(12) United States Patent
Wu et al.

(10) Patent No.: US 10,396,292 B2
(45) Date of Patent: Aug. 27, 2019

(54) COMPOUND AND ORGANIC ELECTRONIC DEVICE USING THE SAME

(71) Applicant: NICHEM FINE TECHNOLOGY CO., LTD., Jhubei, Hsinchu County (TW)

(72) Inventors: Hui-Ling Wu, Jhubei (TW); Liang-Di Liao, Jhubei (TW); Shwu-Ju Shieh, Jhubei (TW); Chi-Chung Chen, Jhubei (TW)

(73) Assignee: SHANGHAI NICHEM FINE CHEMICAL CO., LTD., Shanghai (CN)

( * ) Notice: Subject to any disclaimer, the term of this patent is extended or adjusted under 35 U.S.C. 154(b) by 201 days.

(21) Appl. No.: 15/679,379

(22) Filed: Aug. 17, 2017

(65) Prior Publication Data
US 2018/0053899 A1 Feb. 22, 2018

Related U.S. Application Data

(60) Provisional application No. 62/377,024, filed on Aug. 19, 2016, provisional application No. 62/377,014,
(Continued)

(51) Int. Cl.
*H01L 51/00* (2006.01)
*C07D 313/06* (2006.01)
(Continued)

(52) U.S. Cl.
CPC ........ *H01L 51/0061* (2013.01); *C07D 313/06* (2013.01); *C07D 405/14* (2013.01);
(Continued)

(58) Field of Classification Search
CPC .................................................. C07D 313/06
See application file for complete search history.

(56) References Cited

U.S. PATENT DOCUMENTS

2017/0179397 A1* 6/2017 Kim ..................... H01L 51/0052
2017/0179401 A1* 6/2017 Kim ..................... C09K 11/025
(Continued)

FOREIGN PATENT DOCUMENTS

CN 105793246 A 7/2016
KR 10-2017-0074649 A 6/2017

OTHER PUBLICATIONS

English translation of Japanese Office Action for Appl. No. 2017-157429 dated Aug. 1, 2018.

*Primary Examiner* — Peter F Godenschwager
(74) *Attorney, Agent, or Firm* — Birch, Stewart, Kolasch & Birch, LLP

(57) ABSTRACT

Provided are a novel compound and an organic electronic device using the same. The novel compound is represented by the following Formula (I):

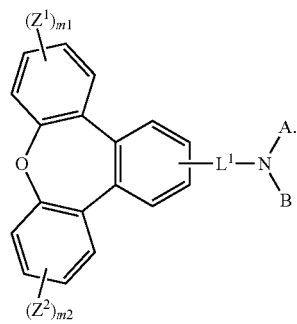

Formula (I)

20 Claims, 44 Drawing Sheets

| Cathode | —18 |
| EIL | —17 |
| ETL | —16 |
| EL | —15 |
| HTL | —14 |
| HIL | —13 |
| Anode | —12 |
| Substrate | —11 |

Related U.S. Application Data filed on Aug. 19, 2016, provisional application No. 62/377,029, filed on Aug. 19, 2016, provisional application No. 62/377,740, filed on Aug. 22, 2016.

(51) Int. Cl.
 *C07D 405/14* (2006.01)
 *H01L 51/50* (2006.01)

(52) U.S. Cl.
 CPC ...... *H01L 51/0059* (2013.01); *H01L 51/0072* (2013.01); *H01L 51/0073* (2013.01); *H01L 51/5056* (2013.01); *H01L 51/5064* (2013.01); *H01L 51/5088* (2013.01); *H01L 51/5096* (2013.01)

(56) References Cited

U.S. PATENT DOCUMENTS

2017/0279050 A1* 9/2017 Chen .................. C07C 211/61
2018/0366647 A1* 12/2018 Jun ..................... H01L 51/0052

* cited by examiner

COMPOUND AND ORGANIC ELECTRONIC DEVICE USING THE SAME

CROSS-REFERENCE TO RELATED APPLICATION

Pursuant to 35 U.S.C. § 119(e), this application claims the benefits of the priority to U.S. Provisional Patent Application No. 62/377,024, filed Aug. 19, 2016, the priority to U.S. Provisional Patent Application No. 62/377,014, filed Aug. 19, 2016, the priority to U.S. Provisional Patent Application No. 62/377,029, filed Aug. 19, 2016, and the priority to U.S. Provisional Patent Application No. 62/377,740, filed Aug. 22, 2016. The contents of the prior applications are incorporated herein by their entirety.

BACKGROUND OF THE INVENTION

1. Field of the Invention

The present invention relates to a novel compound and an organic electronic device using the same, more particularly to a novel compound as hole-transporters and an organic electronic device using the same.

2. Description of the Prior Arts

With the advance of technology, various organic electronic devices that make use of organic materials have been energetically developed. Examples of organic electronic devices include organic light emitting devices (OLEDs), organic phototransistors, organic photovoltaic cells, and organic photodetectors.

OLED was initially invented and proposed by Eastman Kodak Company through a vacuum evaporation method. Dr. Ching Tang and Steven VanSlyke of Kodak Company deposited an electron transport material such as tris(8-hydroxyquinoline)aluminum(III) (abbreviated as $Alq_3$) on a transparent indium tin oxide glass (abbreviated as ITO glass) formed with a hole transport layer of organic aromatic diamine thereon, and subsequently deposited a metal electrode onto an electron transport layer to complete the fabrication of the OLED. OLEDs have attracted lots of attention due to their numerous advantages, such as fast response speed, light weight, compactness, wide viewing angle, high brightness, higher contrast ratio, no need of backlight, and low power consumption. However, the OLEDs still have the problems such as low efficiency and short lifetime.

To overcome the problem of low efficiency, one of the approaches is to interpose some interlayers between the cathode and the anode. With reference to FIG. 1, a modified OLED 1 may have a structure of a substrate 11, an anode 12, a hole injection layer 13 (abbreviated as HIL), a hole transport layer 14 (abbreviated as HTL), an emission layer 15 (abbreviated as EL), an electron transport layer 16 (abbreviated as ETL), an electron injection layer 17 (abbreviated as EIL), and a cathode 18 stacked in sequence. When a voltage is applied between the anode 12 and the cathode 18, the holes injected from the anode 12 move to the EL via HIL and HTL and the electrons injected from the cathode 18 move to the EL via EIL and ETL. Recombination of the electrons and the holes occurs in the EL to generate excitons, thereby emitting a light when the excitons decay from excited state to ground state.

Another approach is to modify the material of HTL to exhibit electron-blocking ability. Examples of conventional hole transport materials include $N^1,N^{1'}$-(biphenyl-4,4'-diyl) bis($N^1$-(naphthalen-1-yl)-$N^4,N^{4'}$-diphenylbenzene-1,4-diamine); or $N^4,N^{4'}$-di(naphthalen-1-yl)-$N^4,N^{4'}$-diphenylbiphenyl-4,4'-diamine (NPB).

However, even using the foresaid hole transport materials, the current efficiency of OLEDs still needs to be improved. Therefore, the present invention provides a novel compound to mitigate or obviate the problems in the prior art.

SUMMARY OF THE INVENTION

An objective of the present invention is to provide a novel compound useful for an organic electronic device, particularly to a novel tertiary amine compound containing at least one tribenzo[b,d,f]oxepinyl group.

Another objective of the present invention is to provide an organic electronic device using the novel compound, so as to improve the efficiency of the organic electronic device.

To achieve the foresaid objectives, the present invention provides a novel compound represented by the following Formula (I):

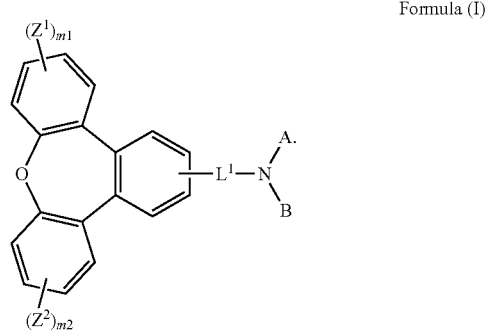

Formula (I)

In an embodiment, the symbol "A" may represent -$L^2$-$R^a$ and the symbol "B" may represent -$L^3$-$R^b$. Or, in another embodiment, A and B are joined together and bonded to the nitrogen atom in Formula (I) to form a substituted or unsubstituted N-carbazolyl group attached with the symbol "$L^1$".

In Formula (I), $L^1$, $L^2$, and $L^3$ are the same or different. $L^1$, $L^2$, and $L^3$ are each independently a single bond or an arylene group having 6 to 60 ring carbon atoms. In the case that $L^1$ is a single bond, the tribenzo[b,d,f]oxepinyl group shown in Formula (I) is directly bonded to the nitrogen atom of the novel compound. In the case that $L^2$ is a single bond, the foresaid $R^a$ group is directly bonded to the nitrogen atom of the novel compound. In the case that $L^3$ is a single bond, the foresaid $R^b$ group is directly bonded to the nitrogen atom of the novel compound.

In Formula (I), $R^a$ and $R^b$ may be the same or different. $R^a$ and $R^b$ may each independently be —Ar-Q, a substituted or unsubstituted tribenzo[b,d,f]oxepinyl group represented by

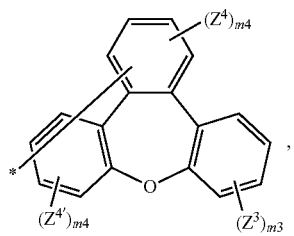

a substituted or unsubstituted tribenzo[b,d,f]azepinyl group represented by

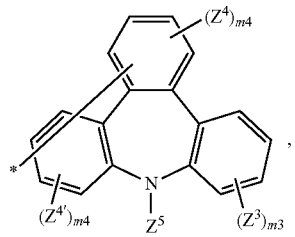

a substituted or unsubstituted dibenzo[b,f]azepinyl group represented by

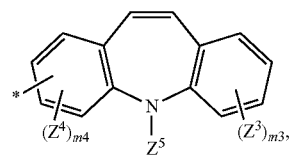

a substituted or unsubstituted carbazolyl group represented by

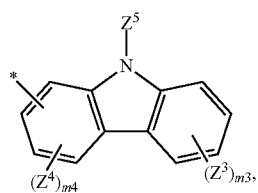

or a substituted or unsubstituted dibenzofuranyl group represented by

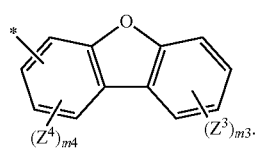

The symbol "Ar" may represent an arylene group having 6 to 60 ring carbon atoms.

The symbol "Q" may represent a hydrogen atom, a deuterium atom, or

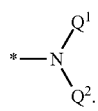

In the case that Q is a hydrogen atom, $R^a$ and/or $R^b$ may each independently be an aryl group having 6 to 60 ring carbon atoms. In the case that Q is a deuterium atom, $R^a$ and/or $R^b$ may each independently be a deuterated aryl group having 6 to 60 ring carbon atoms. In the case that Q is

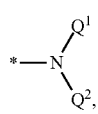

$Q^1$ and $Q^2$ may be the same or different, and $Q^1$ and $Q^2$ may each independently be a substituted or unsubstituted aryl group having 6 to 60 ring carbon atoms, a substituted or unsubstituted tribenzo[b,d,f]oxepinyl group represented by

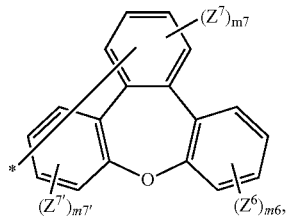

a substituted or unsubstituted tribenzo[b,d,f]azepinyl group represented by

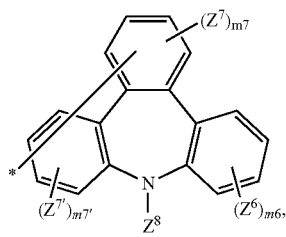

a substituted or unsubstituted dibenzo[b,f]azepinyl group represented by

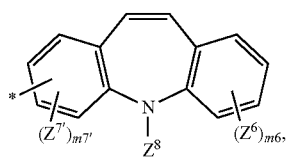

a substituted or unsubstituted carbazolyl group represented by

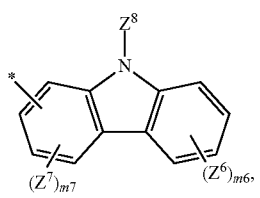

or a substituted or unsubstituted dibenzofuranyl group represented by

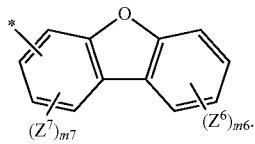

Preferably, the foresaid $Z^1$ to $Z^4$, $Z^{4'}$, $Z^6$, $Z^7$, and $Z^{7'}$ may each independently be a deuterium atom, a trifluoromethyl group, a halogen group, a cyano group, a nitro group, an alkyl group having 1 to 40 carbon atoms, an alkenyl group having 2 to 40 carbon atoms, an alkynyl group having 2 to 40 carbon atoms, a cycloalkyl group having 3 to 60 ring carbon atoms, a heterocycloalkyl group having 3 to 60 ring carbon atoms, an aryl group having 6 to 60 ring carbon atoms, a heteroaryl group having 3 to 60 ring carbon atoms, an alkoxy group having 1 to 40 carbon atoms, an aryloxy group having 6 to 60 ring carbon atoms, an alkylsilyl group having 1 to 40 carbon atoms, an arylsilyl group having 6 to 60 ring carbon atoms, an alkylboron group having 1 to 40 carbon atoms, an arylboron group having 6 to 60 ring carbon atoms, a phosphine group having 1 to 40 carbon atoms, or a phosphine oxide group having 1 to 40 carbon atoms. For example, the foresaid $Z^1$ to $Z^4$, $Z^{4'}$, $Z^6$, $Z^7$, and $Z^{7'}$ may each independently be, but not limited to, a deuterium atom, a trifluoromethyl group, a halogen group, a cyano group, a nitro group, a methyl group, an ethyl group, a propyl group, a hexyl group, an ethynyl group, a phenyl group, a biphenylyl group, a napthyl group, an anthryl group or any deuterated analogs thereof.

Preferably, the foresaid $Z^5$ and $Z^8$ may each independently be a hydrogen atom, a deuterium atom, an alkyl group having 1 to 40 carbon atoms, an alkenyl group having 2 to 40 carbon atoms, an alkynyl group having 2 to 40 carbon atoms, a cycloalkyl group having 3 to 60 ring carbon atoms, a heterocycloalkyl group having 3 to 60 ring carbon atoms, an aryl group having 6 to 60 ring carbon atoms, or a heteroaryl group having 3 to 60 ring carbon atoms. For example, the foresaid $Z^5$ and $Z^8$ may each independently be, but not limited to, a deuterium atom, a trifluoromethyl group, a halogen group, a cyano group, a nitro group, a methyl group, an ethyl group, a propyl group, a hexyl group, an ethynyl group, a phenyl group, a biphenylyl group, a napthyl group, an anthryl group or any deuterated analogs thereof. More preferably, the foresaid $Z^5$ and $Z^8$ may each independently be a phenyl group or its deuterated analogs.

Preferably, m1, m2, m3, and m6 may each independently be an integral of 0 to 4, such as 0, 1, 2, 3, and 4. Preferably, m4, m4', m7, and m7' are each independently an integral of 0 to 3, such as 0, 1, 2, and 3.

Preferably, $R^a$ and $R^b$ are each independently selected from the group consisting of: —Ar-Q,

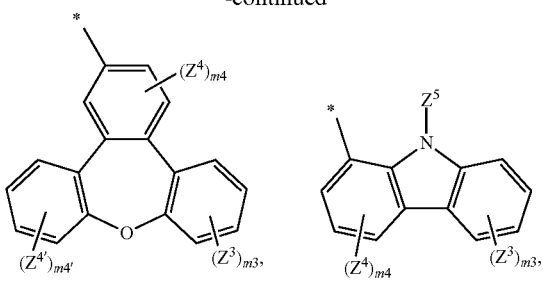

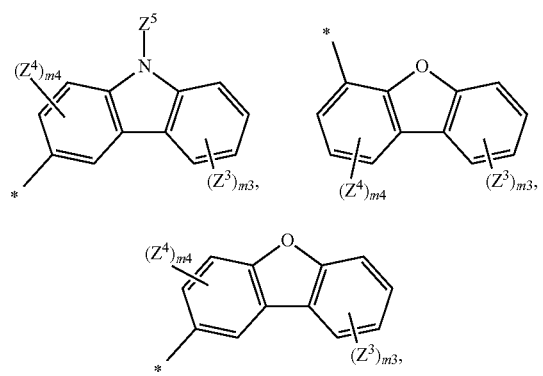

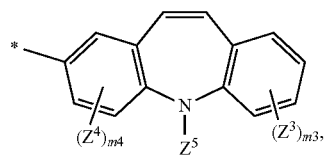

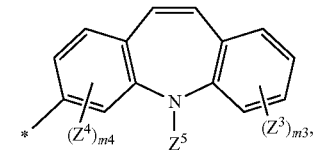

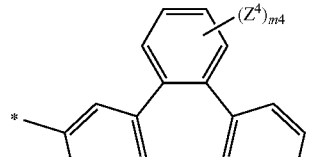

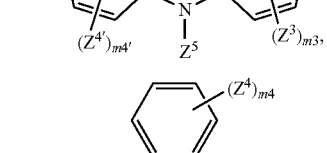

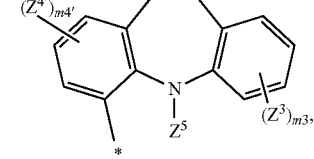

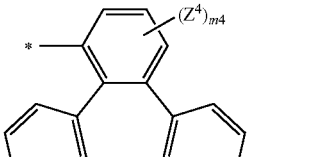

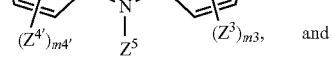

and

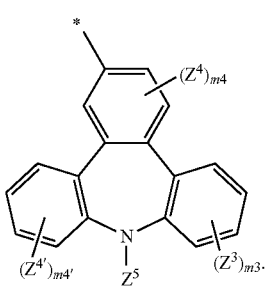
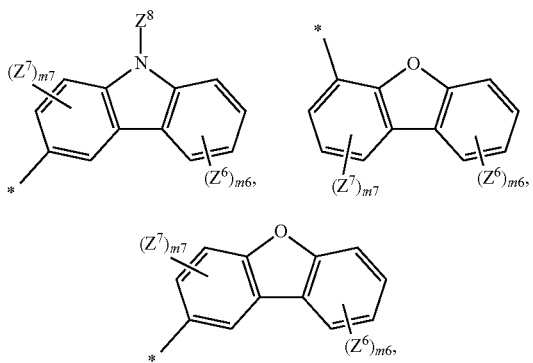
In the case that $R^a$ and/or $R^b$ is —Ar-Q and Q is
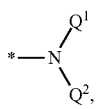
$Q^1$ and $Q^2$ are each independently selected from the group consisting of: a substituted or unsubstituted aryl group having 6 to 60 ring carbon atoms,
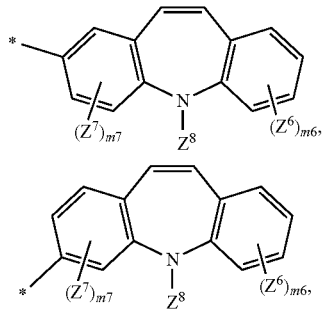
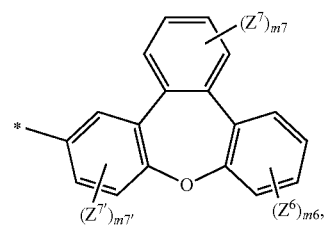
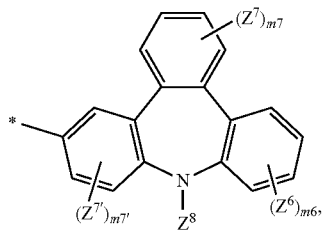
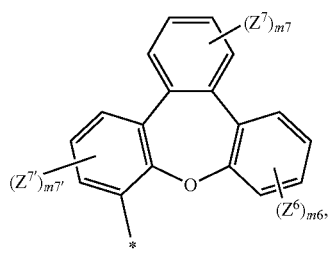
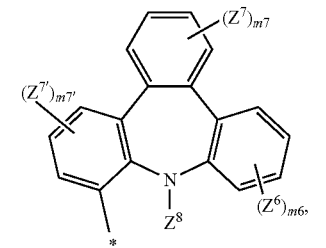
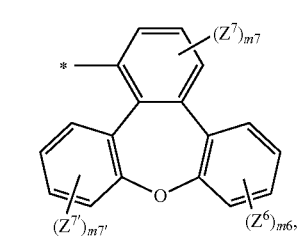
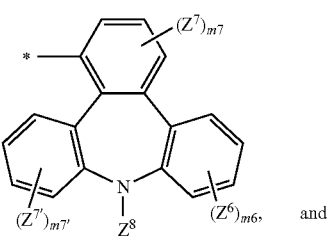
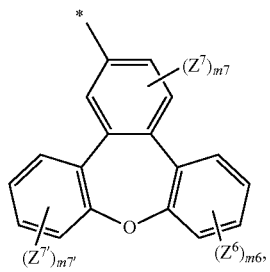
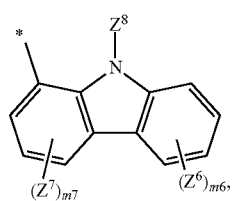
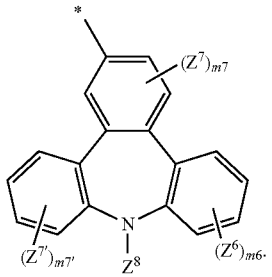
and Preferably, $L^1$, $L^2$, $L^3$, and Ar may be each independently selected from the group consisting of:

a single bond,

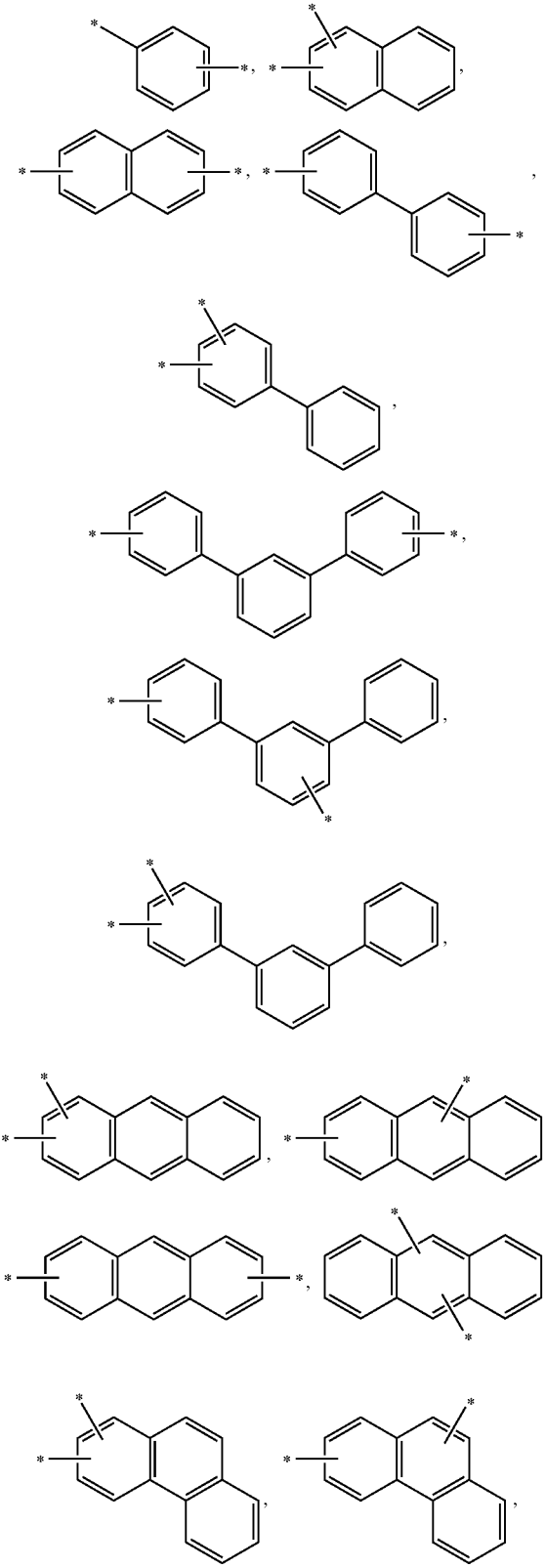

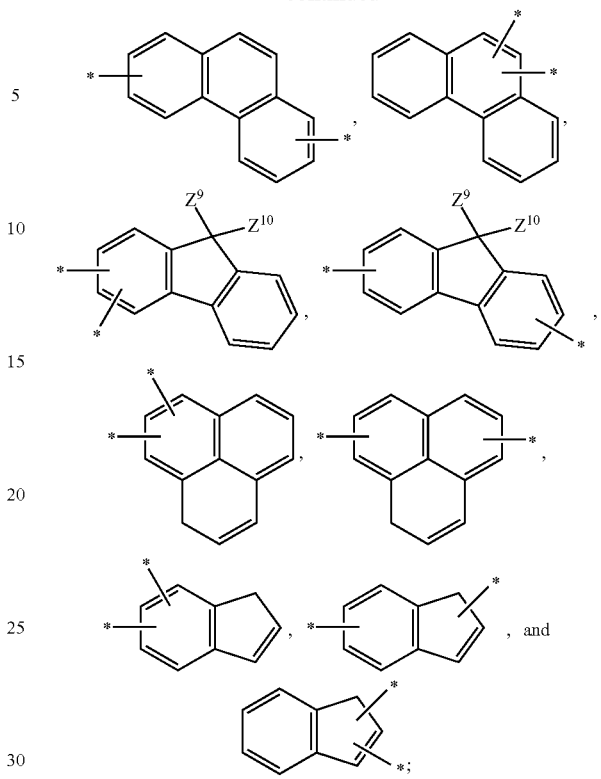

wherein $Z^9$ and $Z^{10}$ may each independently be, for example, but not limited to, a hydrogen atom, a deuterium atom, a methyl group, an ethyl group, a propyl group, a butyl group, a pentyl group, a hexyl group and a phenyl group. Preferably, Ar may not be a single bond.

Preferably, $G^1$, $G^2$, $Z^1$ to $Z^8$, $Z^{4'}$, $Z^{7'}$, $Q^1$, $Q^2$, and —Ar-Q may each independently be, for example, but not limited to, a substituted or unsubstituted phenyl group, a substituted or unsubstituted biphenylyl group, a substituted or unsubstituted terphenyl group, a substituted or unsubstituted naphthyl group, a substituted or unsubstituted phenanthryl group, a substituted or unsubstituted anthryl group, a substituted or unsubstituted benzanthryl group, a substituted or unsubstituted pyrenyl group, a substituted or unsubstituted fluorenyl group, and any deuterated analogs thereof. More specifically, $G^1$, $G^2$, $Z^1$ to $Z^8$, $Z^{4'}$, $Z^{7'}$, $Q^1$, $Q^2$, and —Ar-Q may each independently be, for example, but not limited to:

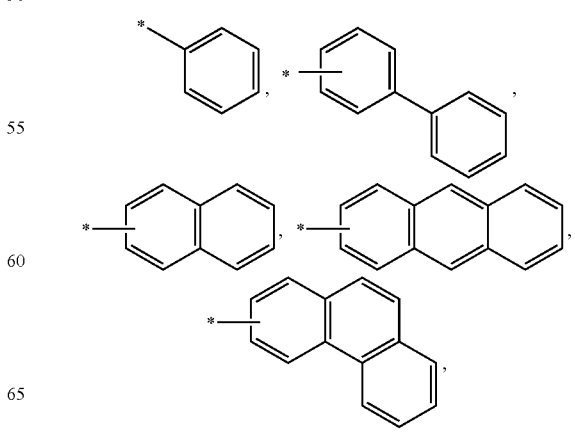

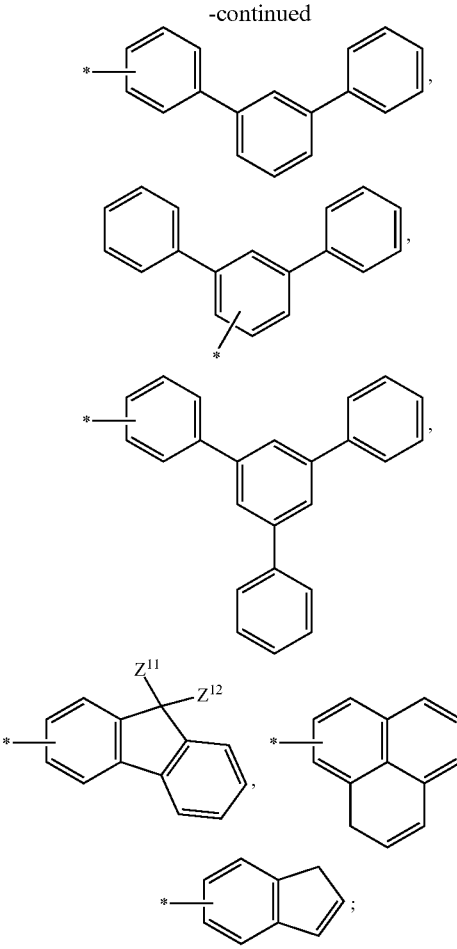

wherein $Z^{11}$ and $Z^{12}$ may each independently be, for example, but not limited to, a hydrogen atom, a deuterium atom, a methyl group, an ethyl group, a propyl group, a butyl group, a pentyl group, a hexyl group and a phenyl group.

More specifically, the novel compound may be represented by

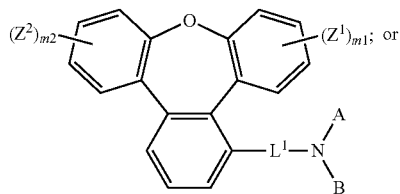

Formula (I-I)

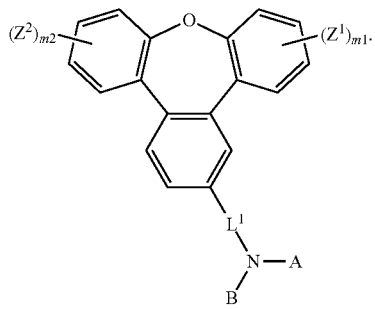

Formula (I-II)

In the case that A is -$L^2$-$R^a$, B is -$L^3$-$R^b$, and both $R^a$ and $R^b$ are each tribenzo[b,d,f]oxepinyl groups, the novel compound contains three tribenzo[b,d,f]oxepinyl groups. For example, the novel compound may be represented by any one of the following formulae:

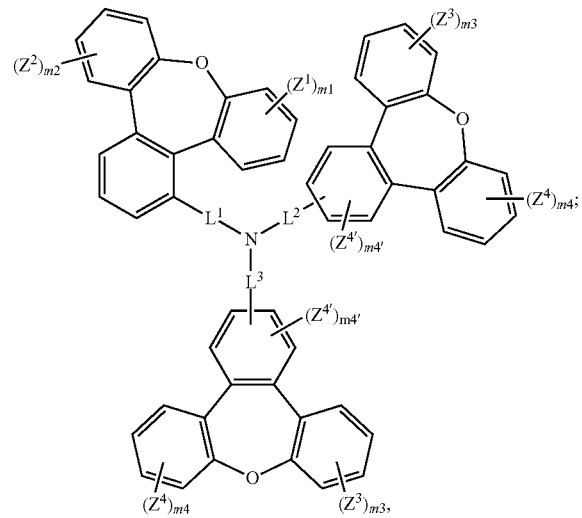

Formula (I-III)

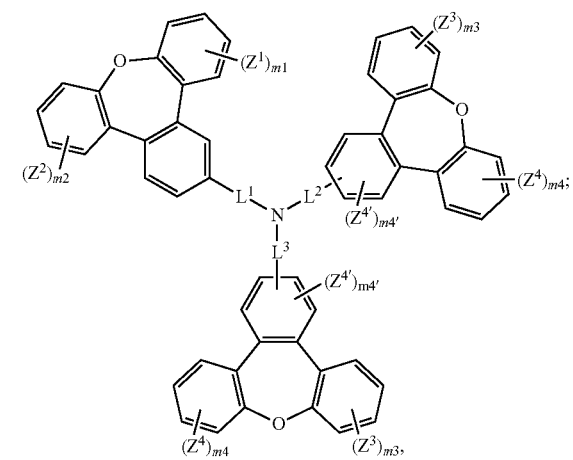

Formula (I-IV)

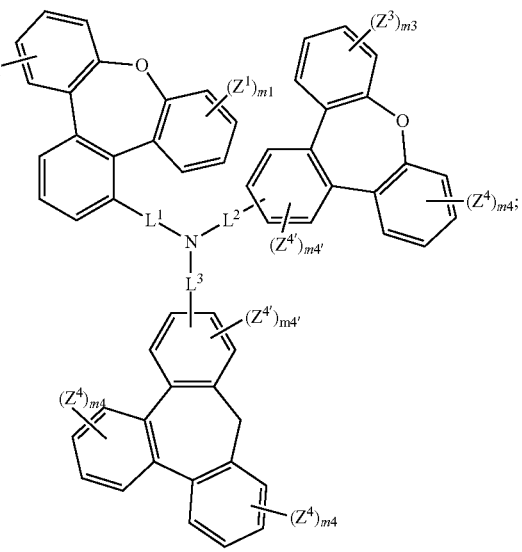

Formula (I-V)

-continued

Formula (I-IV)

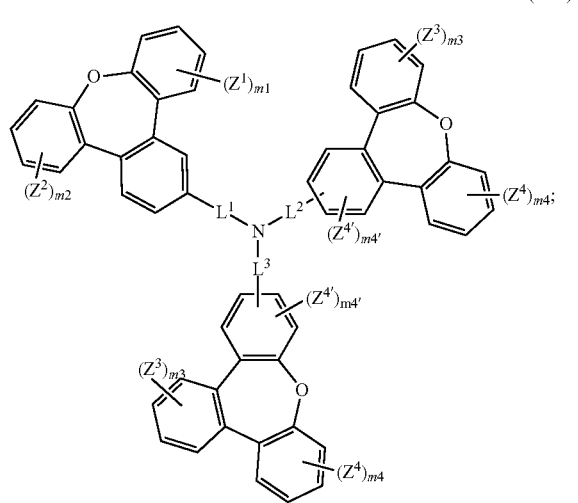

Formula (I-VII)

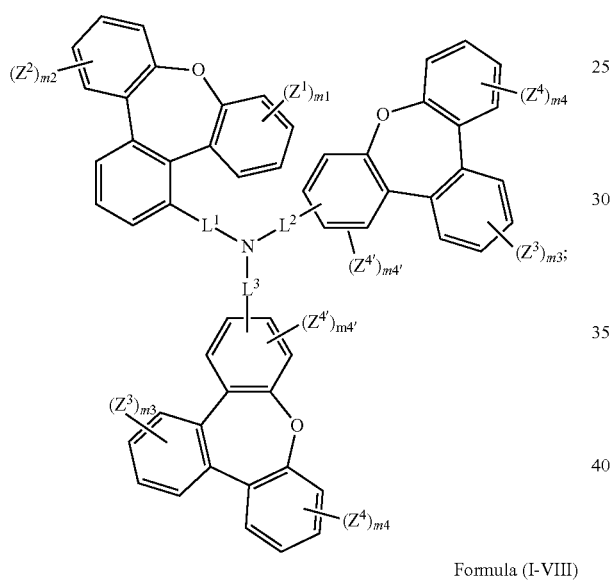

Formula (I-VIII)

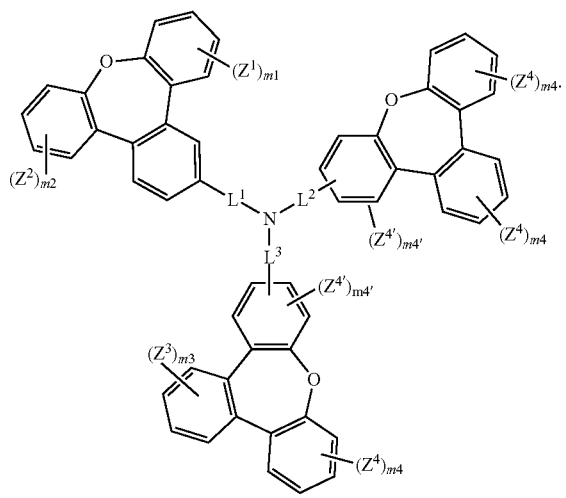

In the case that A is -L²-Rᵃ, B is -L³-Rᵇ, Rᵃ is a tribenzo[b,d,f]oxepinyl group and Rᵇ is an aryl group having 6 to 60 ring carbon atoms, a substituted or unsubstituted carbazolyl group, or a substituted or unsubstituted dibenzofuranyl group, the novel compound contains two tribenzo[b,d,f]oxepinyl groups. For example, the novel compound may be represented by any one of the following formulae:

Formula (I-IX)

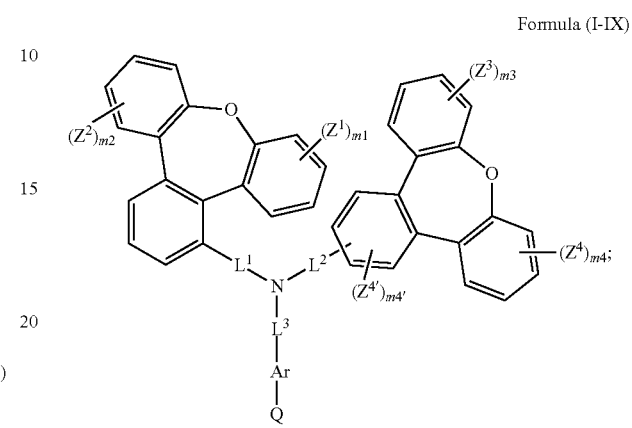

Formula (I-X)

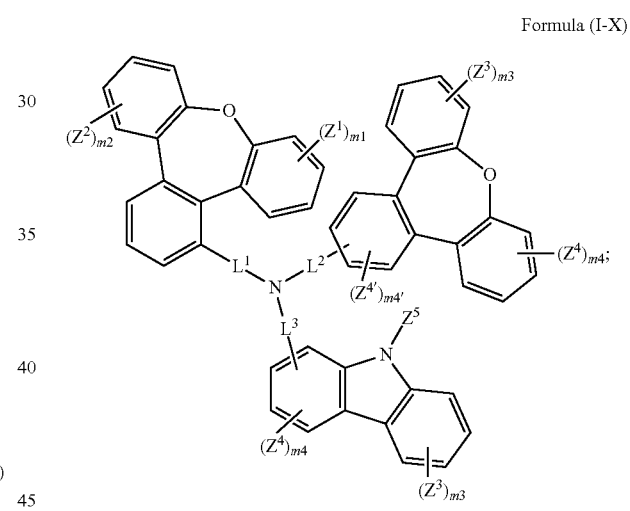

Formula (I-XI)

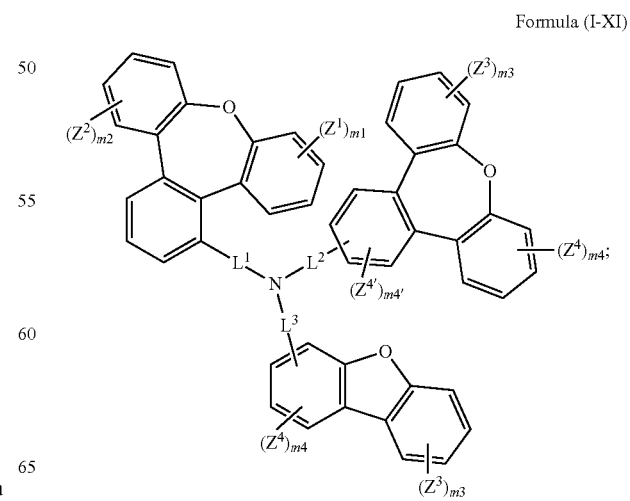

Formula (I-XII)
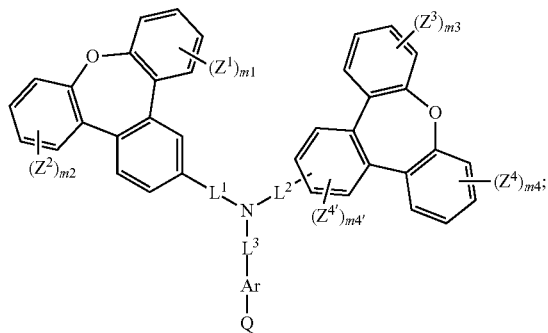
Formula (I-XIII)
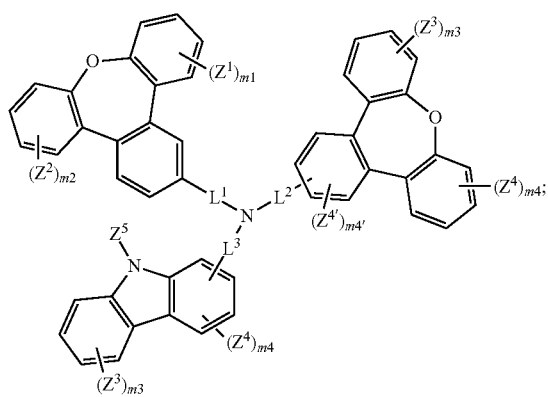
Formula (I-XIV)
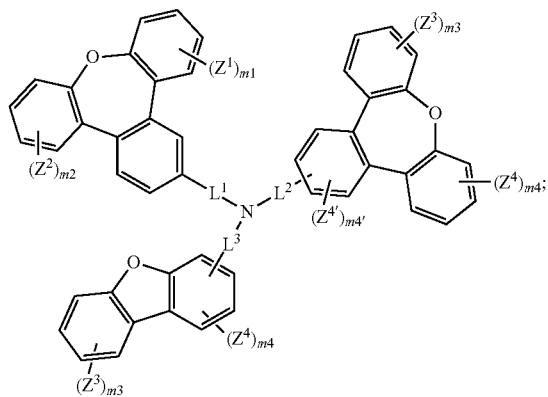
Formula (I-XV)
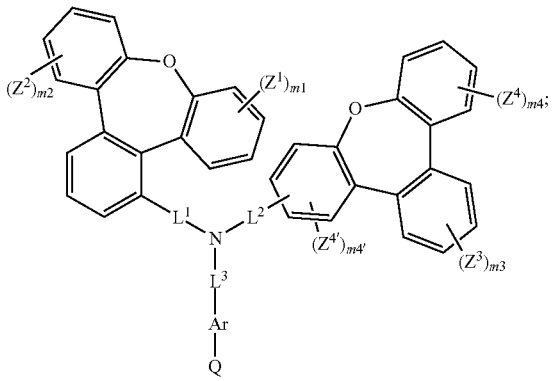
Formula (I-XVI)
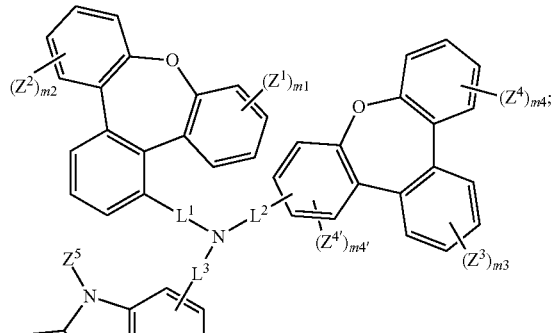
Formula (I-XVII)
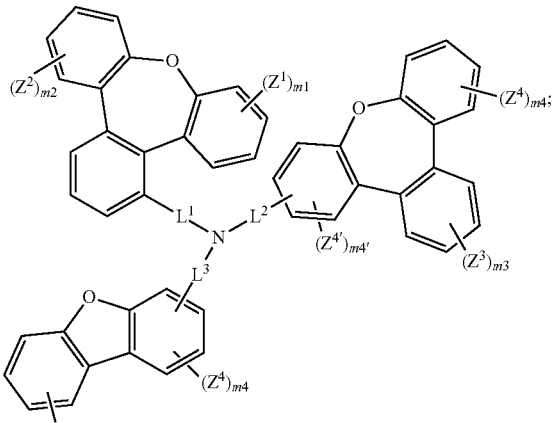
Formula (I-XVIII)
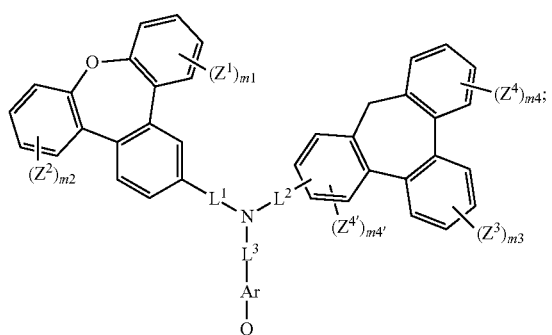
Formula (I-XIX)
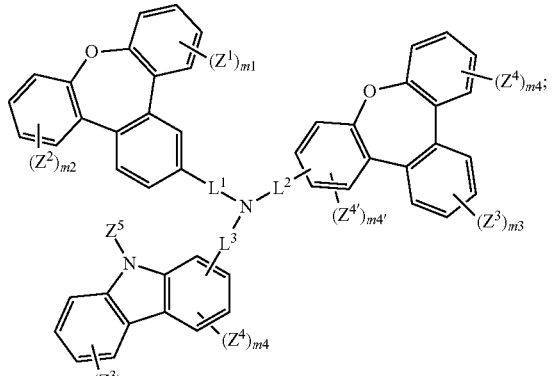

-continued

Formula (I-XX)

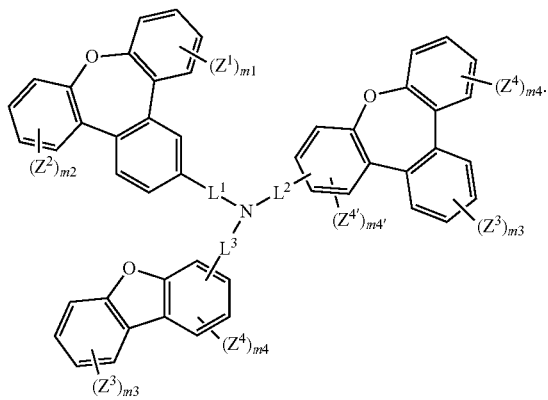

In the case that A is -L$^2$-R$^a$, B is -L$^3$-R$^b$, and each of R$^a$ and R$^b$ is —Ar-Q, the novel compound contains one tribenzo[b,d,f]oxepinyl group and two aryl groups each having 6 to 60 ring carbon atoms. For example, the novel compound may be represented by any one of the following formulae:

Formula (I-XXI)

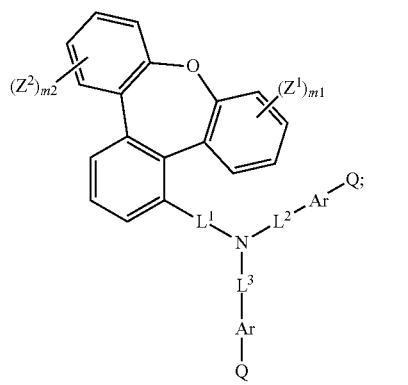

Formula (I-XXIV)

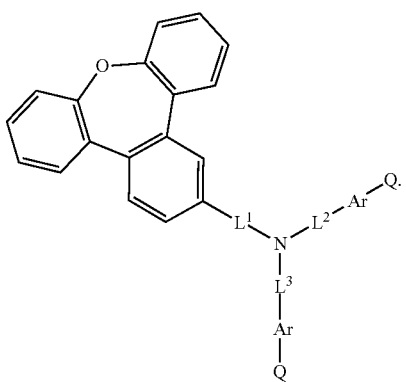

Preferably, in Formulae (I-XXI) and (I-XXIV), Q is a hydrogen atom or a deuterium atom. In this case, R$^a$ and R$^b$ may each independently be an aryl group having 6 to 60 ring carbon atoms or a deuterated aryl group having 6 to 60 ring carbon atoms, and preferably, R$^a$ and R$^b$ are the same.

In the case that A is -L$^2$-R$^a$, B is -L$^3$-R$^b$, R$^a$ is —Ar-Q, and R$^b$ is either a substituted or unsubstituted carbazolyl group or a substituted or unsubstituted dibenzofuranyl group, the novel compound contains two heteroaryl groups bonded to the nitrogen atom of the novel compound. For example, the novel compound may be represented by any one of the following formulae:

Formula (I-XXII)

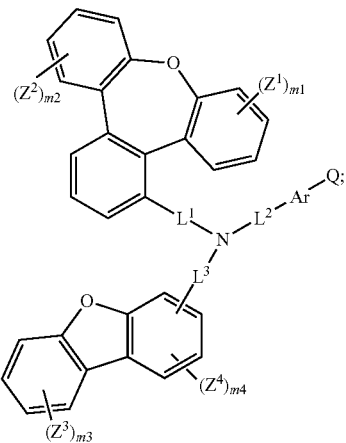

Formula (I-XXIII)

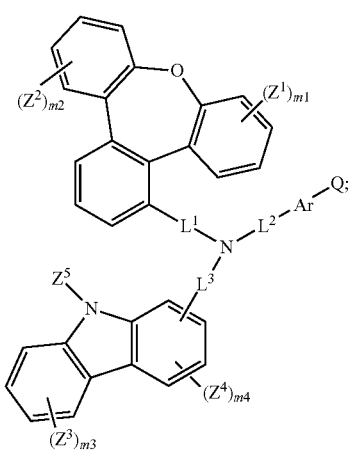

Formula (I-XXV)

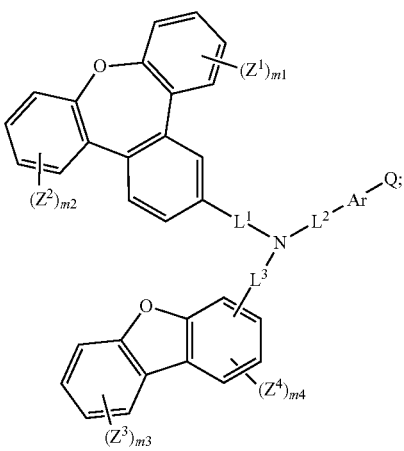

Formula (I-XXVI)

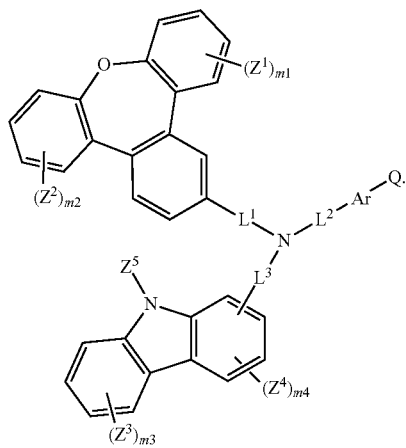

In the case that A is -L²-Rᵃ, B is -L³-Rᵇ, Rᵃ and Rᵇ are each a substituted or unsubstituted carbazolyl group or a substituted or unsubstituted dibenzofuranyl group, the novel compound contains three heteroaryl groups bonded to the nitrogen atom of the novel compound, and one of the heteroaryl groups is tribenzo[b,d,f]oxepinyl group. For example, the novel compound may be represented by any one of the following formulae:

Formula (I-XXVII)

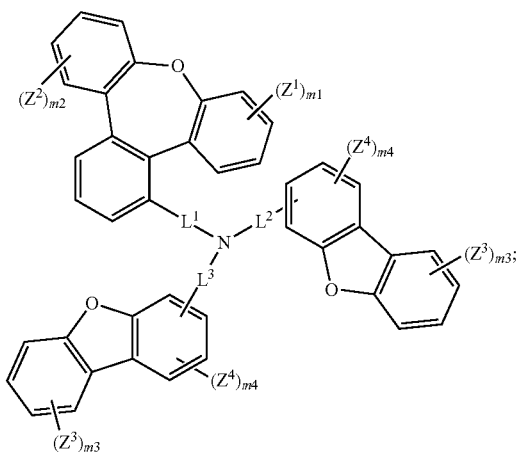

Formula (I-XXVII)

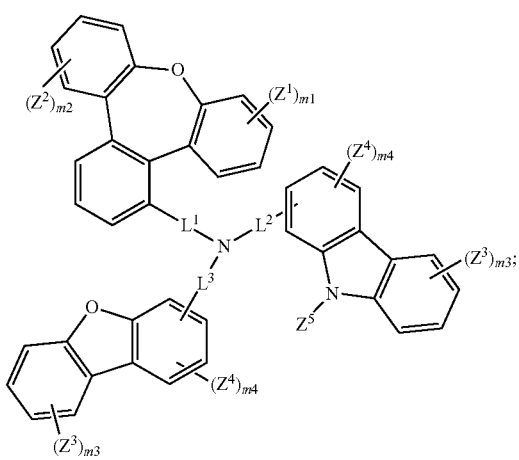

Formula (I-XXIX)

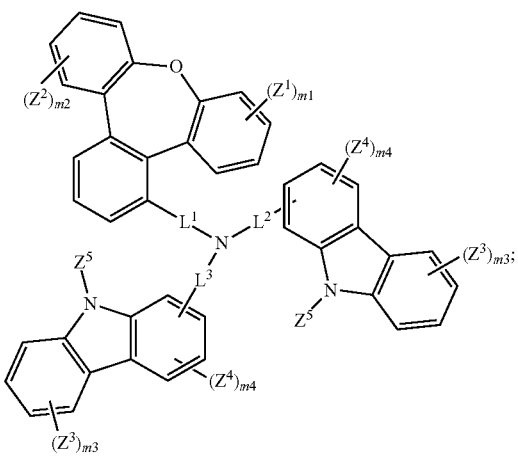

Formula (I-XXX)

Formula (I-XXXI)

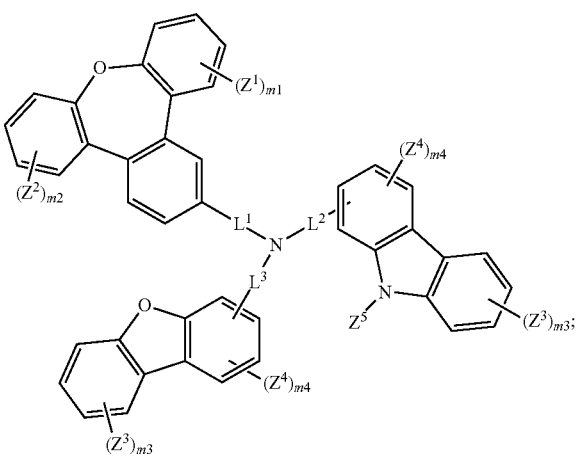

Formula (I-XXXII)

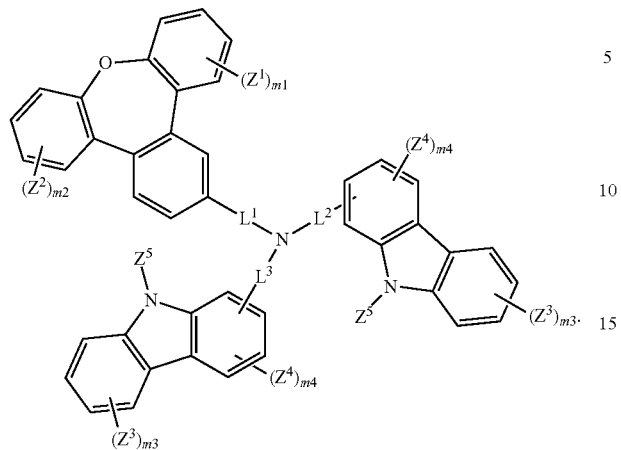

In the case that A and B are joined together and bonded to form a cyclic structure, the nitrogen atom in Formula (I) is bonded to both the carbon atom of A and the carbon atoms of B to form a substituted or unsubstituted N-carbazolyl group. The substituted or unsubstituted N-carbazolyl group constructed from A, B, and the nitrogen atom is bonded to the tribenzo[b,d,f]oxepinyl group in Formula (I). For example, the novel compound may be represented by Formula (I-XXXIII) or (I-XXXIV):

Formula (I-XXXIII)

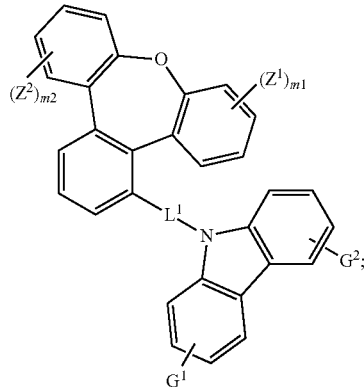

Formula (I-XXXIV)

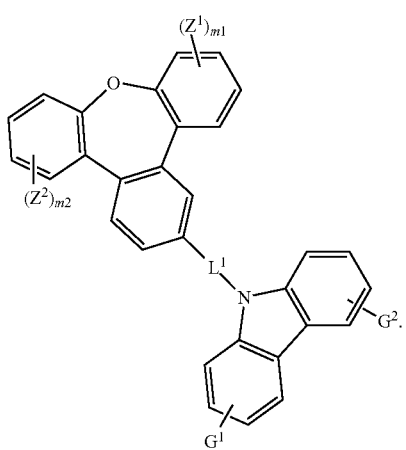

In Formulae (I-XXXIII) and (I-XXXIV), $G^1$ and $G^2$ are the same or different. Preferably, $G^1$ and $G^2$ may each independently be, for example, but not limited to, a hydrogen atom, a deuterium atom, an alkyl group having 1 to 40 carbon atoms, an alkenyl group having 2 to 40 carbon atoms, an alkynyl group having 2 to 40 carbon atoms, a cycloalkyl group having 3 to 60 ring carbon atoms, a heterocycloalkyl group having 3 to 60 ring carbon atoms, an aryl group having 6 to 60 ring carbon atoms, or a heteroaryl group having 3 to 60 ring carbon atoms.

In the case that $R^a$ is —Ar-Q and Q is

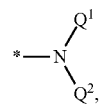

the novel compound is a tertiary diamine compound. For example, the novel compound may be represented by Formula (I-XXXV) or (I-XXXVI):

Formula (I-XXXV)

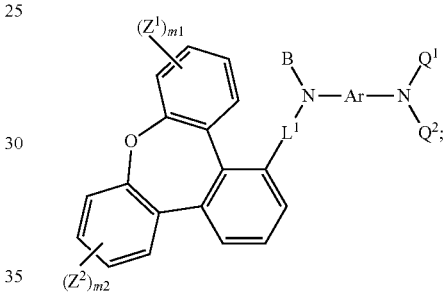

Formula (I-XXXVI)

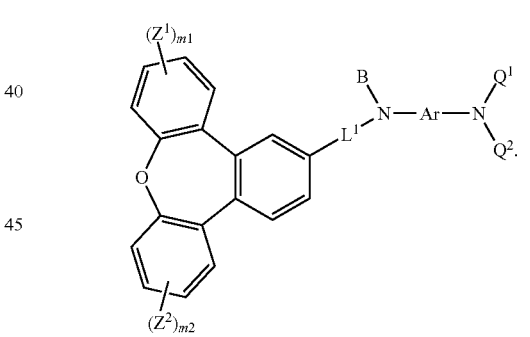

In Formulae (I-XXXV) and (I-XXXVI), said Ar acts as a linker to bond two tertiary amine compounds. The tertiary diamine compound of the present invention may be a symmetrical or unsymmetrical diamine compound.

In this case, B may preferably be a tribenzo[b,d,f]oxepinyl group or a substituted or unsubstituted aryl group having 6 to 60 ring carbon atoms. In this case, $Q^1$ and $Q^2$ may each independently be, for example, but not limited to, a substituted or unsubstituted phenyl group, a substituted or unsubstituted biphenylyl group, a substituted or unsubstituted terphenyl group, a substituted or unsubstituted naphthyl group, a substituted or unsubstituted phenanthryl group, a substituted or unsubstituted anthryl group, a substituted or unsubstituted benzanthryl group, a substituted or unsubstituted pyrenyl group, a substituted or unsubstituted fluorenyl group, or any deuterated analogs thereof.

In the case that $R^a$ is —Ar-Q and Q is

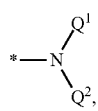

$Q^1$ is preferably a substituted or unsubstituted tribenzo[b,d,f]oxepinyl group, $Q^2$ is preferably a substitution group same as $R^b$, $L^2$ is preferably a single bond, and Ar is an arylene group same as $L^3$, thus the novel compound is a symmetrical tertiary diamine.

Preferably, any one of $G^1$, $G^2$, $Z^1$ to $Z^8$, $Z^{4'}$, $Z^{7'}$, $Q^1$, $Q^2$ may be, for example, but not limited to, More specifically, $Z^5$ and $Z^8$ may each independently be, for example, but not limited to,

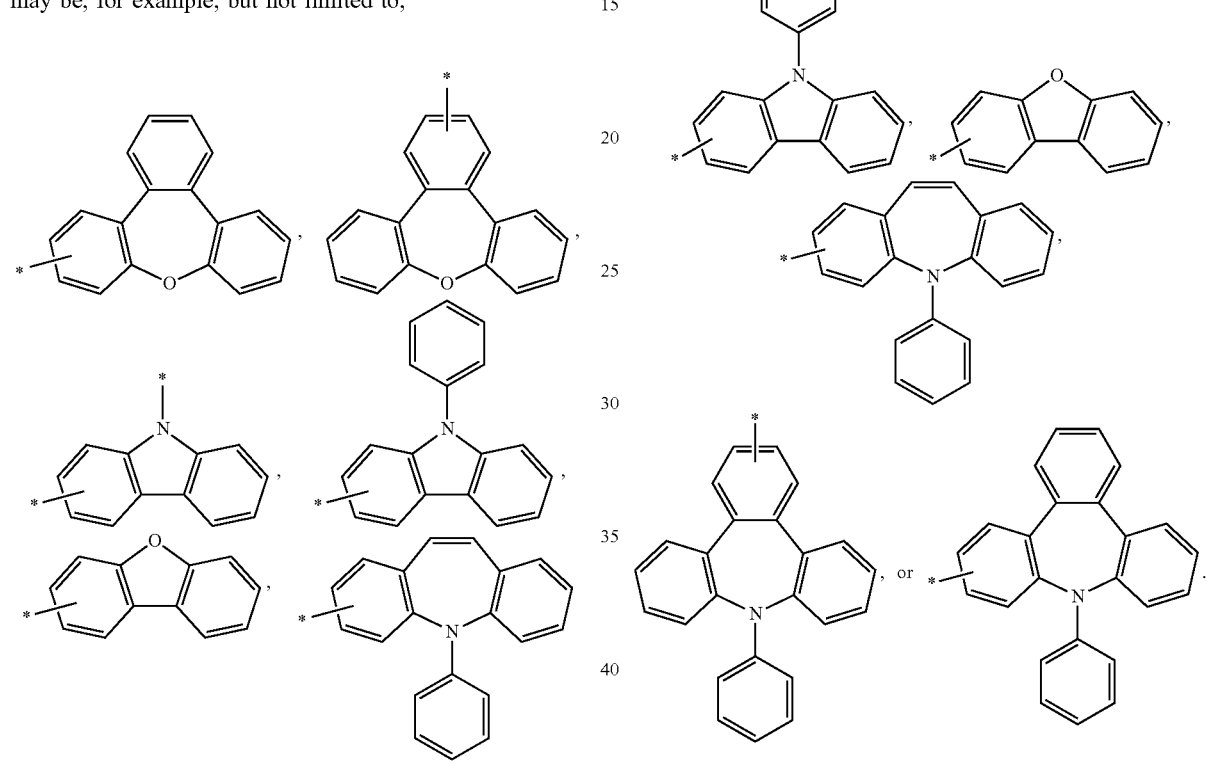

For example, the compound may be, for example, but not limited to:

Compound 1

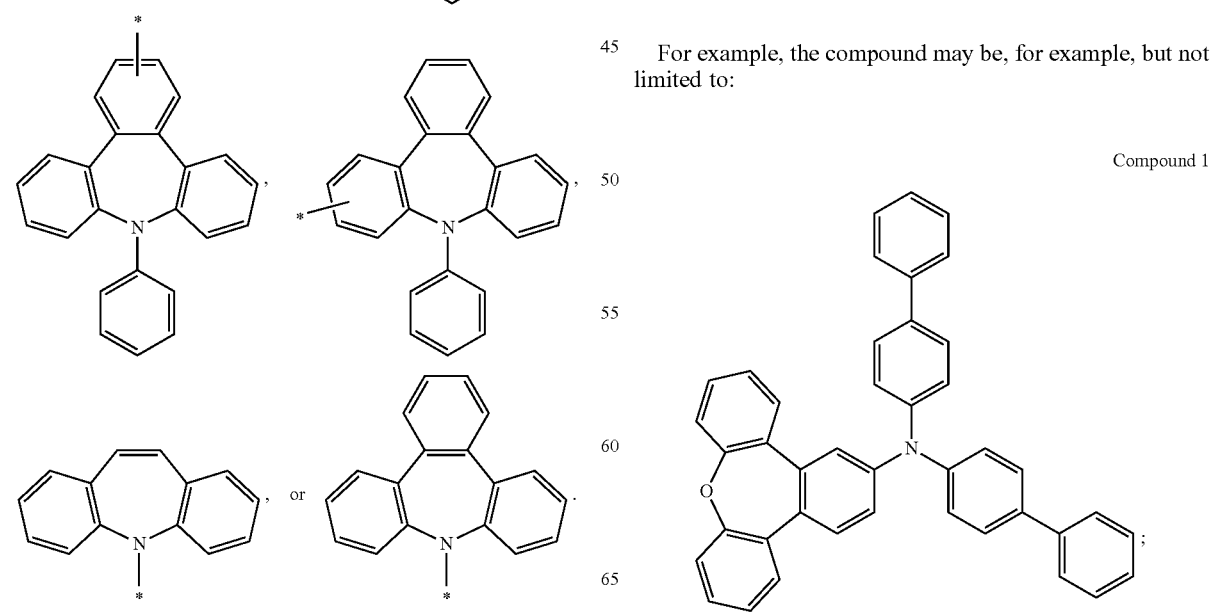

Compound 2
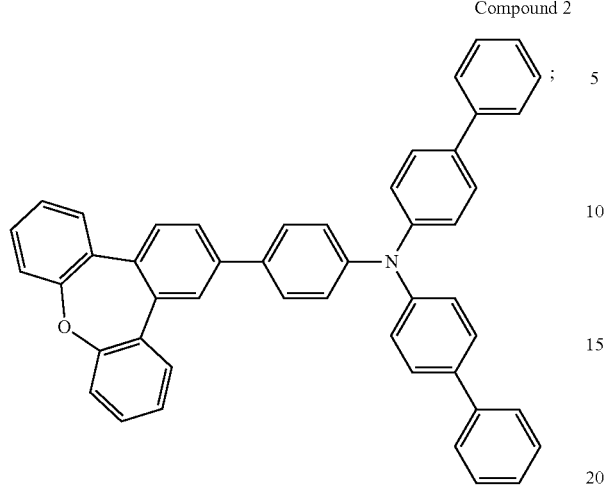
Compound 5
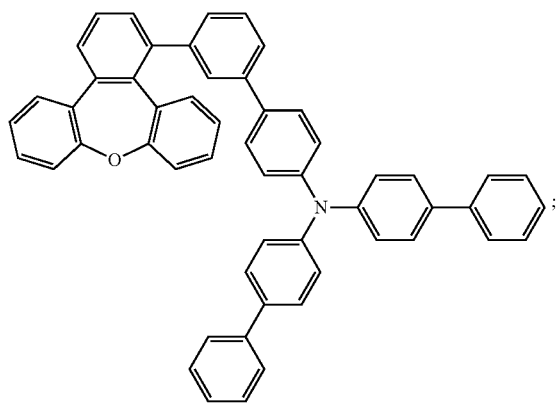
Compound 3
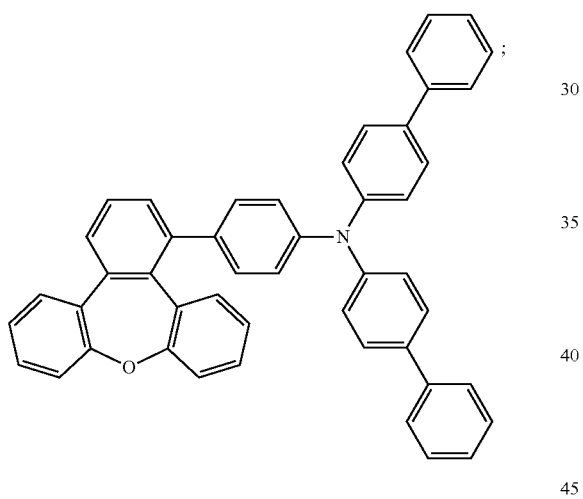
Compound 6
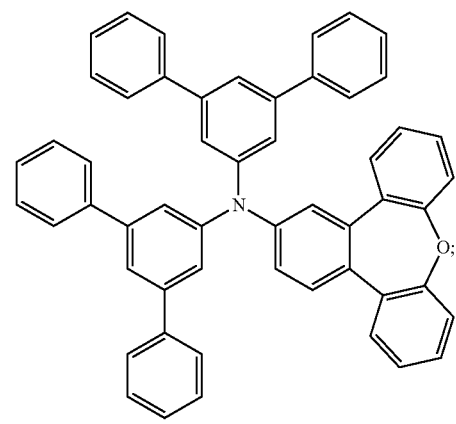
Compound 4
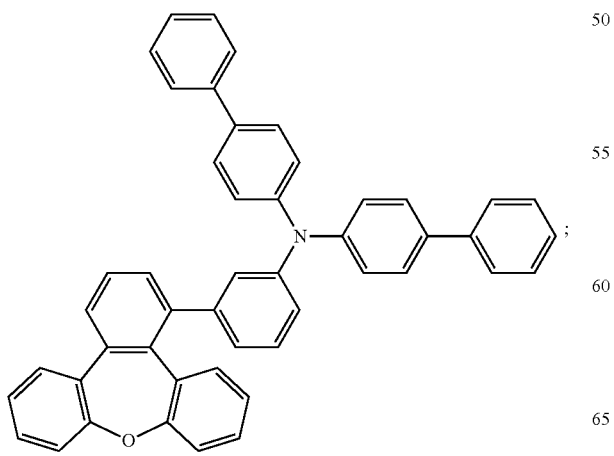
Compound 7
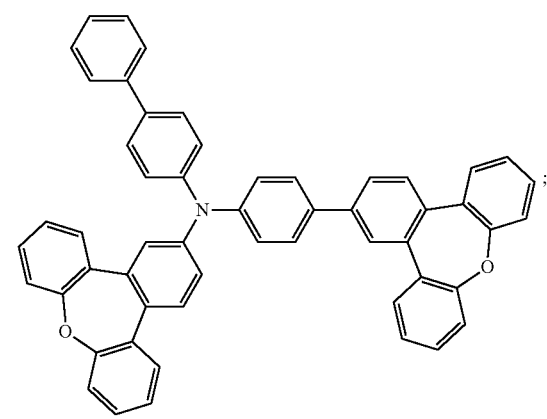

Compound 8
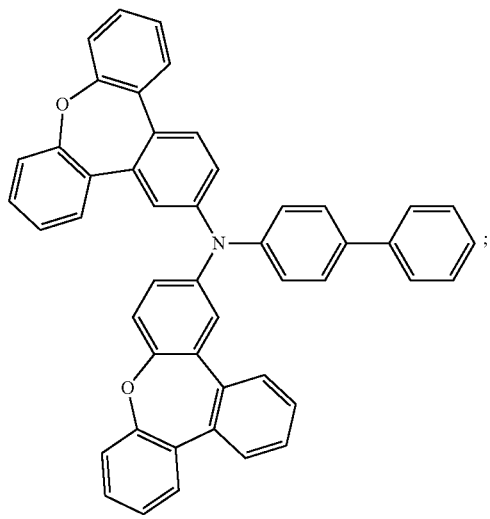
Compound 9
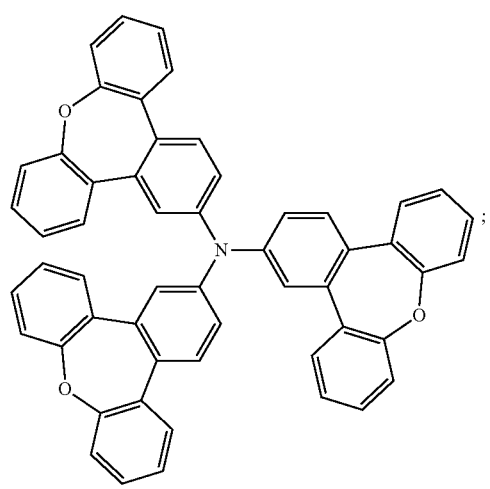
Compound 10
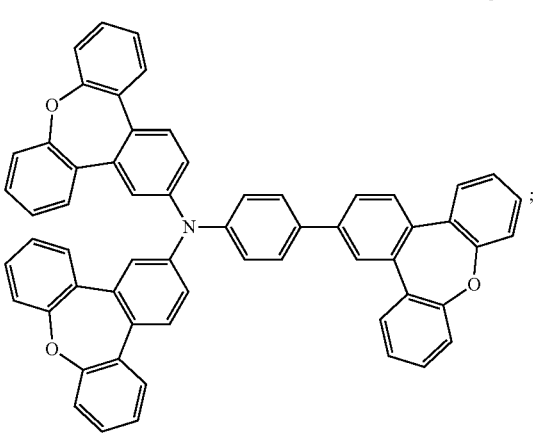
Compound 11
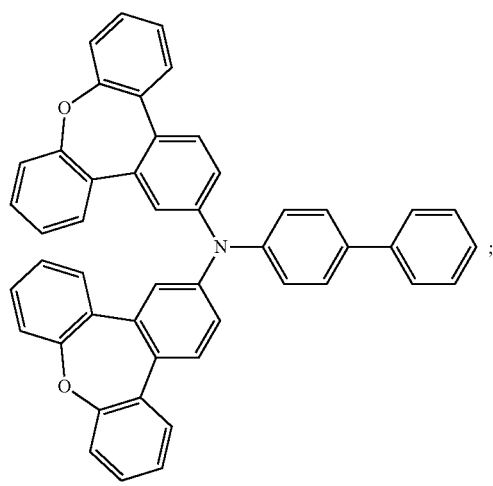
Compound 12
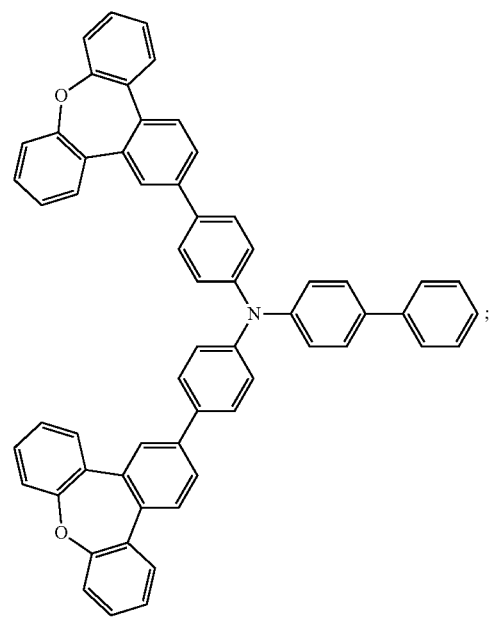
Compound 13
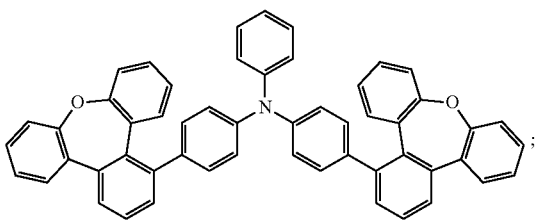

-continued
Compound 14
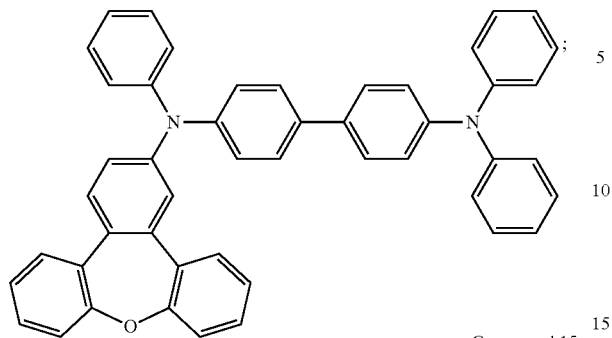
Compound 15
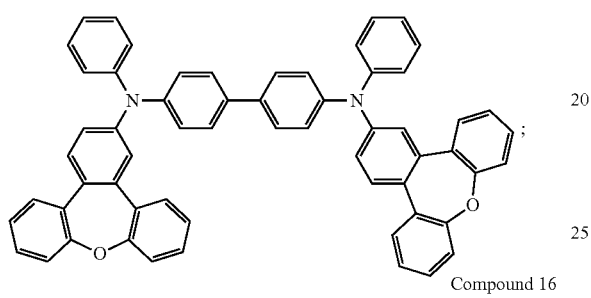
Compound 16
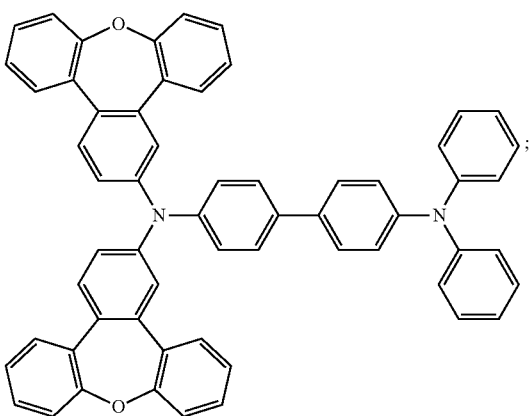
Compound 17
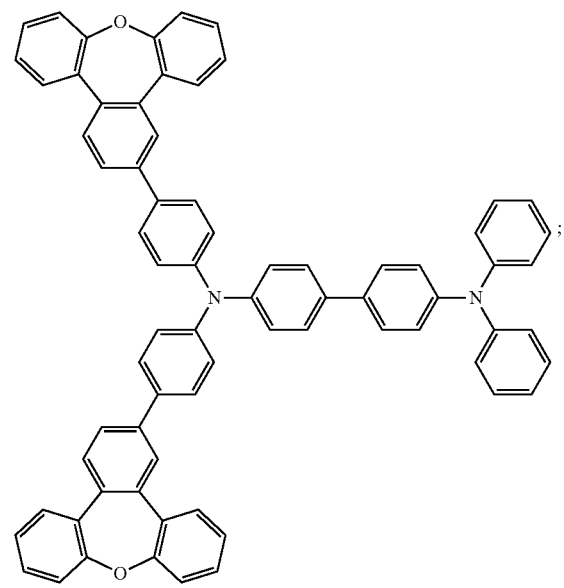
Compound 18
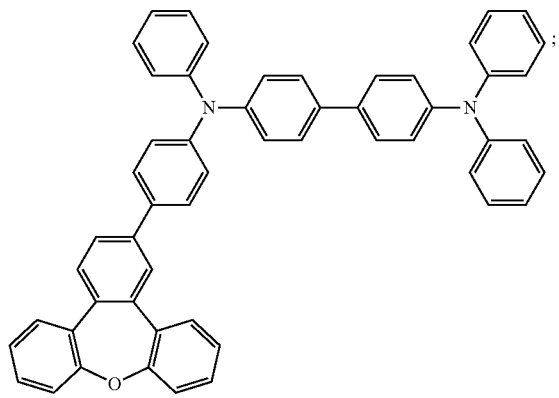
Compound 19
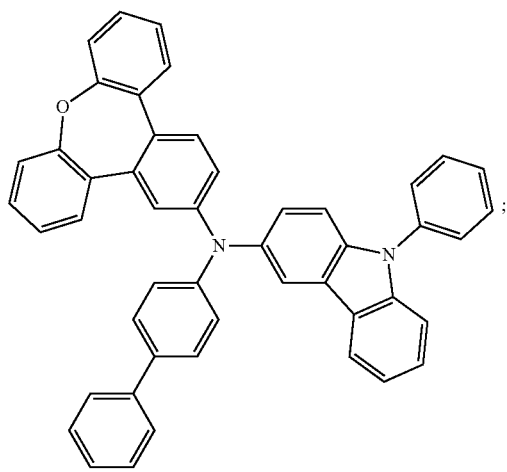
Compound 20
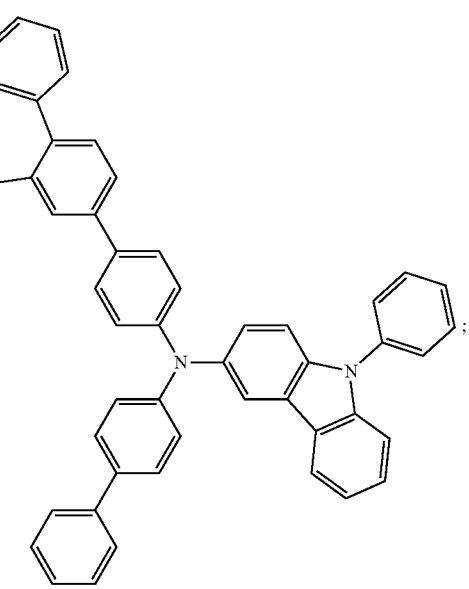

Compound 21
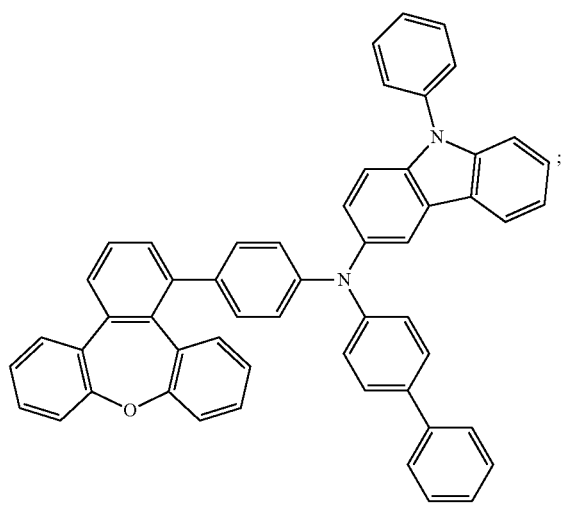
Compound 22
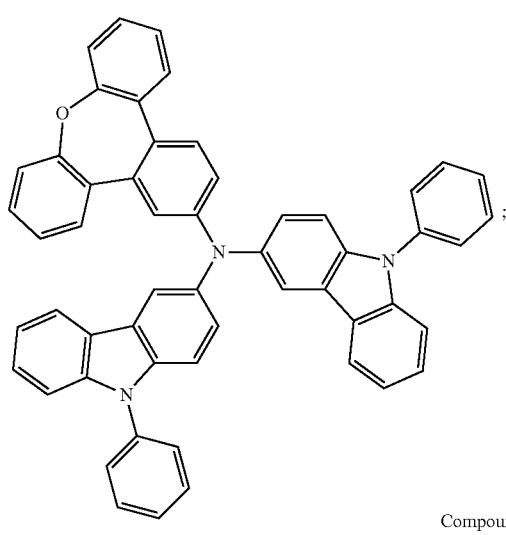
Compound 23
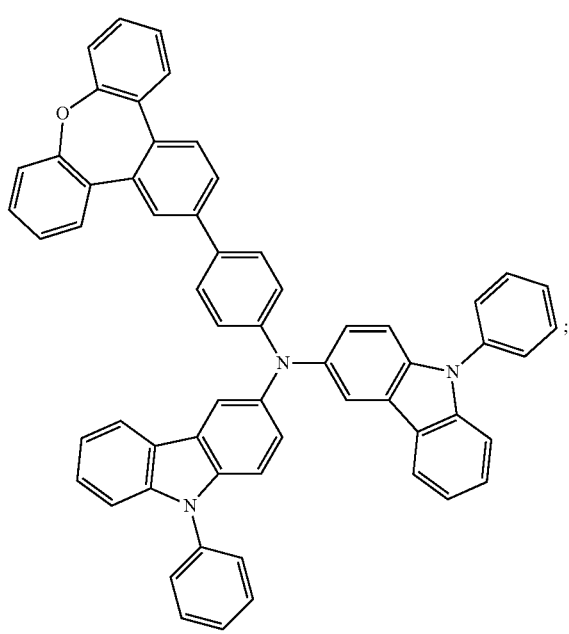
Compound 24
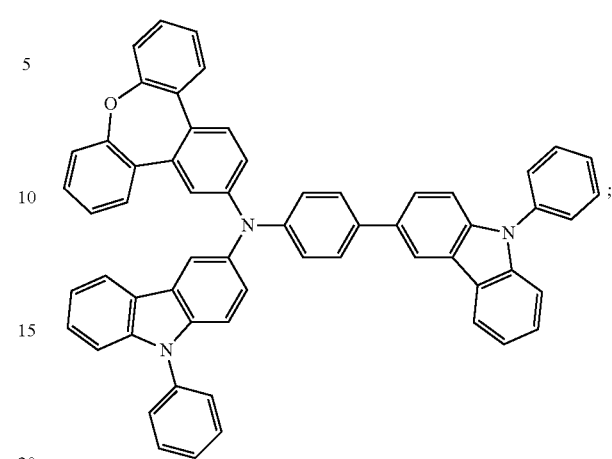
Compound 25
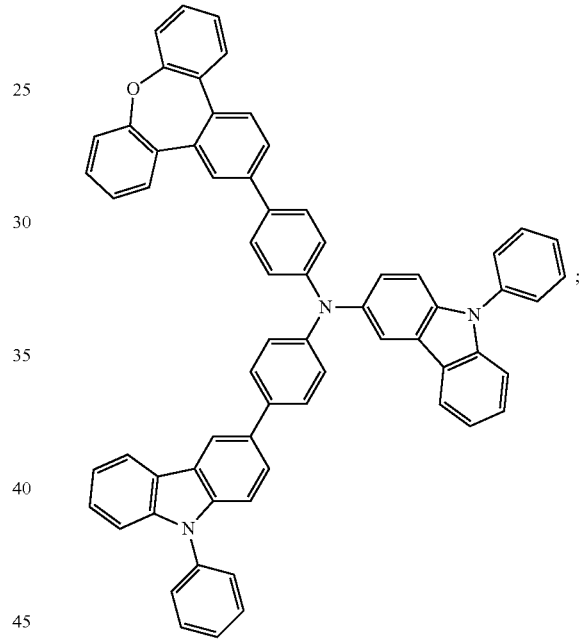
Compound 26

Compound 27
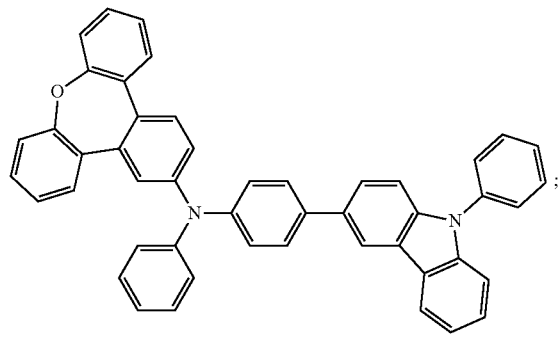
Compound 28
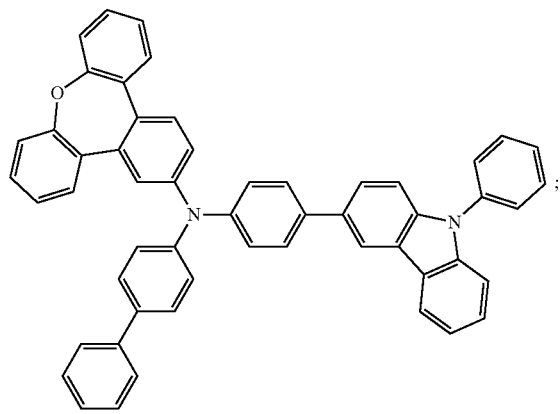
Compound 29
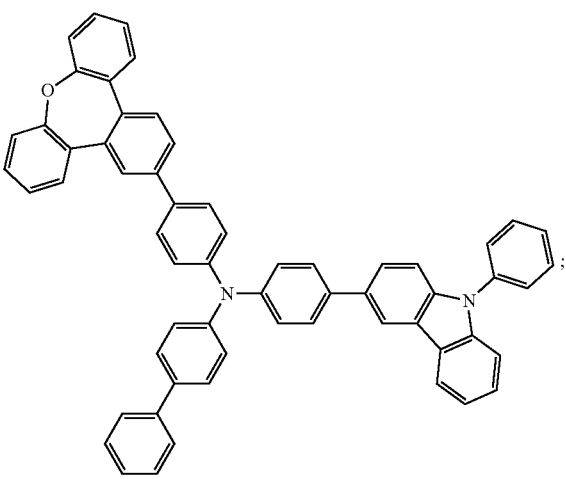
Compound 30
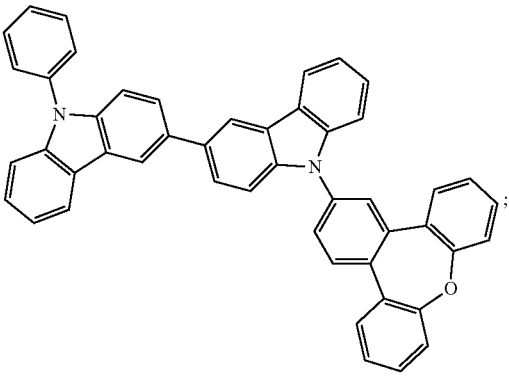
Compound 31
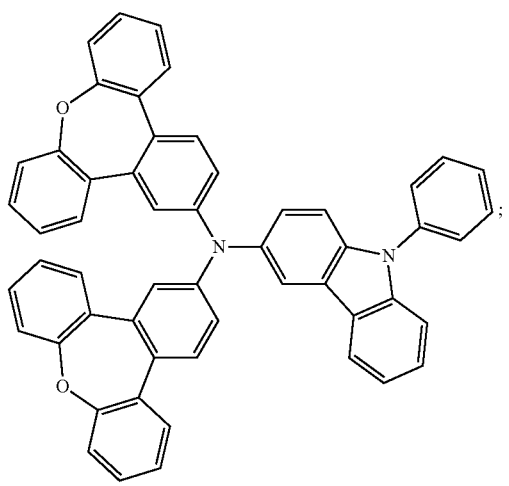
Compound 32
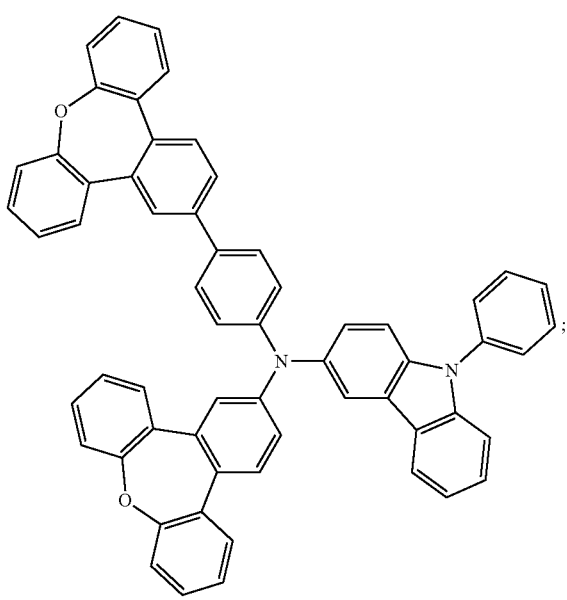

Compound 33
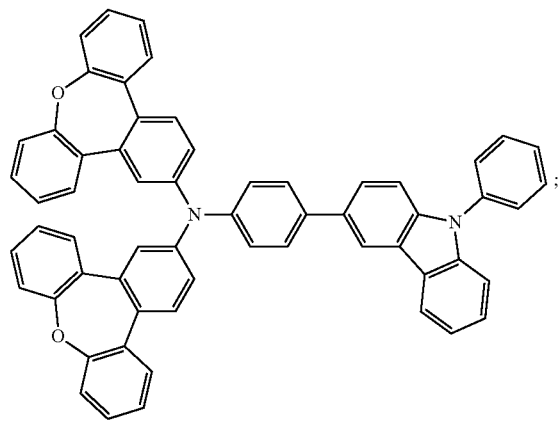
Compound 36
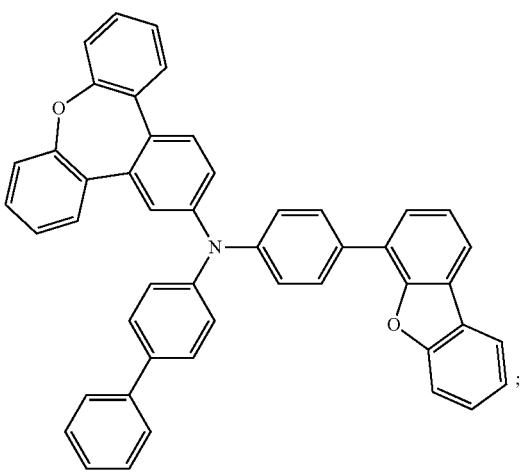
Compound 34
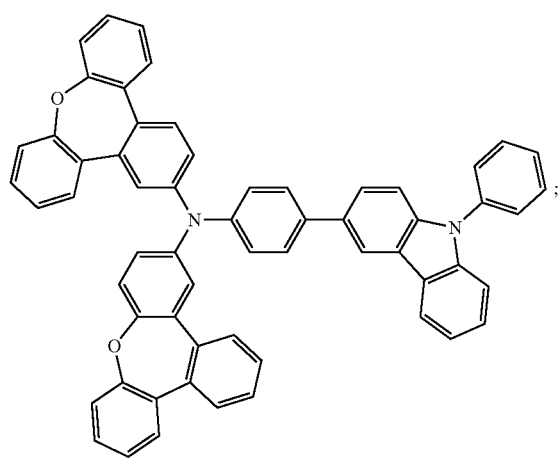
Compound 37
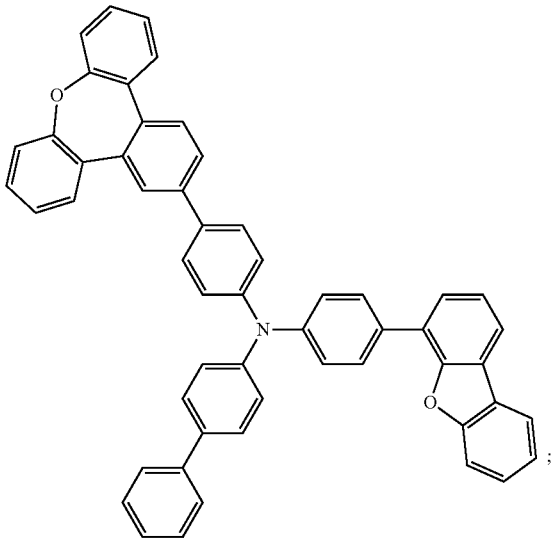
Compound 35
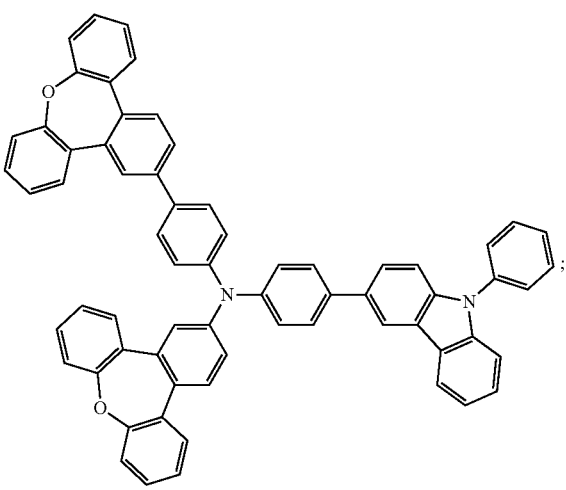
Compound 38
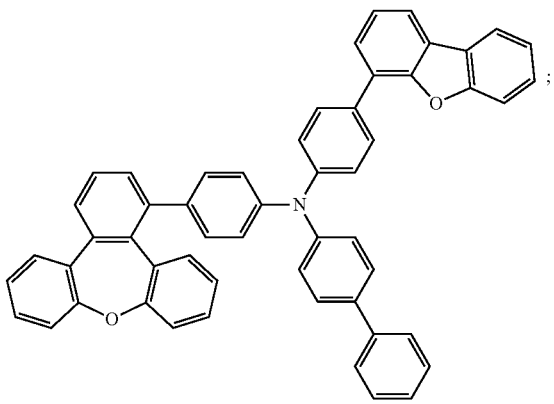

Compound 39
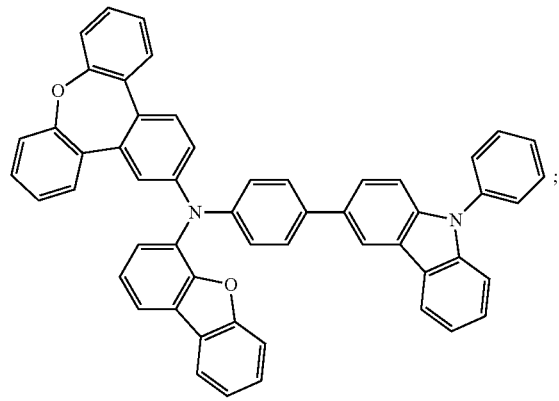
Compound 40
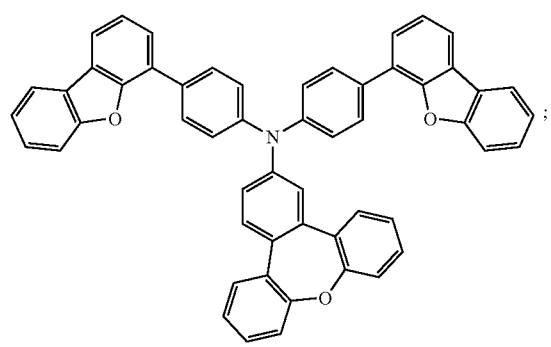
Compound 41
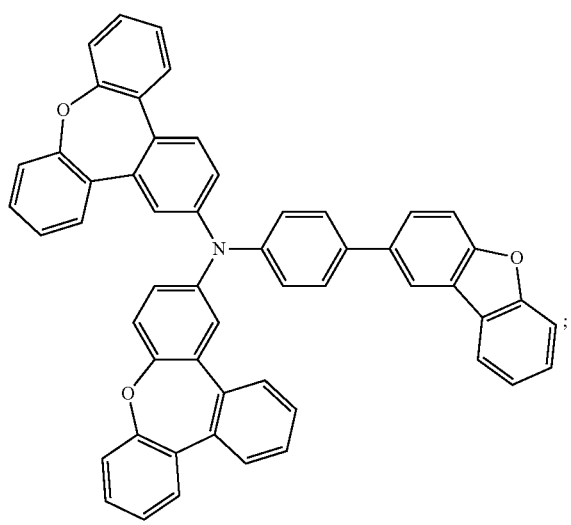
Compound 42
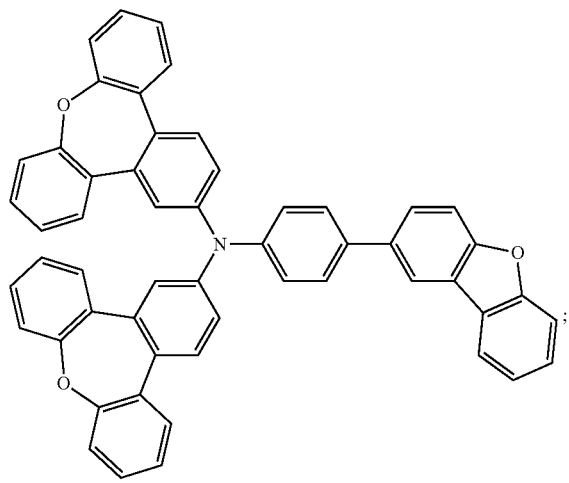
Compound 43
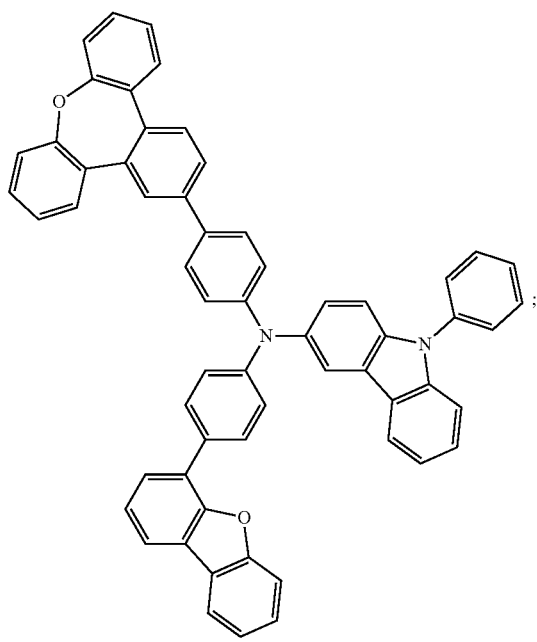
Compound 44
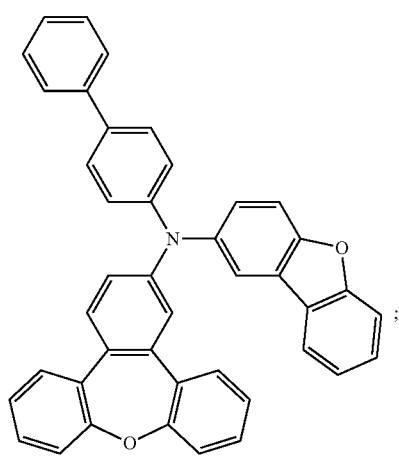

Compound 45
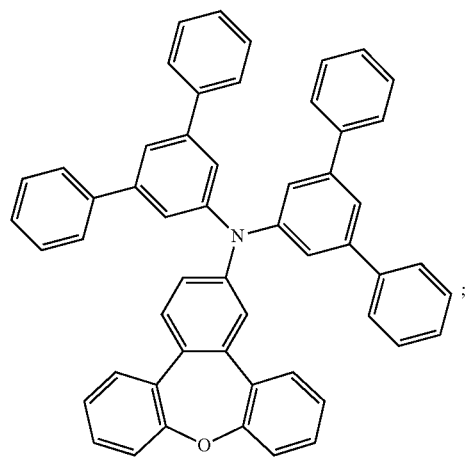
Compound 48
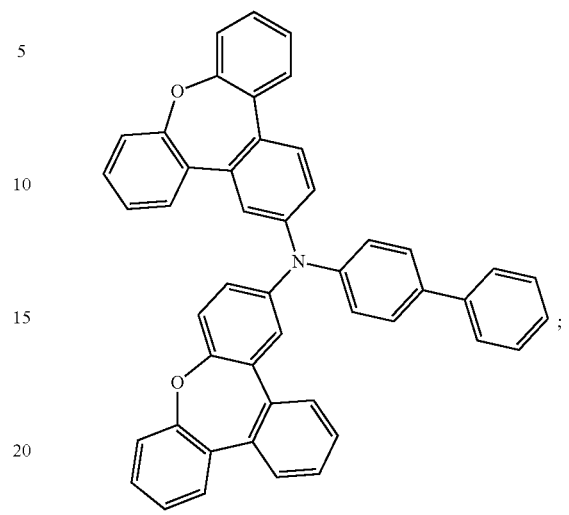
Compound 46
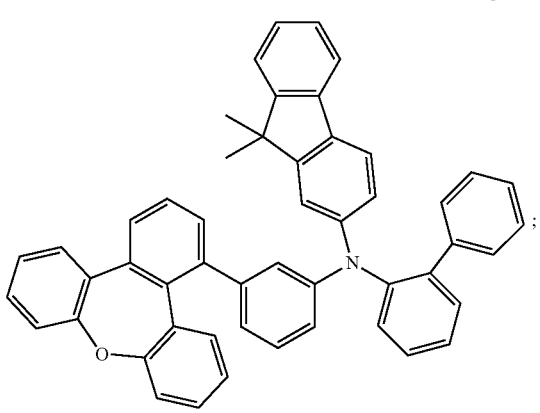
Compound 49
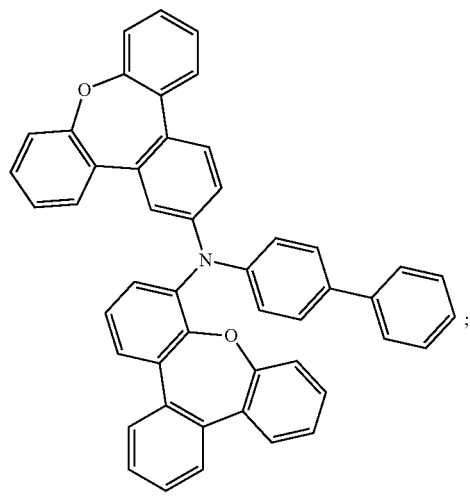
Compound 47
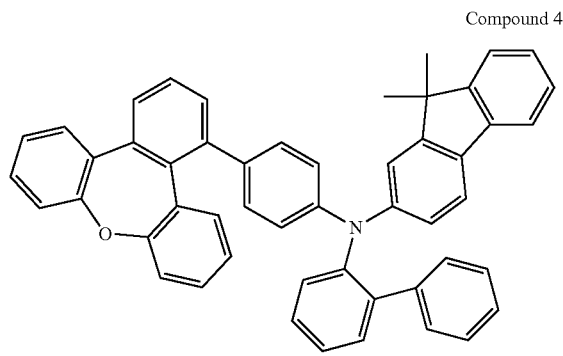
Compound 50
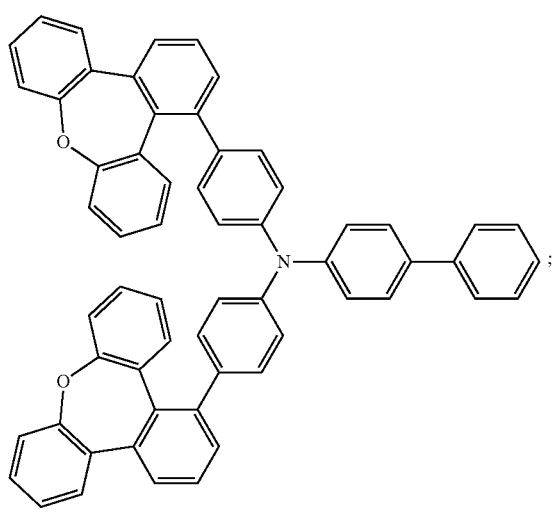

Compound 51
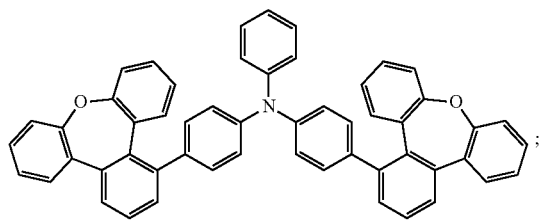
Compound 52
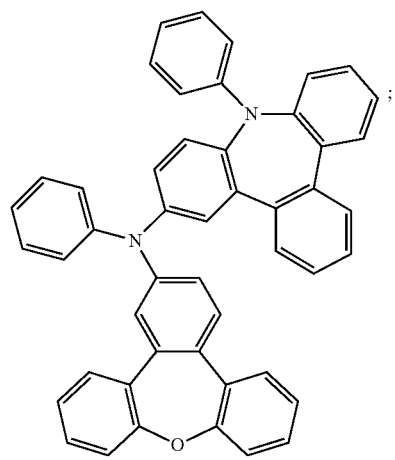
Compound 53
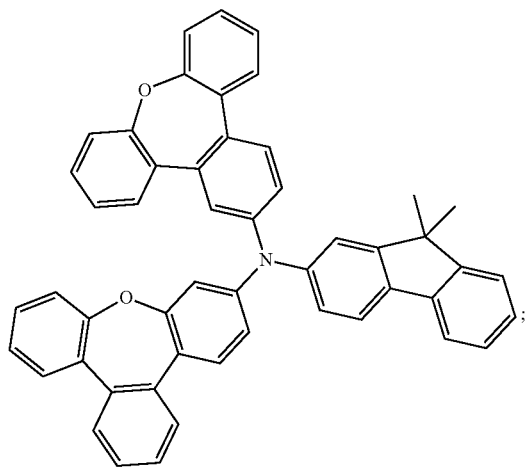
Compound 54
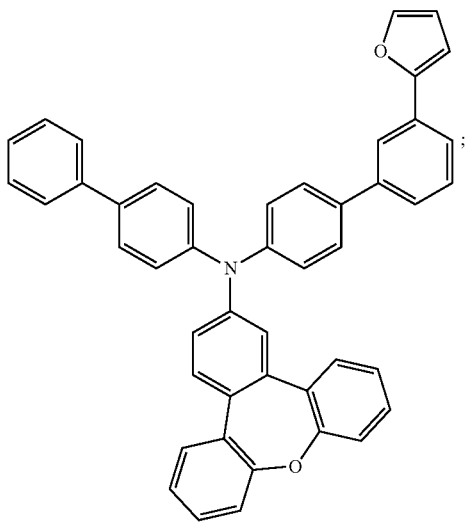
Compound 55
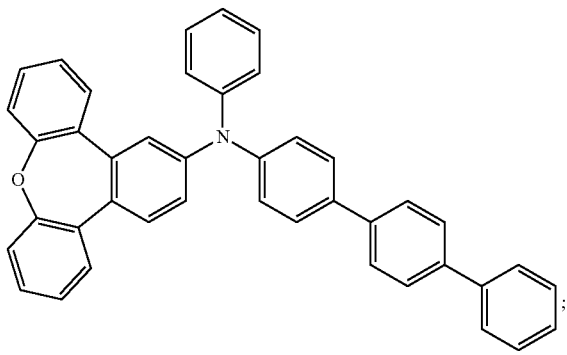
Compound 56
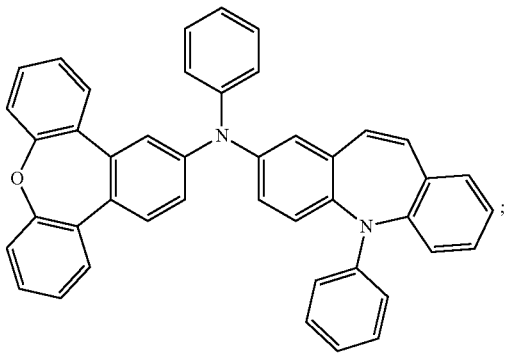

Compound 57
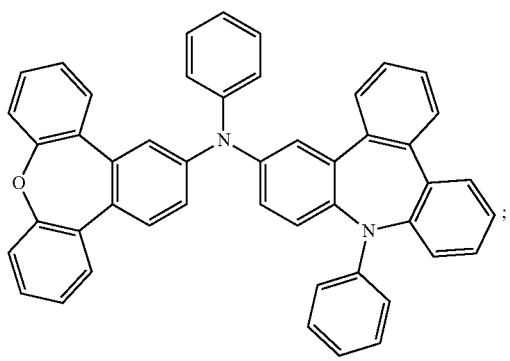
Compound 58
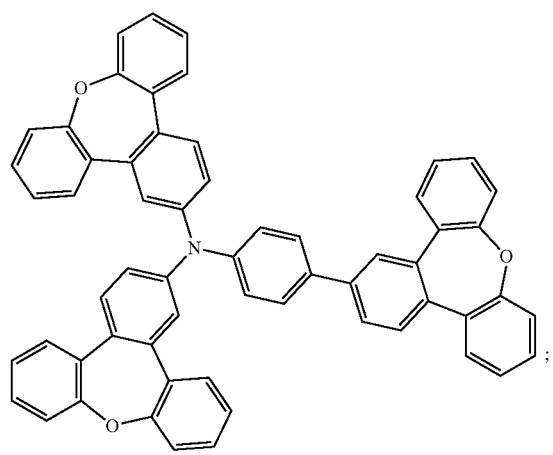
Compound 59
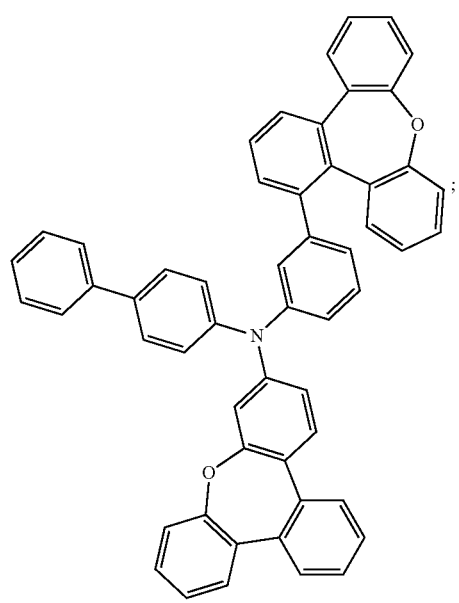
Compound 60
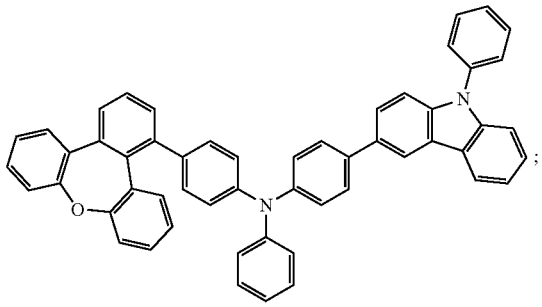
Compound 61
Compound 62
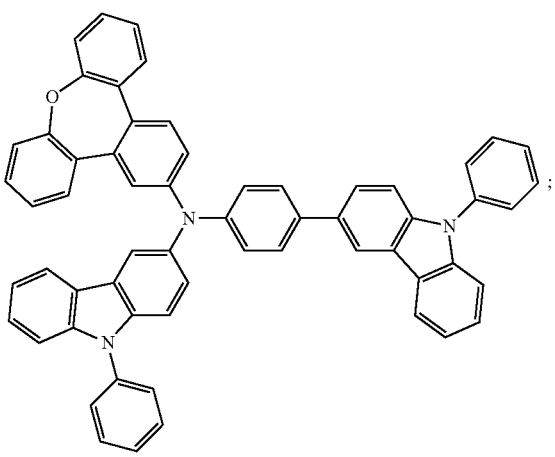

Compound 63
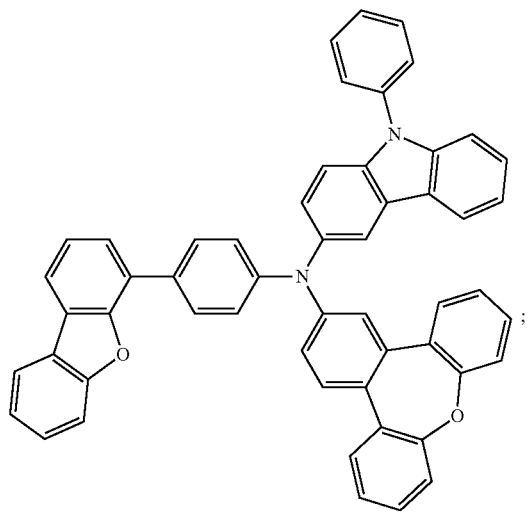
Compound 66
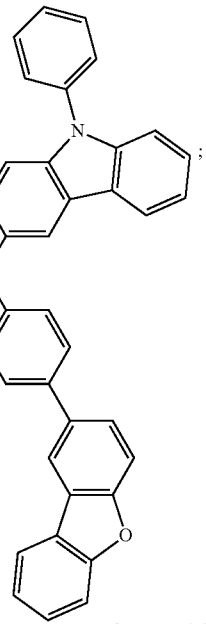
Compound 64
Compound 67
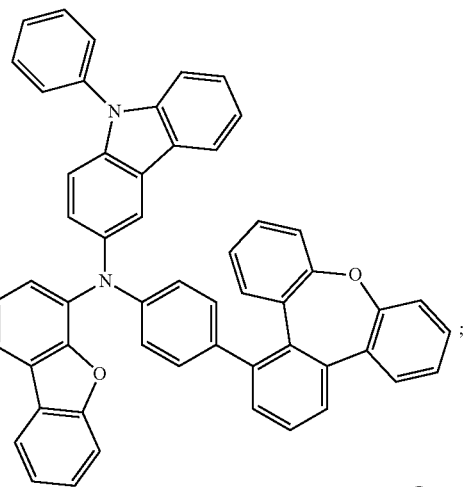
Compound 65
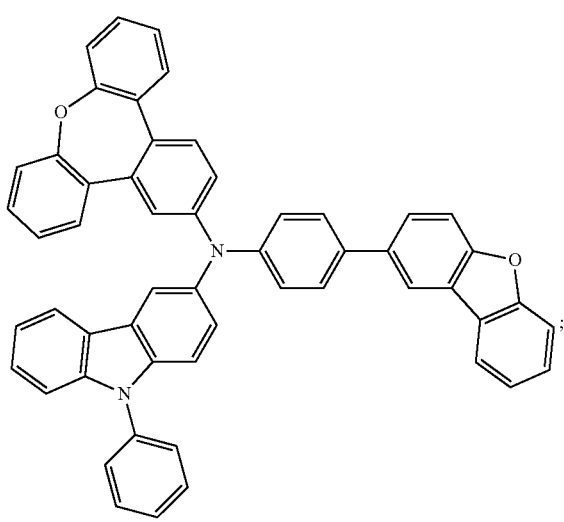
Compound 68
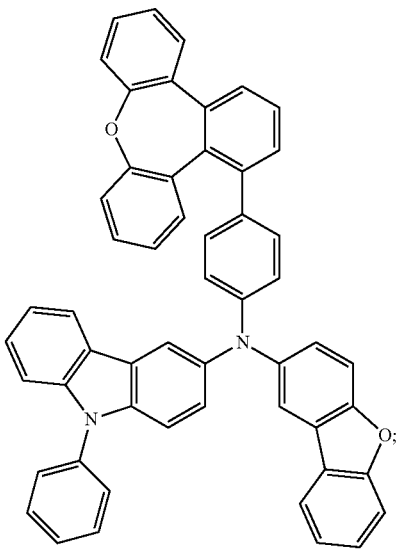

Compound 69
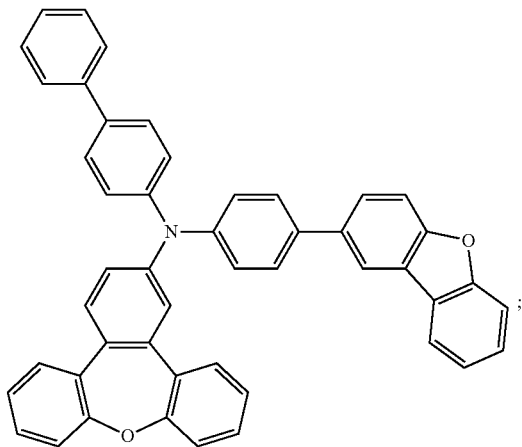
Compound 70
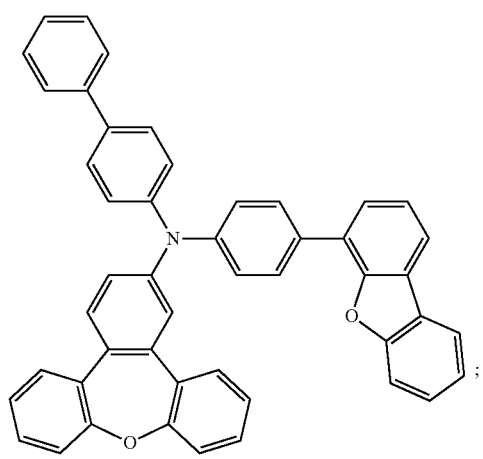
Compound 71
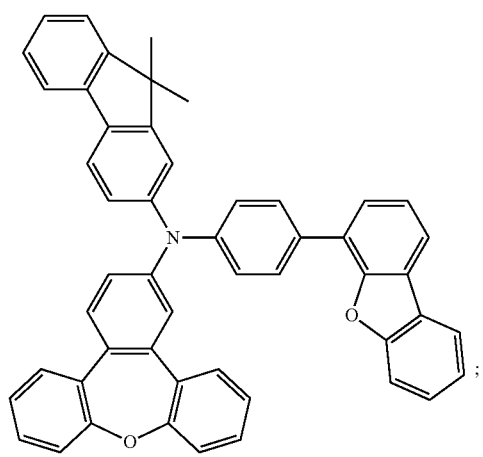
Compound 72
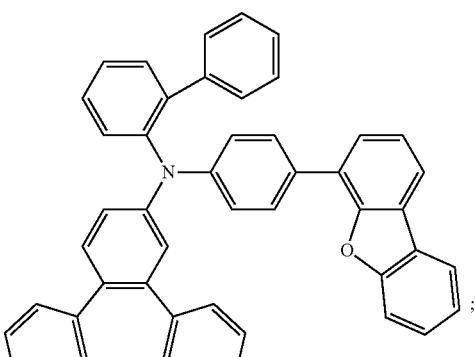
Compound 73
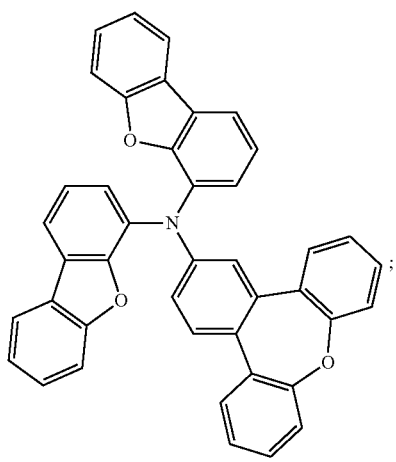
Compound 74
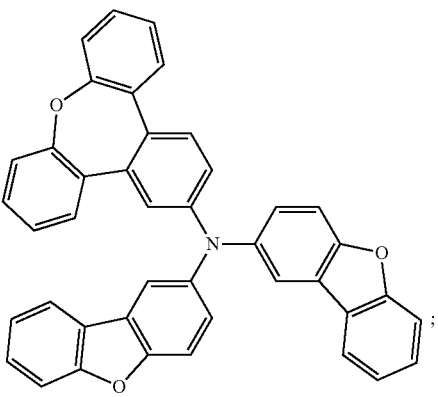

Compound 75
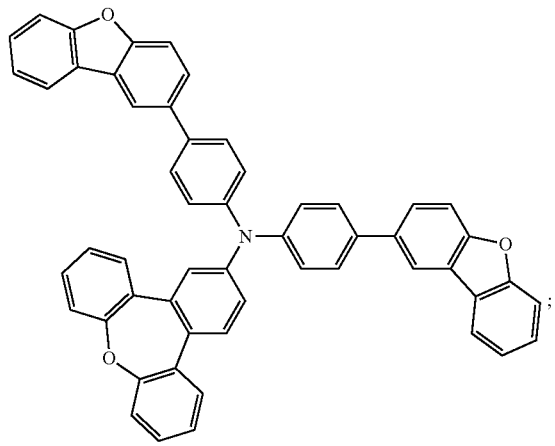
Compound 76
Compound 77
Compound 78
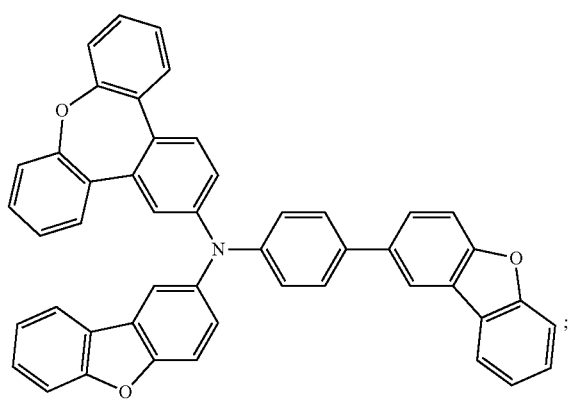
Compound 79
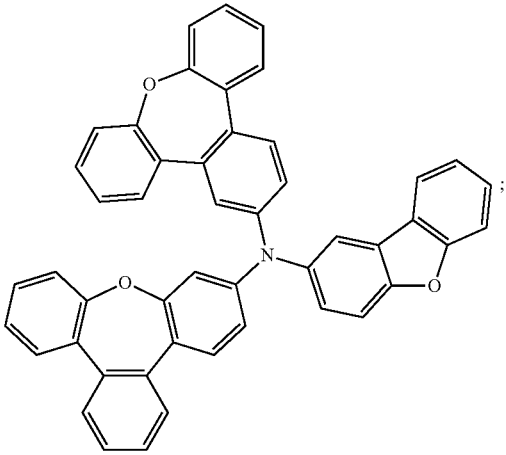
Compound 80
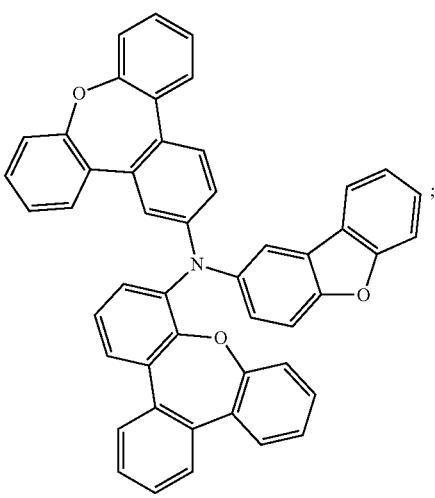
Compound 81
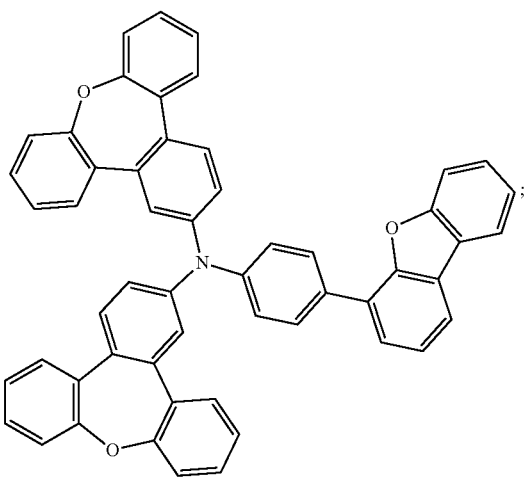

-continued
Compound 82
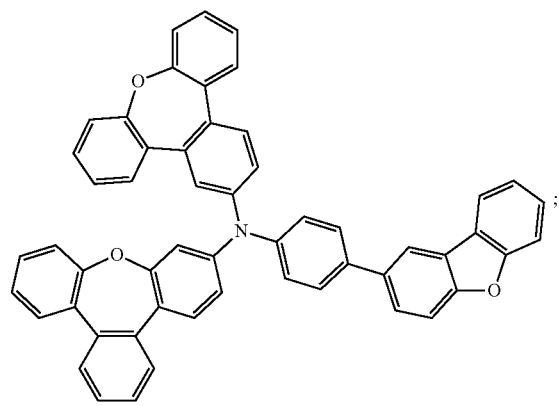
Compound 83
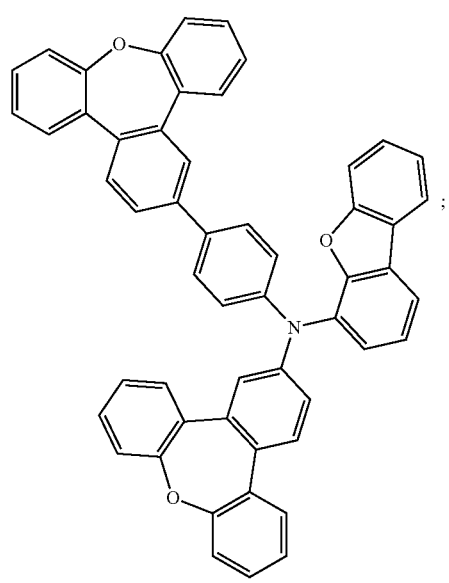
Compound 85
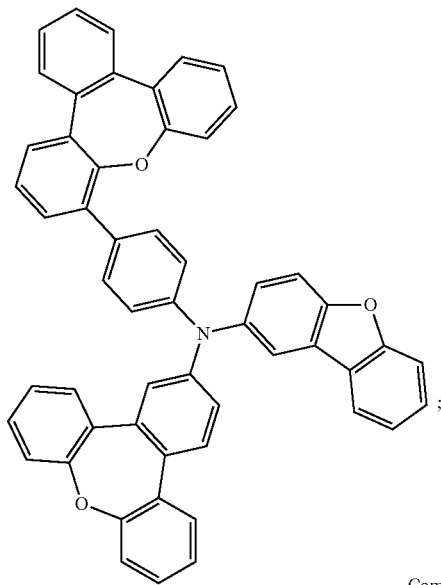
Compound 84
Compound 86
Compound 87
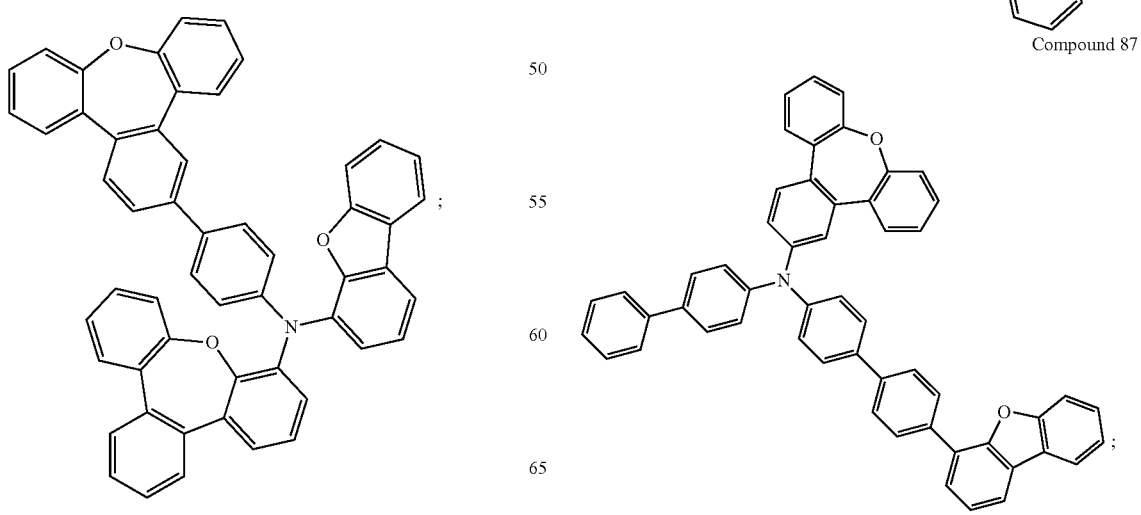

Compound 88
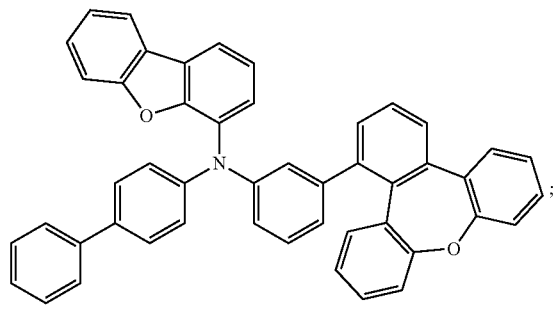
Compound 89
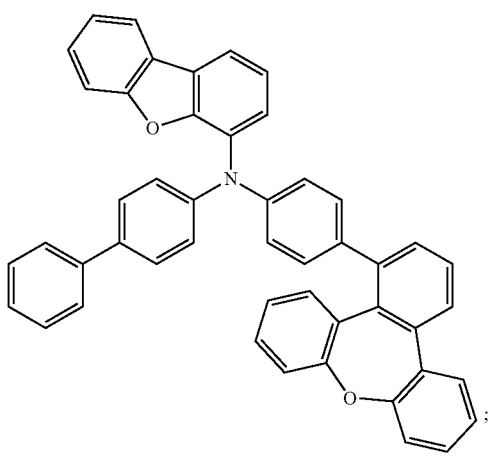
Compound 90
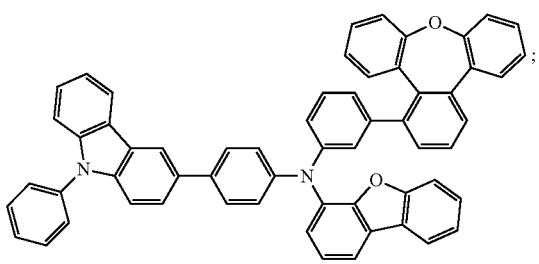
Compound 91
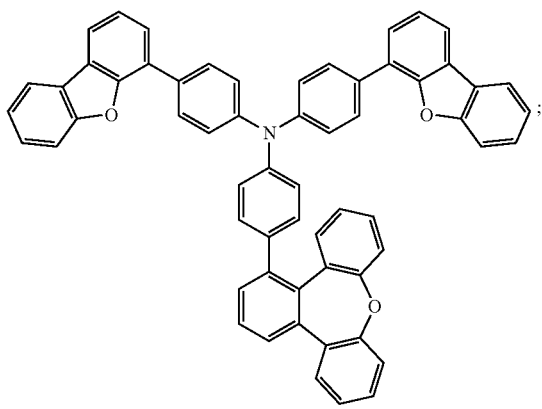
Compound 92
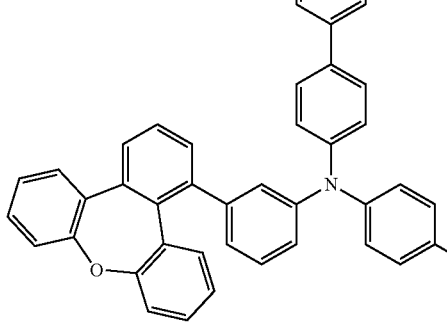
Compound 93
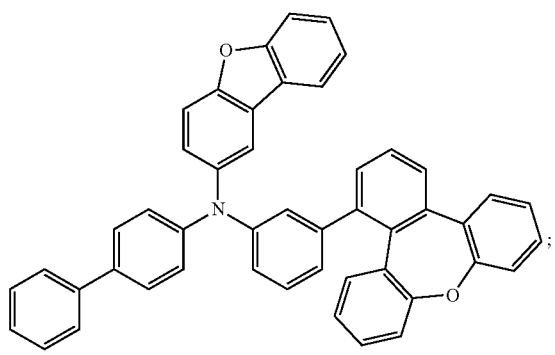
Compound 94
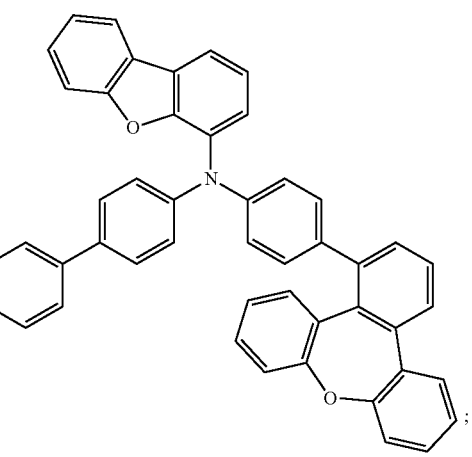

Compound 95
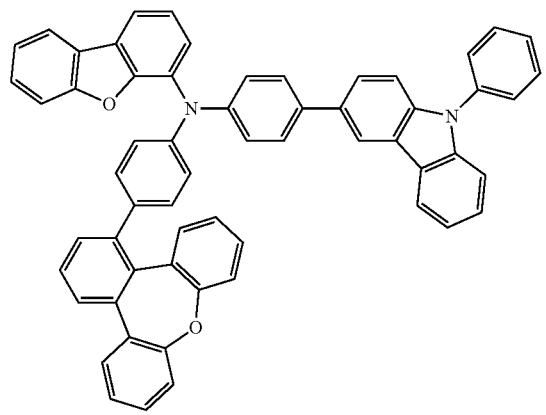
Compound 96
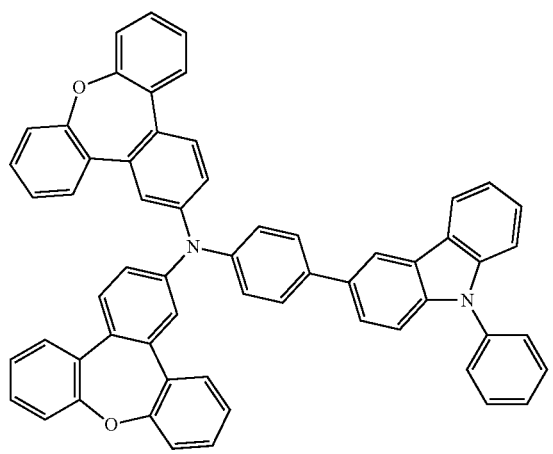
Compound 97
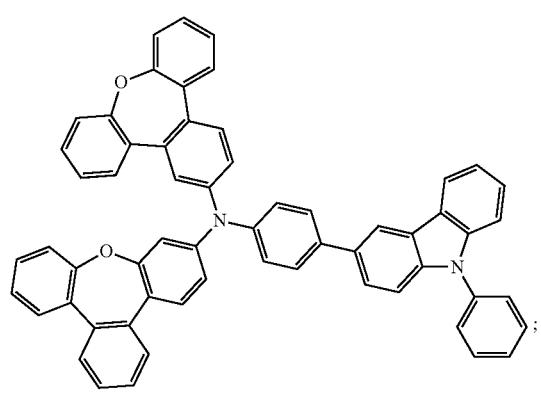
Compound 98
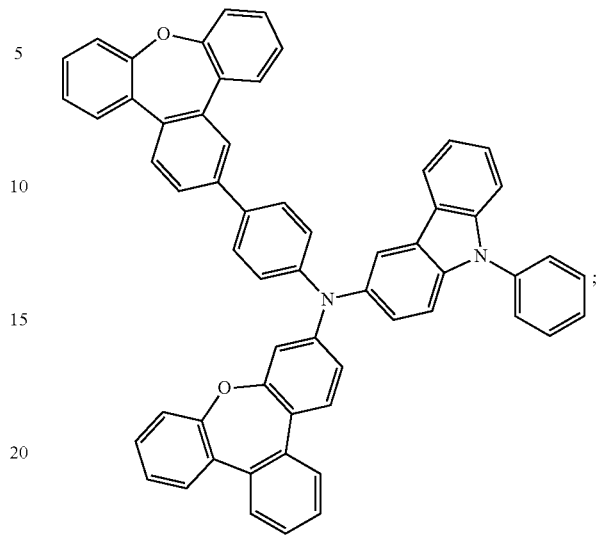
Compound 99
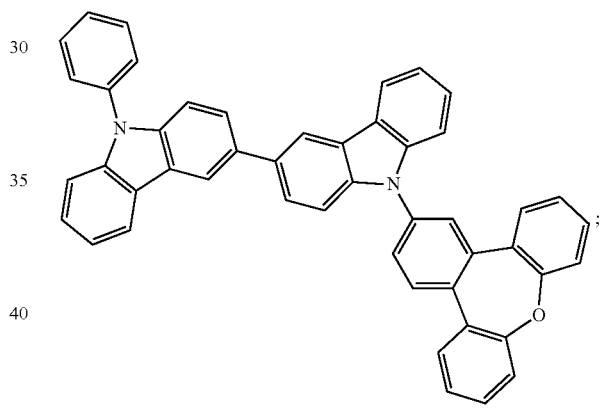
Compound 100
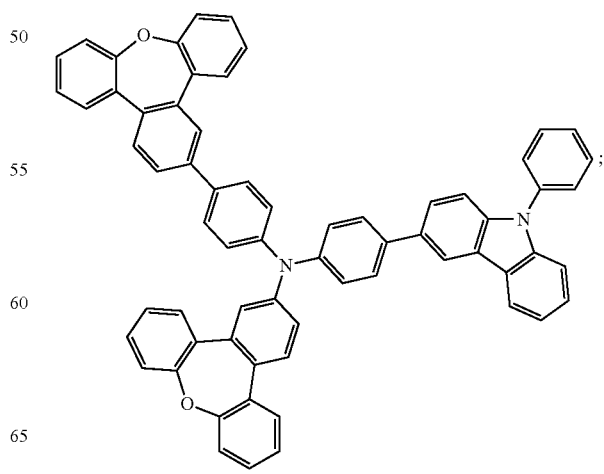

-continued
Compound 101
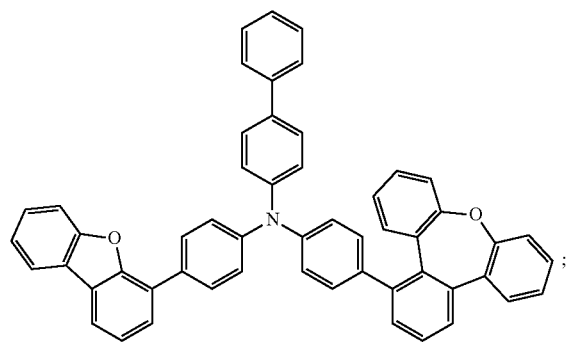
Compound 102
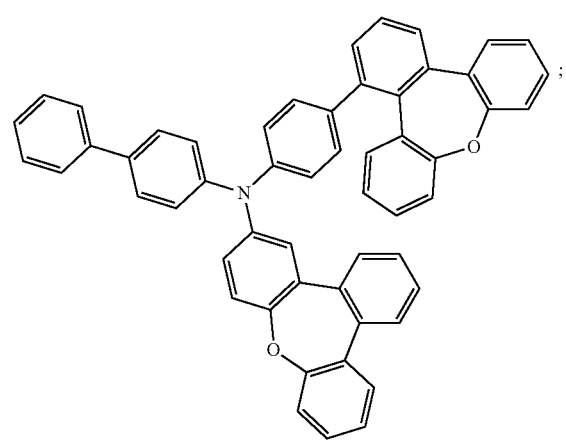
Compound 103
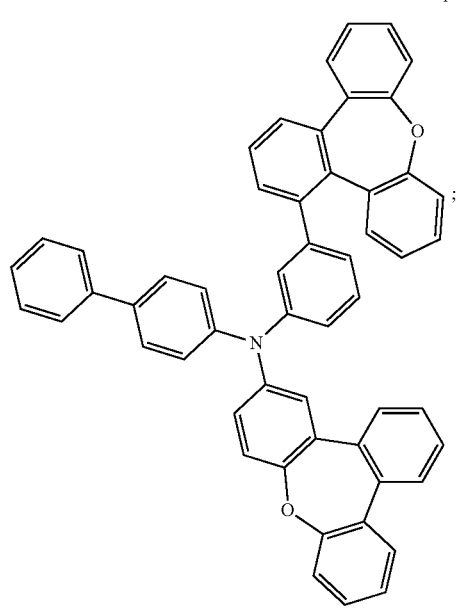
-continued
Compound 104
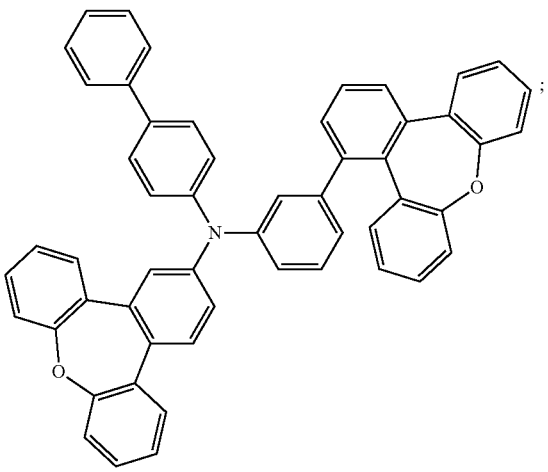
Compound 105
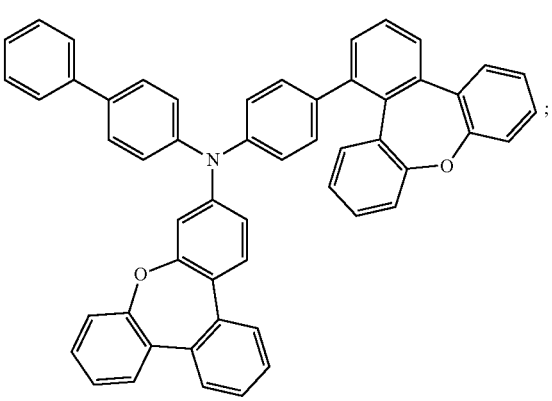
Compound 106
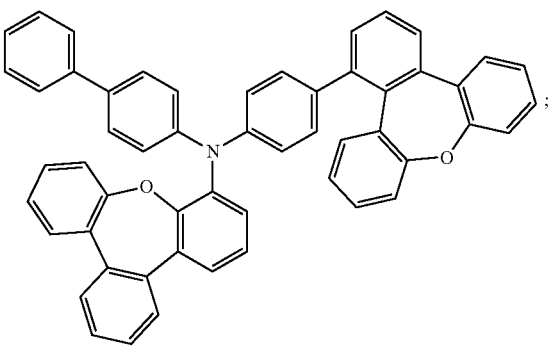

Compound 107
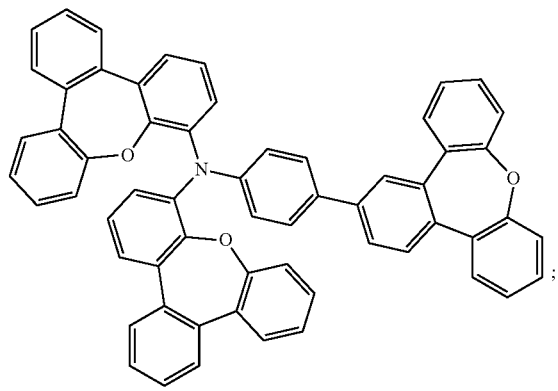
Compound 108
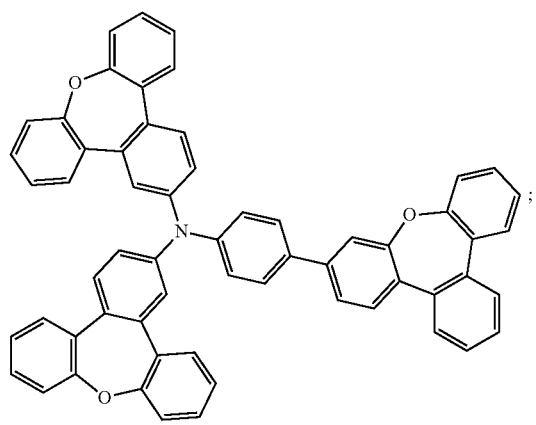
Compound 109
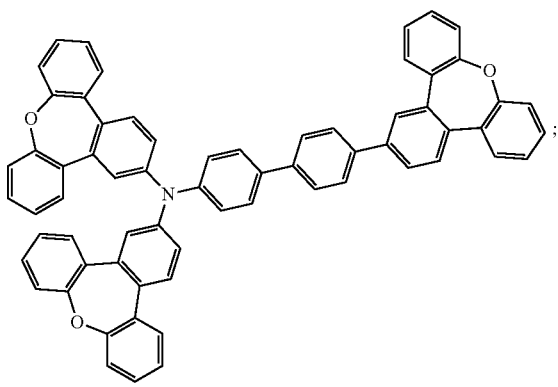
Compound 110
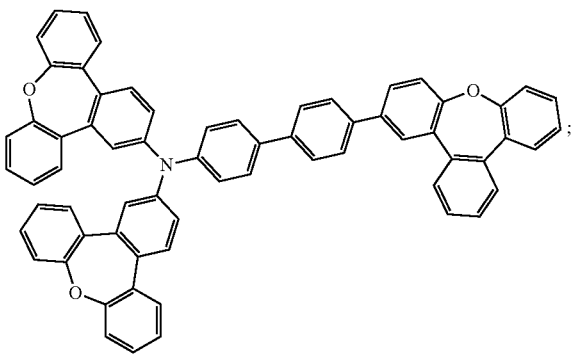
Compound 111
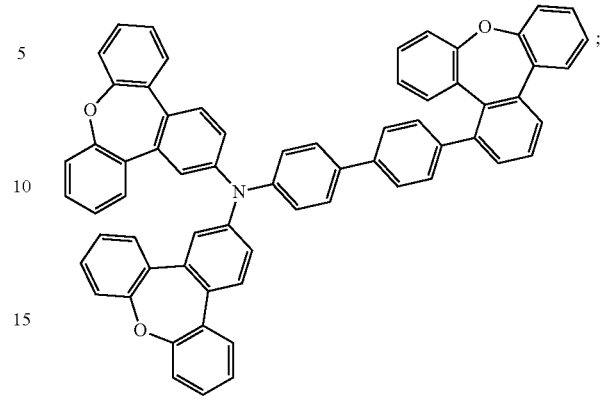
Compound 112
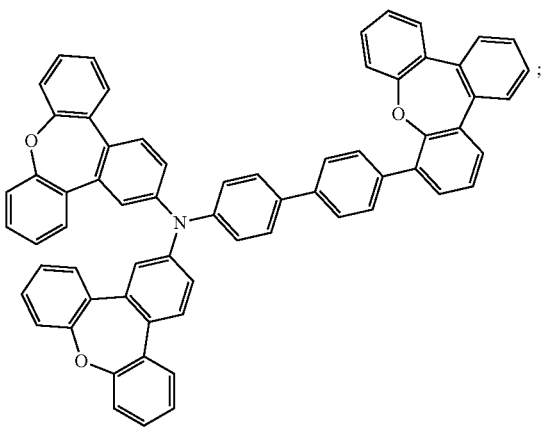
Compound 113
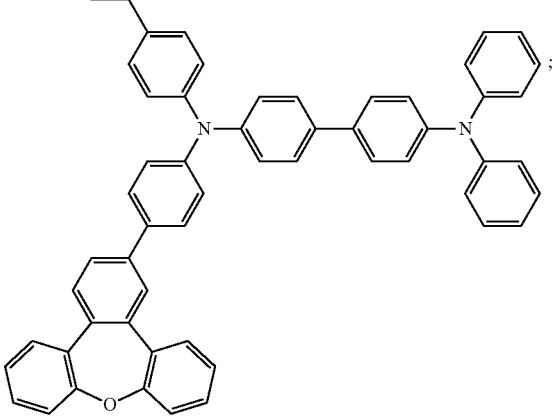

Compound 114
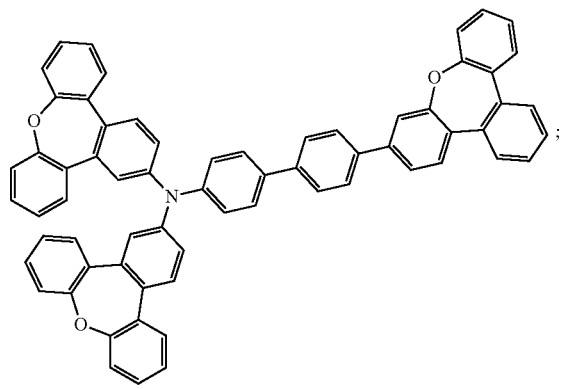
Compound 115
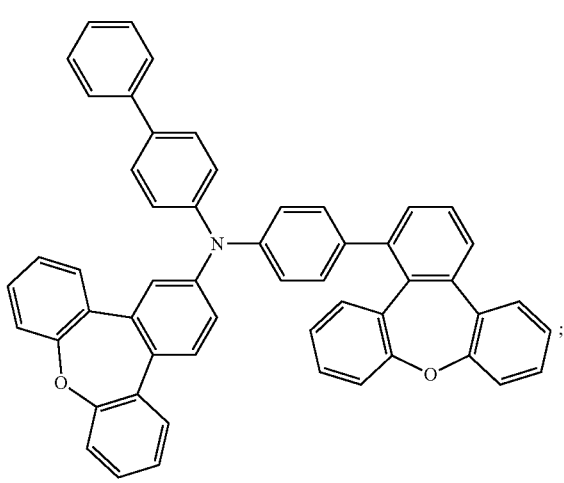
Compound 116
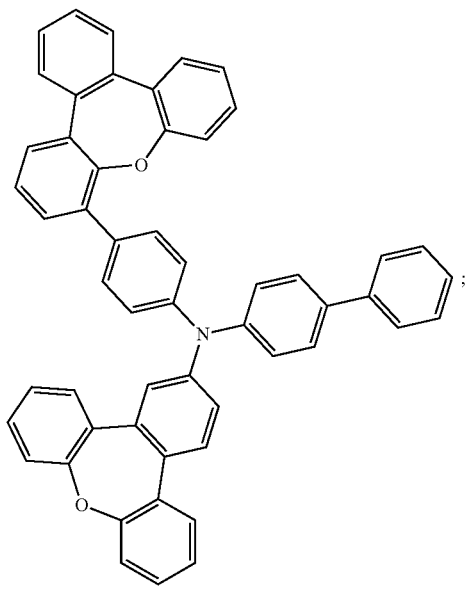
Compound 117
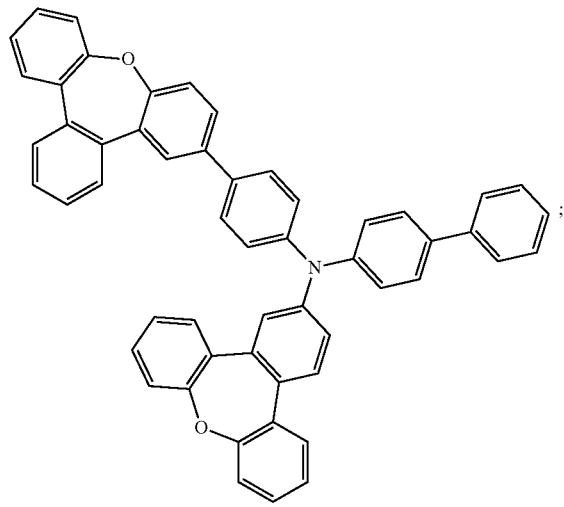
Compound 118
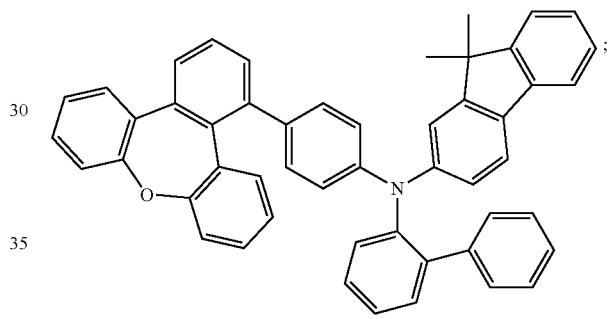
Compound 119
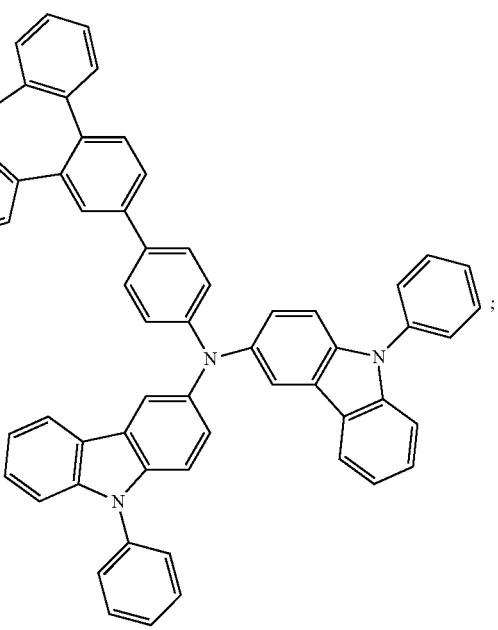

Compound 120
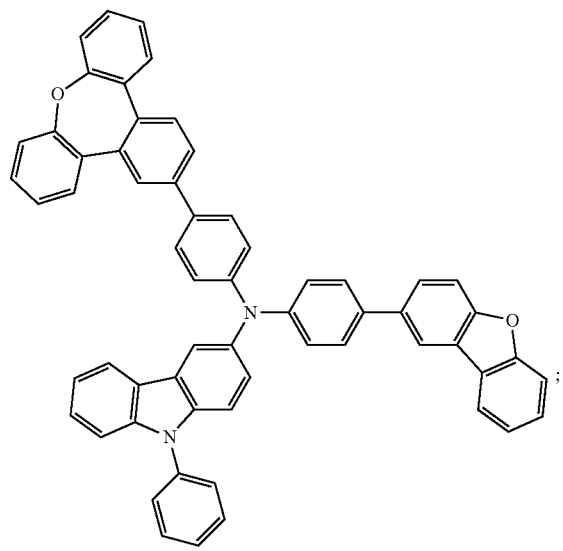
Compound 121
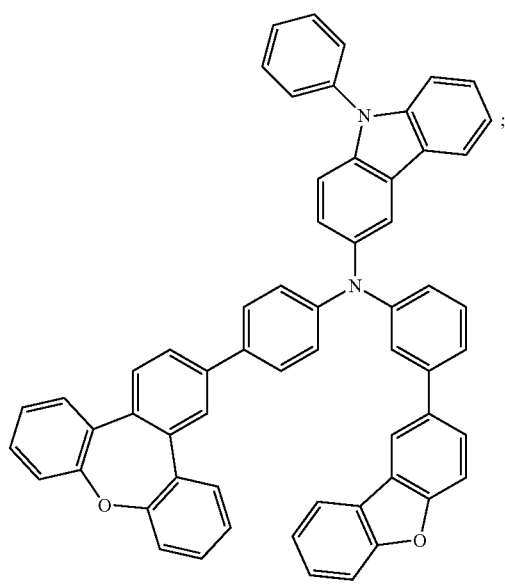
Compound 122
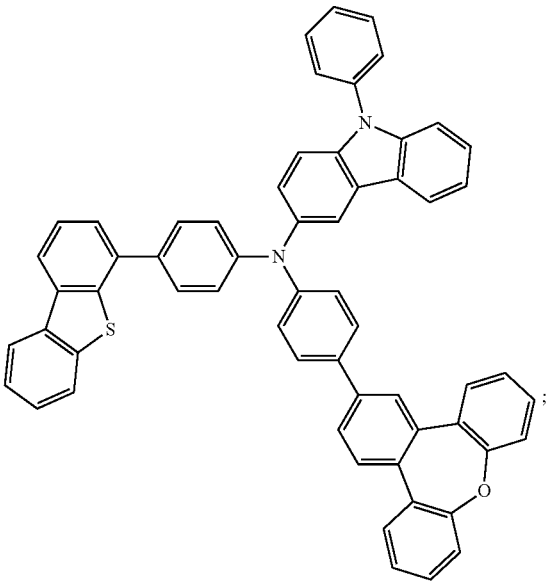
Compound 123
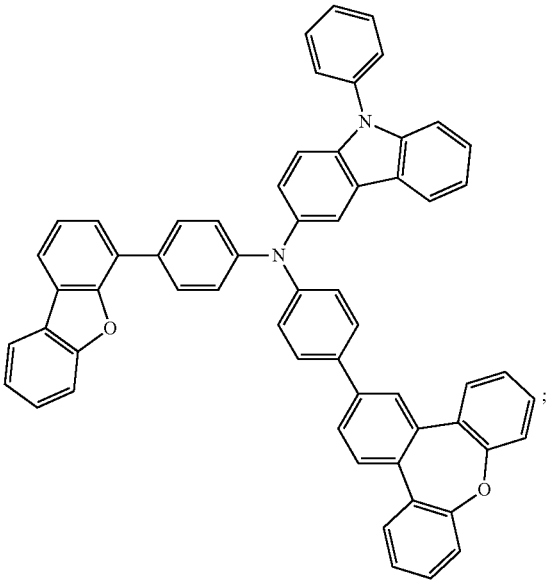

Compound 124
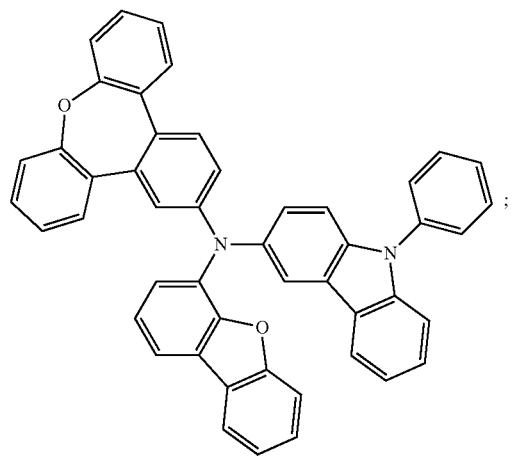
Compound 125
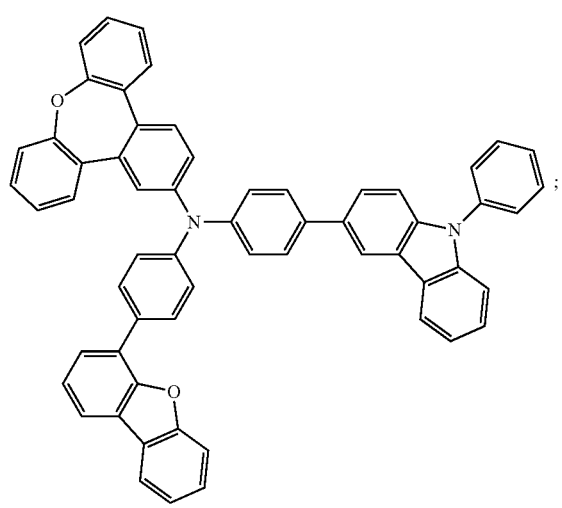
Compound 126
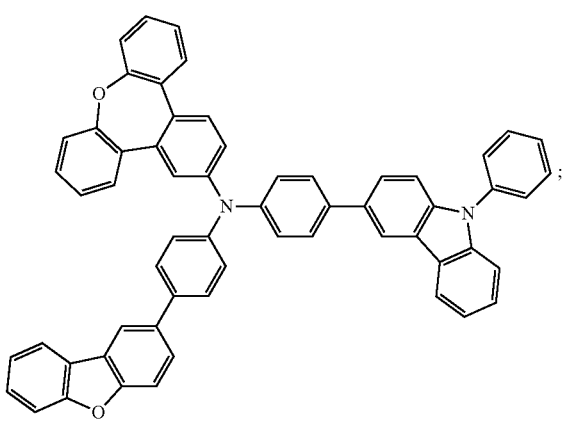
Compound 127
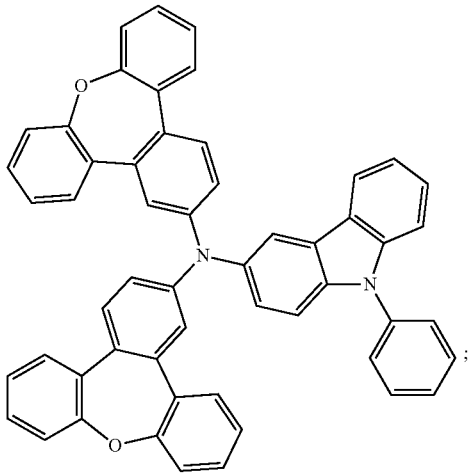
Compound 128
Compound 129
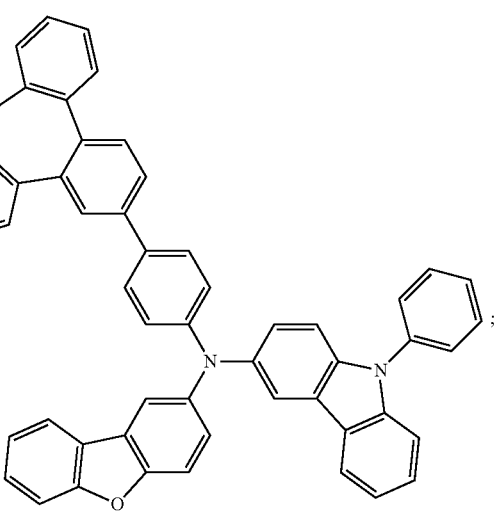

Compound 130
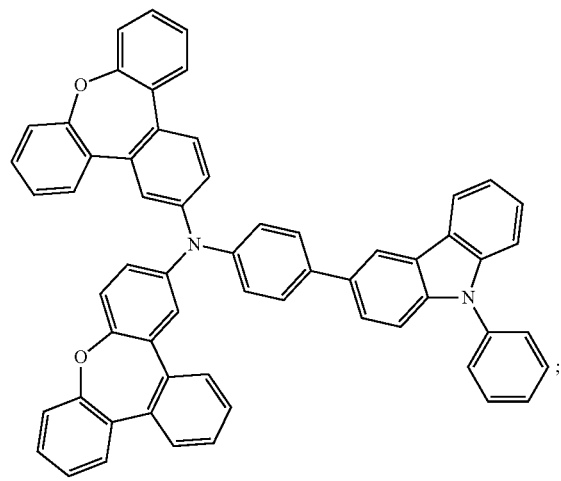
Compound 131
Compound 132
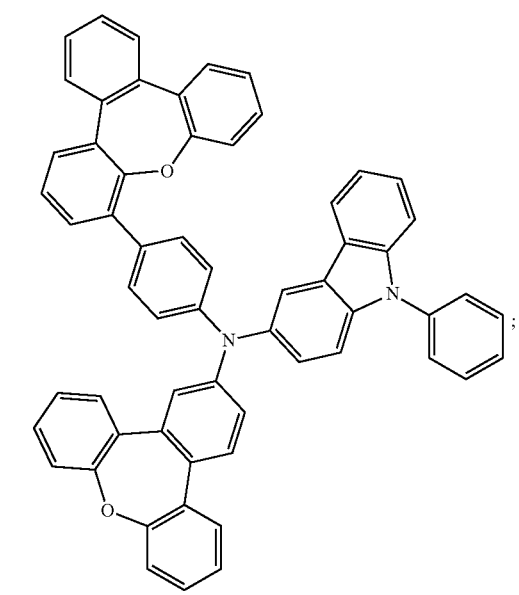
Compound 133
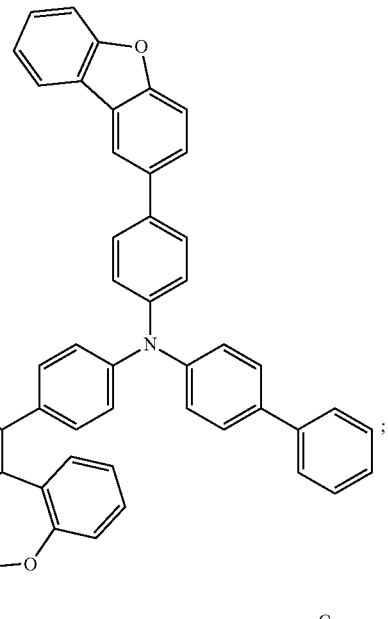
Compound 134
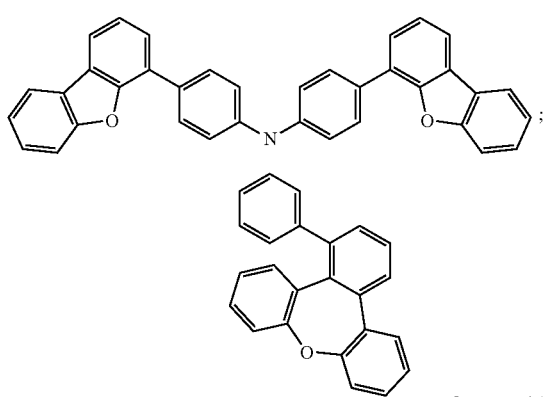
Compound 135
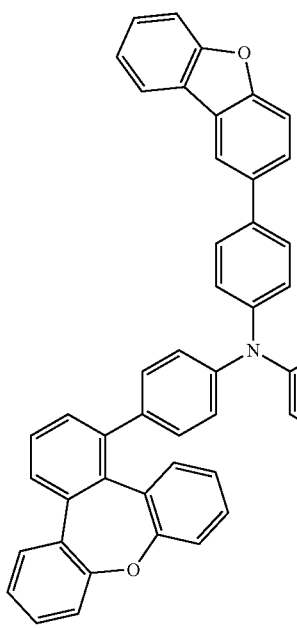

Compound 136
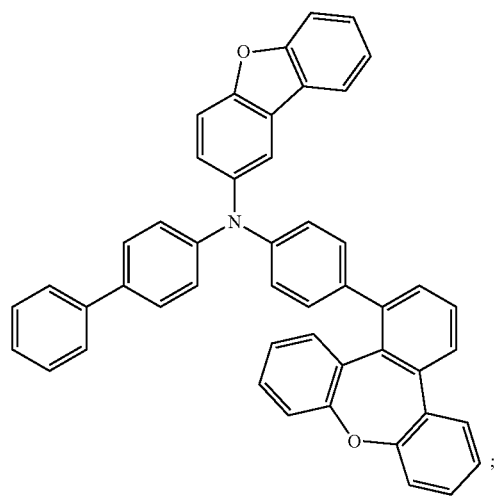
Compound 137
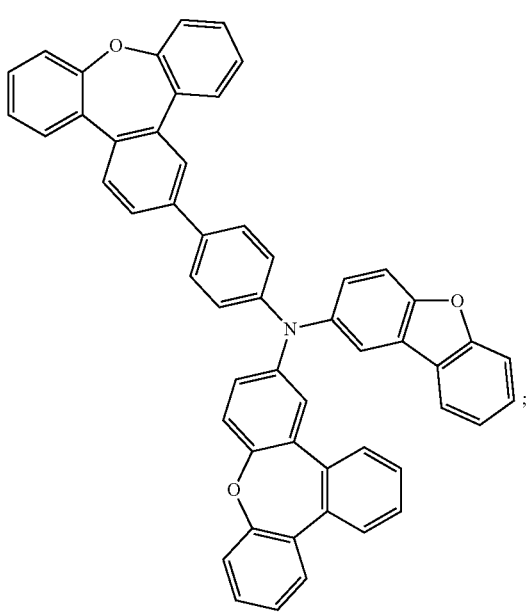
Compound 138
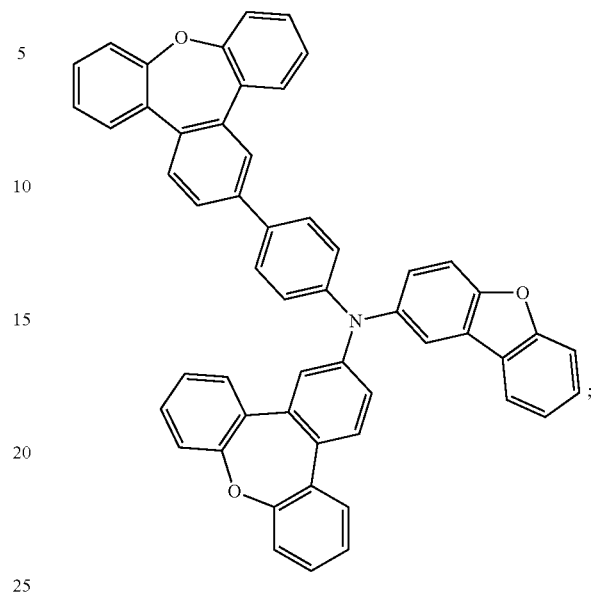
Compound 139
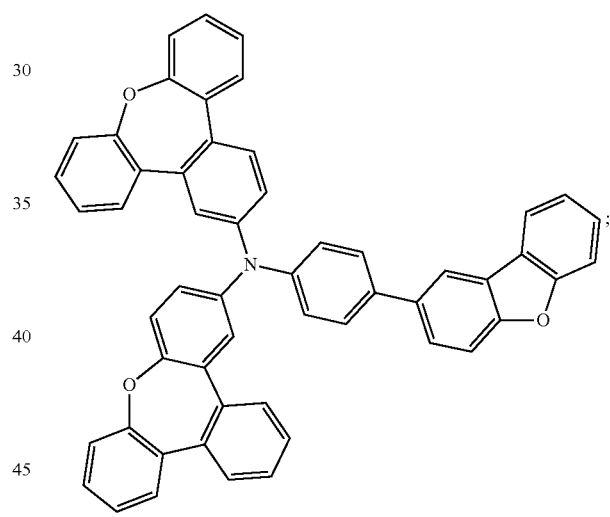
Compound 140
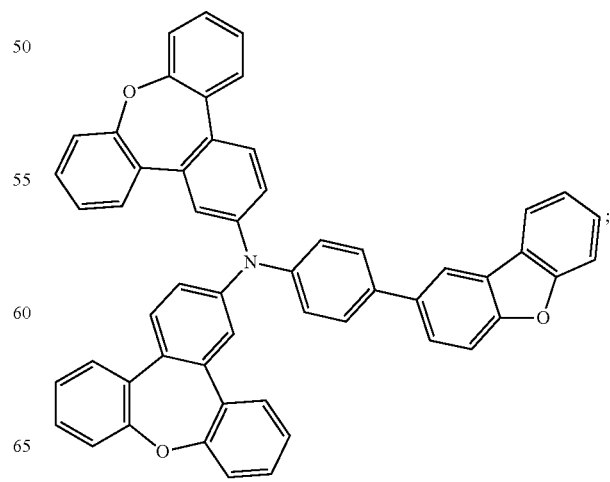

Compound 141
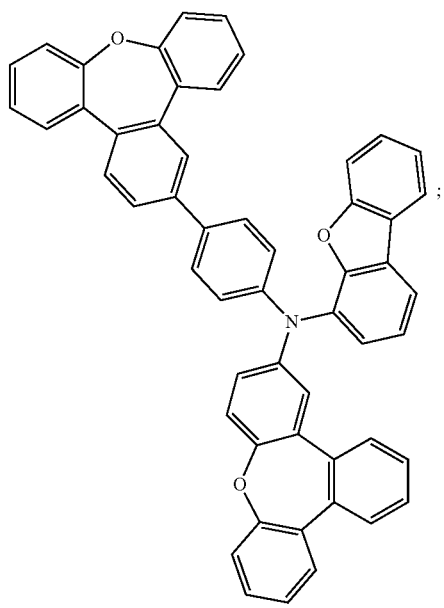
Compound 142
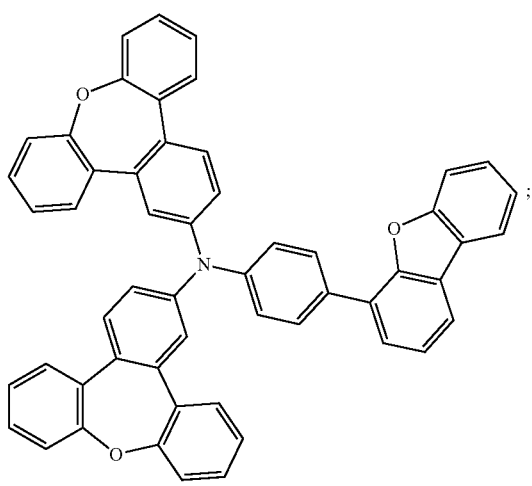
Compound 143
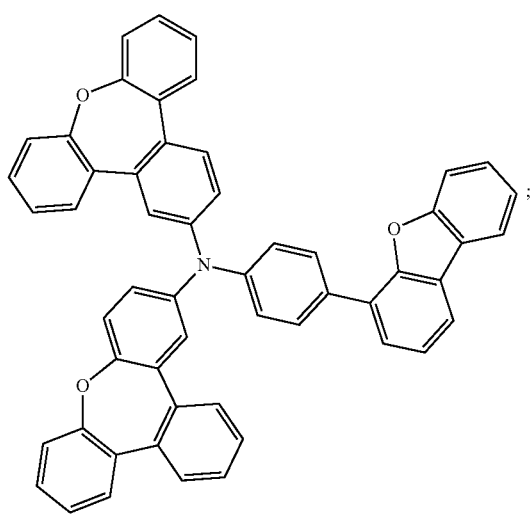
Compound 144
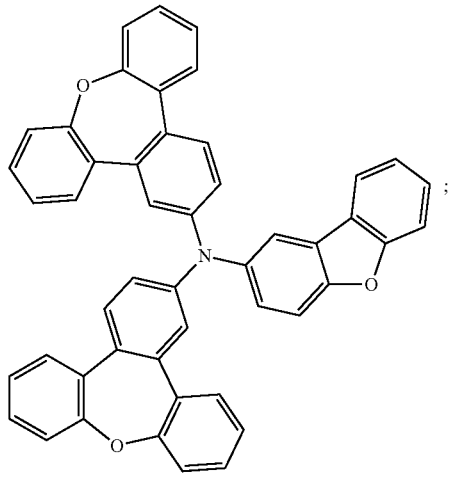
Compound 145
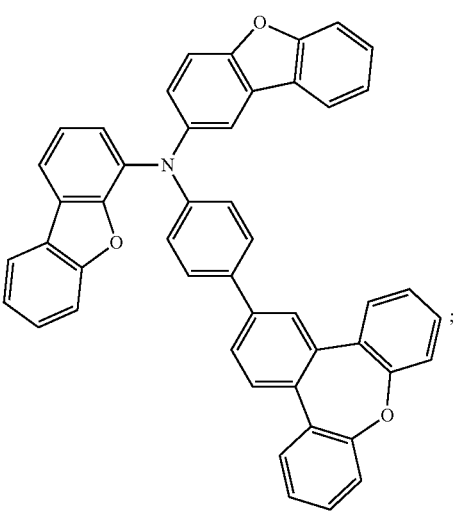
Compound 146
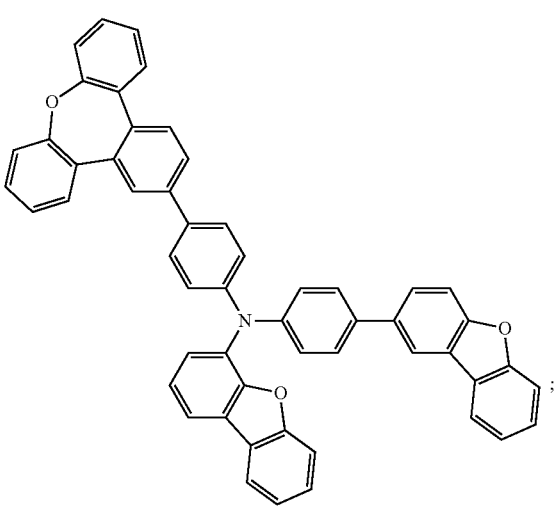

Compound 147
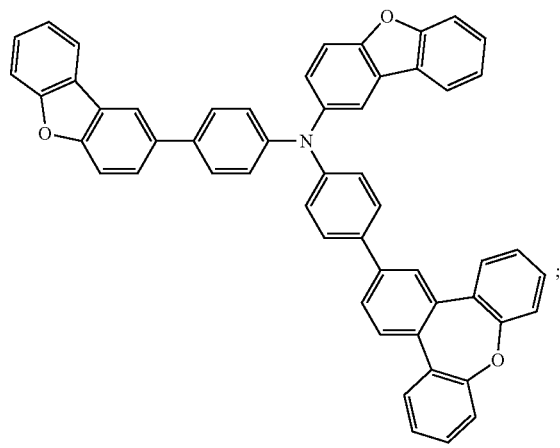
Compound 148
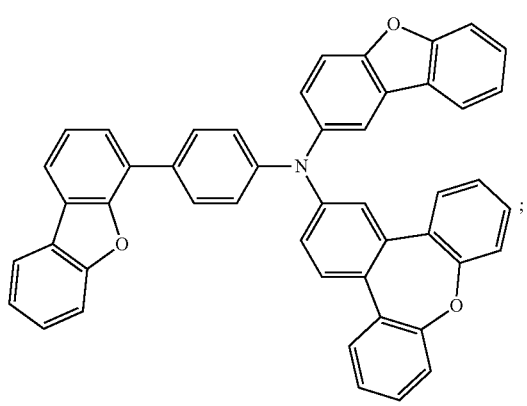
Compound 149
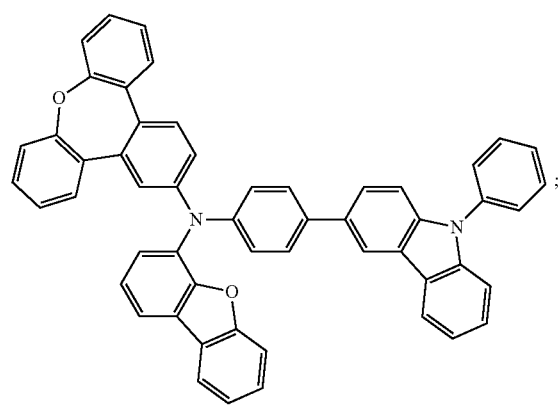
Compound 150
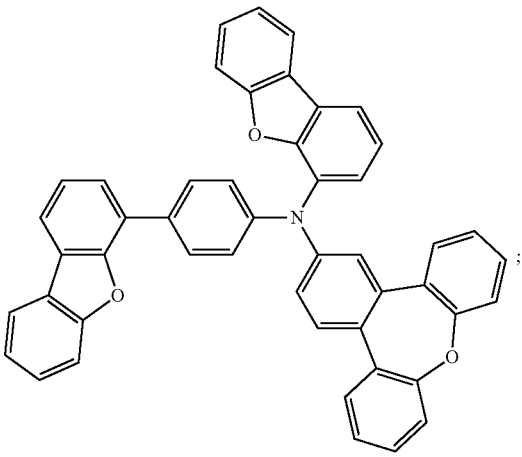
Compound 151
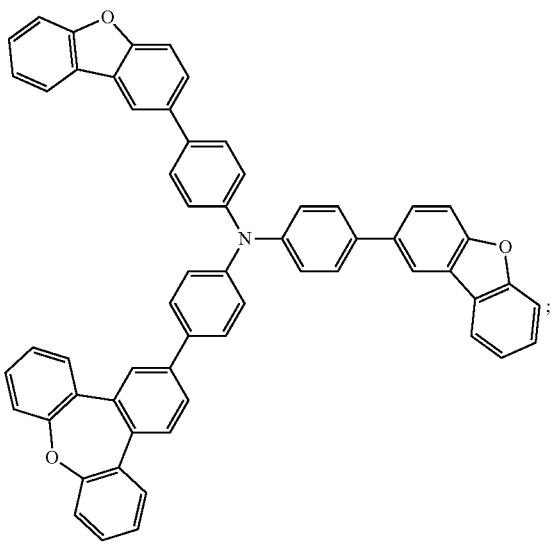
Compound 152
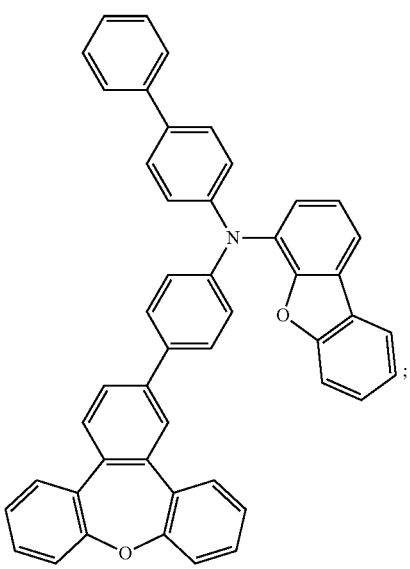

Compound 153

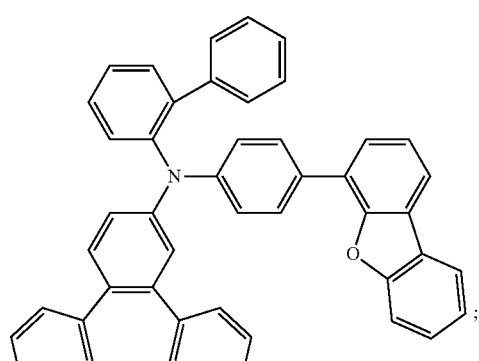

Compound 154

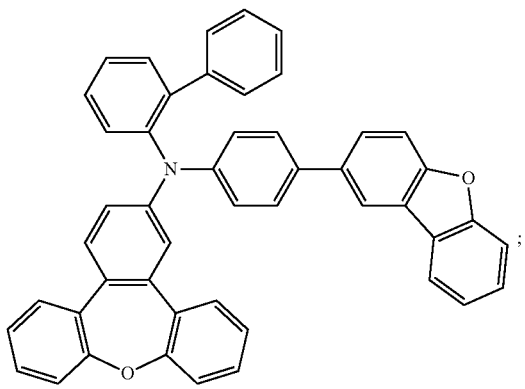

Compound 155

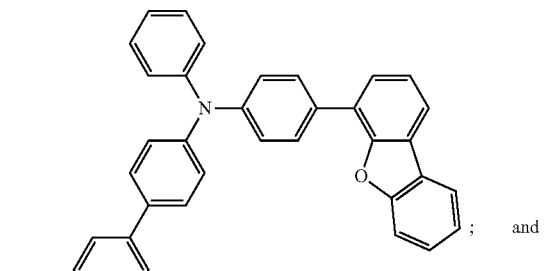

; and

Compound 156

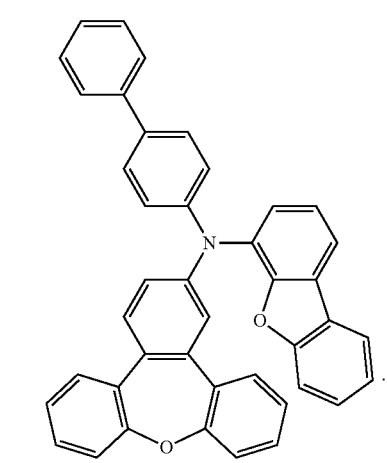

.

In any Formulae shown in the specification, the symbol "N" represents a nitrogen atom, and the symbol "O" represents an oxygen atom. In the specification, the symbol "*" represents a bonding position.

The present invention also provides an organic electronic device, comprising a first electrode, a second electrode, and an organic layer disposed between the first electrode and the second electrode. The organic layer comprises the novel compound as described above.

Preferably, the organic electronic device is an organic light emitting device (OLED). More preferably, the novel compound of the present invention may be used as a hole transport material, a hole injection material, or an electron blocking layer.

Specifically, the organic light emitting device may comprise:
a hole injection layer formed on the first electrode;
a hole transport layer formed on the hole injection layer;
an emission layer formed on the hole transport layer;
an electron transport layer formed on the emission layer;
an electron injection layer formed between the electron transport layer and the second electrode.

In one embodiment, the organic layer may be the hole injection layer, i.e., the hole injection layer comprises the novel compound as stated above. In addition to the novel compounds of the present invention, the hole injection layer may be made of, for example, but not limited to, polyaniline or polyethylenedioxythiophene.

Preferably, the hole injection layer may be a two-layered structure, i.e., the OLED comprises a first hole injection layer and a second hole injection layer disposed between the first electrode and the hole transport layer. More preferably, the organic layer may be the first hole injection layer and/or the second hole injection layer. That is, the first hole injection layer and/or the second hole injection layer comprises the novel compound as stated above or in combination with any other well-known hole injection material.

In another embodiment, the organic layer may be the hole transport layer, i.e., the hole transport layer comprises the novel compound as stated above. Preferably, the hole transport layer may be a two-layered structure, i.e., the OLED comprises a first hole transport layer and a second hole transport layer disposed between the two-layered hole injection layer and the emission layer. More preferably, the organic layer may be the first hole transport layer and/or the second hole transport layer. That is, the first hole transport layer and/or the second hole transport layer comprises the novel compound as stated above or in combination with any other well-known hole transport material.

Preferably, the electron transport layer can be made of, for example, but not limited to: 2-(4-(9,10-di(naphthalen-2-yl)anthracen-2-yl)phenyl)-1-phenyl-1H-benzo[d]imidazole; bis(2-methyl-8-quinolinolato)(p-phenylphenolato) aluminum; or 2-(4-biphenylyl)-5-(4-tert-butylphenyl)-1,3,4-oxadiazole (PBD).

Preferably, the OLED comprises a hole blocking layer formed between the electron transport layer and the emission layer, to block holes overflow from the emission layer to the electron transport layer. Said hole blocking layer may be made of 2,9-dimethyl-4,7-diphenyl-1,10-phenanthroline (BCP) or 2,3,5,6-tetramethyl-phenyl-1,4-(bis-phthalimide) (TMPP), but not limited thereto.

Preferably, the OLED comprises an electron blocking layer formed between the hole transport layer and the emission layer, to block electrons overflow from the emission layer to the hole transport layer. Said electron blocking layer may be made of 9,9'-[1,1'-biphenyl]-4,4'-diylbis-9H-carbazole (CBP) or 4,4',4''-tri(N-carbazolyl)-triphenylamine (TCTA), but not limited thereto. In further another embodiment, the organic layer may be the electron blocking layer, i.e., the electron blocking layer comprises the novel compound as stated above.

More specifically, the organic light emitting device comprises:
a hole injection layer formed on the first electrode;
a hole transport layer formed on the hole injection layer;
an electron blocking layer formed on the hole transport layer;
an emission layer formed on the electron blocking layer;
an electron transport layer formed on the emission layer; and
an electron injection layer formed between the electron transport layer and the second electrode.

Preferably, the organic layer may be the hole transport layer, the hole injection layer, the electron blocking layer, or their combination, i.e., at least one of the hole transport layer, the hole injection layer, and the electron blocking layer may comprise the novel compound as stated above.

In the presence of such a hole blocking layer and/or an electron blocking layer in an OLED, the OLED has a higher luminous efficiency compared to a typical OLED.

The OLEDs using the novel compound as the hole injection material, hole transport material, or the electron blocking material can have an improved efficiency compared to commercial OLEDs using the known hole transport material, such as $N^1,N^{1'}$-(biphenyl-4,4'-diyl)bis($N^1$-(naphthalen-1-yl)-$N^4,N^{4'}$-diphenylbenzene-1,4-diamine); or $N^4,N^{4'}$-di(naphthalen-1-yl)-$N^4,N^{4'}$-diphenylbiphenyl-4,4'-diamine (NPB) as the hole transport material or using the known hole injection layer, such as polyaniline or polyethylenedioxythiophene as the electron injection material.

Said emission layer can be made of an emission material including a host and a dopant. The host of the emission material is, for example, but not limited to, 9-(4-(naphthalen-1-yl)phenyl)-10-(naphthalen-2-yl) anthracene.

For red OLEDs, the dopant of the emission material is, for example, but not limited to: organometallic compounds of iridium (II) having perylene ligands, fluoranthene ligands or periflanthene ligands. For green OLEDs, the dopant of the emission material is, for example, but not limited to: diaminofluorenes; diaminoanthracenes; or organometallic compounds of iridium (II) having phenylpyridine ligands. For blue OLEDs, the dopant of the emission material is, for example, but not limited to: diaminofluorenes; diaminoanthracenes; diaminopyrenes; or organicmetallic compounds of iridium (II) having phenylpyridine ligands. With various host materials of the emission layer, the OLED can emit lights in red, green or blue.

Said electron injection layer may be made of an electron injection material, for example, but not limited to (8-oxidonaphthalen-1-yl)lithium(II).

Said first electrode is, for example, but not limited to, an indium-doped tin oxide electrode.

Said second electrode has a work function lower than that of the first electrode. The second electrode is, for example, but not limited to, an aluminum electrode, an indium electrode, or a magnesium electrode.

Other objectives, advantages and novel features of the invention will become more apparent from the following detailed description when taken in conjunction with the accompanying drawings.

DETAILED DESCRIPTION OF THE PREFERRED EMBODIMENTS

Figure 1:
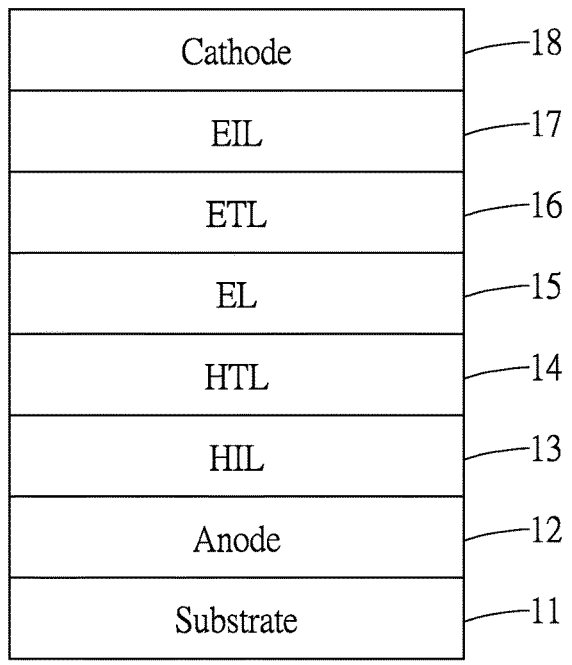
FIG. 1 illustrates a schematic cross-sectional view of an OLED.

Hereinafter, one skilled in the arts can easily realize the advantages and effects of a novel compound and an organic light emitting device using the same in accordance with the present invention from the following examples. It should be understood that the descriptions proposed herein are just preferable examples only for the purpose of illustrations, not intended to limit the scope of the invention. Various modifications and variations could be made in order to practice or apply the present invention without departing from the spirit and scope of the invention.

Preparation of Intermediate A

Intermediates A1 to A32 were adopted to synthesize the novel compound. Intermediates A1 to A32 could be purchased or synthesized by the following steps. Hereinafter, Intermediates A1 to A6, A9 to A14, A19 to A27 were purchased from Aldrich or Alfa, and their CAS No. were listed in Table 1. The other Intermediates A were synthesized by the following steps. The following syntheses are carried out, unless indicated otherwise, under a protected-gas atmosphere. The specific chemical structures of the Intermediates A1 to A32 were listed in Table 1.

TABLE 1 chemical structures and CAS No. of Intermediates A1 to A32.

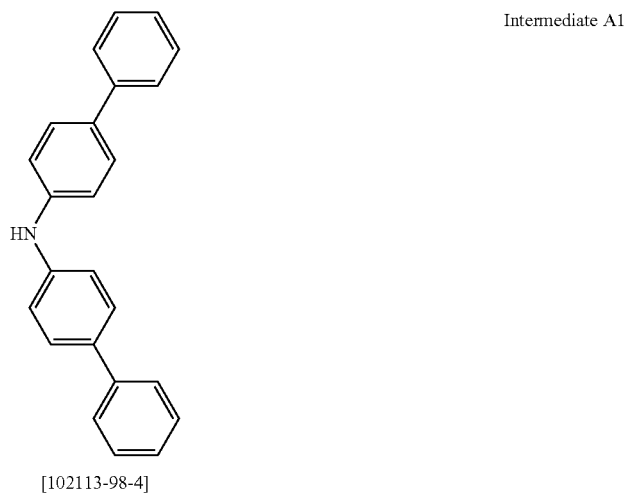

Intermediate A1

TABLE 1-continued
chemical structures and CAS No. of Intermediates A1 to A32.
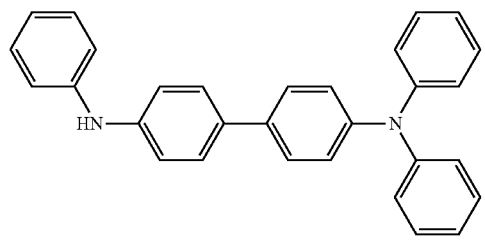
[167218-30-6]
Intermediate A2
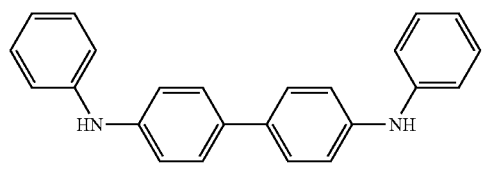
[531-91-9]
Intermediate A3
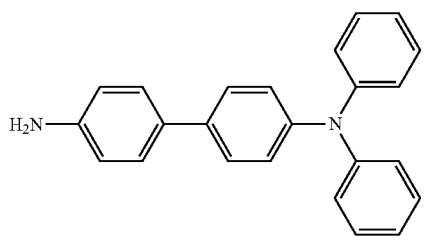
[84161-87-5]
Intermediate A4
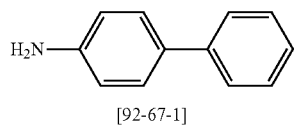 [SMILES: Nc1ccc(-c2ccccc2)cc1]
[92-67-1]
Intermediate A5
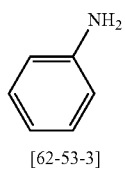
[62-53-3]
Intermediate A6
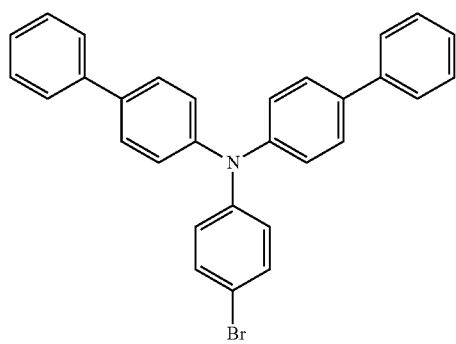
Intermediate A7

TABLE 1-continued
chemical structures and CAS No. of Intermediates A1 to A32.
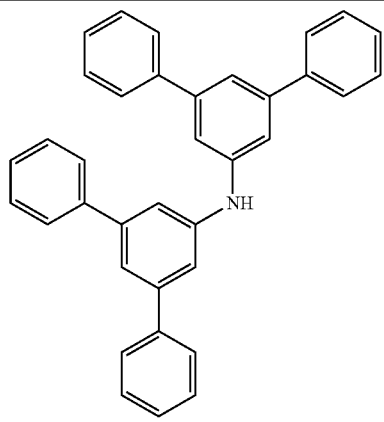
Intermediate A8
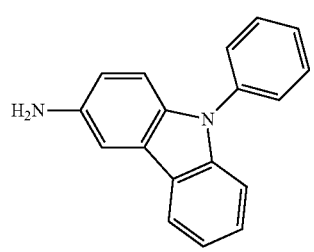
[318253-36-9]
Intermediate A9
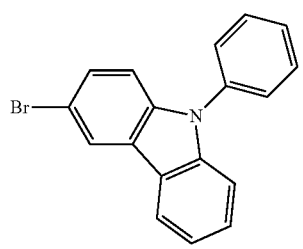 [SMILES: Brc1ccc2c(c1)c1ccccc1n2-c1ccccc1]
[1153-85-1]
Intermediate A10
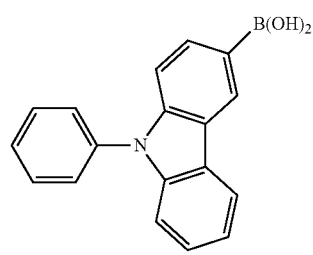
[854952-58-2]
Intermediate A11
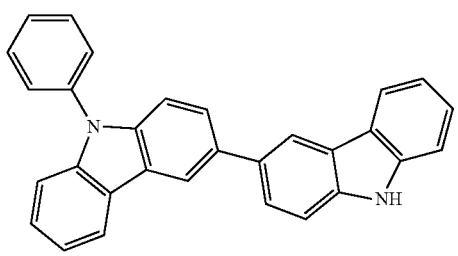
[1060735-14-9]
Intermediate A12

TABLE 1-continued
chemical structures and CAS No. of Intermediates A1 to A32.
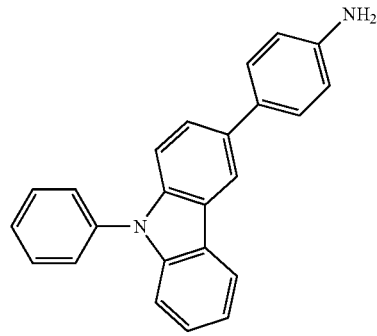 [SMILES: Nc1ccc(-c2ccc3c(c2)c2ccccc2n3-c2ccccc2)cc1]
[1370034-59-5]
Intermediate A13
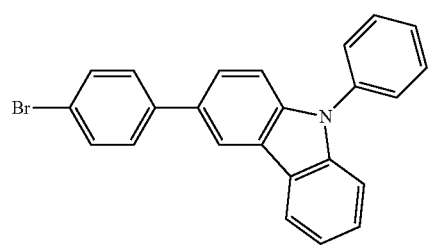
[1028647-93-9]
Intermediate A14
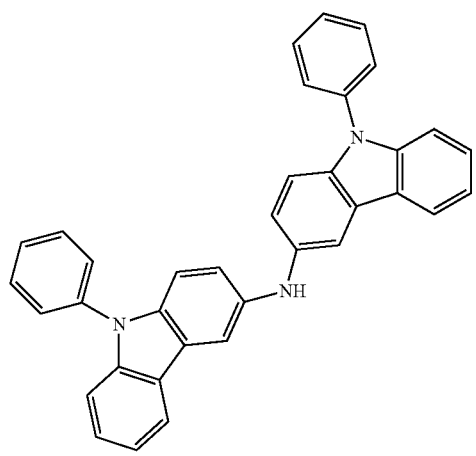
Intermediate A15

TABLE 1-continued
chemical structures and CAS No. of Intermediates A1 to A32.
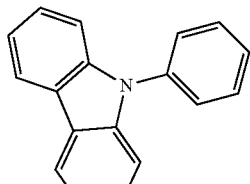
Intermediate A16
—
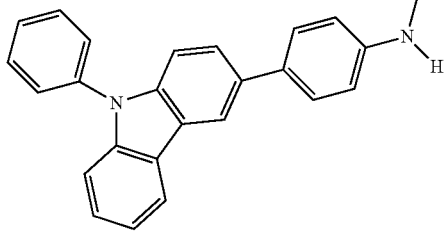
Intermediate A17
—
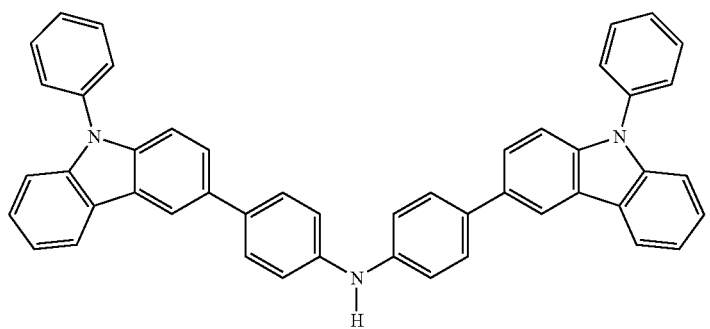
Intermediate A18
—
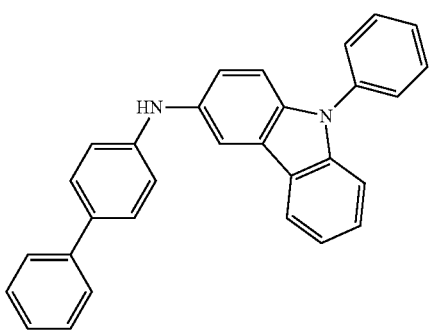
Intermediate A19
[1072194-21-8]

TABLE 1-continued
chemical structures and CAS No. of Intermediates A1 to A32.
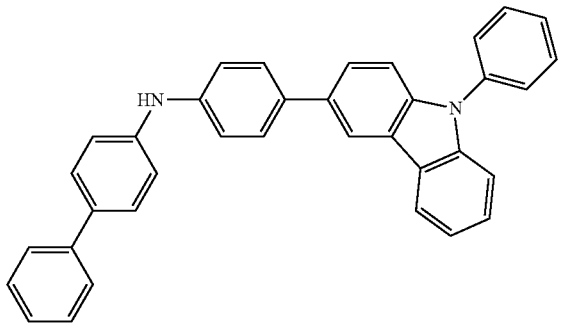
Intermediate A20
[1160294-96-1]
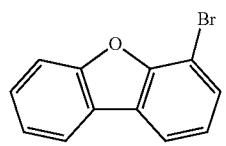 [SMILES: Brc1cccc2c1oc1ccccc12]
Intermediate A21
[89827-45-2]
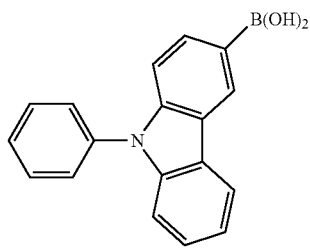
Intermediate A22
[854952-58-2]
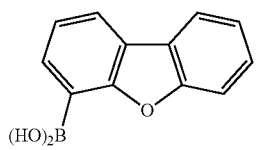
Intermediate A23
[100124-06-9]
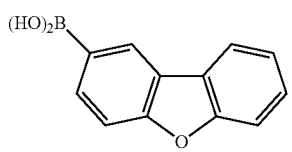
Intermediate A24
[402936-15-6]
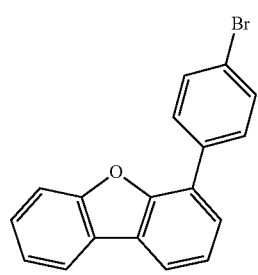 [SMILES: Brc1ccc(-c2cccc3c2oc2ccccc23)cc1]
Intermediate A25
[955959-84-9]

TABLE 1-continued
chemical structures and CAS No. of Intermediates A1 to A32.
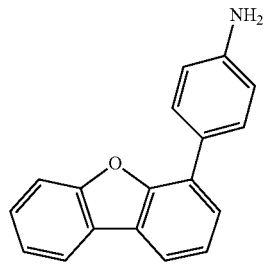 [SMILES: Nc1ccc(-c2cccc3c2oc2ccccc23)cc1]
[578027-21-1]
Intermediate A26
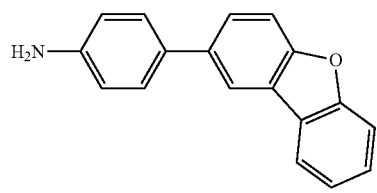
[1178274-17-3]
Intermediate A27
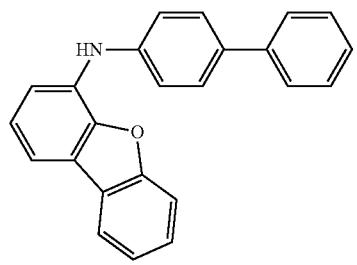
—
Intermediate A28
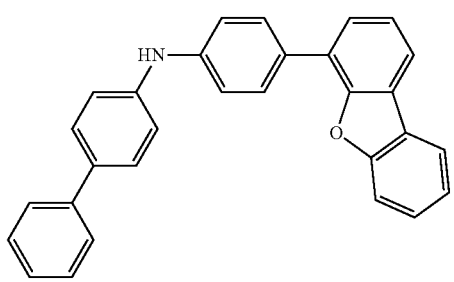
—
Intermediate A29
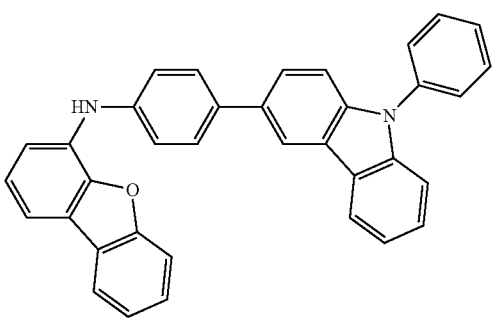
—
Intermediate A30

TABLE 1-continued chemical structures and CAS No. of Intermediates A1 to A32.

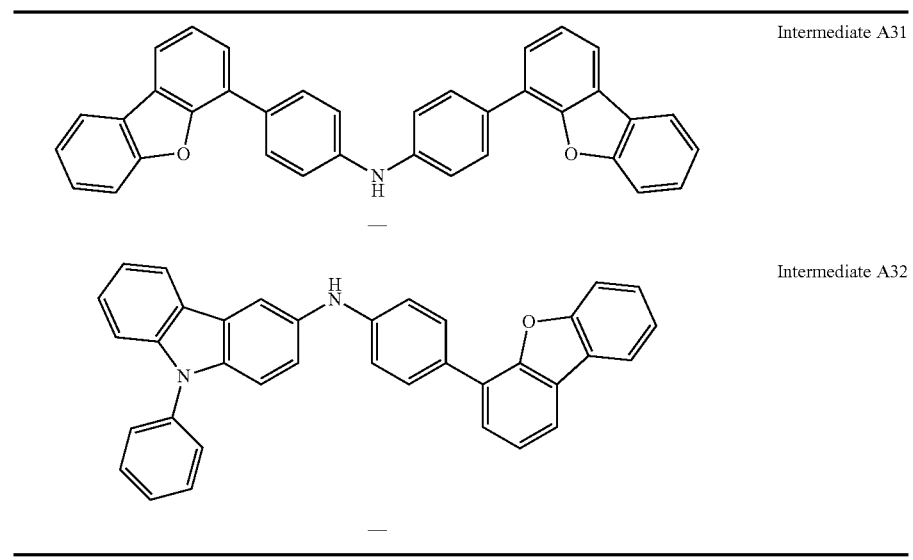

Intermediate A31

Intermediate A32

Synthesis of Intermediate A7

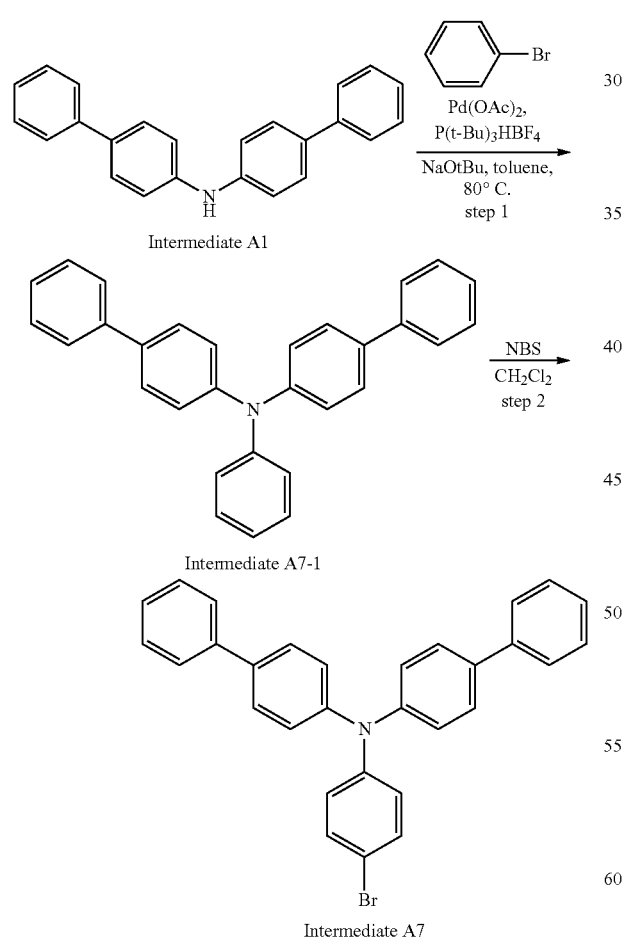

Step 1:
A mixture of intermediate A1 (1.0 eq), bromobenzene (1.05 eq), Pd(OAc)$_2$ (0.005 eq), P(t-Bu)$_3$HBF$_4$ (0.02 eq), and NaO$^t$Bu (1.5 eq) in toluene (0.3M) was heated at 80° C. for 8 h. After the completion of the reaction, the volatiles were removed under vacuum, and the resulting solution extracted with dichloromethane (3×60 mL). The combined organic extract was washed with brine solution, dried over Na$_2$SO$_4$, and concentrated to leave a yellow solid. Further, the crude product was purified by column chromatography on silica gel to give Intermediate A7-1 with white solid.

Step 2:

Intermediate A7-1 (1.0 eq) was dissolved in dichloromethane (10 times to Intermediate A7-1) and N-bromosuccinimide (1.05 eq) was slowly put into the round bottom flask for 10 min, and agitated for 4 hours. After 100 ml of the sodium thiosulfate aqueous solution was put and agitated for 20 min, the organic layer was separated. The separated organic layer was washed by 50 ml of the sodium chloride aqueous solution and then dried by magnesium sulfate anhydride. The crude product was purified by column chromatography on silica gel to give Intermediate A7 with white solid, yield 75%.

Synthesis of Intermediate A8

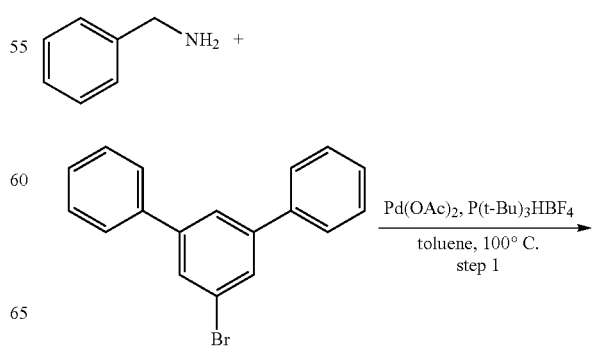

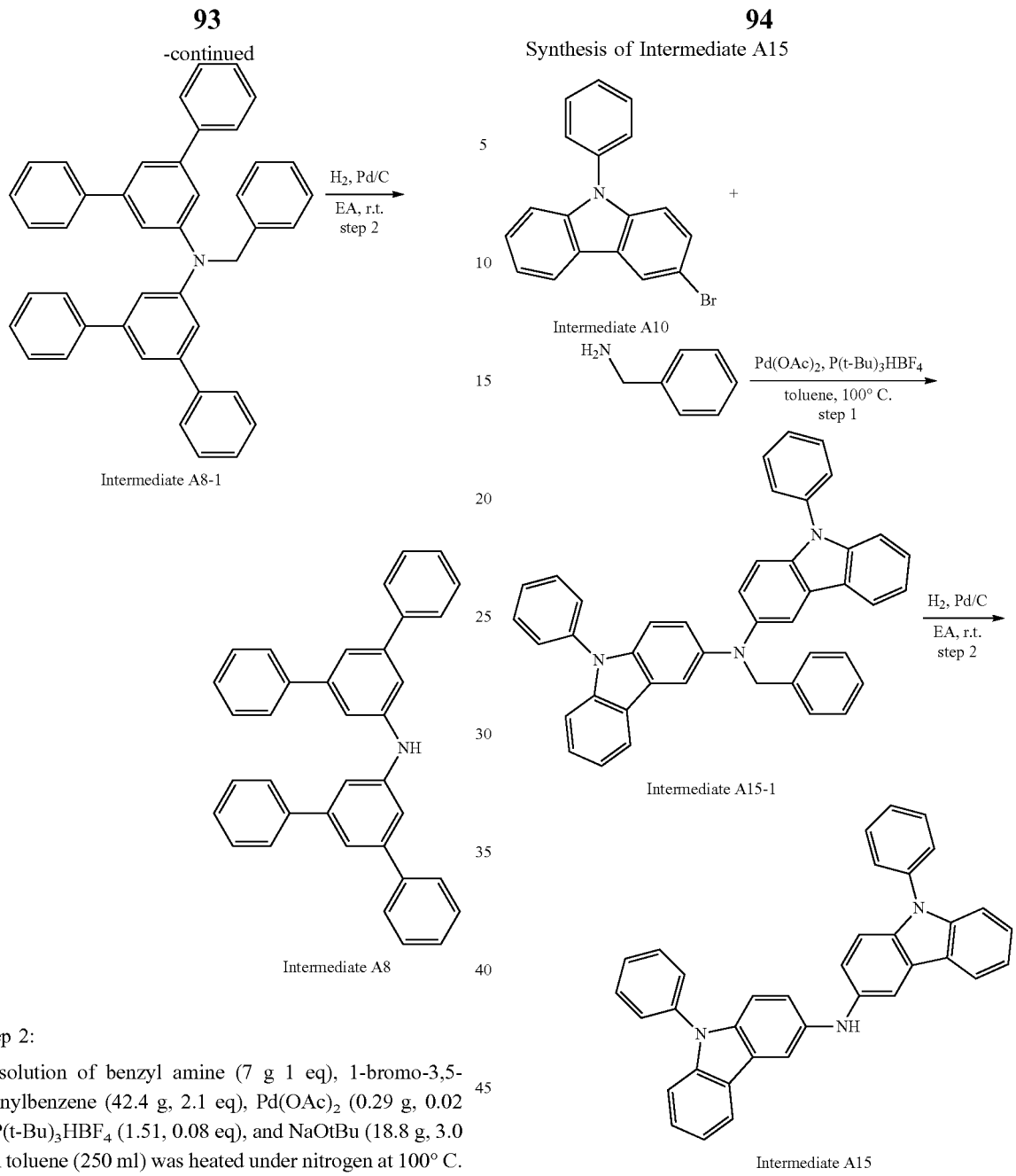

Synthesis of Intermediate A15

Step 2:

A solution of benzyl amine (7 g 1 eq), 1-bromo-3,5-diphenylbenzene (42.4 g, 2.1 eq), Pd(OAc)$_2$ (0.29 g, 0.02 eq), P(t-Bu)$_3$HBF$_4$ (1.51, 0.08 eq), and NaOtBu (18.8 g, 3.0 eq) in toluene (250 ml) was heated under nitrogen at 100° C. for 12 hour. After cooling to room temperature, the solvent was then removed using a rotary evaporator, and the remaining substance was purified with column chromatography to obtain Intermediate A8-1: N,N-di((3,5diphenyl) phenyl) benzylamine (29 g, yield: 78.7%). MS: [M]$^+$=563.73

Step 2:

A solution of N,N-di((3,5diphenyl)phenyl)benzylamine (29 g, 1.0 eq), 5% Pd/C (8.2 g, 0.075 eq) in DCM (300 ml) was hydrogenated under hydrogen balloon at room temperature. The reaction was monitored by HPLC. After the completion of reaction, the mixture was filtered over a celite bed with DCM, and concentrated under reduced pressure. The remaining substance was purified with column chromatography to obtain intermediate A8. (18 g, yield: 73.9%). MS: [M]$^+$=473.61.

Step 1:

A solution of benzylamine (5.0 g, 1.0 eq), Intermediate A10 (31.6 g, 2.1 eq), Pd(OAc)$_2$ (0.10 g, 0.01 eq), DPPF (0.54 g, 0.04 eq), and NaOtBu (13.5 g, 3.0 eq) in toluene (180 mL) was heated under nitrogen at 100° C. for 12 hours. After cooling to room temperature, the solvent was then removed using a rotary evaporator, and the remaining substance was purified with column chromatography to obtain Intermediate A15-1 (N-benzyl-9-phenyl-N-(9-phenyl-9H-carbazol-3-yl)-9H-carbazol-3-amine (20.3 g, yield: 73.8%)). MS: [M]$^+$=589.73.

Step 2:

A suspension of N-benzyl-9-phenyl-N-(9-phenyl-9H-carbazol-3-yl)-9H-carbazol-3-amine (20.3 g, 1.0 eq) and 5% Pd/C (0.025 eq) in 200 ml ethyl acetate was stirred for 3 to 6 hours under a hydrogen atmosphere provided by a balloon of hydrogen. The resulting mixture was filtered through a pad of celite and washed with ethyl acetate, and the filtrate was concentrated under reduced pressure to obtain Intermediate A15 (17.2 g, yield: 100%). MS: [M]$^+$=499.6.

Synthesis of Intermediate A17

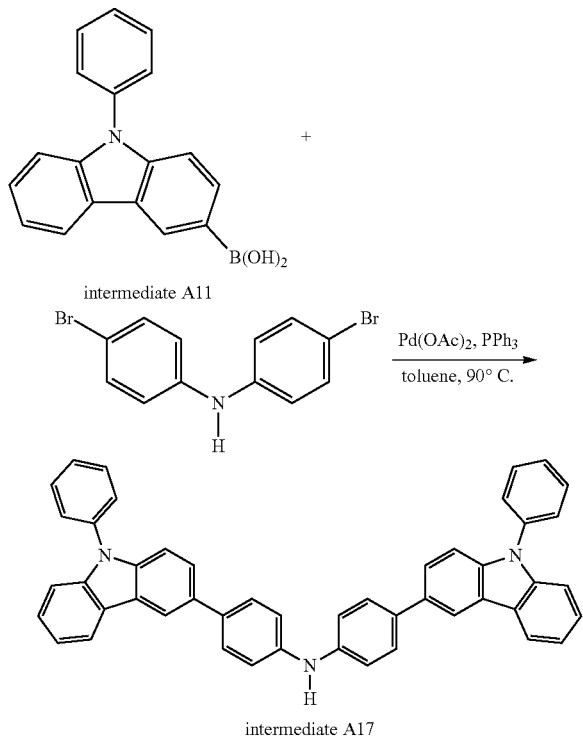

intermediate A17

A solution of bis(4-bromophenyl)amine (35.4 g, 1.0 eq), (9-Phenyl-9H-carbazol-3-yl)boronic acid (2.1 eq), Pd(OAc)$_2$ (0.02 eq), PPh$_3$ (0.08 eq), and 3M of K$_2$CO$_3$ aqueous solution (3.0 eq in H$_2$O) in toluene (0.3M) was heated under nitrogen at 90° C. for 12 hour. After cooling to room temperature, the solvent was then removed using a rotary evaporator, and the remaining substance was purified with column chromatography to obtain Intermediate A17 (58.7 g, yield: 83.2%). MS: [M]$^+$=651.8.

Synthesis of Intermediates A16, A18, and A28 to A32

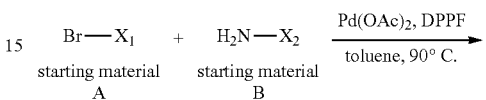

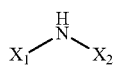

A solution of bromo-hetrocyclic compounds (1.0 eq), amine (1.1 eq), Pd(OAc)$_2$ (0.01 eq), DPPF (0.04 eq), and NaOtBu (1.5 eq) in toluene (0.3 M) was heated under nitrogen at 90° C. for 12 hours. After cooling to room temperature, the solvent was then removed using a rotary evaporator, and the remaining substance was purified with column chromatography to obtain Intermediate A16, A18 and A28 to A32, and their yields and MS data were given in the following table.

TABLE 2
The starting materials A and B used for preparing Intermediates A16, A18 and A28 to A32 and their yields and MS data.
| Starting Material A | Starting Material B | Intermediates | Yield (%) | Mass(M⁺) |
|---|---|---|---|---|
| 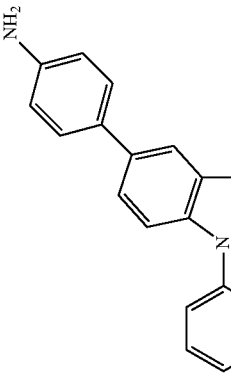 | 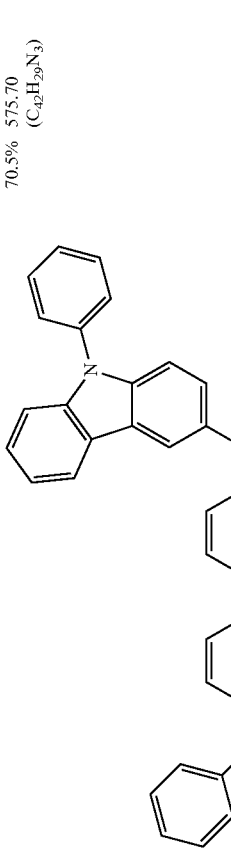 | 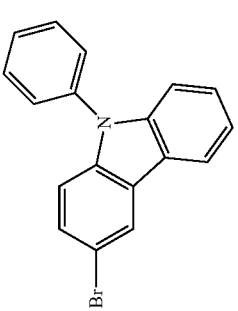<br>Intermediate A16 | 70.5% | 575.70 ($C_{42}H_{29}N_3$) |
| 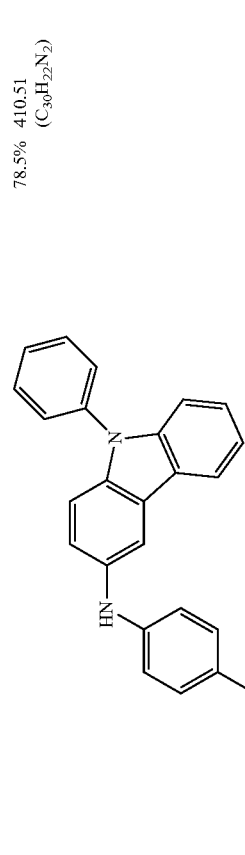 | 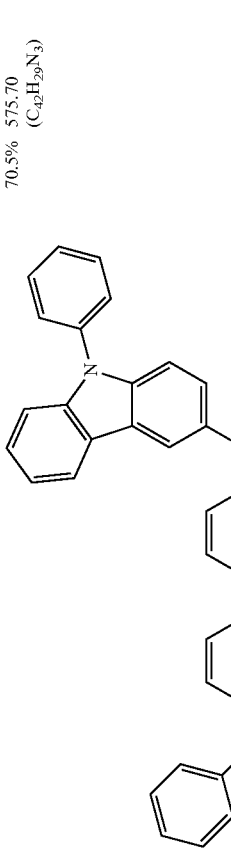 | 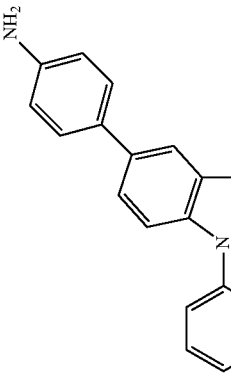<br>Intermediate A18 | 78.5% | 410.51 ($C_{30}H_{22}N_2$) |

TABLE 2-continued
The starting materials A and B used for preparing Intermediates A16, A18 and A28 to A32 and their yields and MS data.
| Starting Material A | Starting Material B | Intermediates | Yield (%) | Mass(M⁺) |
|---|---|---|---|---|
| 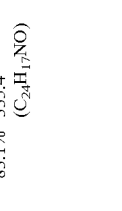 | 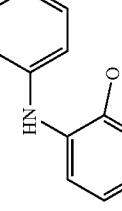 | 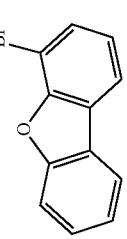 Intermediate A28 | 83.1% | 335.4 ($C_{24}H_{17}NO$) |
| 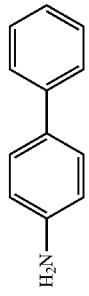 | 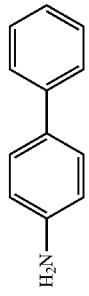 | 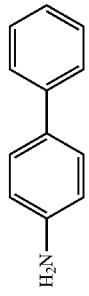 Intermediate A29 | 74.8% | 411.49 ($C_{30}H_{21}NO$) |
| 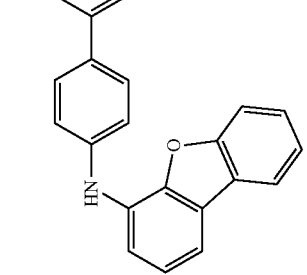 | 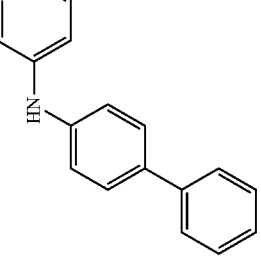 | 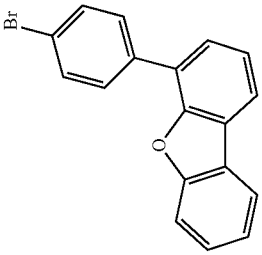 Intermediate A30 | 40.0% | 500.59 ($C_{36}H_{24}N_2O$) |

TABLE 2-continued
The starting materials A and B used for preparing Intermediates A16, A18 and A28 to A32 and their yields and MS data.
| Starting Material A | Starting Material B | Intermediates | Yield (%) | Mass(M+) |
|---|---|---|---|---|
| 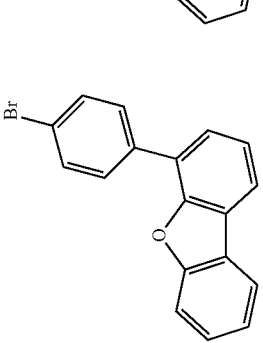 | 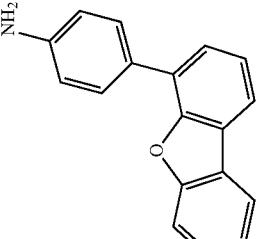 | 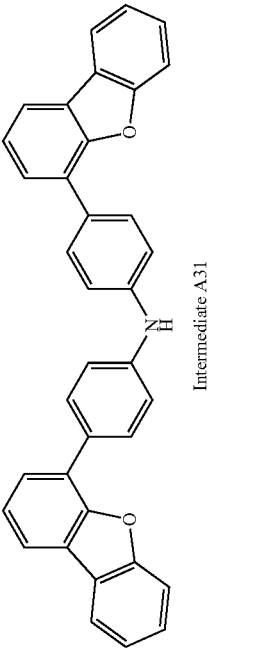 Intermediate A31 | 78.5% | 501.57 (C$_{36}$H$_{23}$NO$_2$) |
| 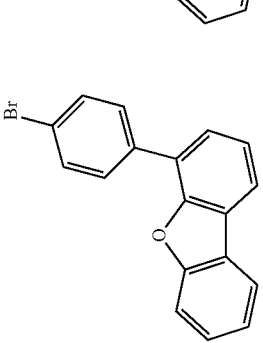 | 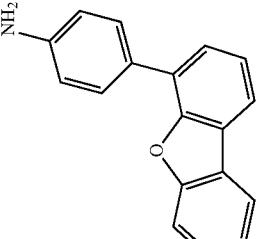 | 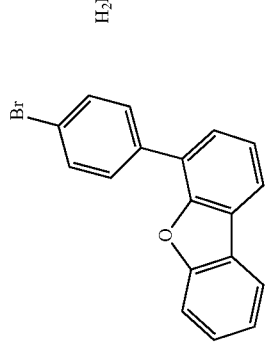 Intermediate A32 | 85.0% | 500.59 (C$_{36}$H$_{24}$N$_2$O) |

Intermediate B

To prepare the novel compound of the present invention, Intermediate B may be, for example, but not limited to as follows.

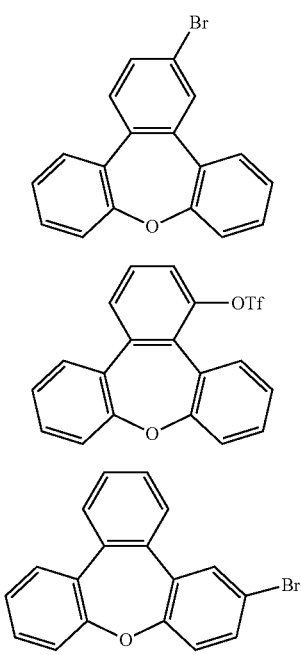

Intermediate B1

Intermediate B2

Intermediate B3

Synthesis of Intermediate B1

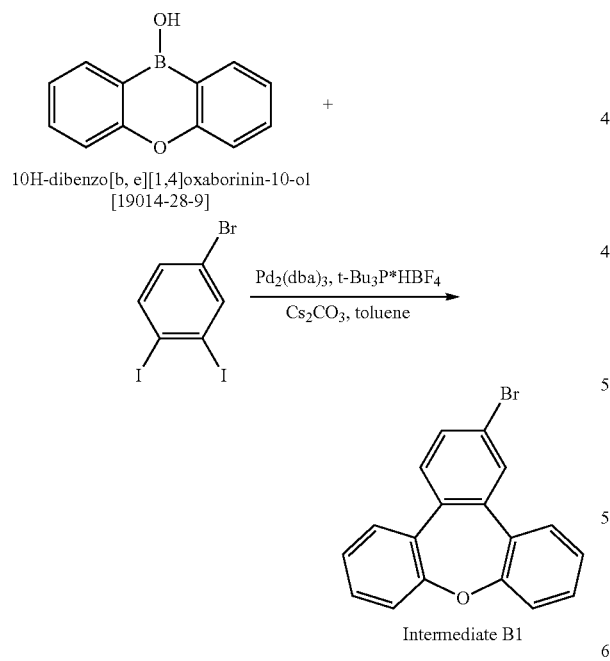

10H-dibenzo[b, e][1,4]oxaborinin-10-ol
[19014-28-9]

1-Bromo-3,4-diiodobenzene (300.0 g, 1.0 eq), 10H-dibenzo[b,e][1,4]oxaborinin-10-ol (151.0 g, 1.05 eq) and t-Bu₃P(HBF₄) (10.0 g, 0.015 eq) were put into 3M Cs₂CO₃ aqueous solution (717.0 g, 3.0 eq in 770 ml H₂O) and toluene (1350 ml), and refluxed and agitated for about 24 hours. It was cooled to room temperature, the organic layer was separated from the reaction mixture solution, and the organic layer was dried with anhydrous magnesium sulfate, and filtered. The filtered solution was concentrated under the reduced pressure and purified by silica gel chromatography (evaluation solvent: toluene/n-hexane=1:1) to give the Intermediate B1 (175 g, yield: 73.4%). MS: [M]⁺=323.18

Synthesis of Intermediate B2

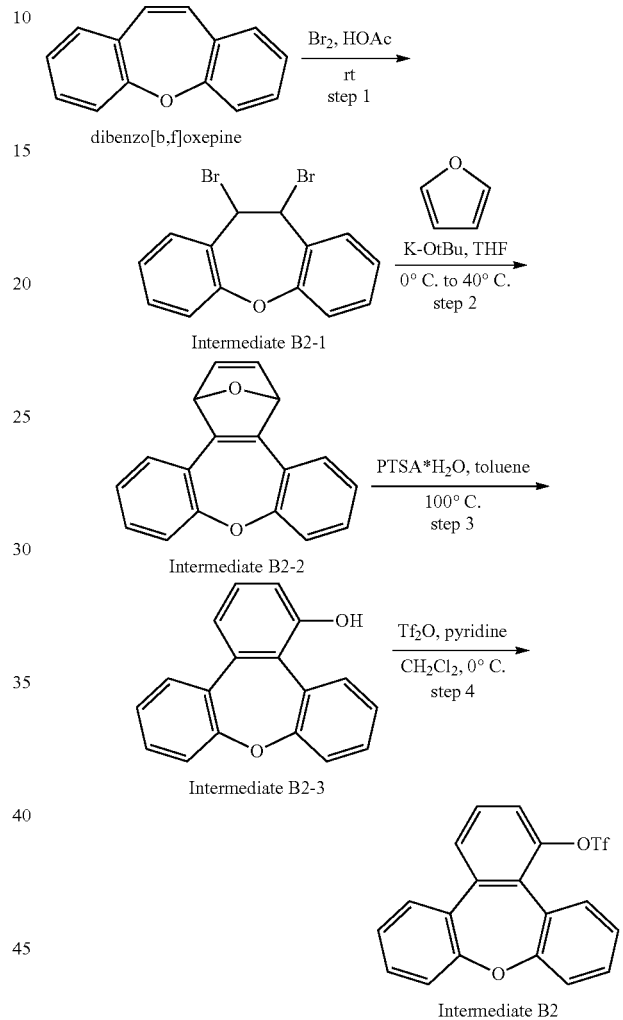

Step 1:

A mixture of dibenzo[b,f]oxepine (100 g, 1.0 eq) in acetic acid (600 ml) was added bromine (1.1 eq) diluted with acetic acid (200 ml) slowly at 5° C., and the reaction mixture was allowed to be warmed to room temperature. The reaction was monitored by HPLC. After the completion of a reaction, the precipitate was separated by filtration and washed with MeOH then purified by recrystallization. The purified product was concentrated to dryness, whereby a white solid product was obtained in 96.0% yield. The solid product was identified as intermediate B2-1 by a field desorption mass spectroscopy (FD-MS) analysis. FD-MS analysis: $C_{14}H_{10}Br_2O$: theoretical value of 354.04 and observed value of 354.04.

Step 2:

The obtained Intermediate B2-1 (116.0 g, 1.0 eq) was dissolved in 700 mL of furan/THF(v/v=2/1), the reaction was cooled to 0° C. and then treated with potassium tertbutoxide (KO-tBu) (3.0 eq). The reaction was allowed to stir at 0° C. for 1 h, and then heated to 40° C. for another 12 h. After the completion of the reaction, the reaction was quenched by DI water and the organic layer was recovered by solvent extraction operation, which was then dried over sodium sulfate. The solvent was removed from the organic layer by distillation under reduced pressure, and the resulting residue was purified by silica gel column chromatography. The purified product was concentrated to dryness, whereby a light yellow solid product was obtained in 51.1% yield. The solid product was identified as Intermediate B2-2 by FD-MS analysis. FD-MS analysis $C_{18}H_{12}O_2$: theoretical value of 260.29 and observed value of 260.29.

Step 3:

Intermediate B2-2 (20 g, 1.0 eq) and p-toluenesulfonic acid (PTSA) (1.2 eq) in 200 mL of toluene (10 times to B4-2) was heated to reflux for 6 h. The reaction mixture was cooled to room temperature and then quenched with a saturated aqueous solution of $NaHCO_3$ and extracted with $CH_2Cl_2$. The organic layer was washed with water, brine and dried with anhydrous $Na_2SO_4$ subsequently. Then the resulting solution was concentrated under reduced pressure and purified by column chromatography to obtain product as brown oil in a yield of 100%. The oil product was identified as intermediate B2-3 by FD-MS analysis. FD-MS analysis $C_{18}H_{12}O_2$: theoretical value of 260.29 and observed value of 260.29.

Step 4:

Intermediate B2-3 (20 g, 1.0 eq) and pyridine (2.0 eq) in 200 mL of $CH_2Cl_2$ (10 times to B2-3) was cooled to 0° C. Trifluoromethanesulfonic anhydride (1.2 eq) was slowly added, and then the reaction is allowed to be warmed to room temperature and stirred for 2 hours. The reaction was quenched with water and extracted with $CH_2Cl_2$. The organic layer was washed with water and dried with anhydrous $Na_2SO_4$ subsequently. Then the resulting solution was concentrated under reduced pressure and purified by column chromatography to obtain white solid in 85.9% yield. The solid product was identified as intermediate B2 by FD-MS analysis. FD-MS analysis $C_{19}H_{11}F_3O_4S$: theoretical value of 392.35 and observed value of 392.35.

Synthesis of Intermediate B3

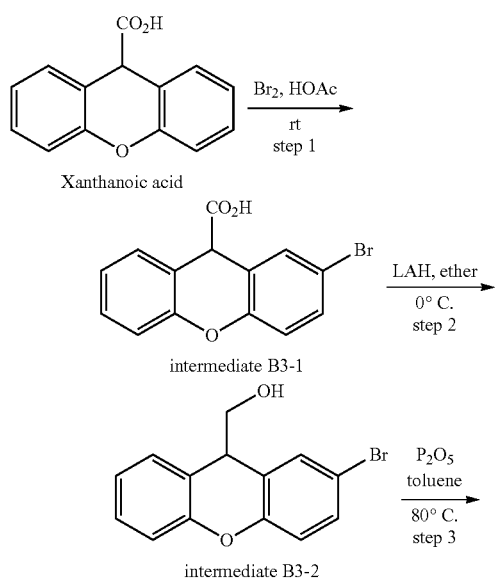

Step 1:

A mixture of 9H-xanthene-9-carboxylic acid (1.0 eq) in acetic acid was added bromine (1.05 eq) diluted with acetic acid slowly at ambient temperature for 18 hours. The reaction was monitored by HPLC. After completion of a reaction, the reaction was quenched with DI water (2800 ml) and stirred for 2 hours. The precipitate was separated by filtration and washed with water again. The precipitate was separated by filtration and dissolved with ethyl acetate, and then the layer of water was separated and the organic layer dried with magnesium sulfate. After drying, this mixture was subjected to suction filtration, and the filtrate was concentrated to obtain white powdery solid in 97% yield. The solid product was identified as intermediate B3-1 by FD-MS analysis. FD-MS analysis: $C_{14}H_9BrO_3$: theoretical value of 305.12 and observed value of 305.12.

Step 2:

Intermediate B3-1 (1.0 eq) was added slowly into a stirred solution of LiAlH4 (1.5 eq) in anhydrous ether under $N_2$ and 0° C. The system was stirred for 1 h at room temperature. The reaction was monitored by HPLC. After the completion of the reaction, 3N of HCl solution was slowly dropped. The mixture was extracted with diethyl ether and the combined organic phase was dried over $MgSO_4$. The excess solvent was removed under reduced pressure, and the resulting residue was purified by silica gel column chromatography to obtain yellow solid in 93% yield. The solid product was identified as intermediate B3-2 by FD-MS analysis. FD-MS analysis: $C_{14}H_{11}BrO_2$: theoretical value of 291.14 and observed value of 291.14.

Step 3:

Intermediate B3-2(1 eq) was dissolved in toluene that was added to a suspension of phosphorous pentoxide (6.0 eq) in toluene under $N_2$ and refluxed at 80° C. for 0.5 hours. The reaction was monitored by HPLC. After the completion of the reaction, the reaction mixture was cooled to 0° C., and 3N HCl solution (400 mL) was slowly dropped. The organic layer was recovered by solvent extraction operation and dried over $MgSO_4$. The solvent was removed from the organic layer by distillation under reduced pressure, and the resulting residue was purified by silica gel column chromatography to obtain white solid in 93% yield. The solid product was identified as intermediate B3-3 by FD-MS analysis. FD-MS analysis: $C_{14}H_9BrO$: theoretical value of 273.12 and observed value of 273.12.

Step 4:

A mixture of intermediate B3-3 (1.0 eq) in acetic acid was added bromine (1.0 eq) diluted with acetic acid slowly at 5° C., and the reaction mixture was allowed to be warmed to room temperature. The reaction was monitored by HPLC. After the completion of the reaction, the precipitate was separated by filtration and washed with MeOH and then purified by recrystallization. The purified product was concentrated to dryness, whereby a white solid product was obtained in 96% yield. The solid product was identified as intermediate B3-4 by FD-MS analysis. FD-MS analysis: $C_{14}H_9Br_3O$: theoretical value of 432.93 and observed value of 432.93.

Step 5:

Intermediate B3-4 (1.0 eq) was dissolved in furan and THF, the reaction was cooled to 0° C. and then treated with potassium t-butoxide (3.0 eq). The reaction was allowed to stir for 1 hour at 0° C. prior to raise up to 50° C. and stirred for another 12 hours. Quenched by DI water, the organic layer was recovered by solvent extraction operation and dried over $MgSO_4$. The solvent was removed from the organic layer by distillation under reduced pressure, and the resulting residue was purified by silica gel column chromatography. The purified product was concentrated to dryness, whereby a light yellow solid bridge furan compound was obtained in 72% yield. The solid product was identified as Intermediate B3-5 by FD-MS analysis. FD-MS analysis: $C_{18}H_{11}BrO_2$: theoretical value of 339.18 and observed value of 339.18.

Step 6:

A suspension of Intermediate B3-5 (1.0 eq) and 5% Pd/C (0.025 eq) in ethyl acetate was stirred for 3 to 6 hours under a hydrogen atmosphere provided by a balloon of hydrogen. The resulting mixture was filtered through a pad of celite and washed with ethyl acetate, and the filtrate was concentrated under reduced pressure to obtain product as a yellow solid in 100% yield, and the compound could be directly used in the following reaction without further purified. The product was identified as Intermediate B3-6 by FD-MS analysis. FD-MS analysis: $C_{18}H_{13}BrO_2$: theoretical value of 3412 and observed value of 341.2.

Step 7:

A mixture of Intermediate B3-6 (1.0 eq) and p-toluene-sulfonic acid (2.0 eq) in toluene was heated to reflux for 12 hours. The reaction mixture was cooled to room temperature and then quenched with a saturated aqueous solution of $NaHCO_3$ and extracted with toluene. The organic layer was washed with water, brine and dried with anhydrous $Na_2SO_4$ subsequently. Then the resulting solution was concentrated under reduced pressure and purified by column chromatography on silica gel to obtain white solid in 94% yield. The product was identified as intermediate B3 by FD-MS analysis. FD-MS analysis: $C_{18}H_{11}BrO$: theoretical value of 323.18 and observed value of 323.18.

Intermediate C

To prepare the novel compound of the present invention, Intermediate C may be, for example, but not limited to as follows.

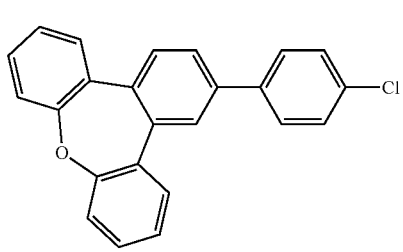

Intermediate C1

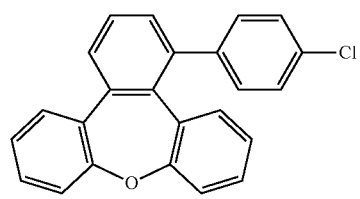

Intermediate C2

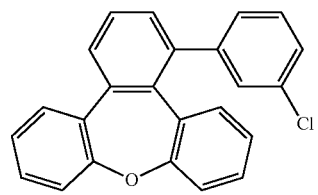

Intermediate C3

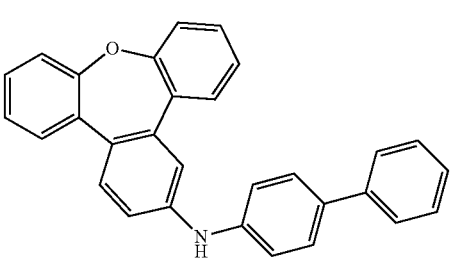

Intermediate C4

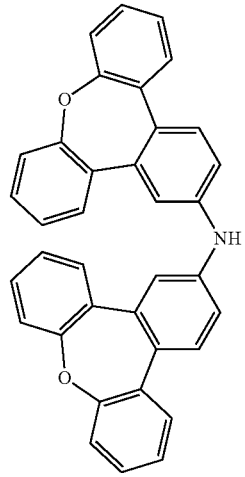

Intermediate C5

-continued

Intermediate C6

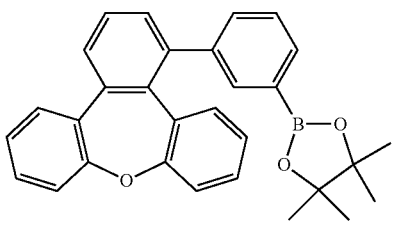

Intermediate C7

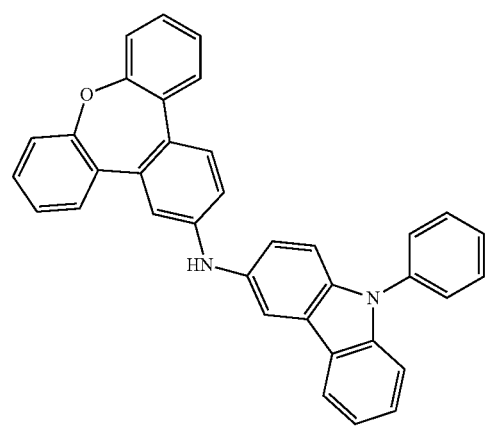

Intermediate C8

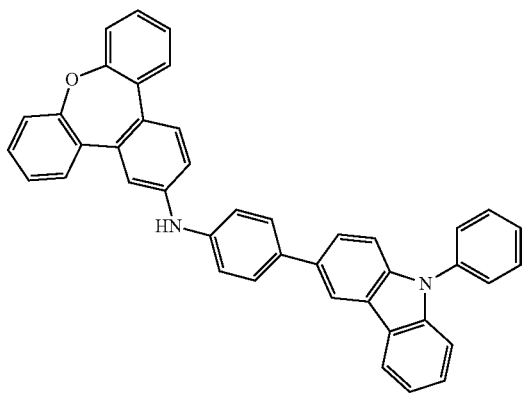

-continued

Intermediate C9

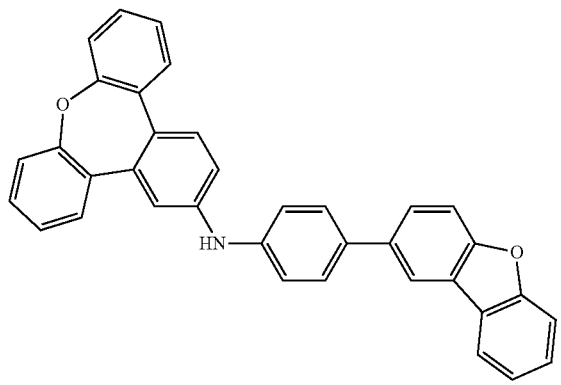

Synthesis of Intermediate C1 to C3

Intermediate B1 or B2 $\xrightarrow[\text{K}_2\text{CO}_{3(aq)}, \text{Toluene/EtOH}]{\text{Pd(OAc)}_2, \text{PPh}_3}$ Intermediate C1~C3
$100°$ C.

Intermediate B1 or B2 (1.0 eq), chlorophenylboronic acid (1.2 eq, CAS 1679-18-1), Pd(OAc)$_2$ (0.015 eq), PPh$_3$ (0.06 eq), K$_2$CO$_3$ (1.5 eq, 3M) in toluene (0.3M) were heated at 100° C. for 12 hours. After the completion of the reaction, the volatiles were removed under vacuum, and the resulting solution extracted with CH$_2$Cl$_2$. The combined organic extract was washed with brine solution, dried over Na$_2$SO$_4$. Then the resulting solution was concentrated under reduced pressure and purified by column chromatography to obtain white solid. The analysis data of the obtained products, i.e. Intermediates C1 to C3 as listed in the following Table 3.

TABLE 3

The starting materials, including Intermediate B and chlorophenyl boronic acid, used for preparing Intermediates C1 to C3 and their yields and MS data.

| Intermediate B | Chlorophenyl boronic acid | Intermediate C | Yield (%) | Formula (FD-MS) |
|---|---|---|---|---|
| Intermediate B1 | Cl—⌬—B(OH)$_2$ [1679-18-1] | Intermediate C1 | 90 | C$_{24}$H$_{15}$ClO (354.83) |

TABLE 3-continued

The starting materials, including Intermediate B and chlorophenyl boronic acid, used for preparing Intermediates C1 to C3 and their yields and MS data.

| Intermediate B | Chlorophenyl boronic acid | Intermediate C | Yield (%) | Formula (FD-MS) |
|---|---|---|---|---|
| Intermediate B2 | Cl—⌬—B(OH)₂  [1679-18-1] | Intermediate C2 | 95 | $C_{24}H_{15}ClO$ (354.83) |
| Intermediate B2 | Cl—⌬—B(OH)₂  [63503-60-6] | Intermediate C3 | 93 | $C_{24}H_{15}ClO$ (354.83) |

Synthesis of Intermediate C4

Synthesis of Intermediate C5

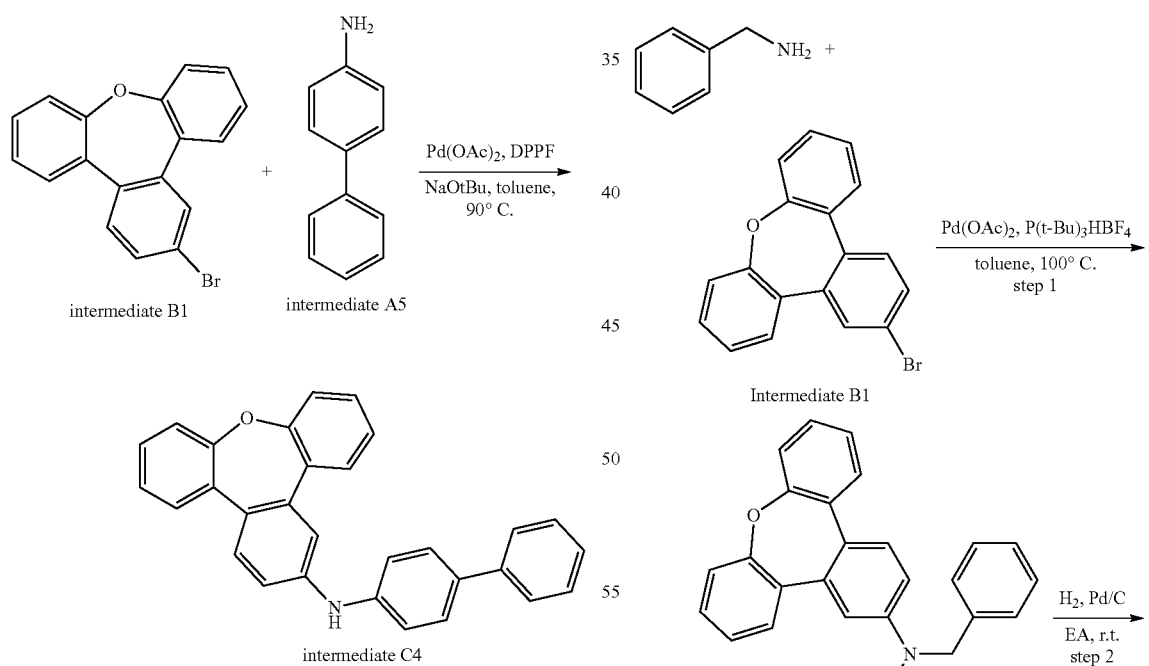

A solution of Intermediate A5 (11.50 g, 1.1 eq), Intermediate B1 (20.00 g, 1 eq), Pd(OAc)₂ (0.14 g, 0.01 eq), DPPF (1.37 g, 0.04 eq), and NaOtBu (8.92 g, 1.5 eq) in toluene (160 ml) was heated under nitrogen at 90° C. for 12 hours. After cooling to room temperature, the solvent was then removed using a rotary evaporator, and the remaining substance was purified with column chromatography to obtain Intermediate C4. (25.3 g, yield: 81.5%). MS: [M]⁺=411.49.

Synthesis of Intermediate C6

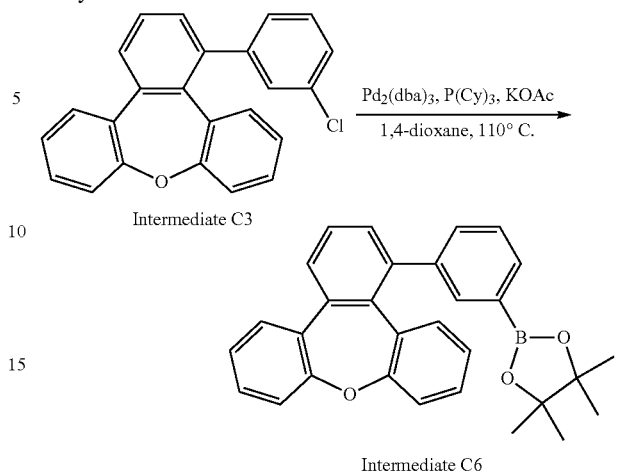

Intermediate C3

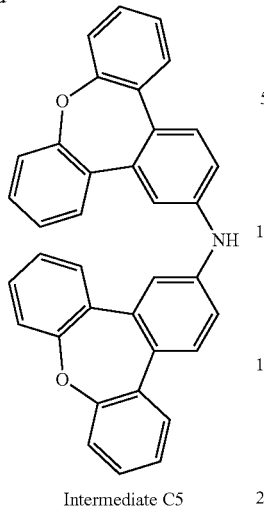

Intermediate C5

A solution of benzyl amine (5 g, 1 eq), Intermediate B1 (31.7 g, 2.1 eq), Pd(OAc)$_2$ (0.1 g, 0.01 eq), P(t-Bu)$_3$HBF$_4$ (0.5, 0.04 eq), and NaOtBu (13.5 g, 3.0 eq) in toluene (185 ml) was heated under nitrogen at 100° C. for 12 hours. After cooling to room temperature, the solvent was then removed using a rotary evaporator, and the remaining substance was purified with column chromatography to obtain N,N-diTBObenzylamine (17.5 g, yield: 74.8%). MS: [M]$^+$=591.7.

Step 2:

A solution of N,N-diTBObenzylamine (20 g, 1.0 eq), 5% Pd/C (5.4 g, 0.075 eq) and acetic acid (12.6 g, 6.2 eq) in DCM (100 ml) was hydrogenated under hydrogen balloon at room temperature. The reaction was monitored by HPLC. After completion of reaction, the mixture was filtered over a celite bed with DCM, and concentrated under reduced pressure. The remaining substance was purified with column chromatography to obtain Intermediate C5 (12.8 g, yield: 75.5%). MS: [M]$^+$=501.57.

A mixture of Intermediate C3 (1.0 eq), bis(pinacolato)diboron (1.2 eq), Pd$_2$(dba)$_3$ (0.015 eq), P(Cy)$_3$HBF$_4$ (0.06 eq), KOAc (3.0 eq) in 1,4-Dioxane (0.3M) was heated at 110° C. for 8 hours under nitrogen atmosphere. After cooling to room temperature, the solvent was then removed under reduced pressure, and the residue was purified via column chromatography to obtain white solids in 98.6% yield. The solid product was identified as intermediate C6 by FD-MS analysis. FD-MS analysis: C$_{30}$H$_{27}$BO$_3$: theoretical value of 446.34 and observed value of 446.34.

Synthesis of Intermediates C7 and C8

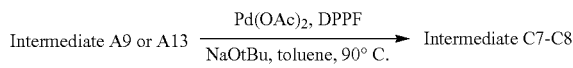

A solution of Intermediate B1 (1.0 eq), Intermediate A9 or A13 (1.1 eq), Pd(OAc)$_2$ (0.01 eq), DPPF (0.04 eq), and NaOtBu (1.5 eq) in toluene (0.5M) was heated under nitrogen at 90° C. for 12 hours. After cooling to room temperature, the solvent was then removed using a rotary evaporator, and the remaining substance was purified with column chromatography to respectively obtain Intermediate C7 and C8 as listed in the following Table 4.

TABLE 4

The starting materials, including Intermediate A and B, used for preparing Intermediates C7 and C8 and their yields and MS data.

| Intermediate B | Intermediate A | Intermediate C | Yield (%) | Mass (M$^+$) |
|---|---|---|---|---|
| Intermediate B1 | Intermediate A9 | 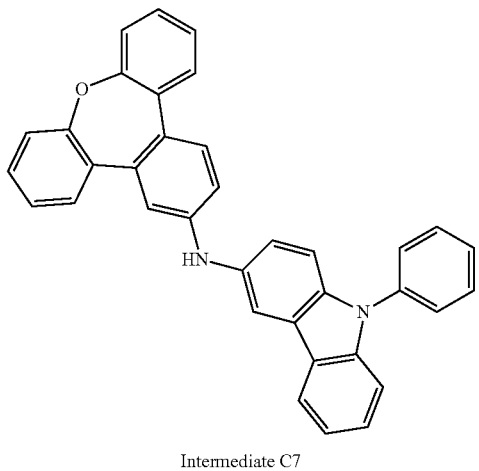 [SMILES: c1ccc(-n2c3ccccc3c3cc(Nc4ccc5c(c4)-c4ccccc4Oc4ccccc4-5)ccc32)cc1]<br>Intermediate C7 | 54.4% | 500.59 (C$_{36}$H$_{24}$N$_2$O) |

TABLE 4-continued

The starting materials, including Intermediate A and B, used for preparing Intermediates C7 and C8 and their yields and MS data.

| Intermediate B | Intermediate A | Intermediate C | Yield (%) | Mass (M+) |
|---|---|---|---|---|
| Intermediate B1 | Intermediate A13 | 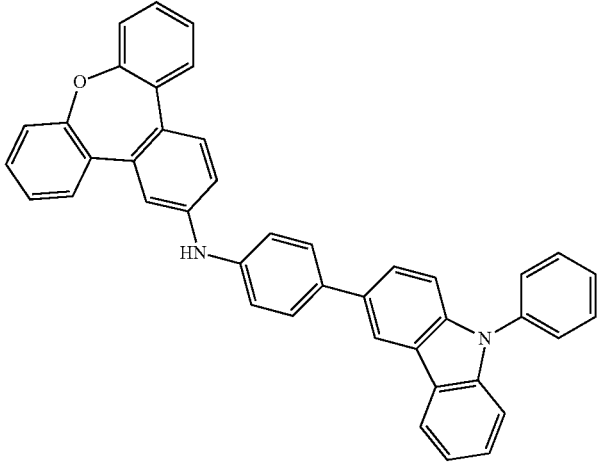<br>Intermediate C8 | 80.6% | 576.68 ($C_{42}H_{28}N_2O$) |

Synthesis of intermediate C9

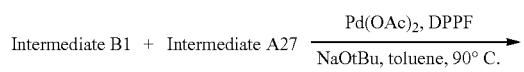

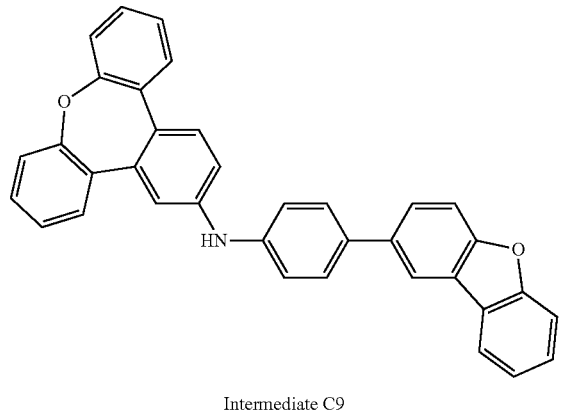

Intermediate C9

A solution of Intermediate B1(8 g, 1.0 eq), Intermediate A27 (1.1 eq), Pd(OAc)$_2$ (0.01 eq), DPPF (0.04 eq), and NaOtBu (1.5 eq) in toluene (0.5 M) was heated under nitrogen at 90° C. for 12 hours. After cooling to room temperature, the solvent was then removed using a rotary evaporator, and the remaining substance was purified with column chromatography to obtain intermediate C9 (8.5 g, yield: 68.5%). MS: [M]$^+$=501.57.

Synthesis of Novel Compounds

The general synthesis pathway of the claimed novel compound was summarized in Scheme I-A or Scheme I-B. In the following Scheme I-A or Scheme I-B, "Reactant A" may be any one of Intermediate A1 to A32 as listed in Table 1 or Intermediates C1 to C9 as stated above, and "Reactant B" may be any one of Intermediate B1 to B3 or C1 to C9 as stated above. The compounds were each synthesized by the following method A or B and results were listed in Table 5.

Scheme I-A
Method A

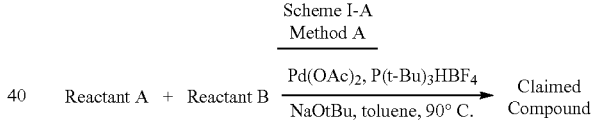

General Procedure A:

A mixture of Reactant A (1.00 eq), Reactant B (1.00 eq), Pd(OAc)$_2$ (0.005 eq), P(t-Bu)$_3$HBF$_4$ (0.02 eq), and NaOtBu (1.5 eq) in toluene (0.3M) was heated at 90° C. for 12 h. The solvent was evaporated, and the residue was dissolved in methylene dichloride and filtered. The filtrate was washed with DI water (2 times), and the organic layer was dried with MgSO$_4$. This was filtered, and the solvent was evaporated to give the novel compound with white solid. Herein, Compounds 1 to 4, 6 to 10, 14, 15, 18 to 29, 31 to 41, and 43 were synthesized through method A.

Scheme I-B
Method B

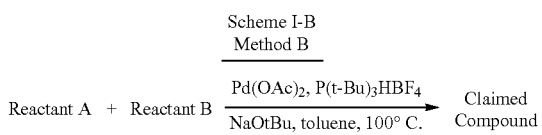

General Procedure B:

A mixture of Reactant A (1.0 eq), Reactant B (1.00 eq), Pd$_2$(dba)$_3$ (0.015 eq), P(t-Bu)$_3$HBF$_4$ (0.06 eq), and NaOtBu (3.0 eq) in toluene (0.3M) was heated at 100° C. for 12 hours. The solvent was evaporated, and the residue was dissolved in methylene dichloride and filtered. The filtrate was washed with DI water (2 times), and the organic layer was dried with $MgSO_4$. This was filtered, and the solvent was evaporated to give the novel compound with white solid. Herein, Compounds 11 to 13, 16, 17, 30, and 42 were synthesized through method B.

Synthesis of Compound 5

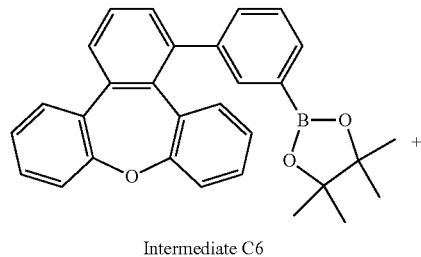

Intermediate C6

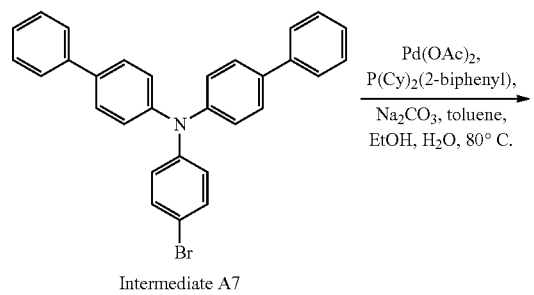

Intermediate A7

Pd(OAc)$_2$,
P(Cy)$_2$(2-biphenyl),
Na$_2$CO$_3$, toluene,
EtOH, H$_2$O, 80° C.

-continued

Compound 5

A solution of Intermediate A7 (1 eq), Intermediate C6 (1.2 eq), Pd(OAc)$_2$ (0.01 eq), P(Cy)$_2$(2-biphenyl) (0.04 eq), and Na$_2$CO$_3$ (3.0 eq) in toluene (0.54 M), EtOH (0.05M) and water (2 M) was heated under nitrogen at 80° C. for 12 hours. After cooling to room temperature, the solvent was then removed using a rotary evaporator, and the remaining substance was purified with column chromatography to obtain Compound 5.

Figure 2:
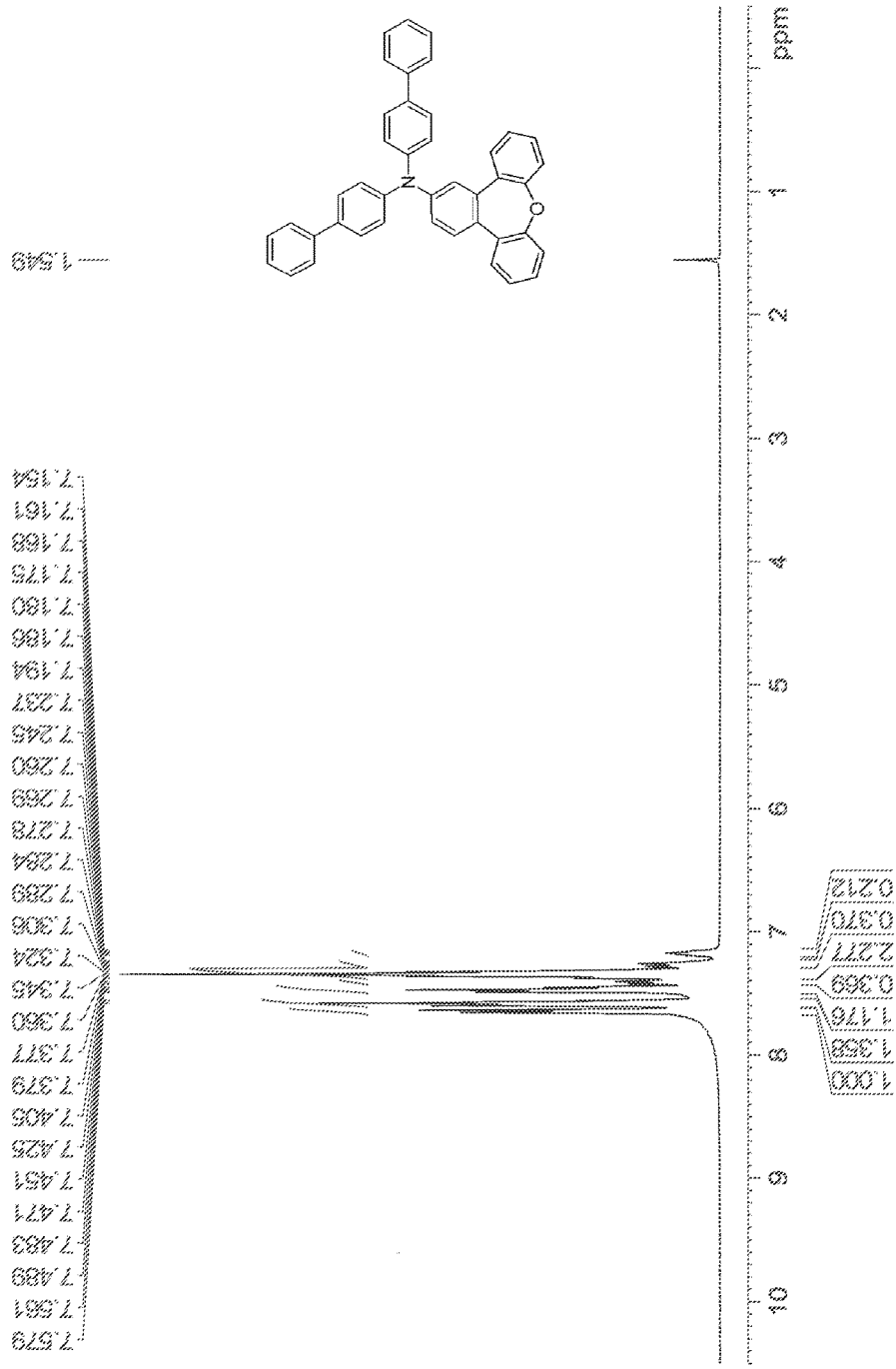
FIGS. 2 to 44 are $^1$H nuclear magnetic resonance (NMR) spectra of Compounds 1 to 43.
Figure 3:
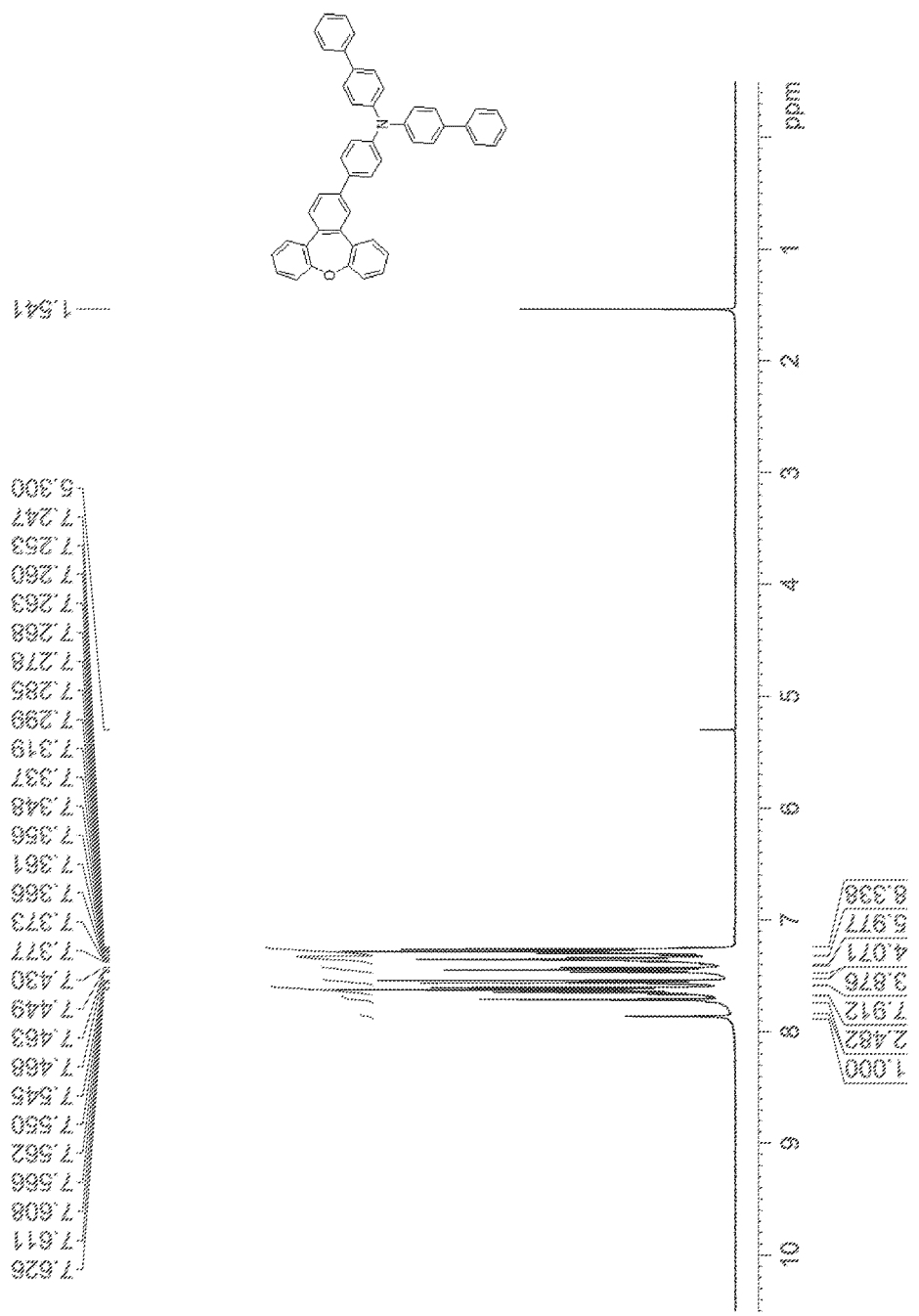
Figure 4:
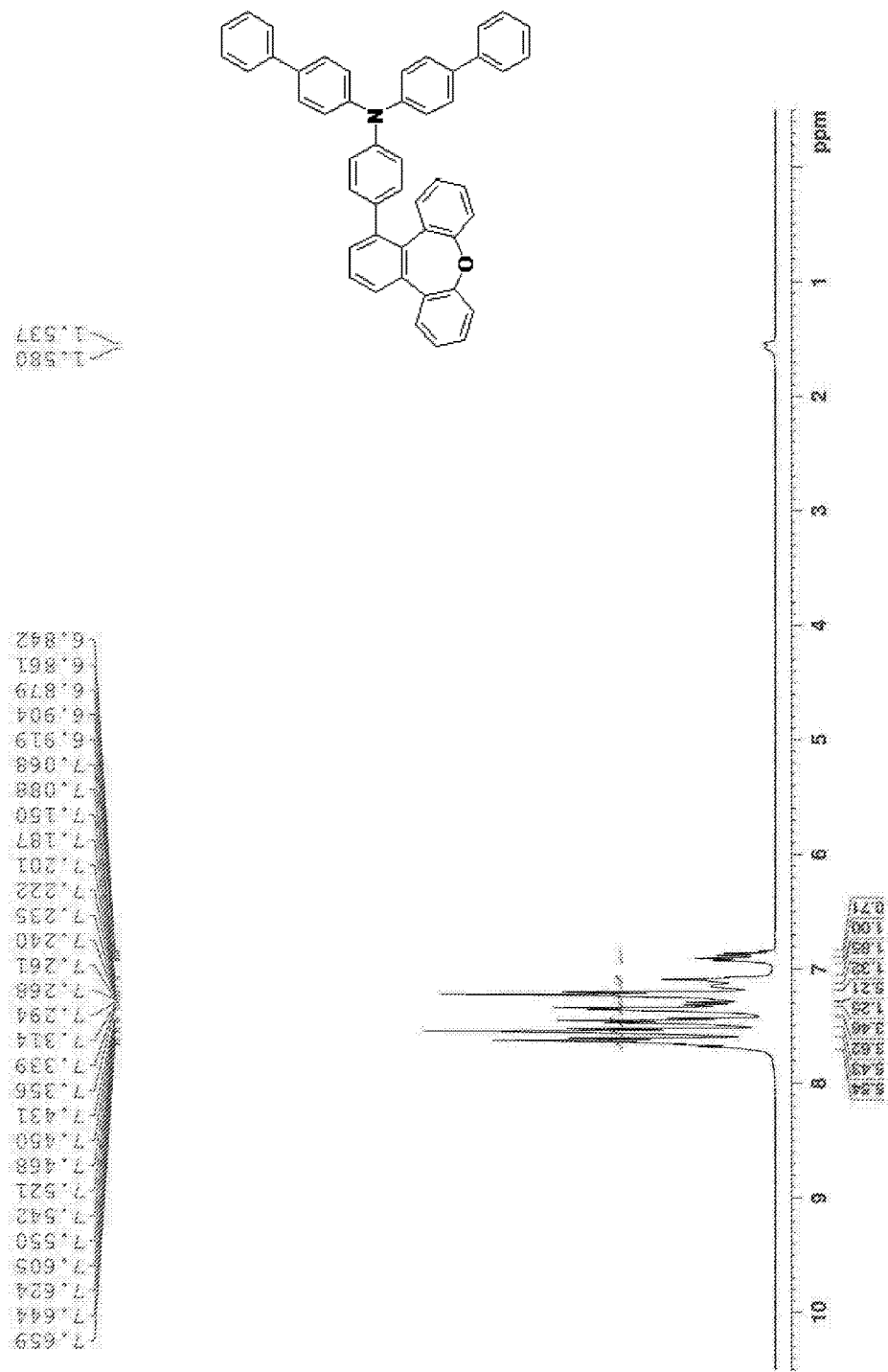
Figure 5:
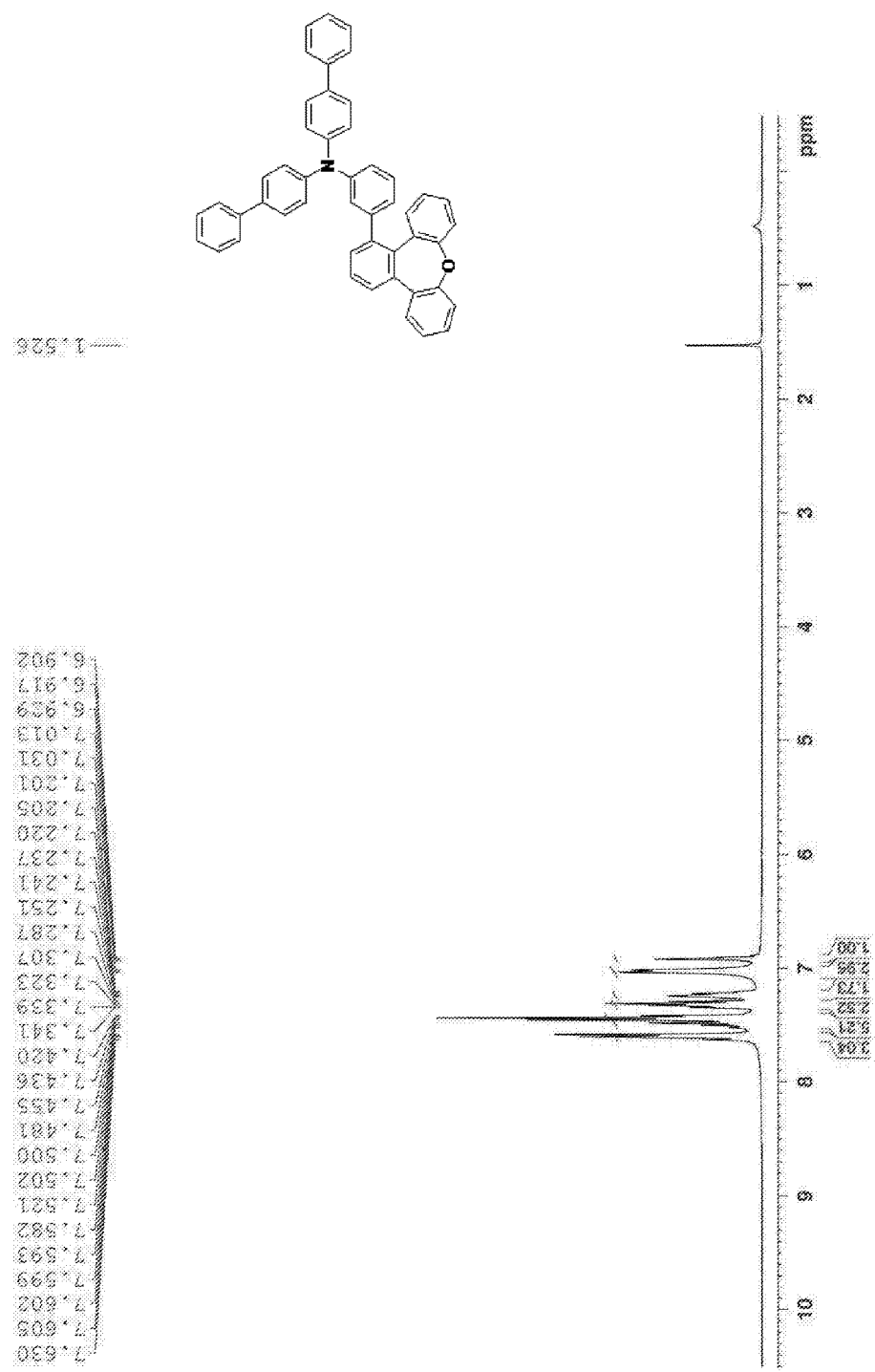
Figure 6:
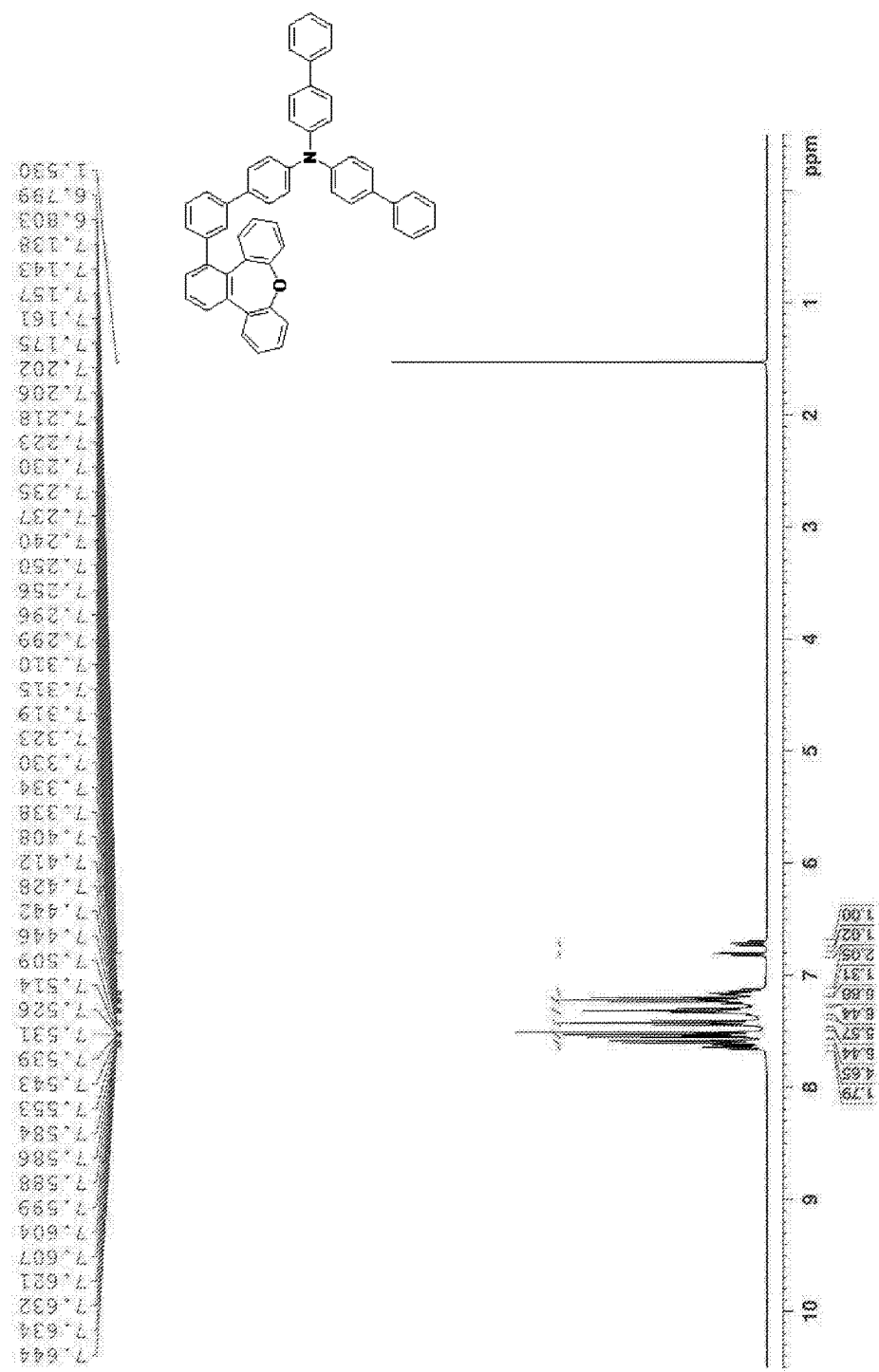
Figure 7:
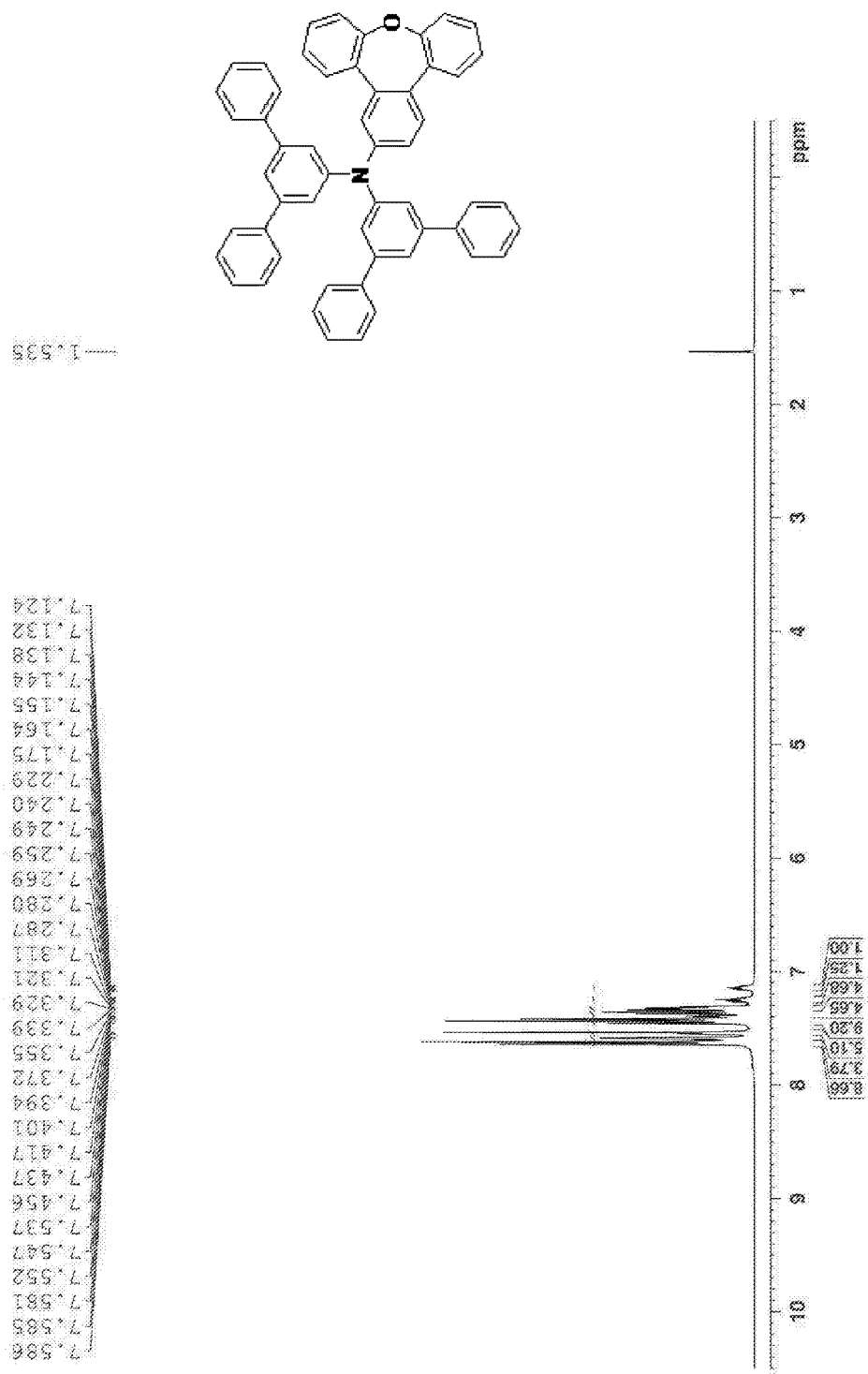
Figure 8:
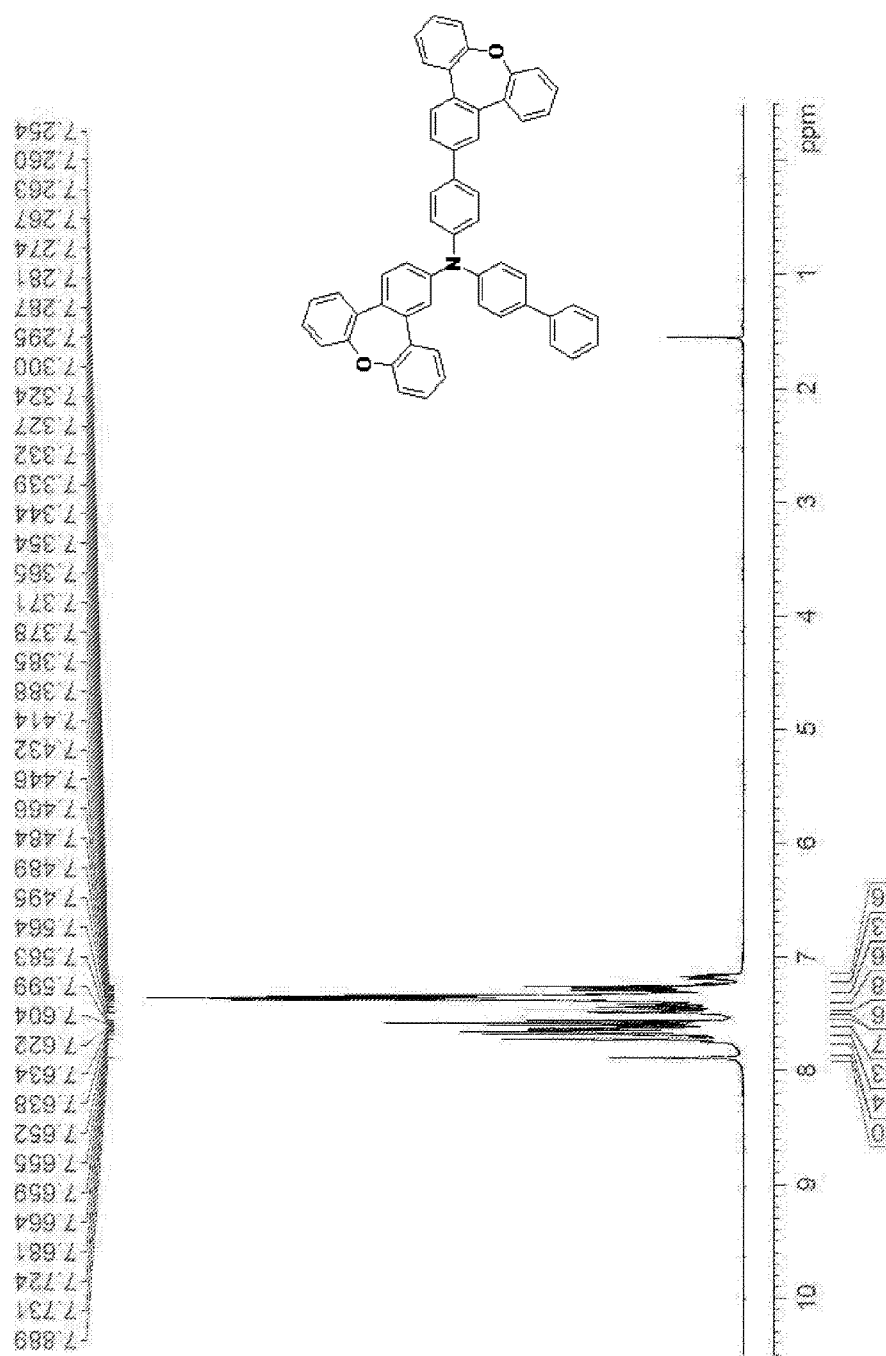
Figure 9:
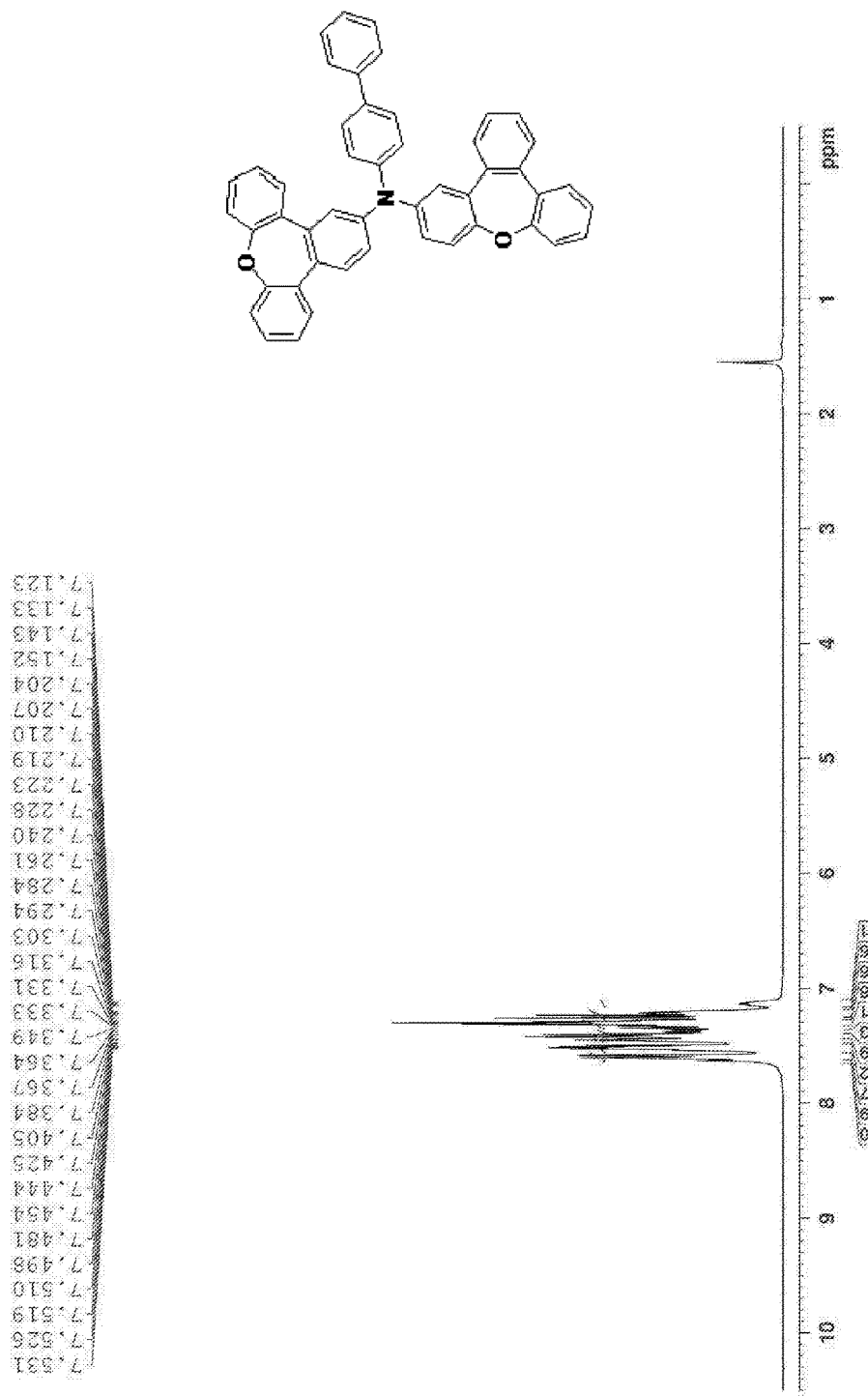
Figure 10:
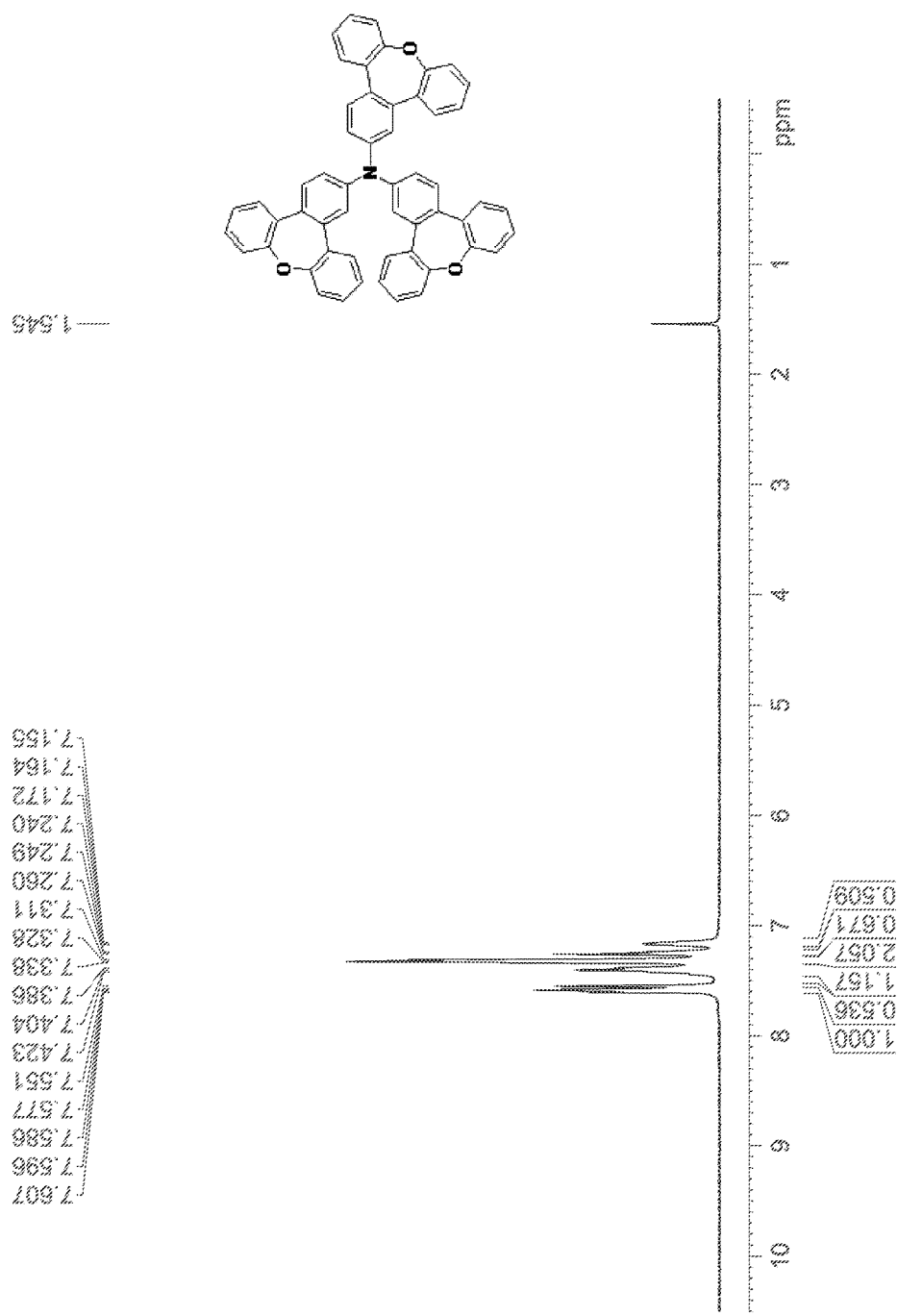
Figure 11:
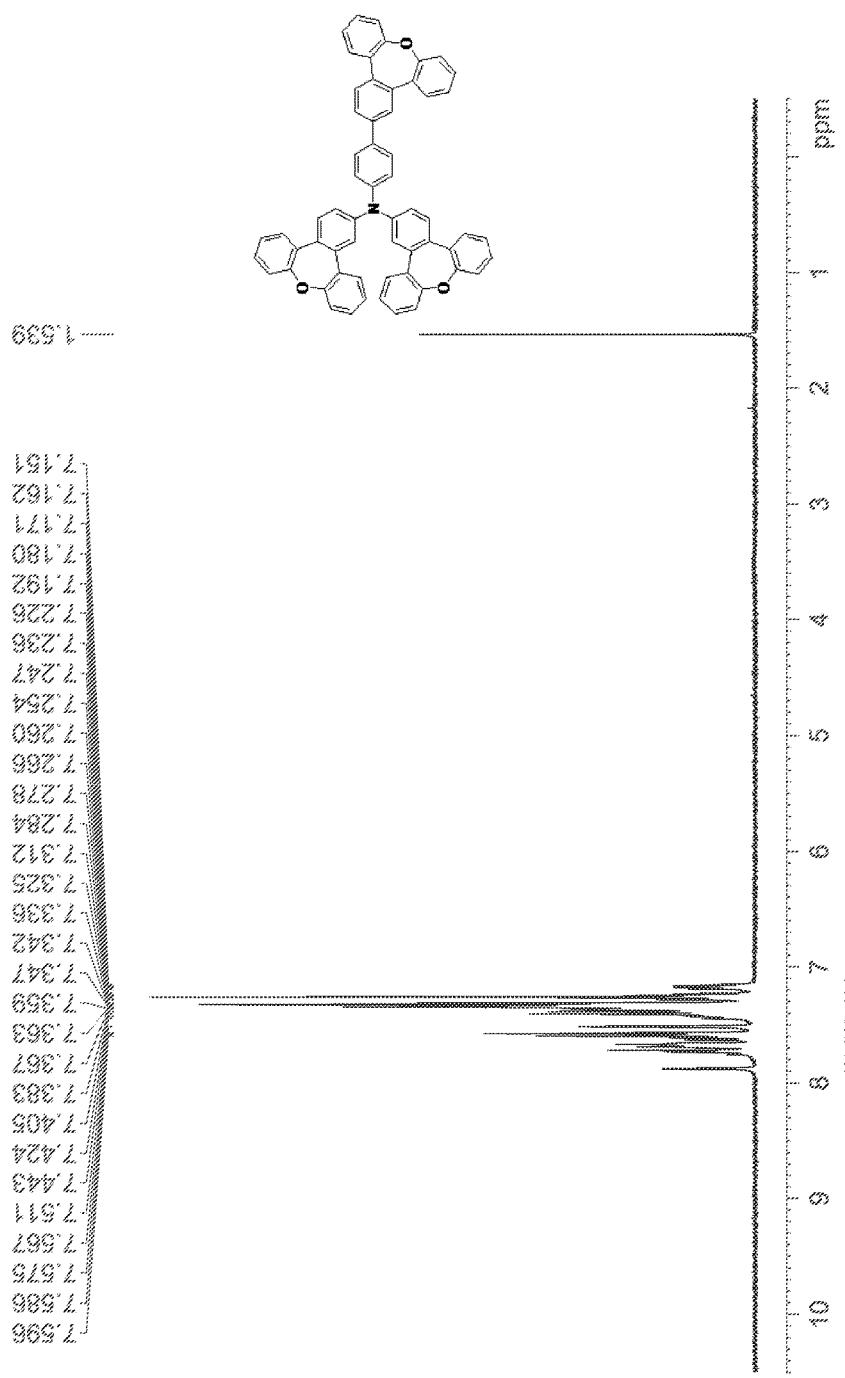
Figure 12:
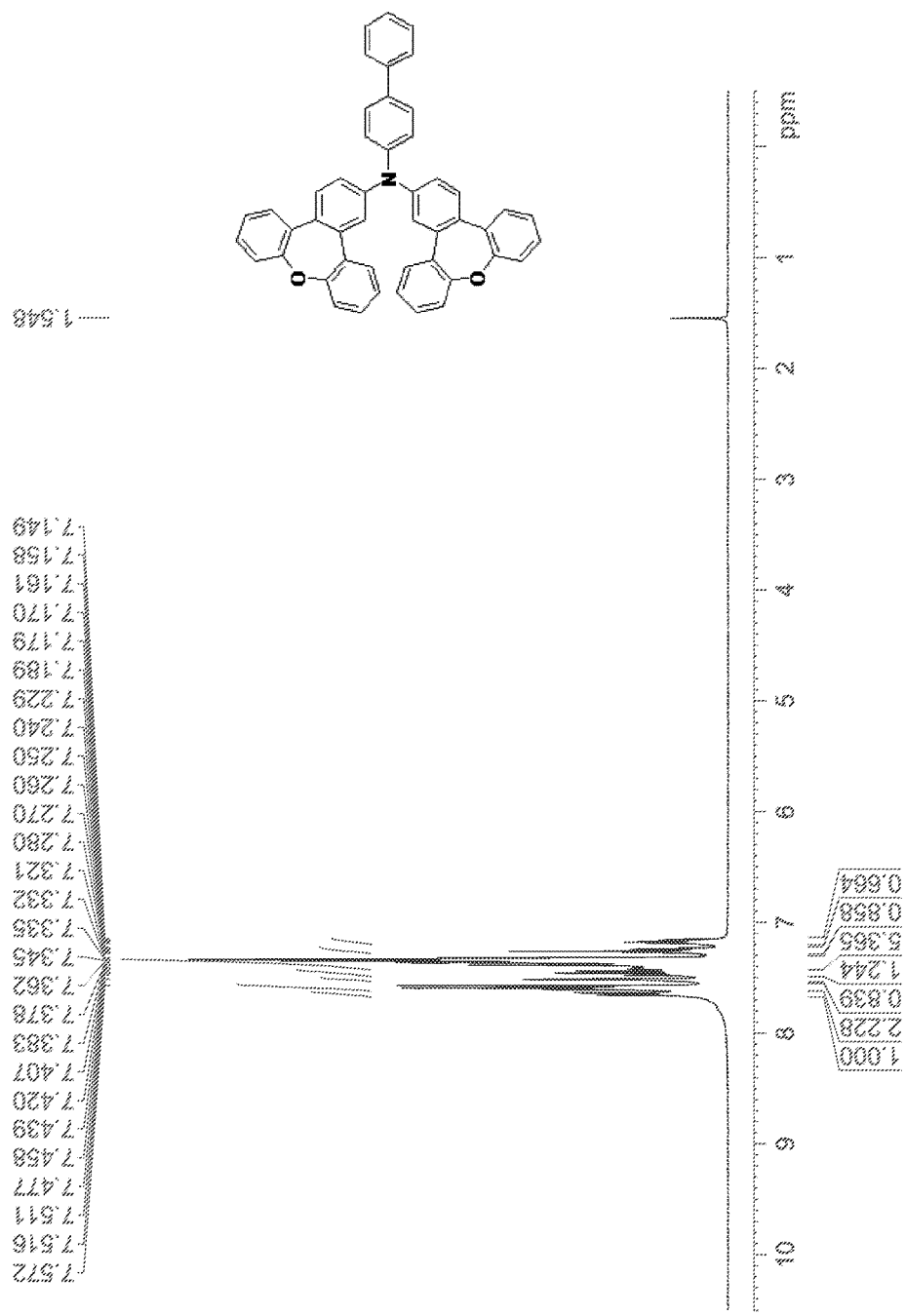
Figure 13:
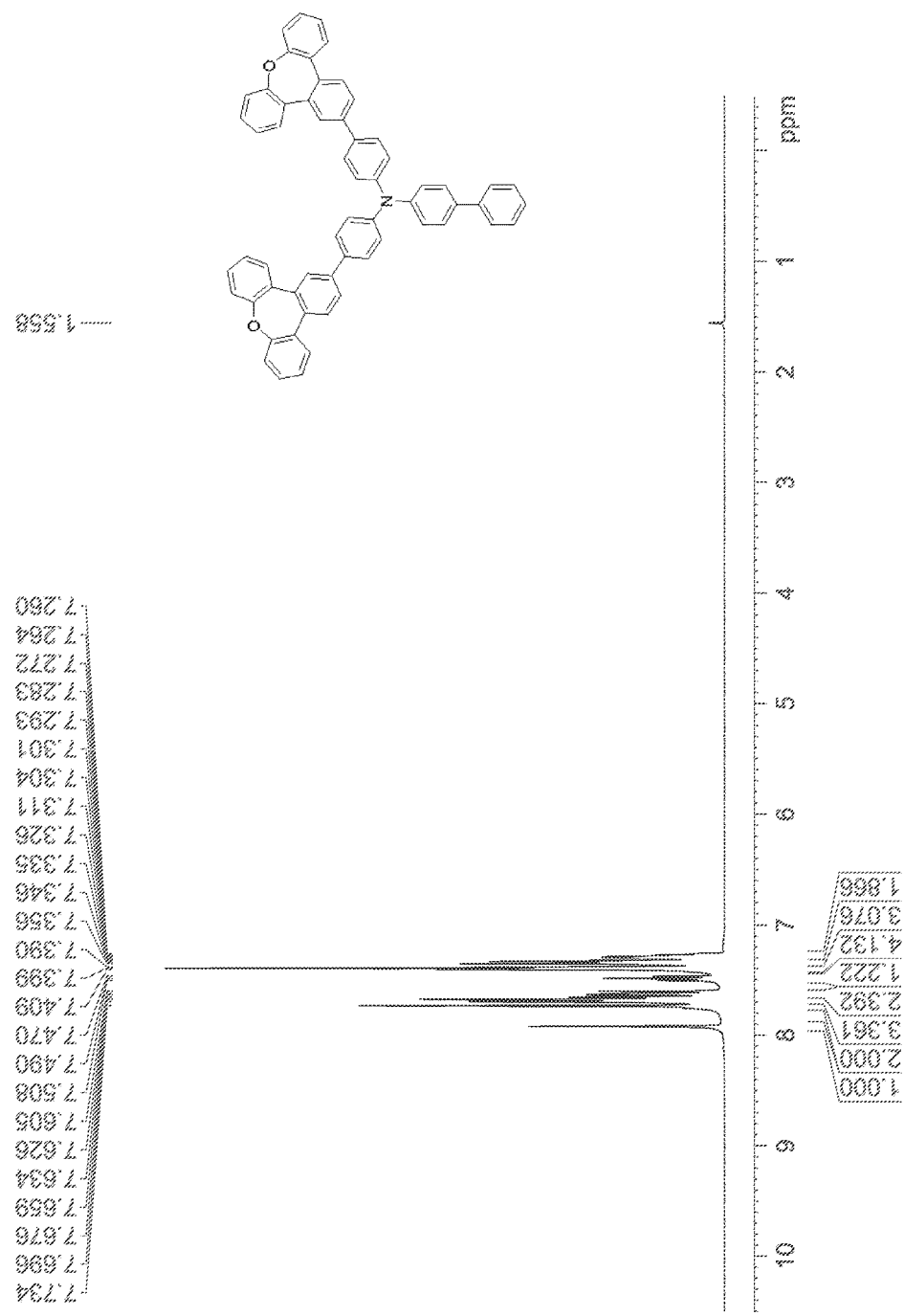
Figure 14:
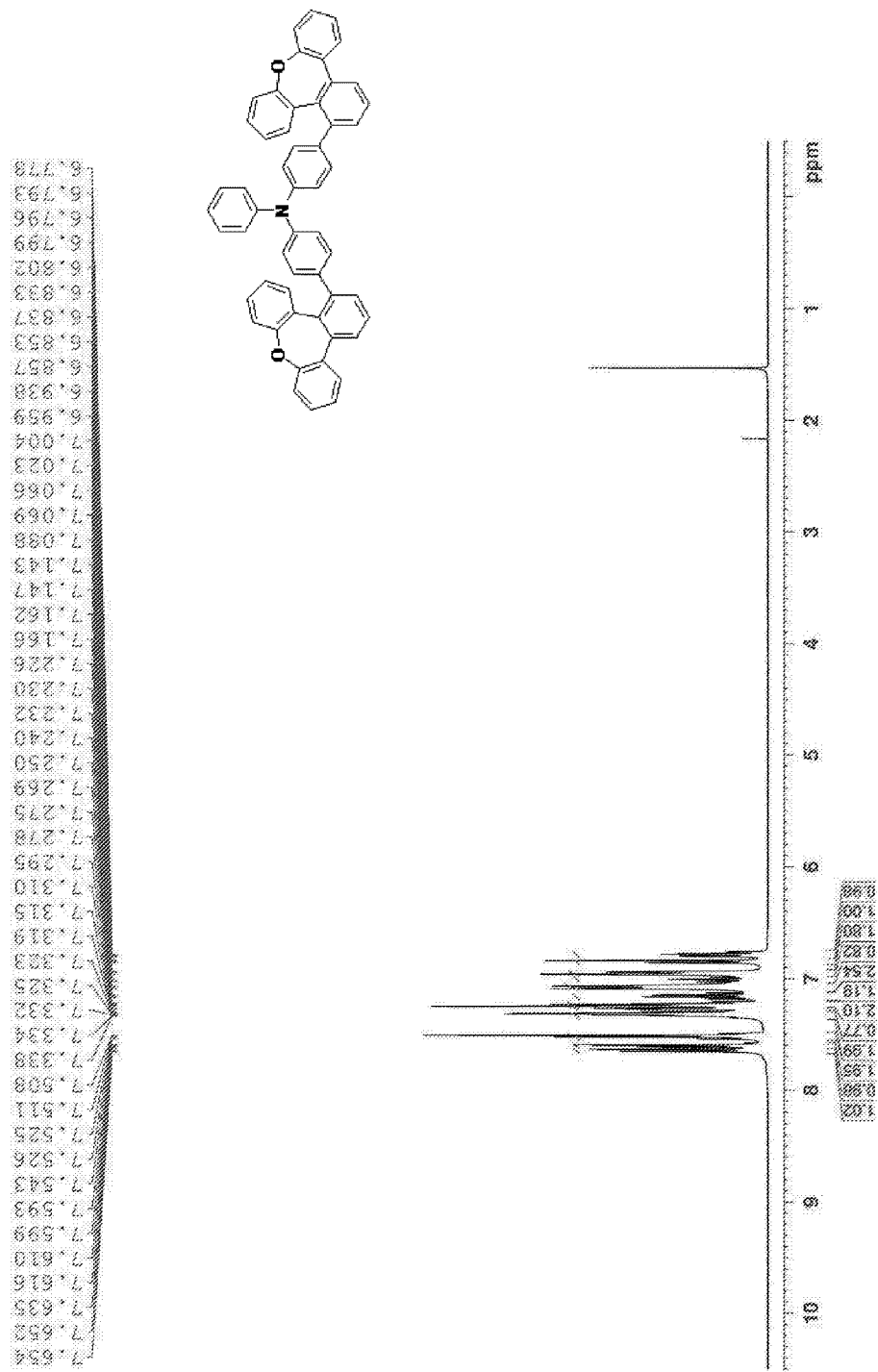
Figure 15:
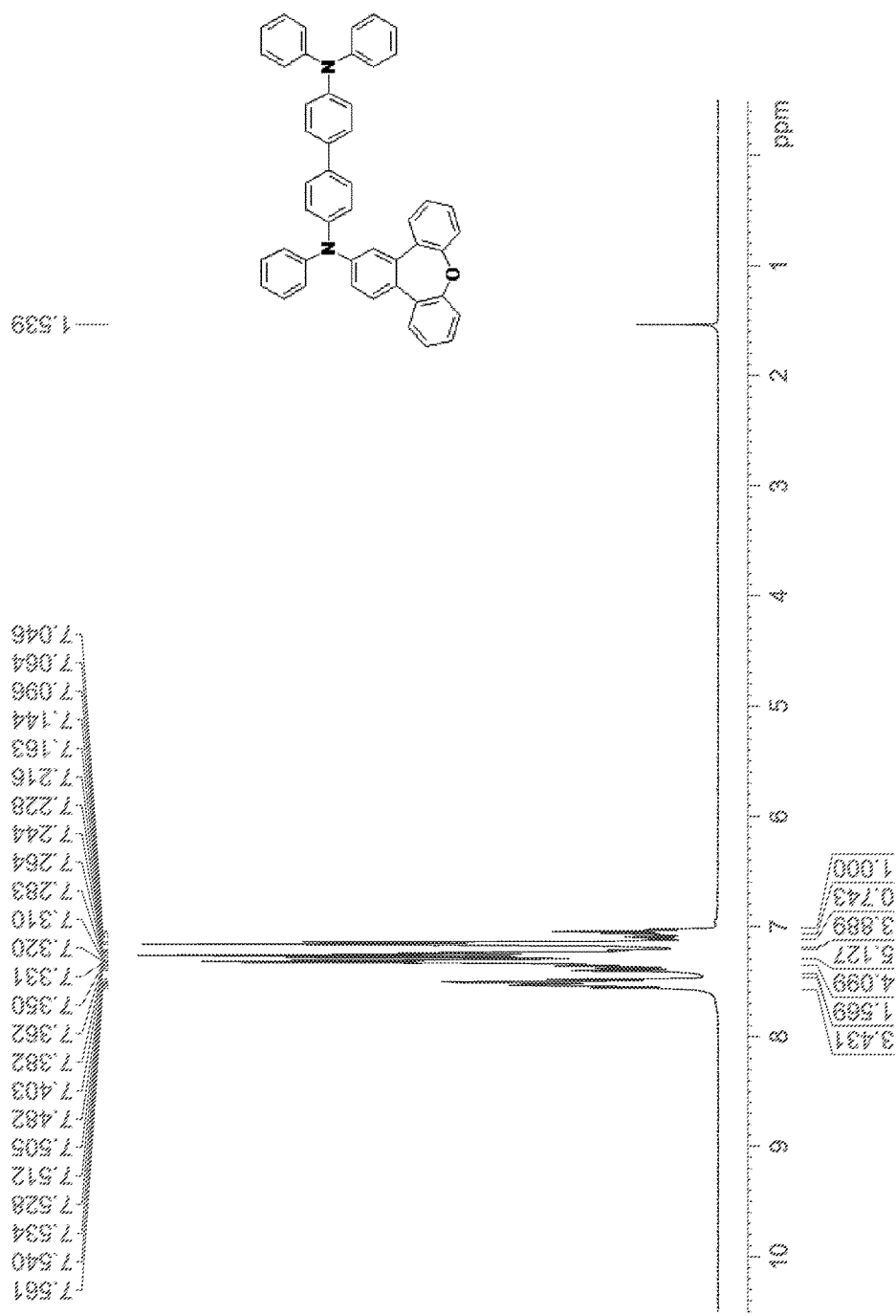
Figure 16:
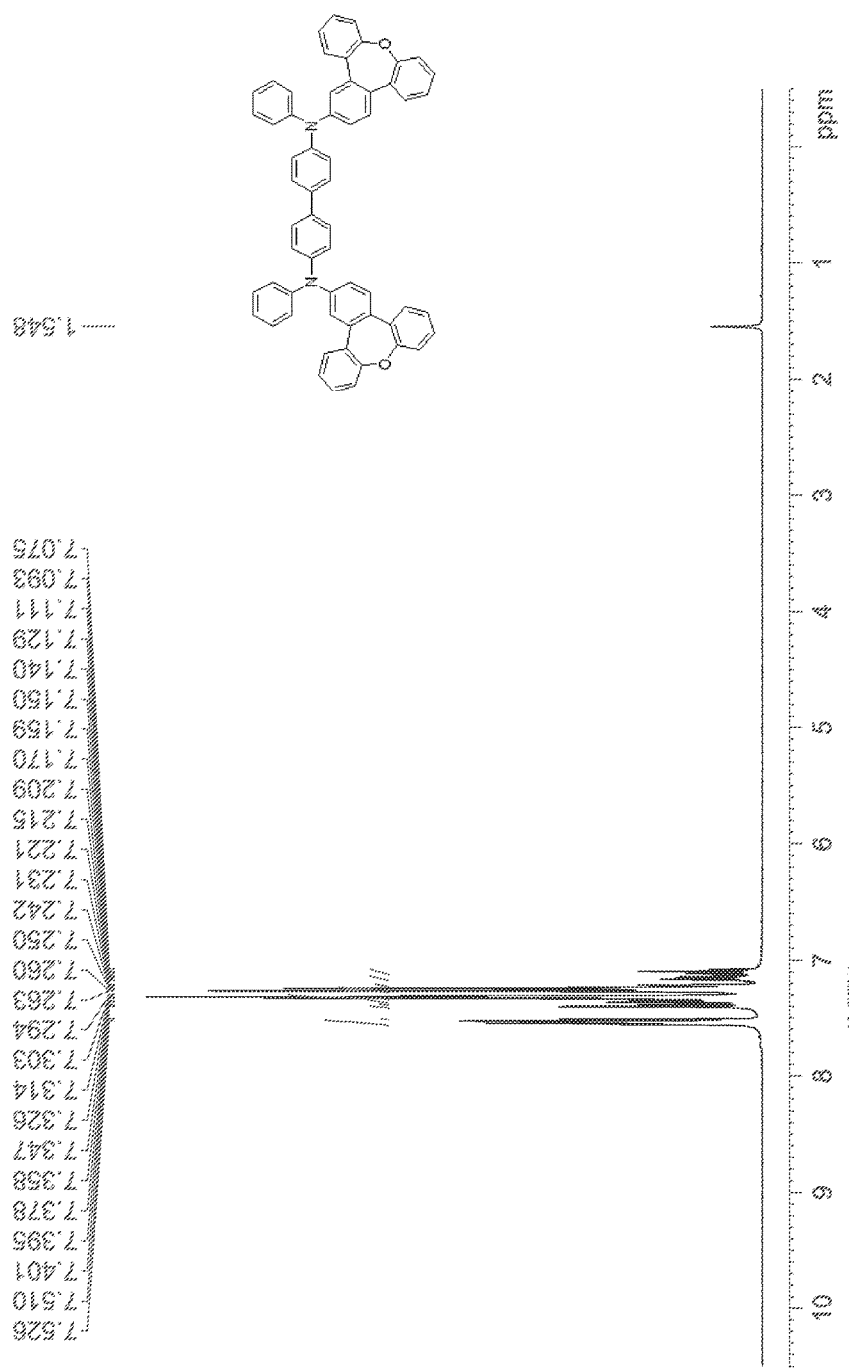
Figure 17:
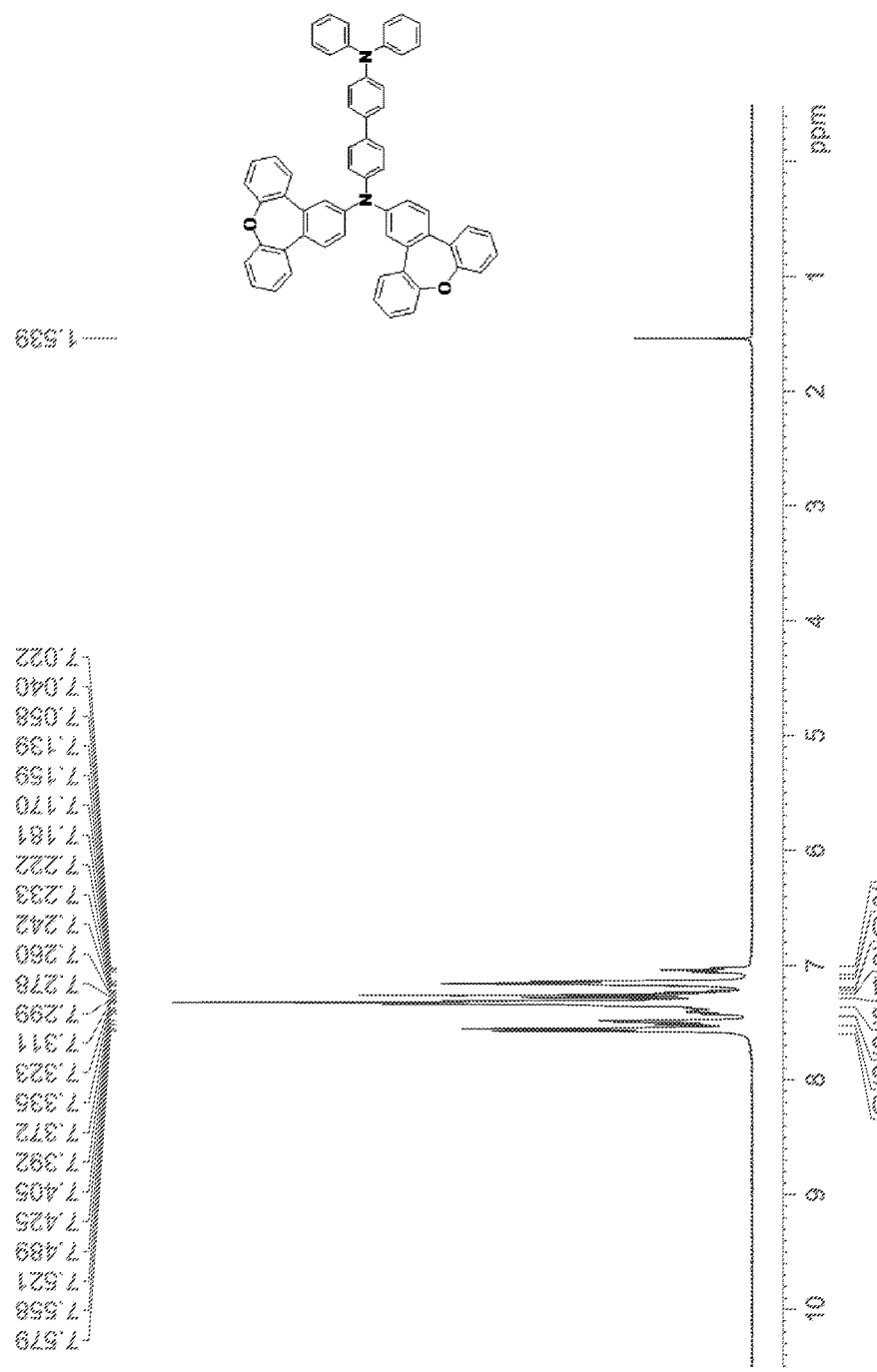
Figure 18:
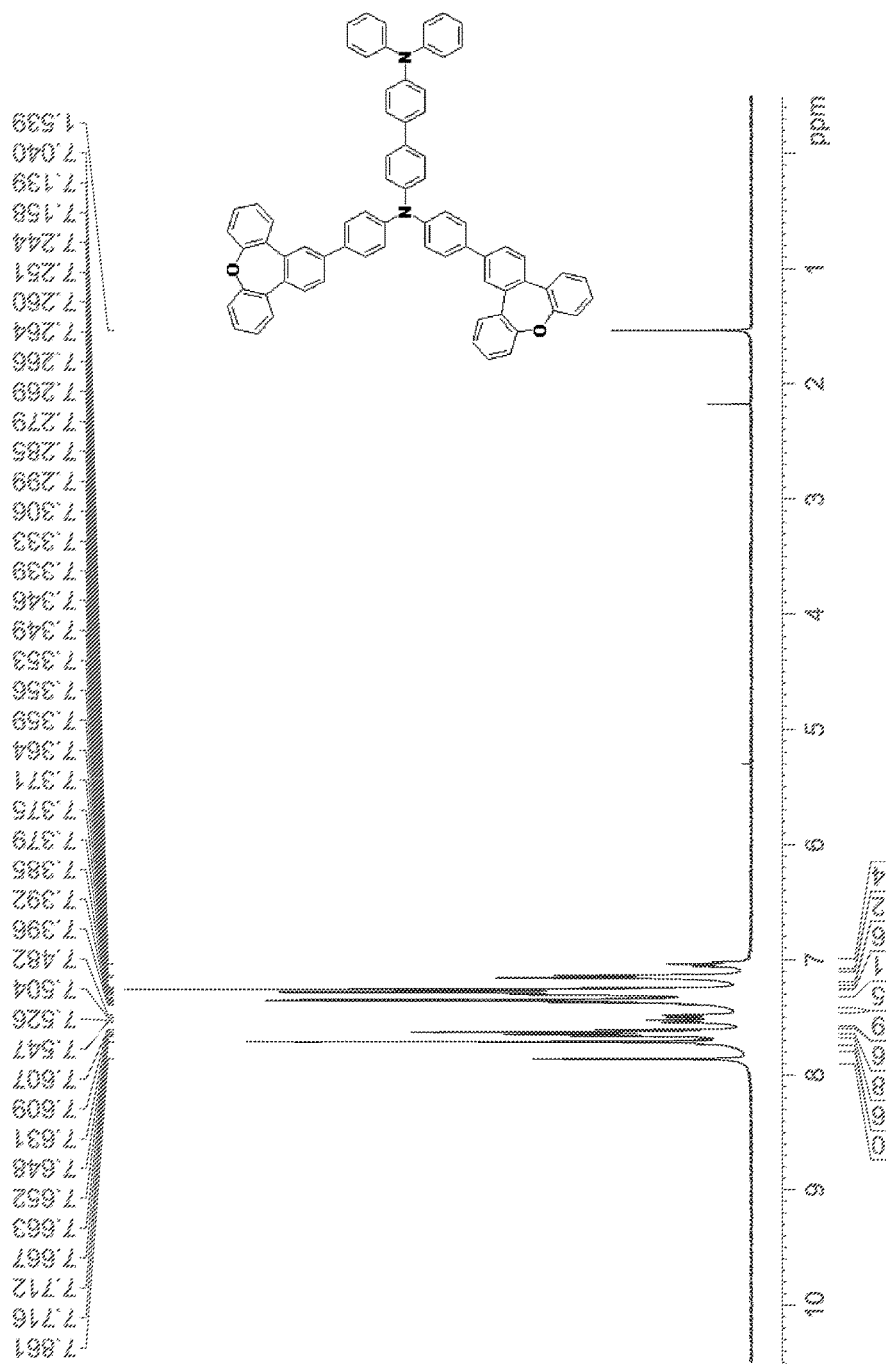
Figure 19:
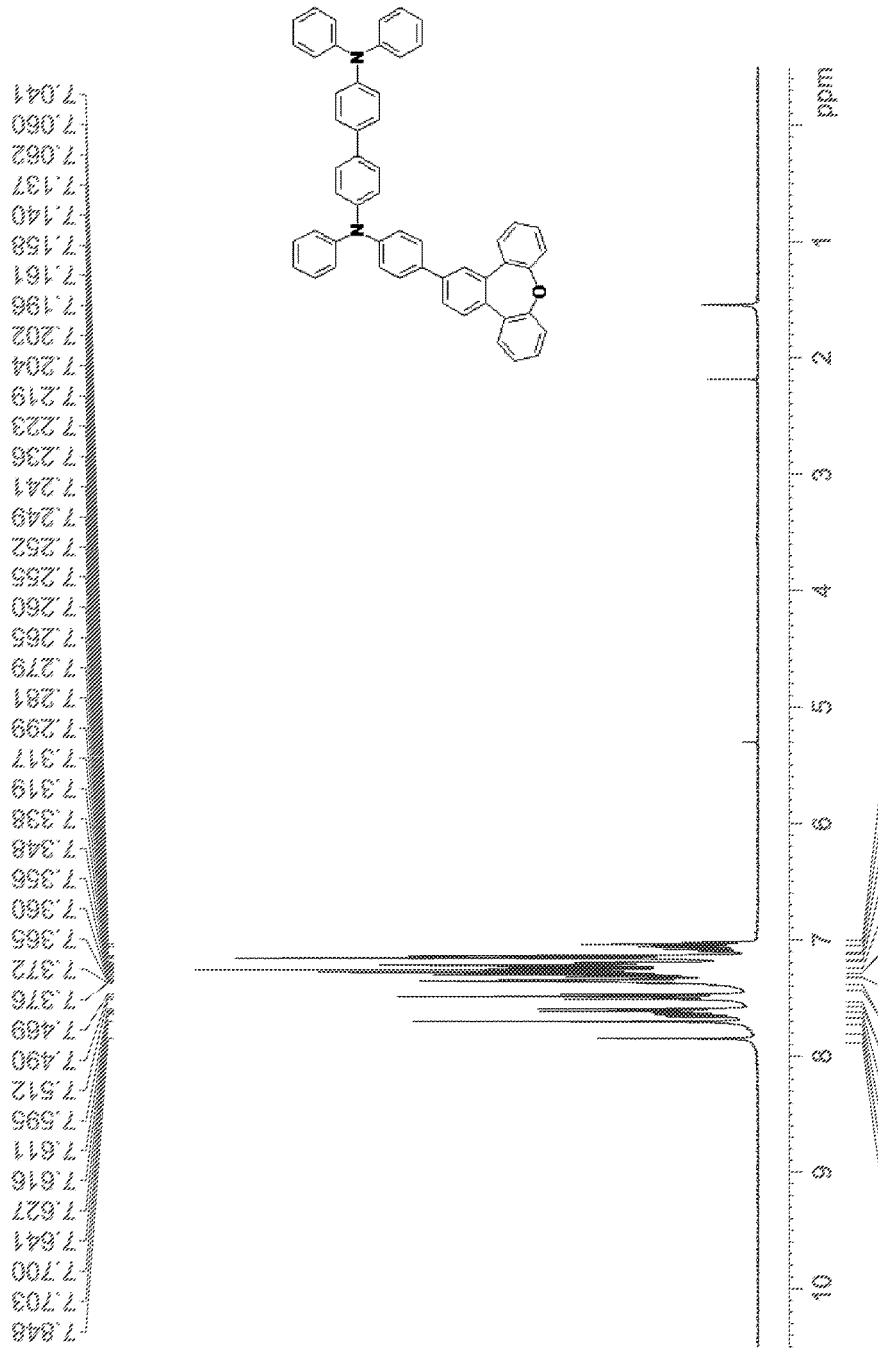
Figure 20:
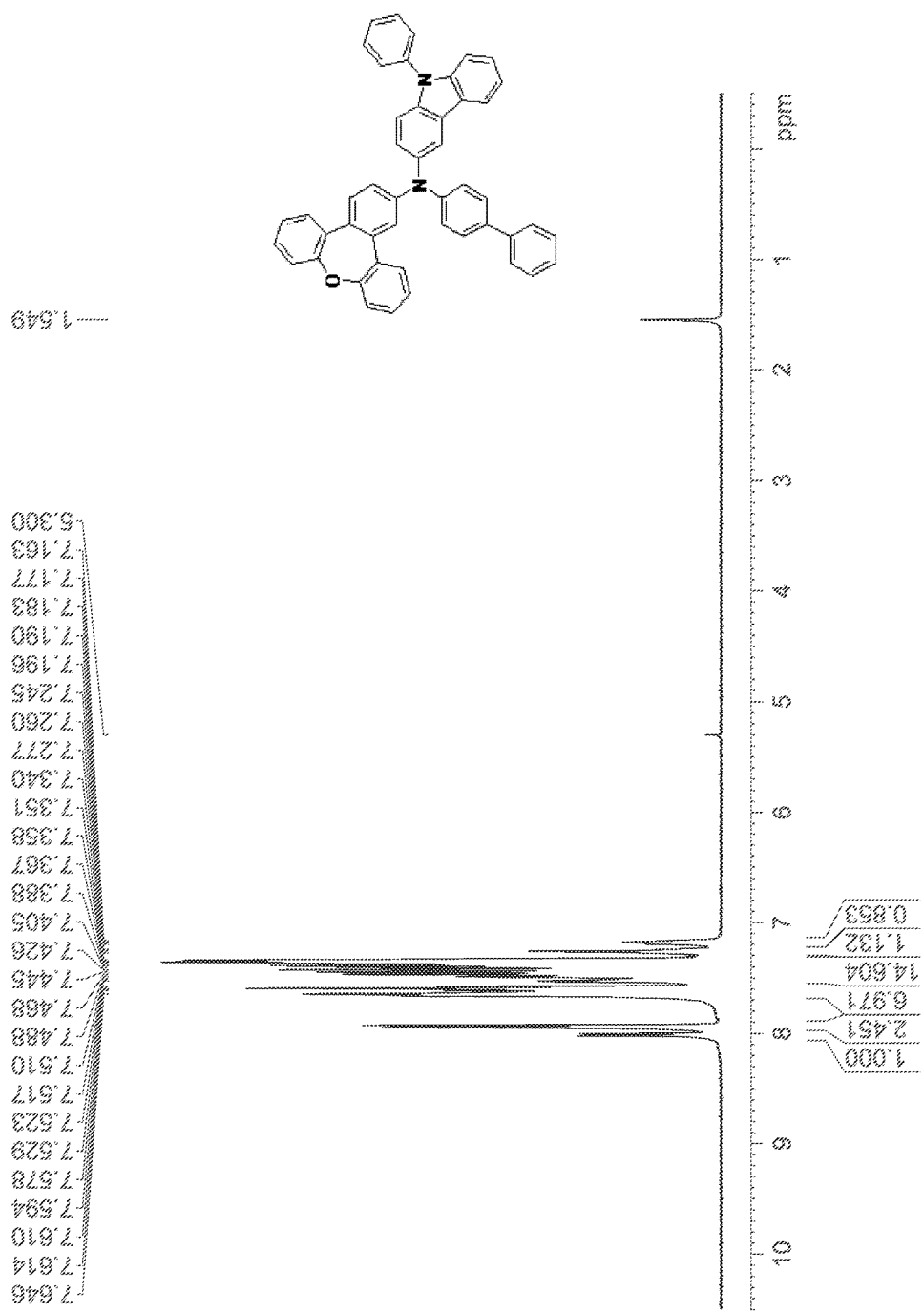
Figure 21:
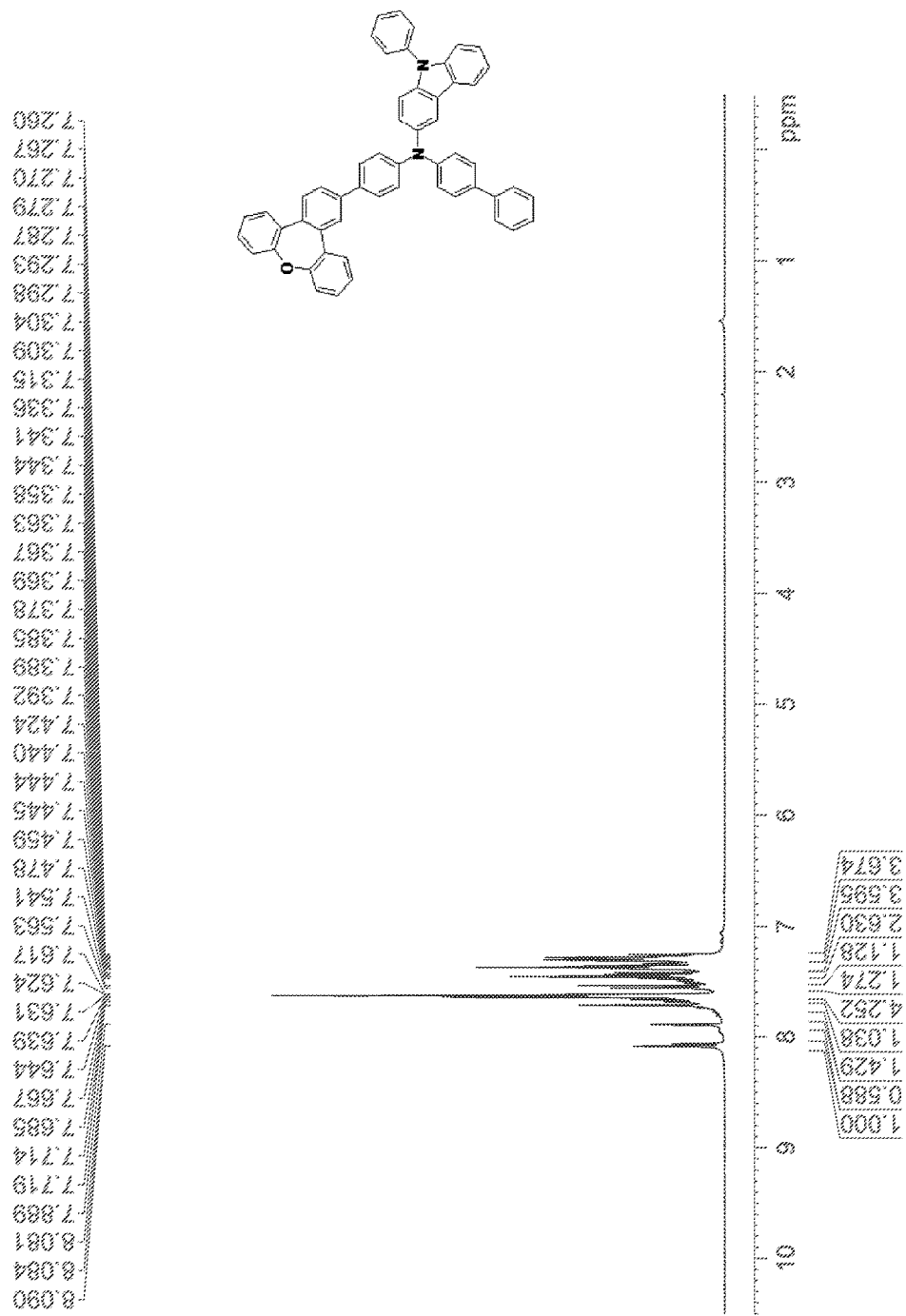
Figure 22:
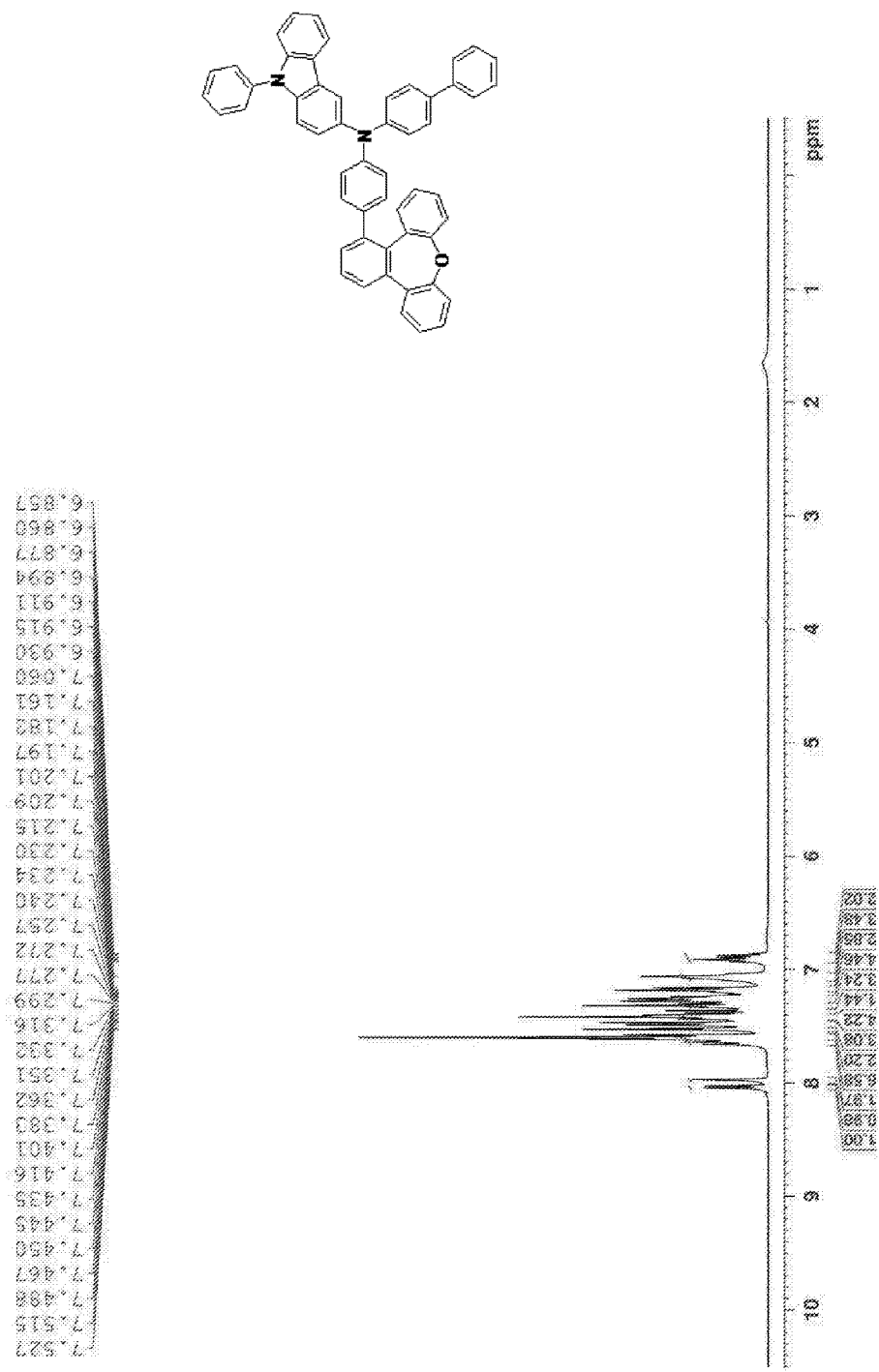
Figure 23:
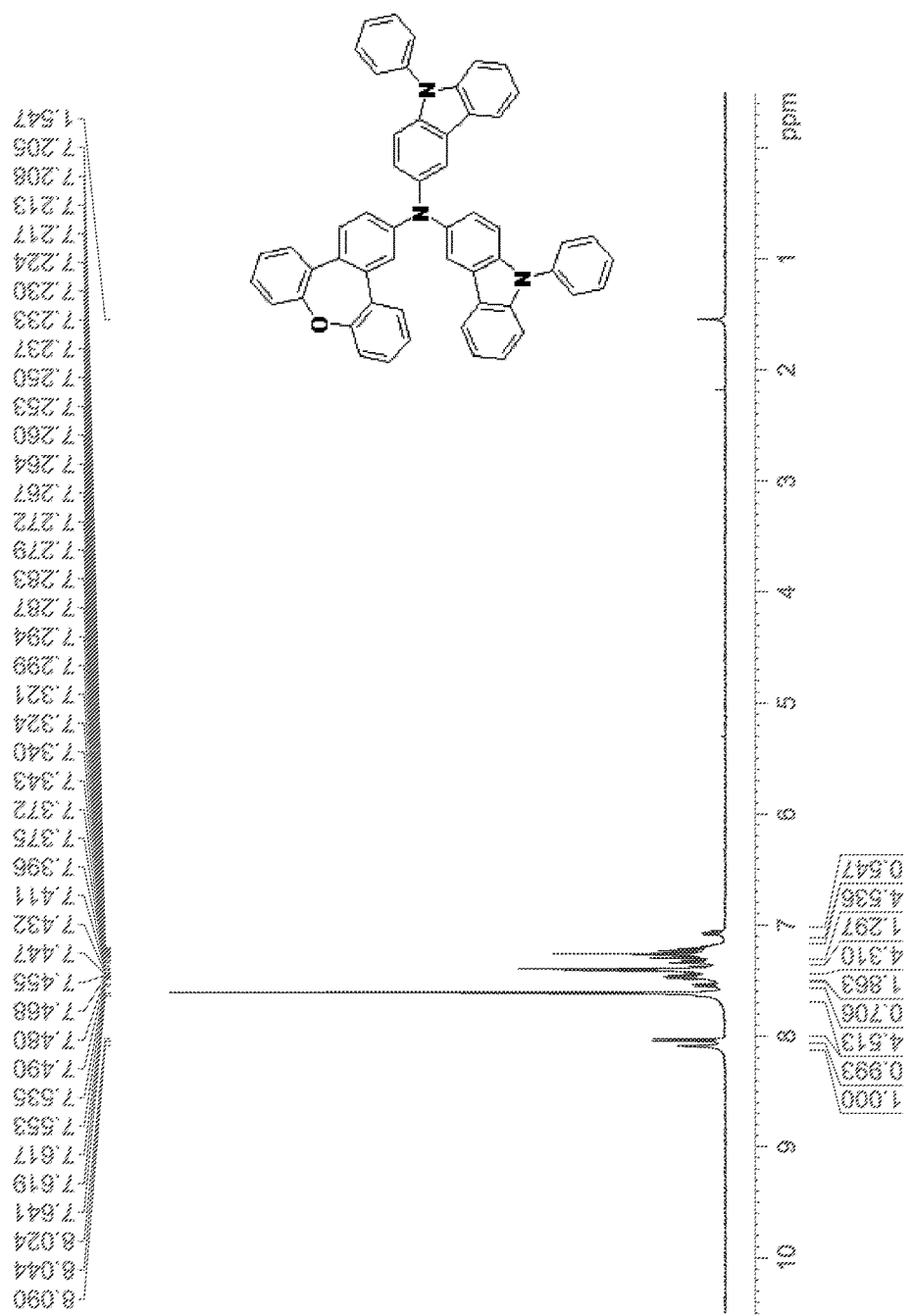
Figure 24:
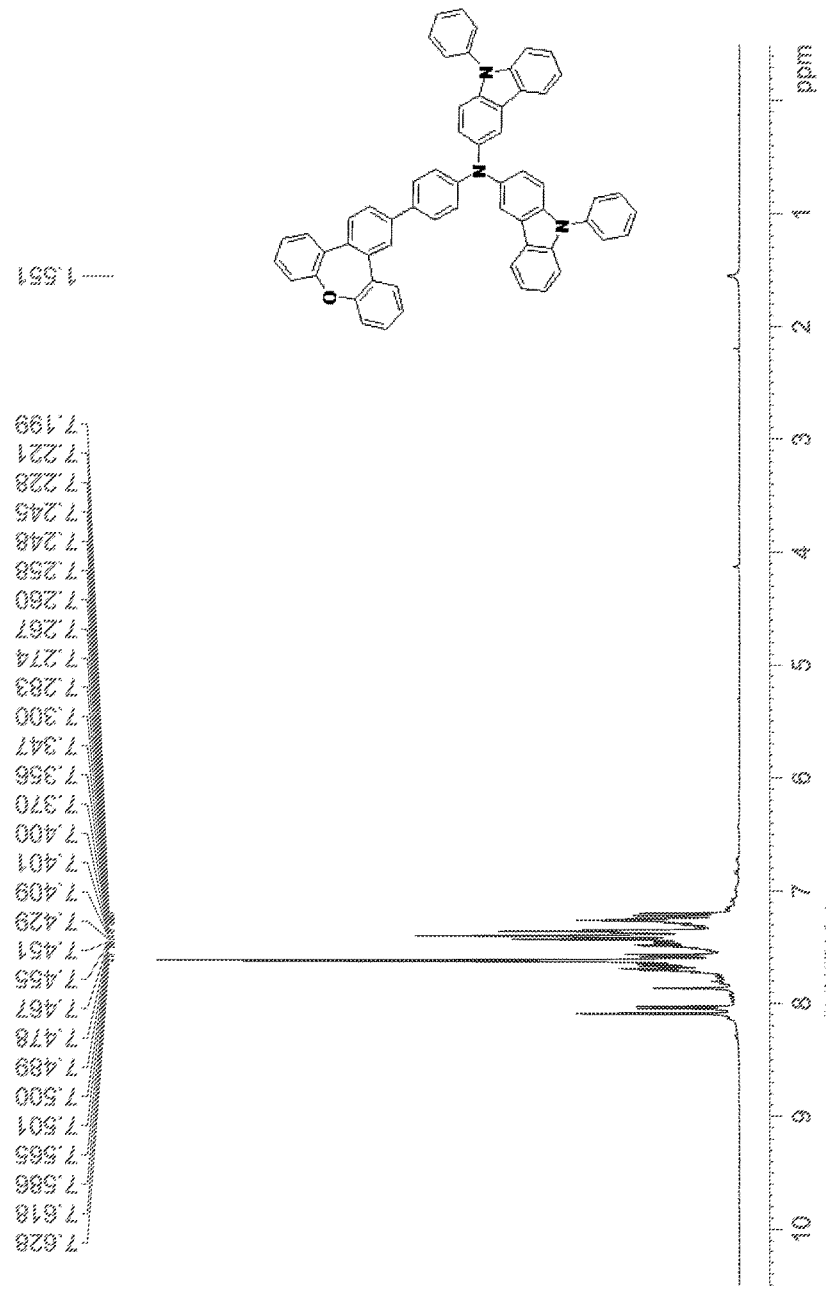
Figure 25:
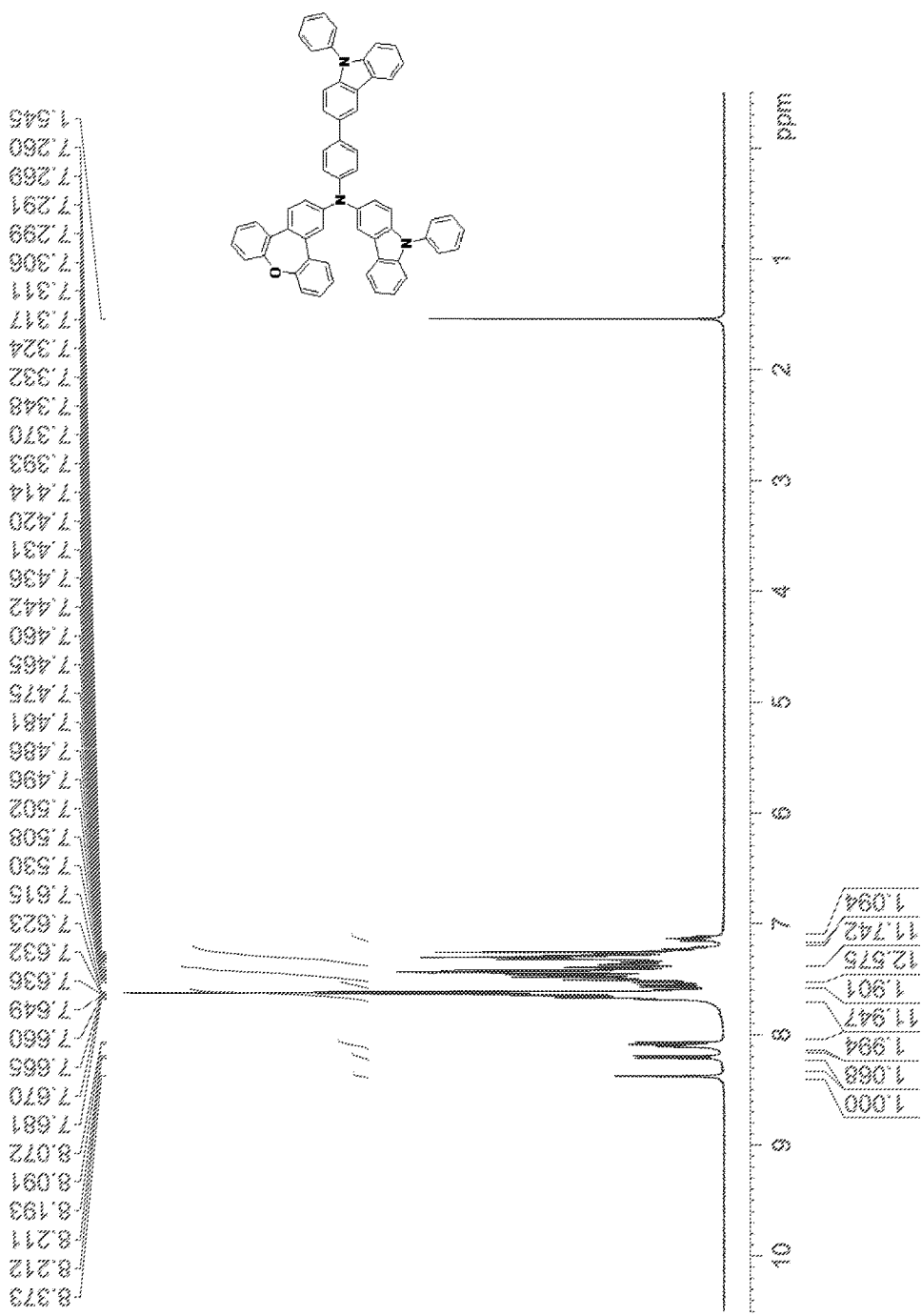
Figure 26:
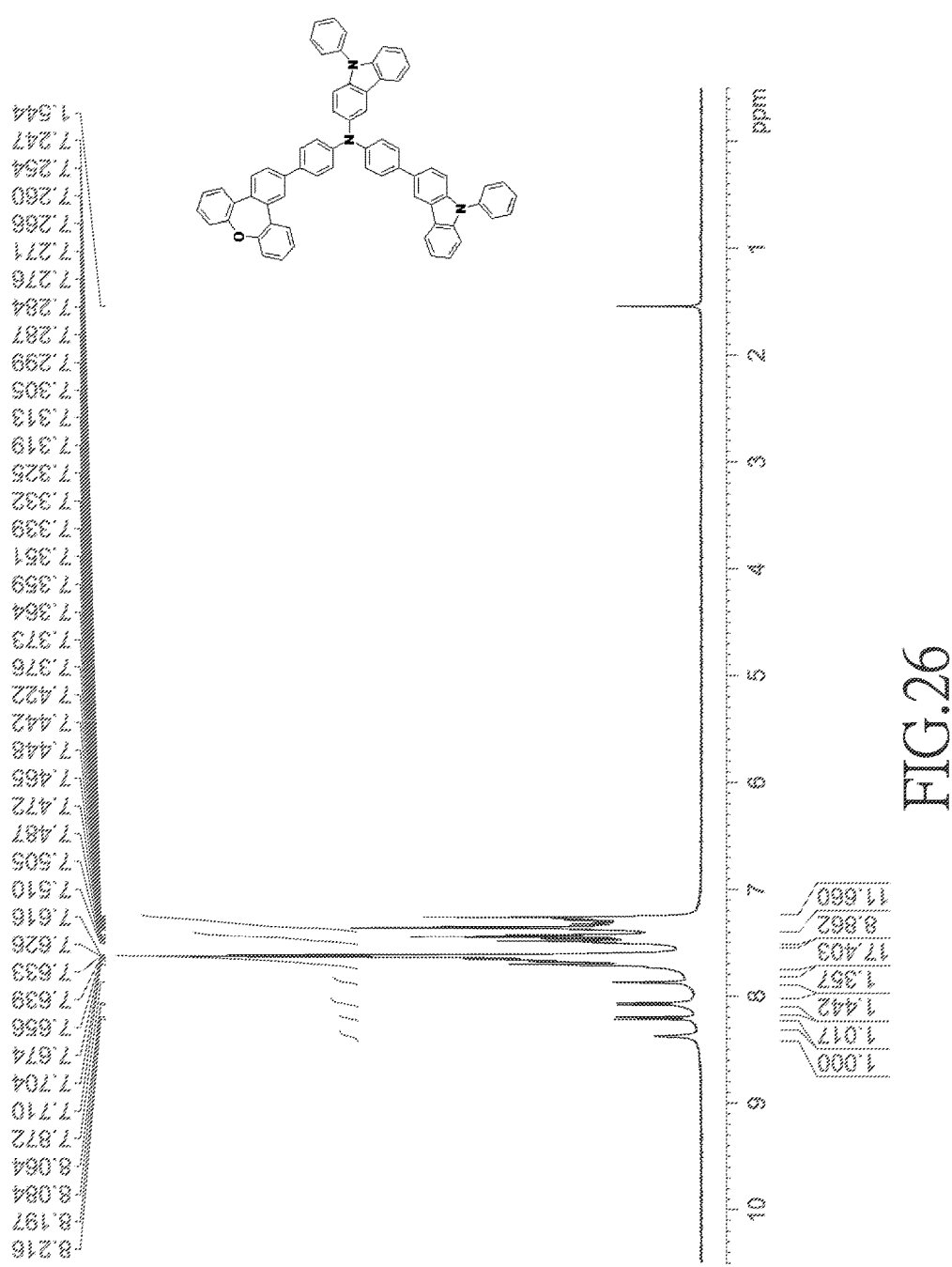
Figure 27:
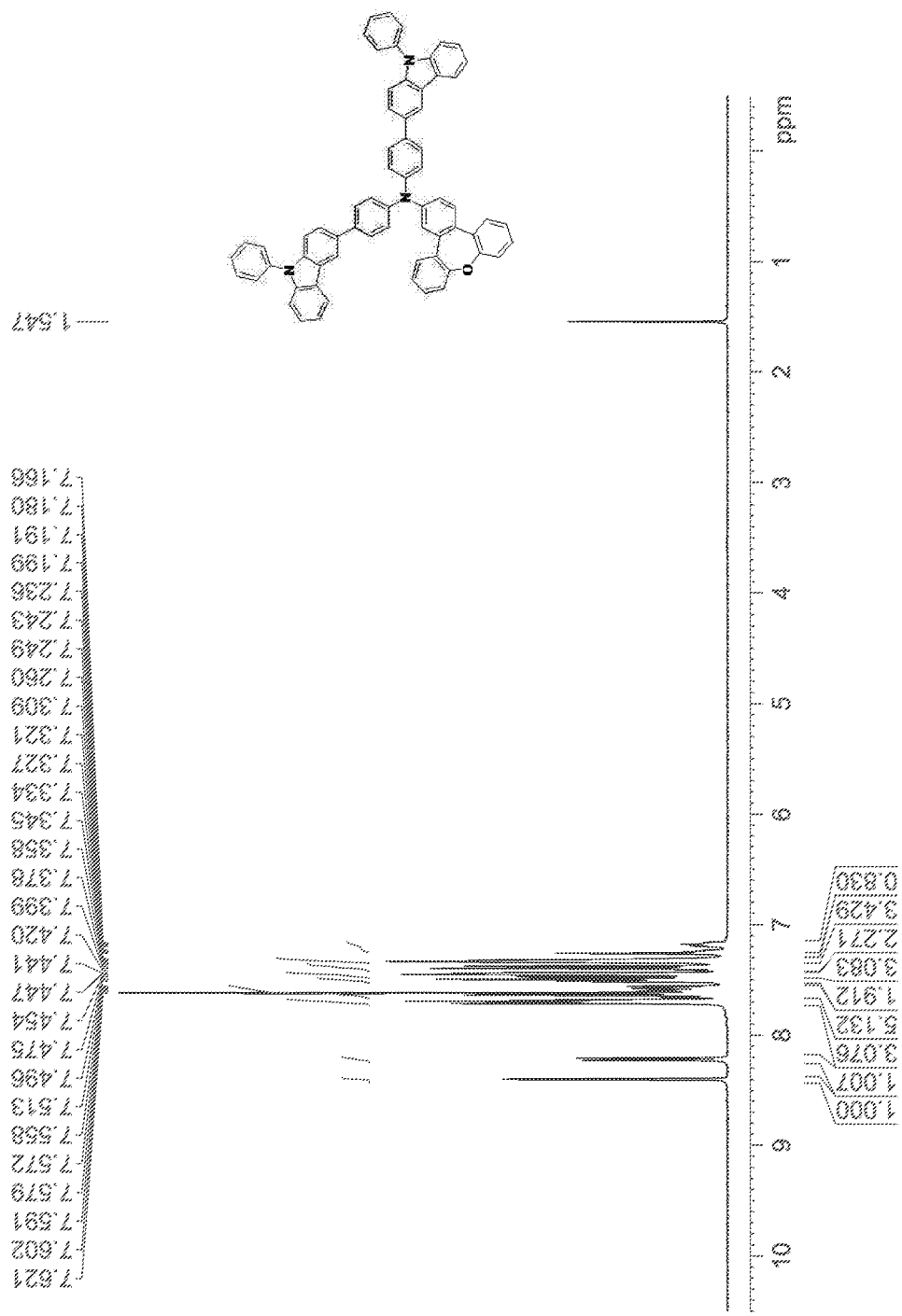
Figure 28:
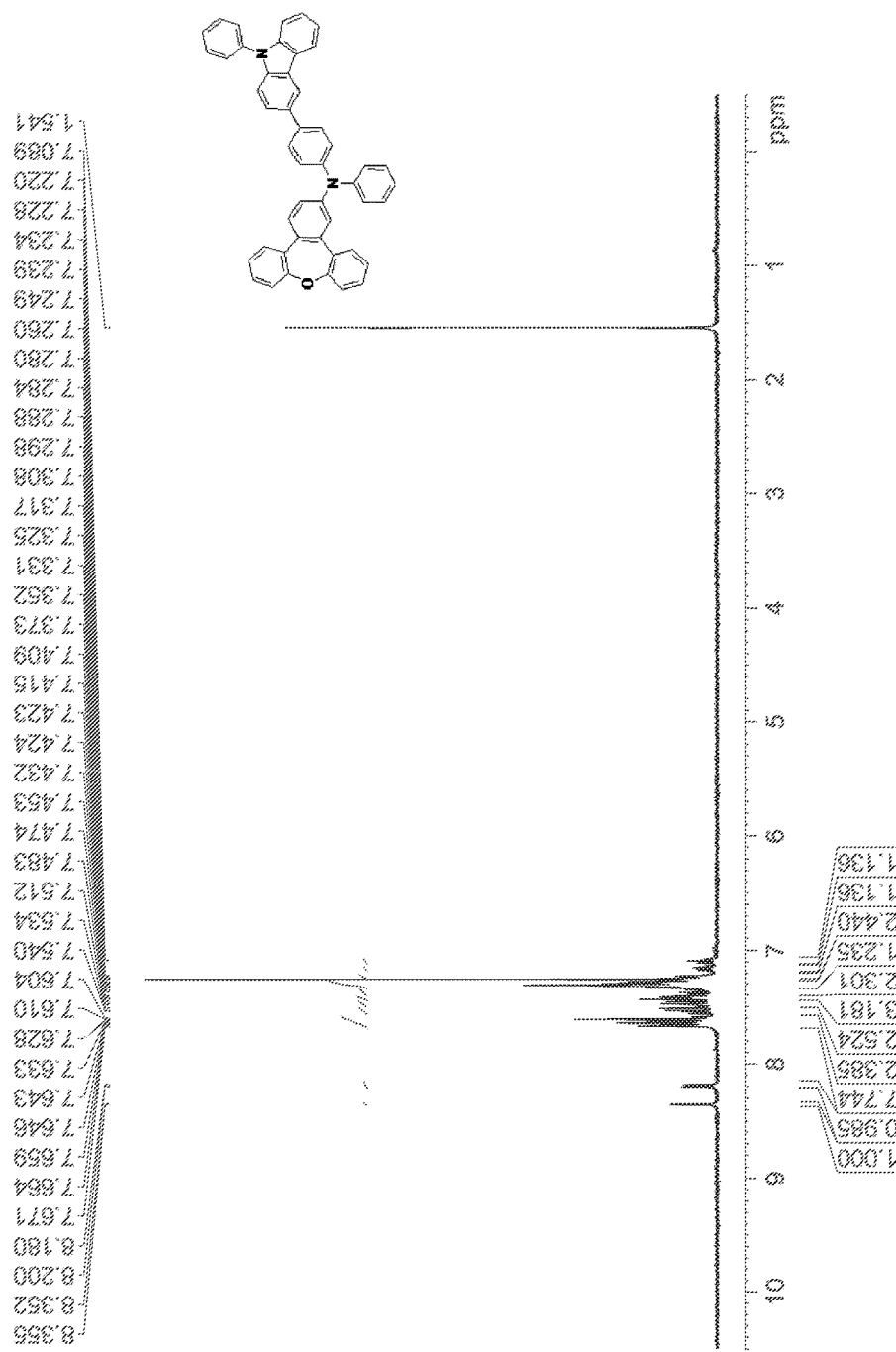
Figure 29:
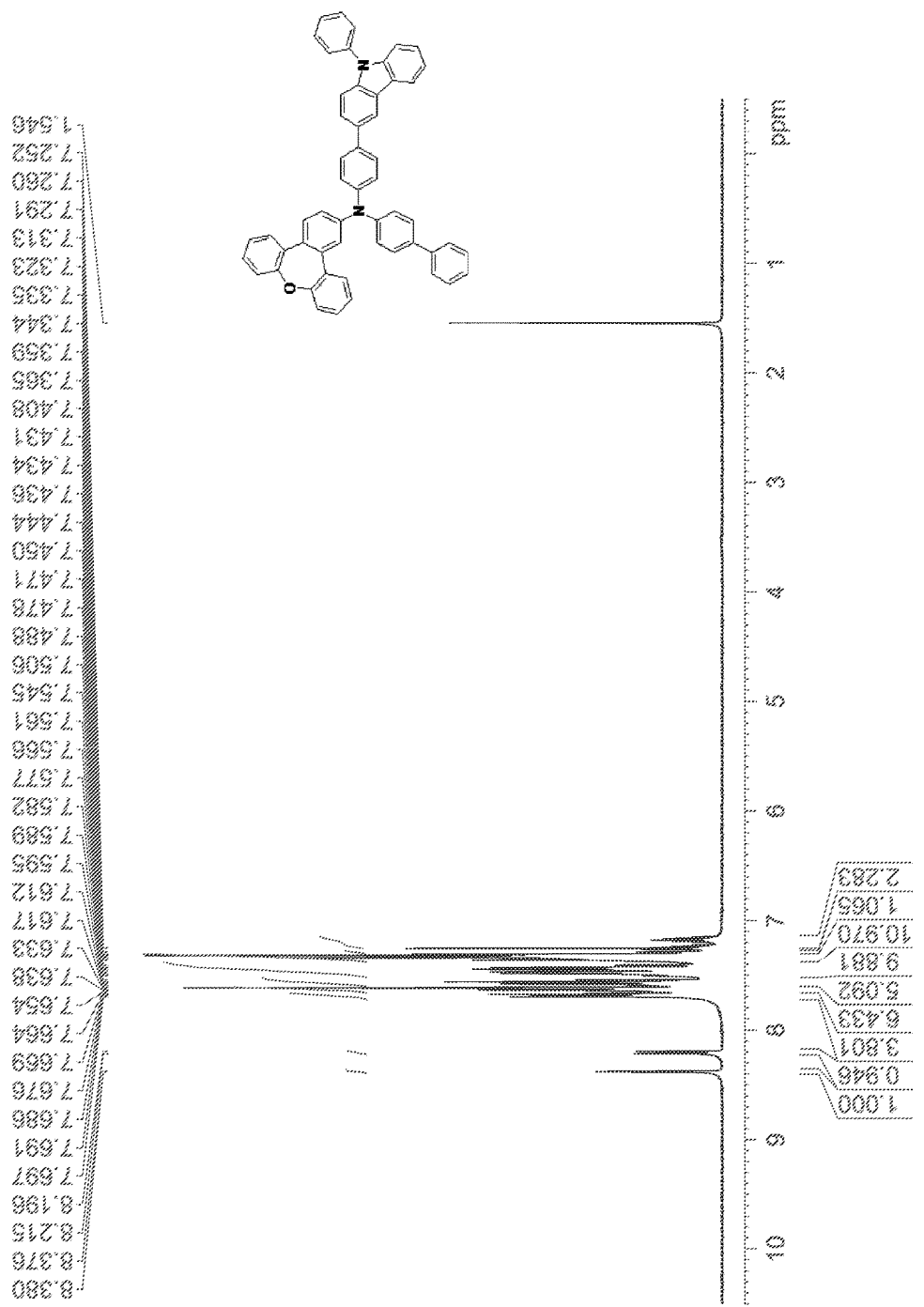
Figure 30:
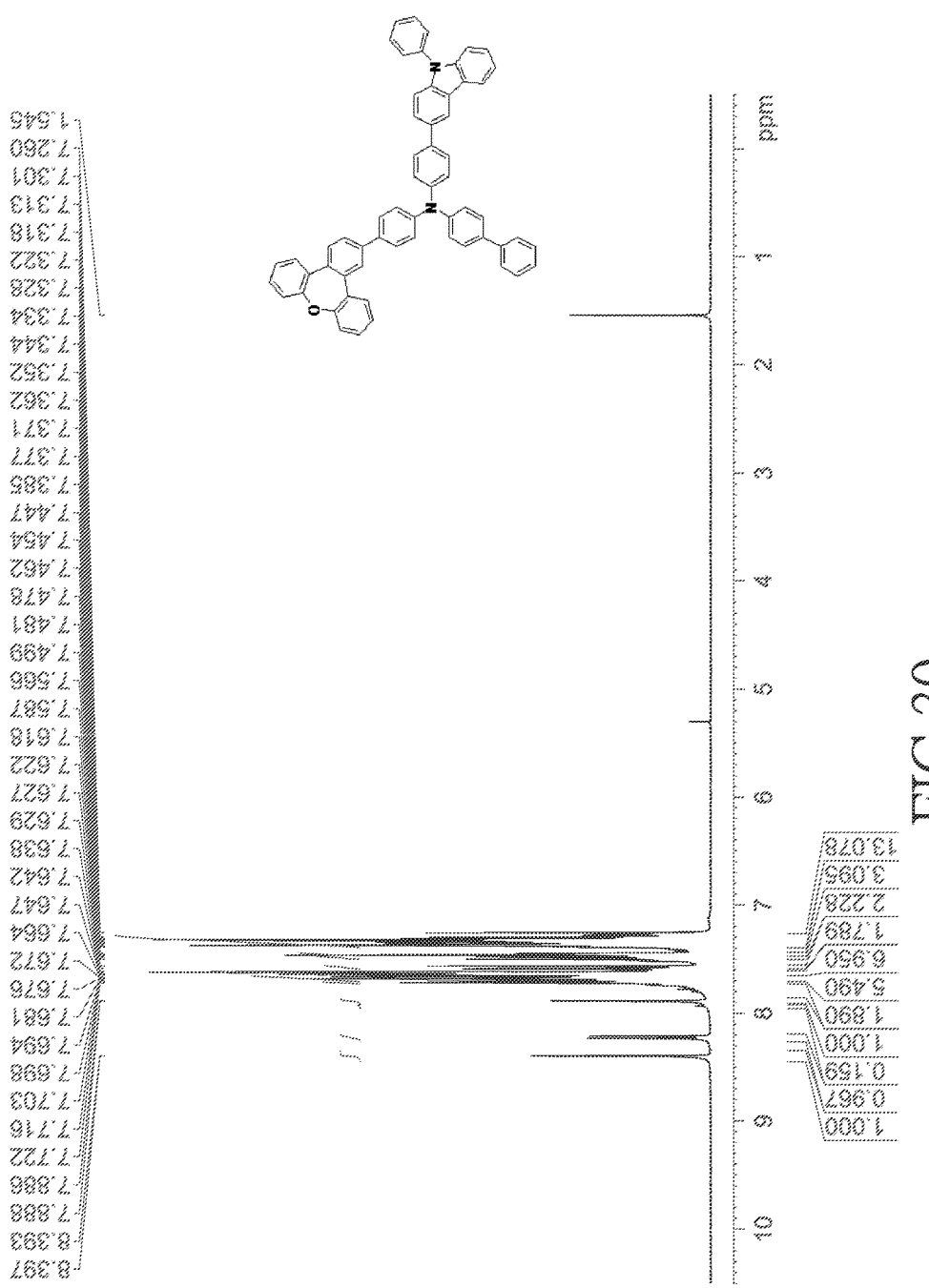
Figure 31:
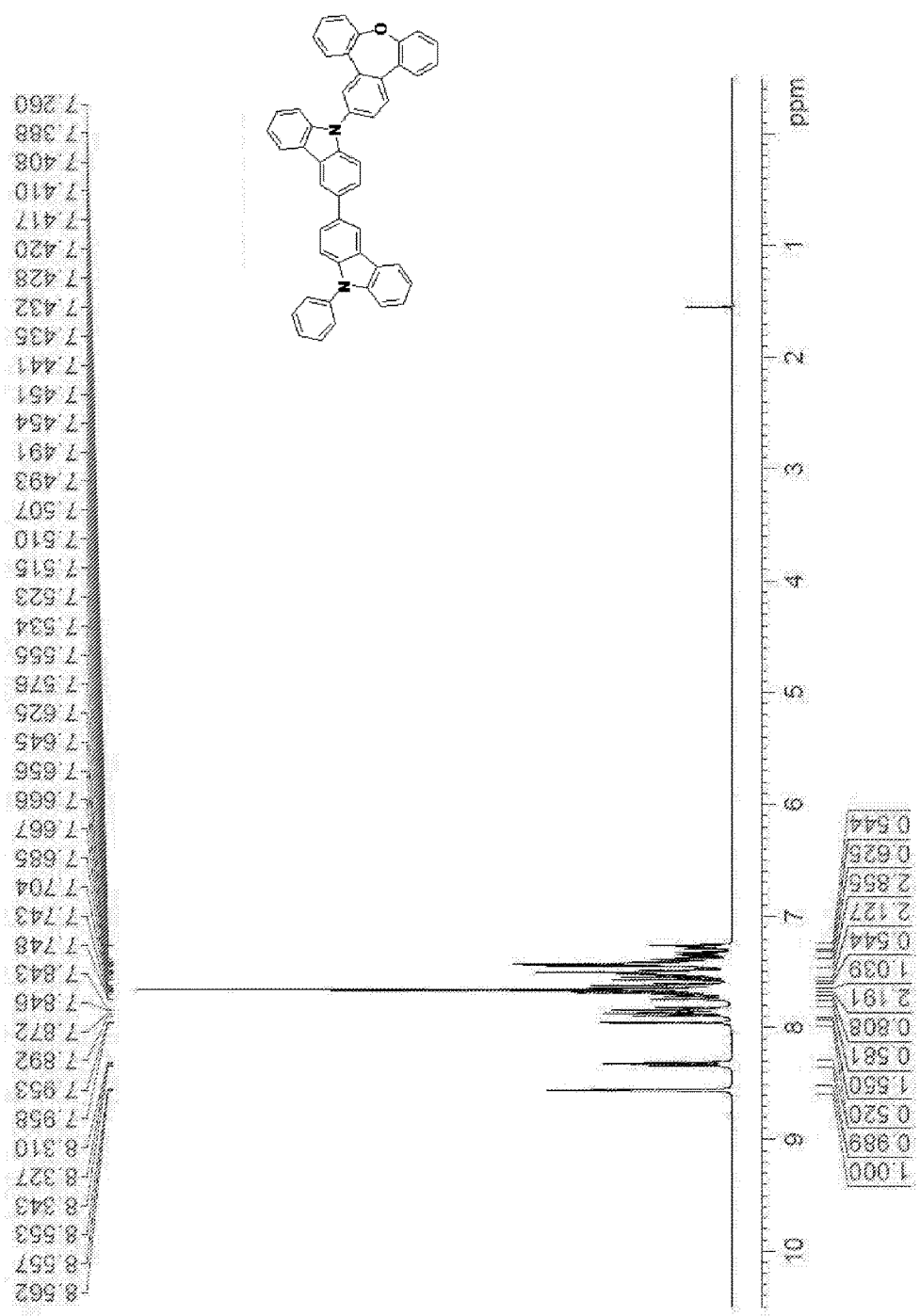
Figure 32:
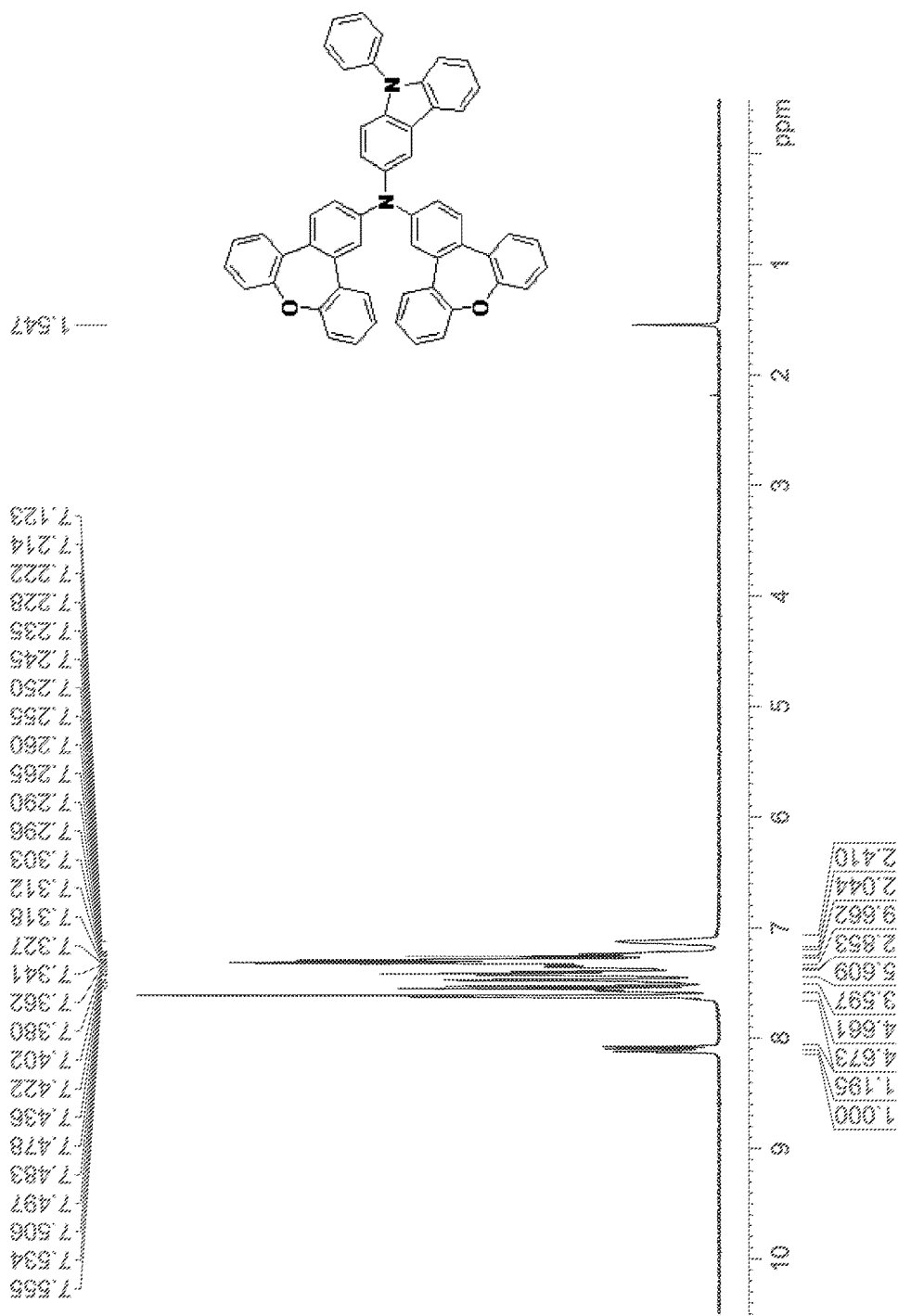
Figure 33:
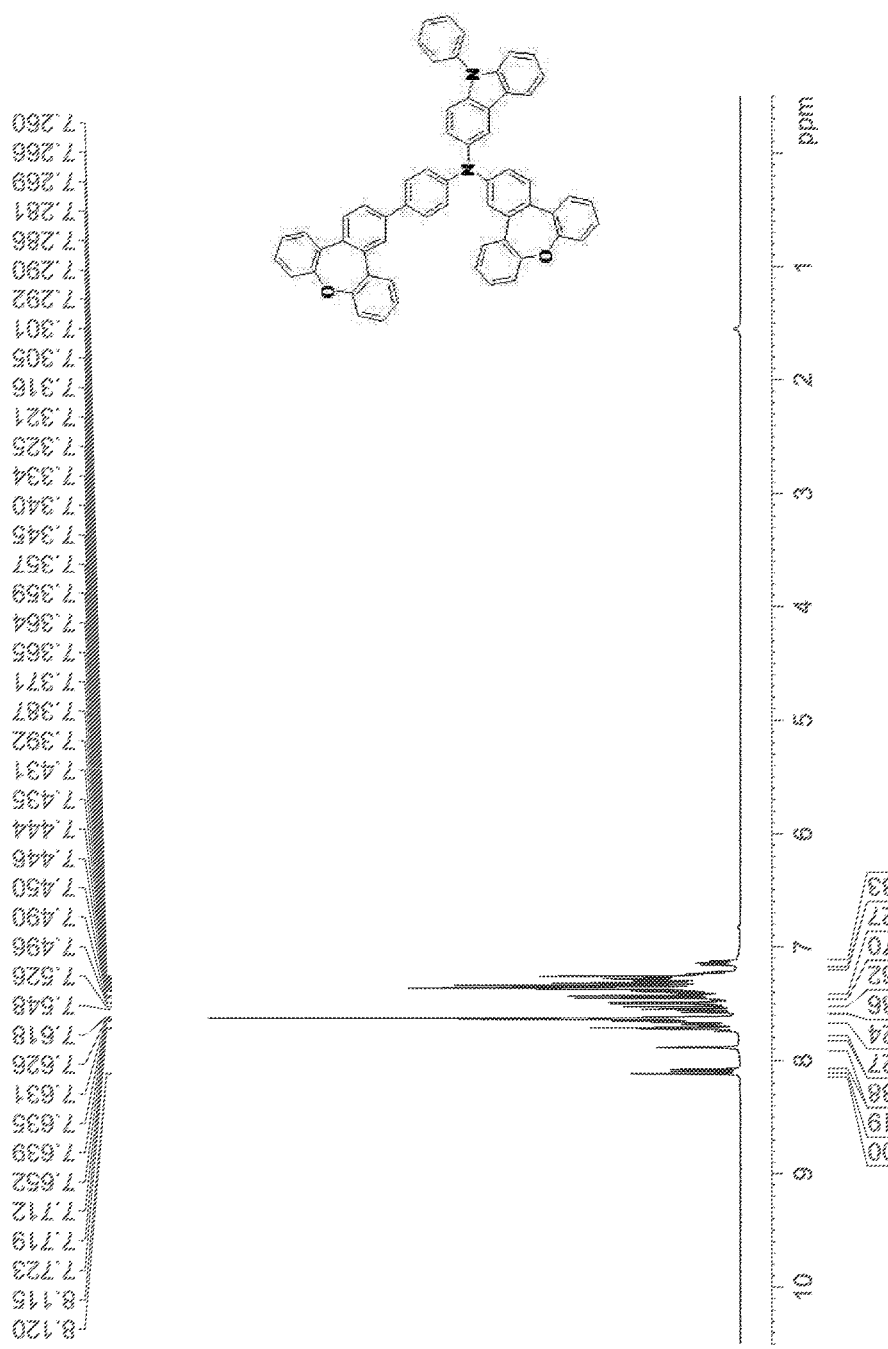
Figure 34:
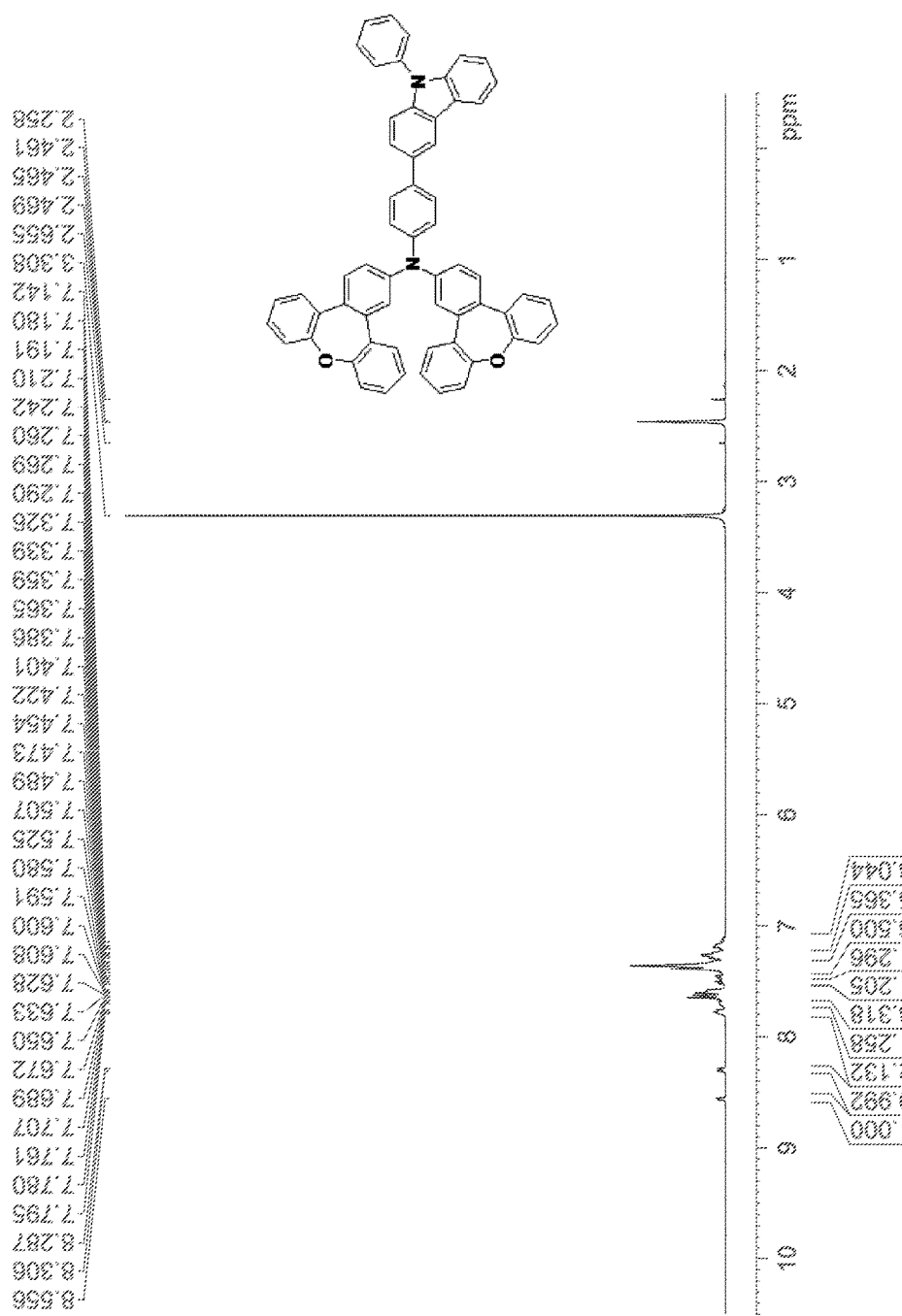
Figure 35:
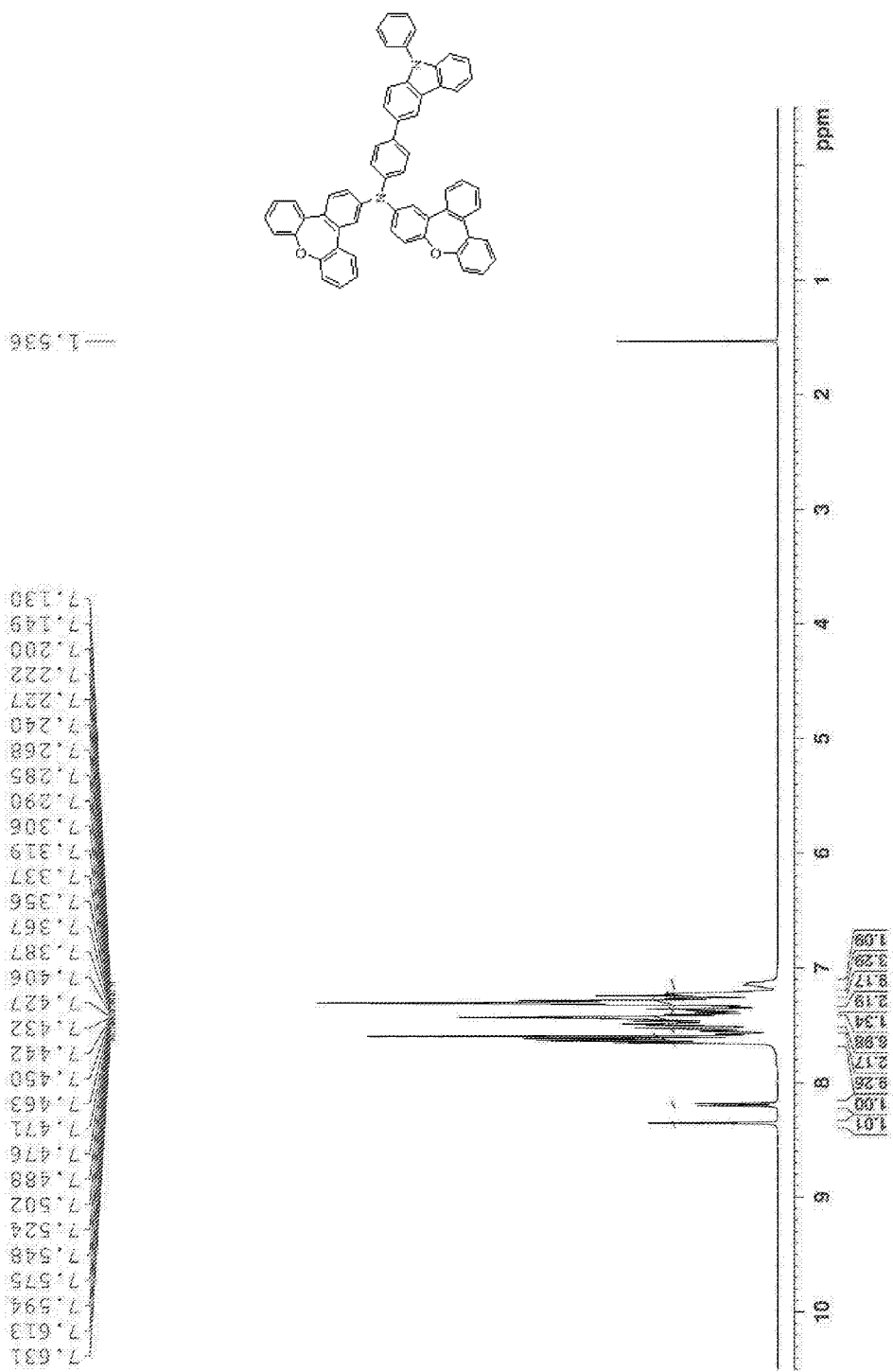
Figure 36:
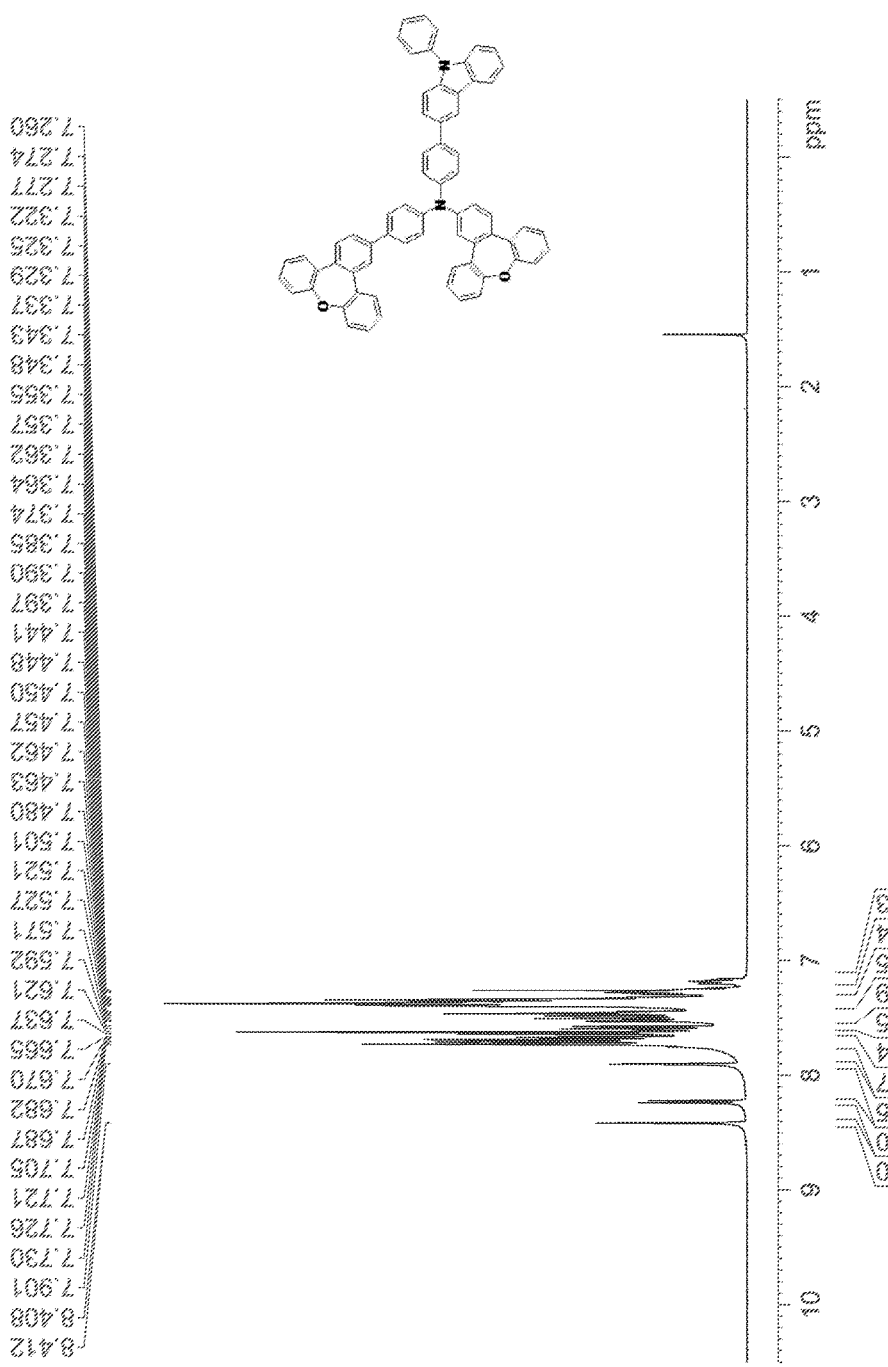
Figure 37:
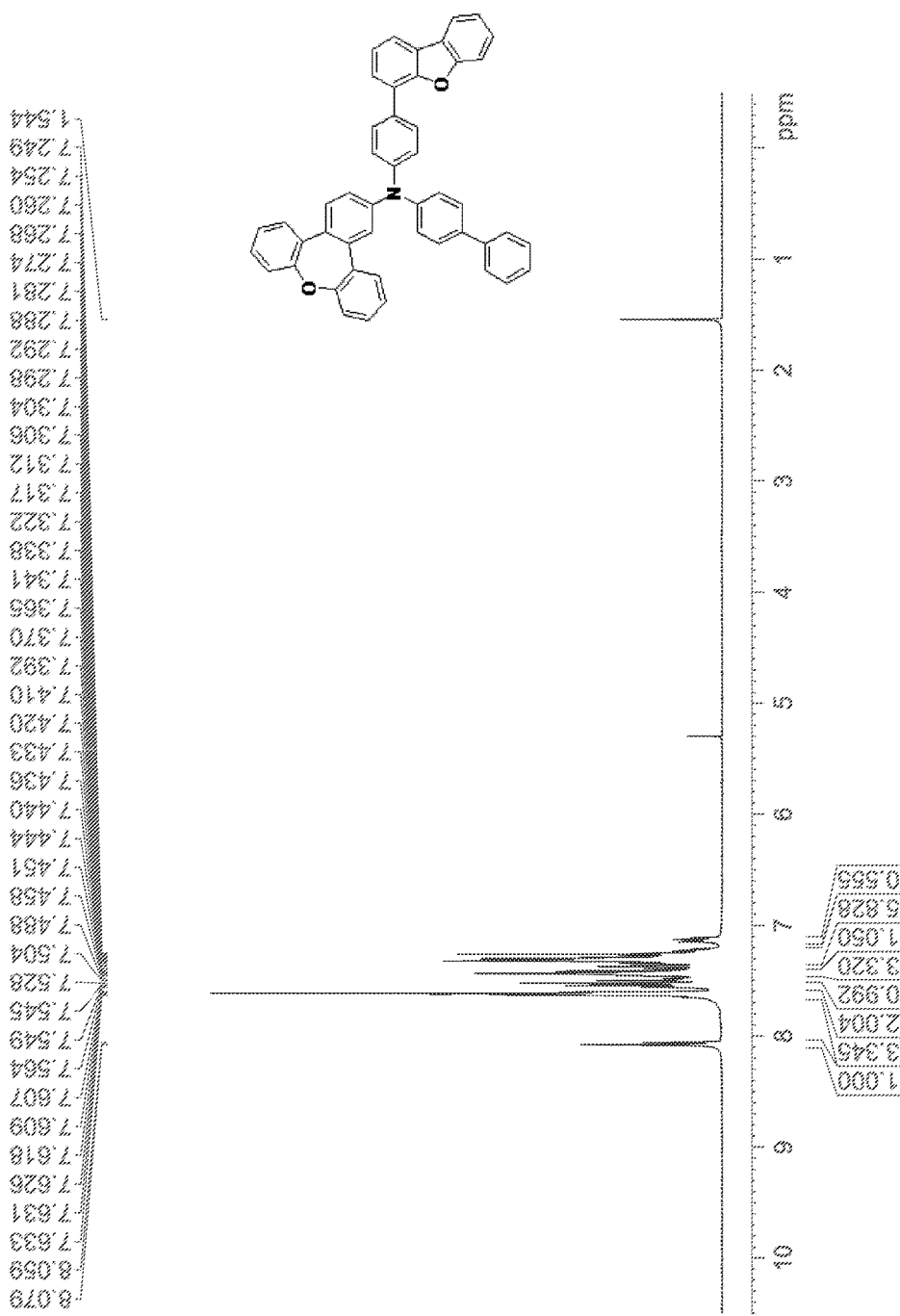
Figure 38:
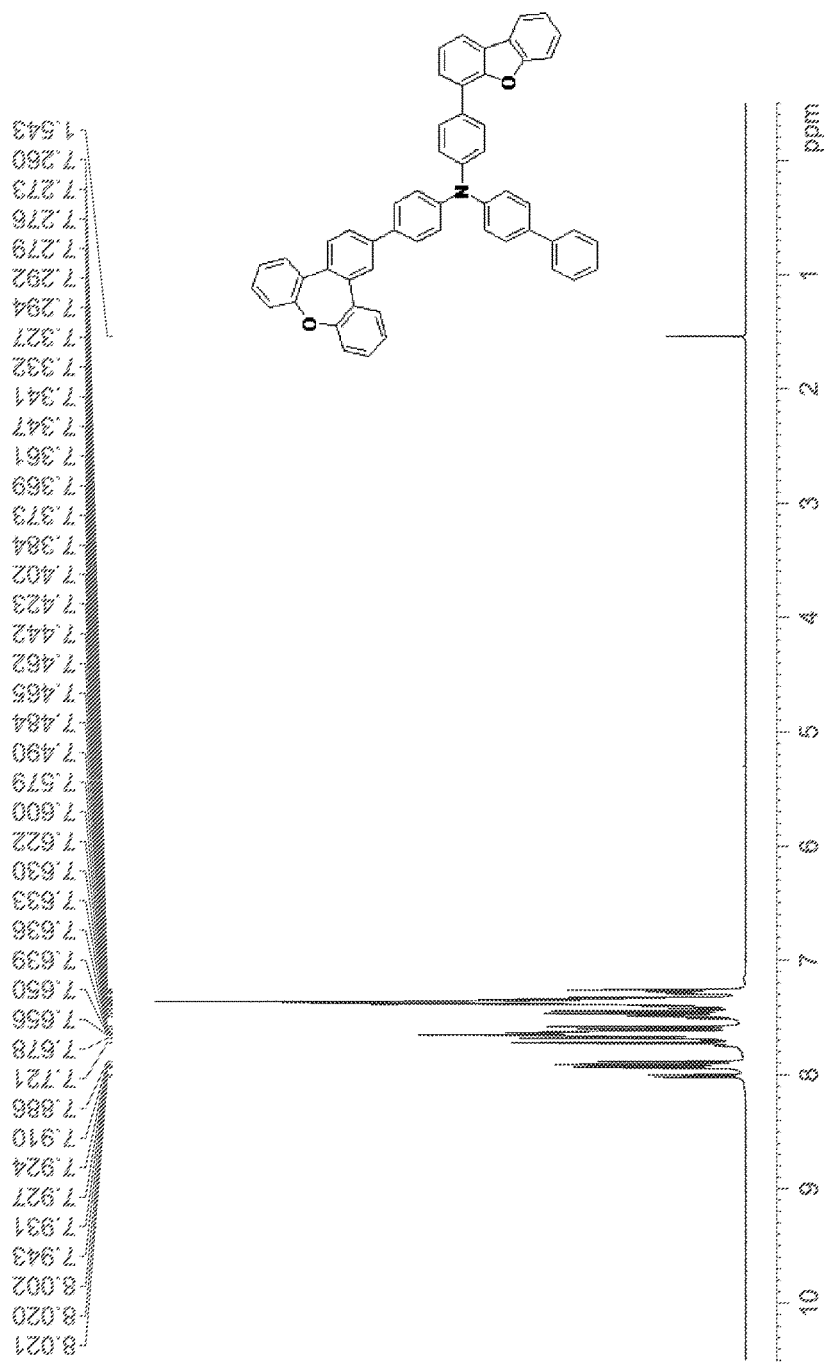
Figure 39:
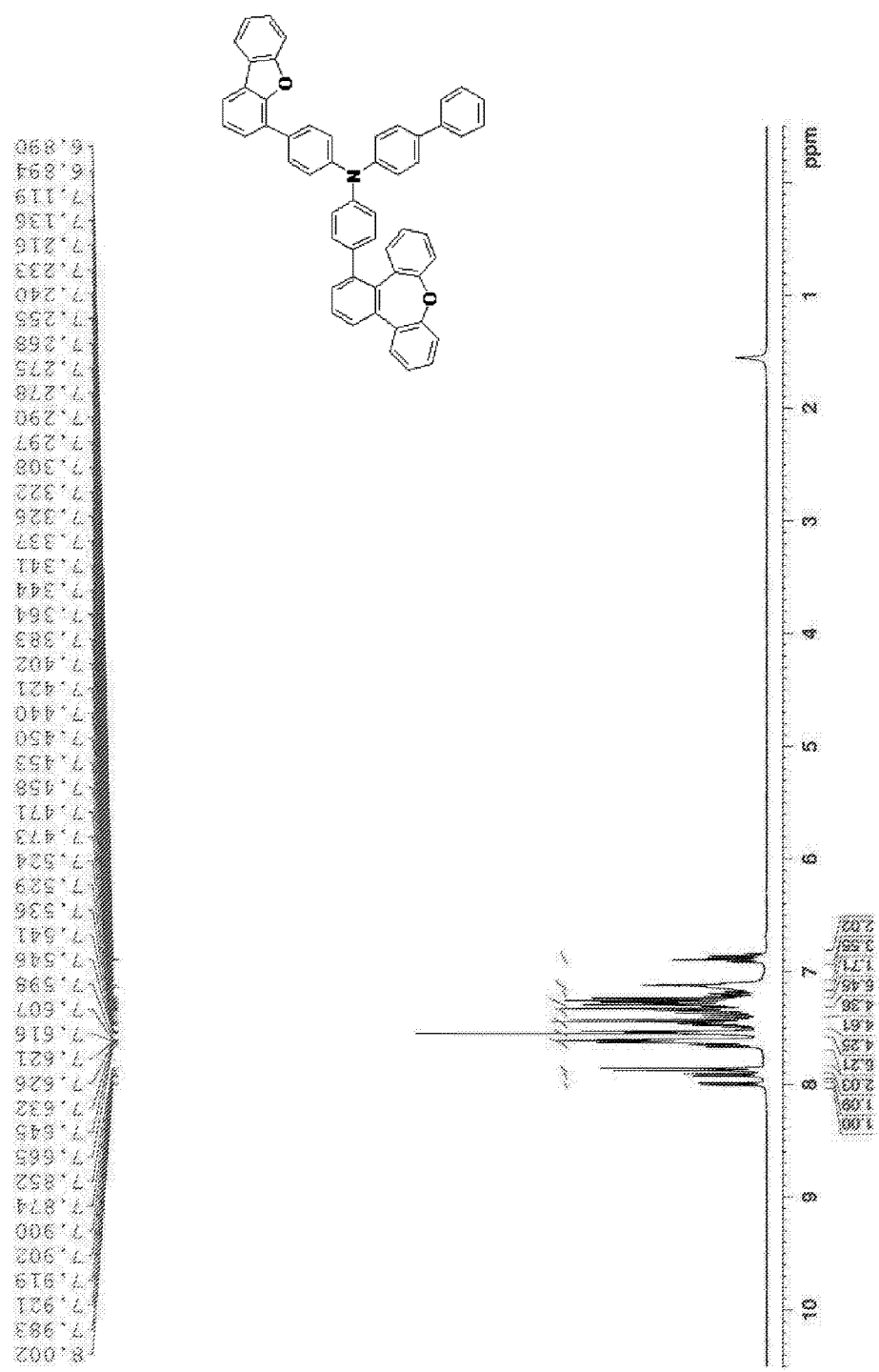
Figure 40:
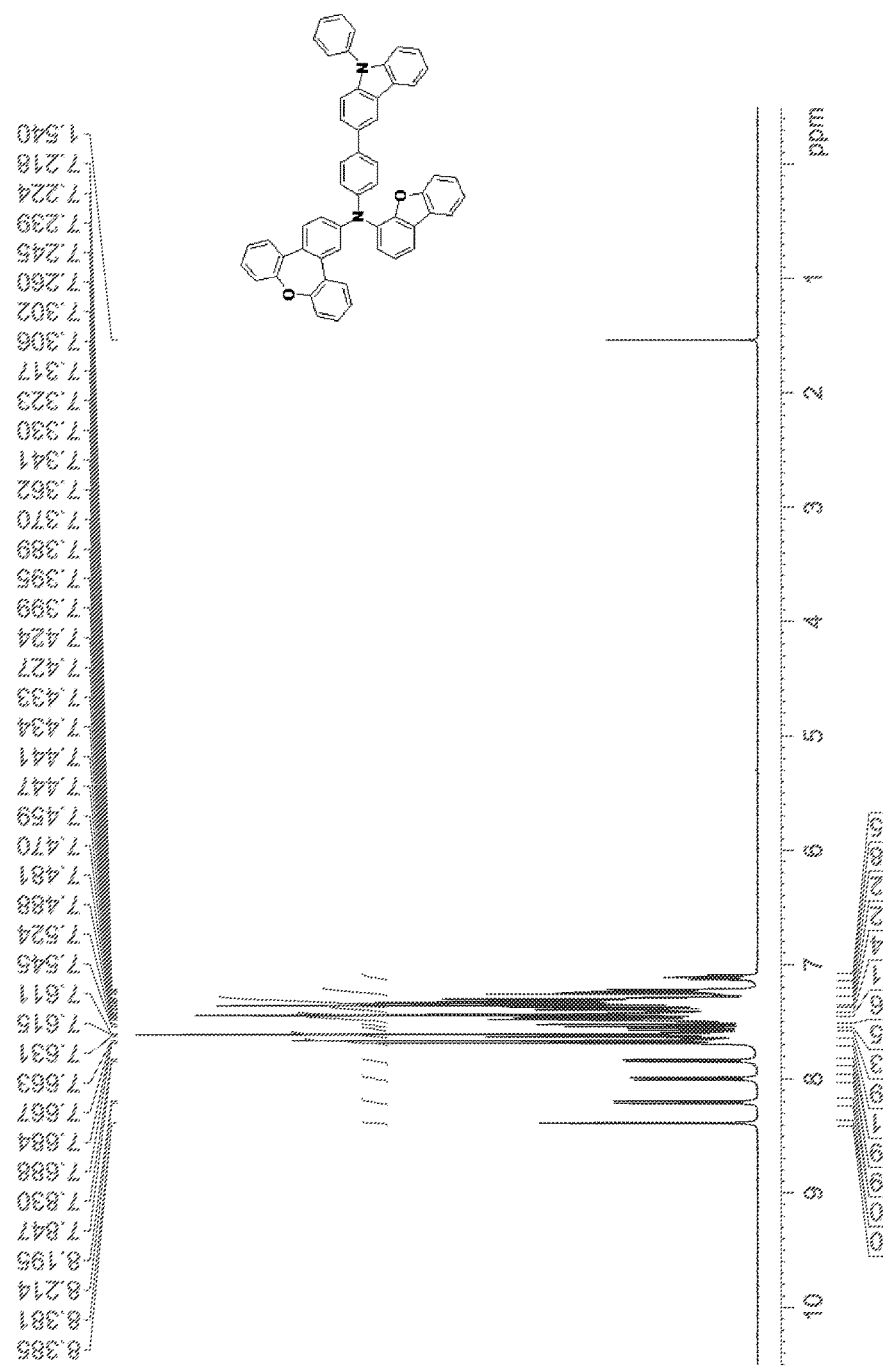
Figure 41:
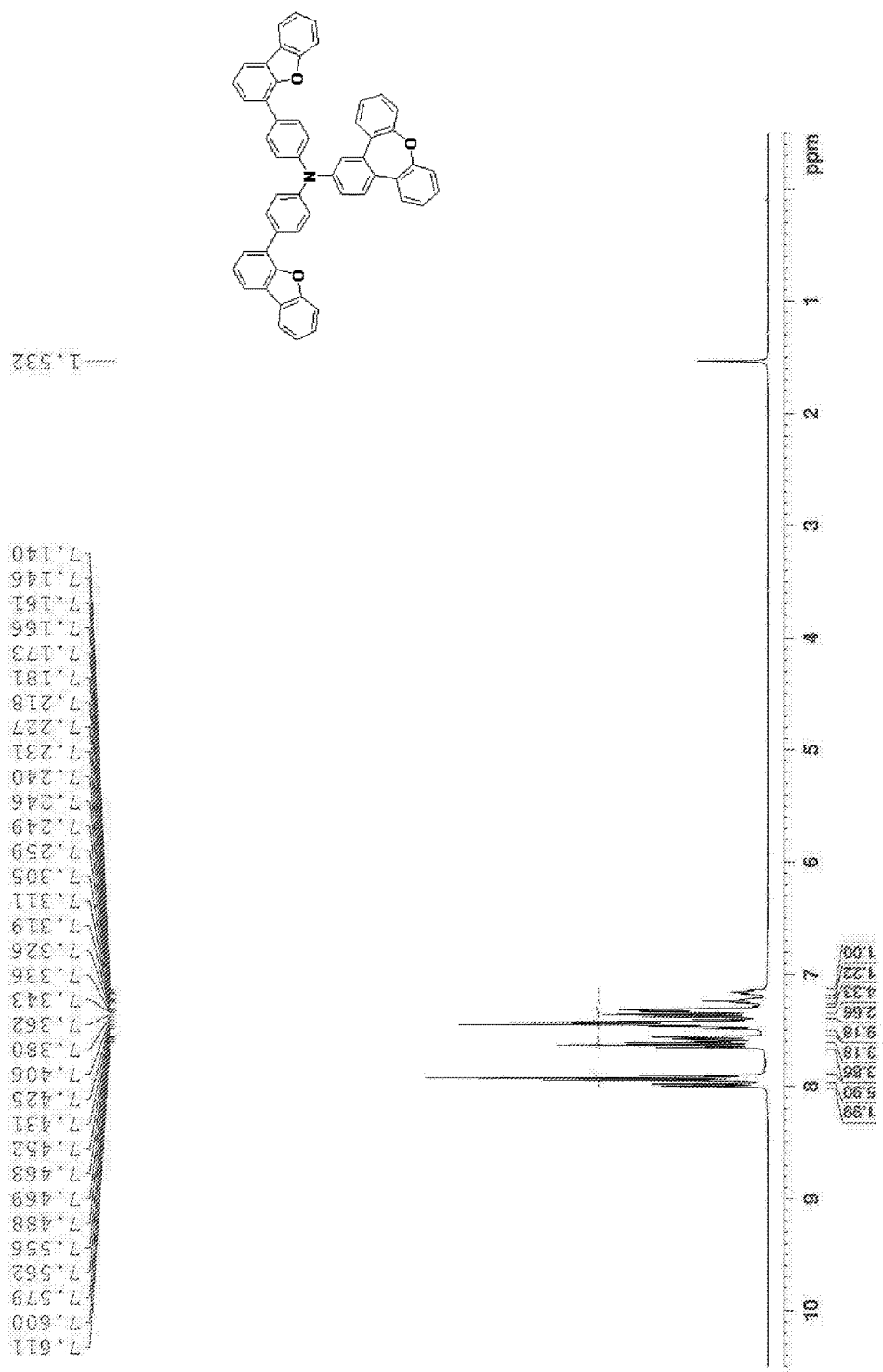
Figure 42:
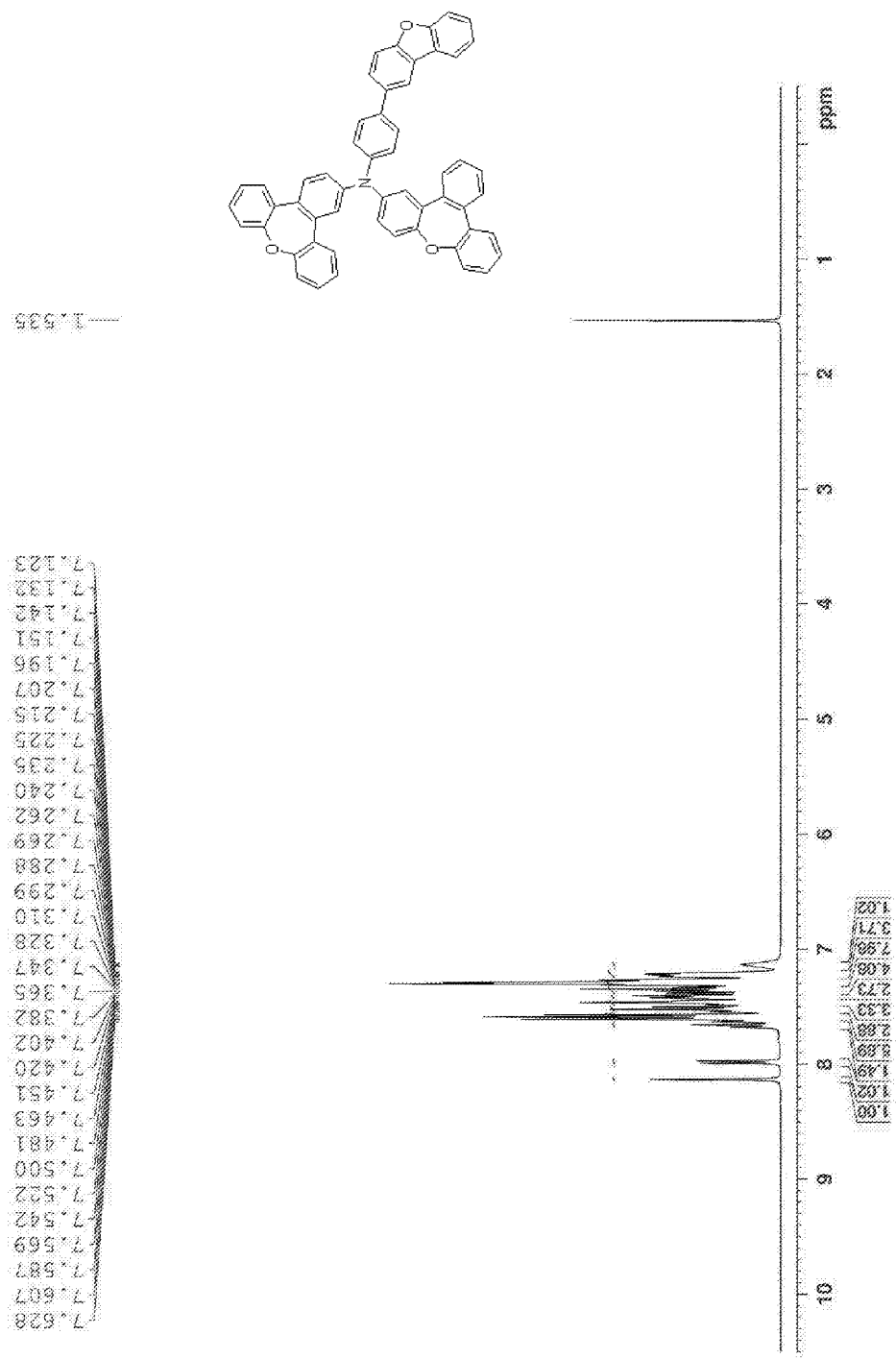
Figure 43:
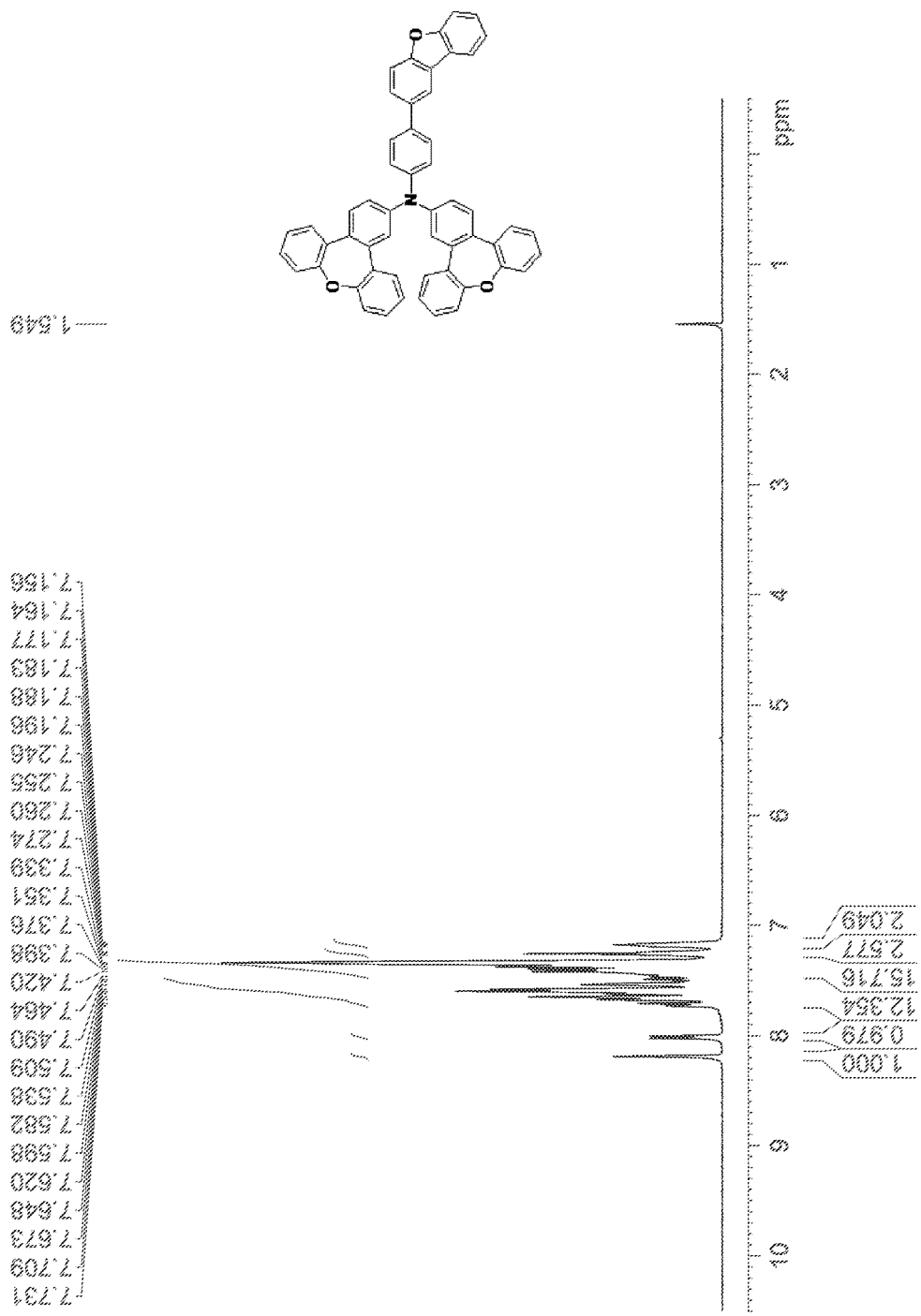
Figure 44:
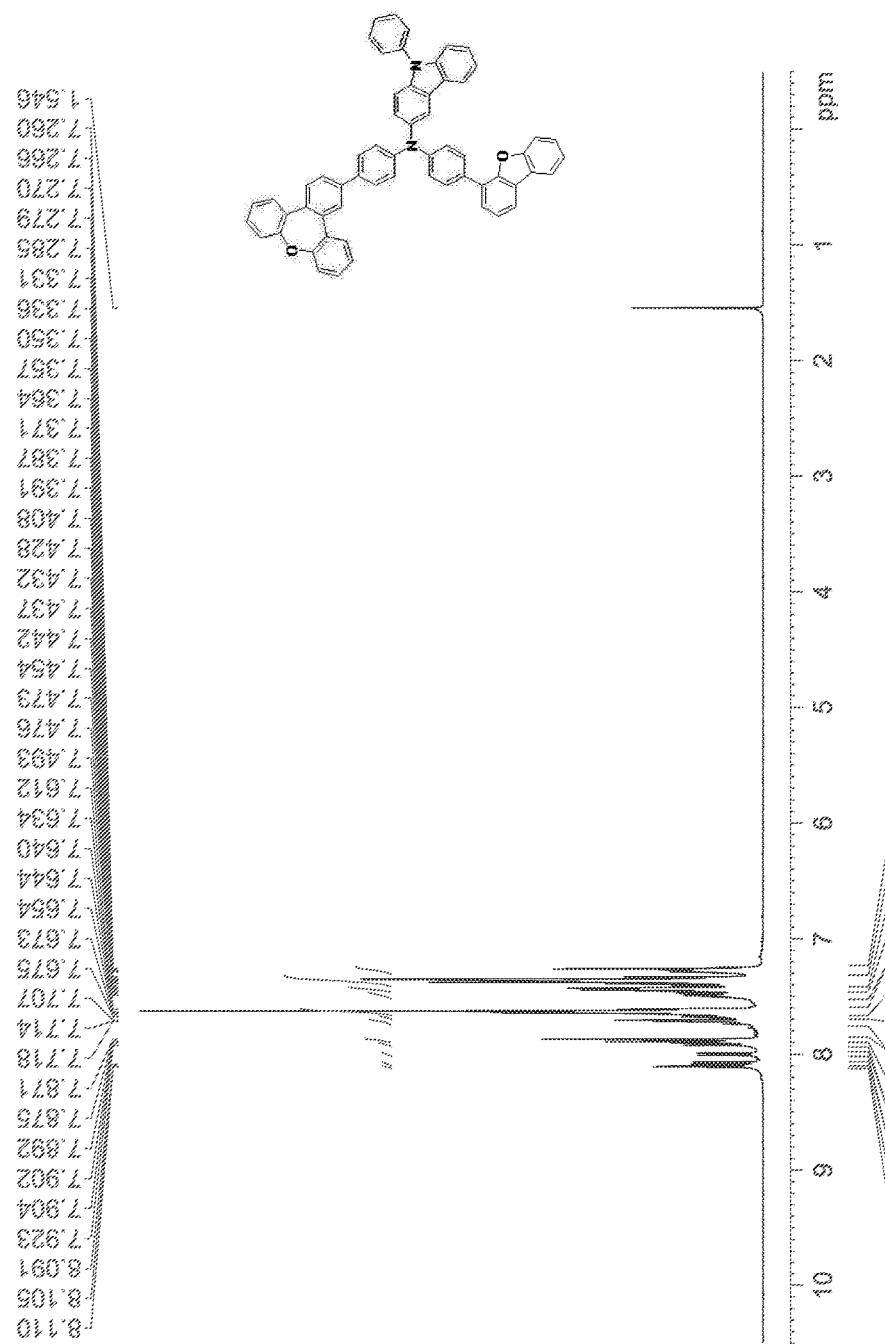

Reactant A and Reactant B adopted to synthesize Compounds 1 to 43 were listed in Table 5. Compounds 1 to 43 were identified by $H^1$-NMR and FD-MS, and the chemical structure, yield, formula and mass of each of Compounds 1 to 43 were also listed in Table 5. According to FIGS. 2 to 44 and the results of FD-MS, the chemical structure of Compounds 1 to 43 were identified as follows.

TABLE 5

The reactants A and B used for preparing the novel compounds and their yields and MS data.

| Reactant A | Reactant B | Chemical Structure of Novel Compound | Yield (%) | Mass(M$^+$) Theoretical (found) |
|---|---|---|---|---|
| Intermediate A1 | Intermediate B1 | Compound 1 | 85.2% | 563.69 (C$_{42}$H$_{29}$NO) |

TABLE 5-continued
The reactants A and B used for preparing the novel compounds and their yields and MS data.
| Reactant A | Reactant B | Chemical Structure of Novel Compound | Yield (%) | Mass(M+) Theoretical (found) |
|---|---|---|---|---|
| Intermediate A1 | Intermediate C1 | 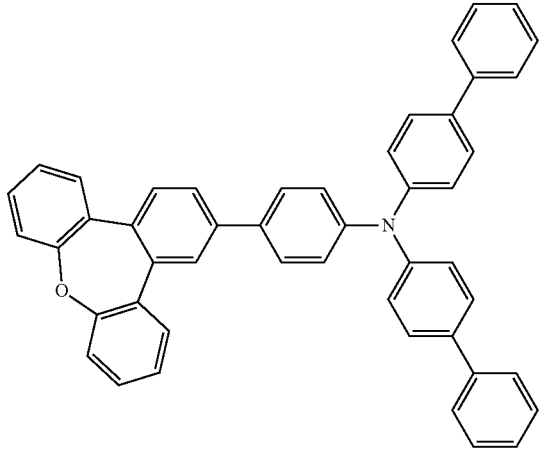<br>Compound 2 | 90.1% | 639.78 ($C_{48}H_{33}NO$) |
| Intermediate A1 | Intermediate C2 | 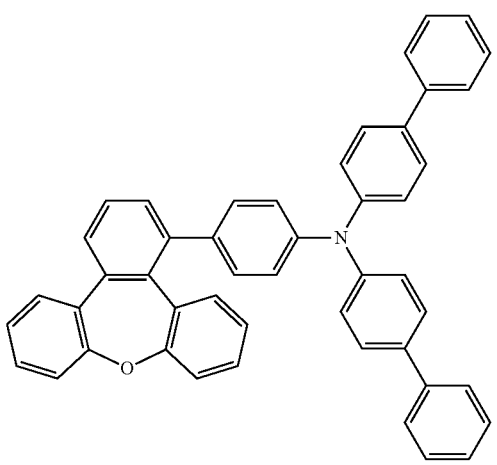<br>Compound 3 | 80.5% | 639.78 ($C_{48}H_{33}NO$) |
| Intermediate A1 | Intermediate C3 | 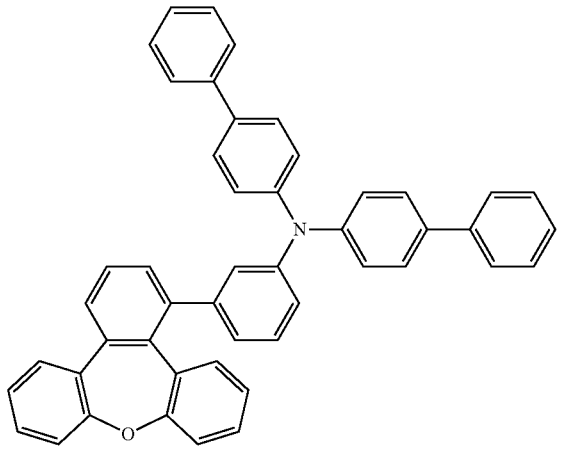<br>Compound 4 | 88.9% | 639.78 ($C_{48}H_{33}NO$) |

TABLE 5-continued
The reactants A and B used for preparing the novel compounds and their yields and MS data.
| Reactant A | Reactant B | Chemical Structure of Novel Compound | Yield (%) | Mass(M+) Theoretical (found) |
|---|---|---|---|---|
| Intermediate A7 | Intermediate C6 | 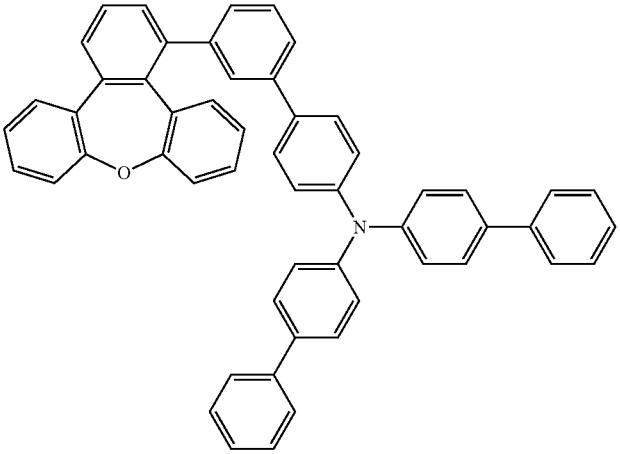<br>Compound 5 | 86.3% | 715.88 ($C_{57}H_{37}NO$) |
| Intermediate A8 | Intermediate B1 | 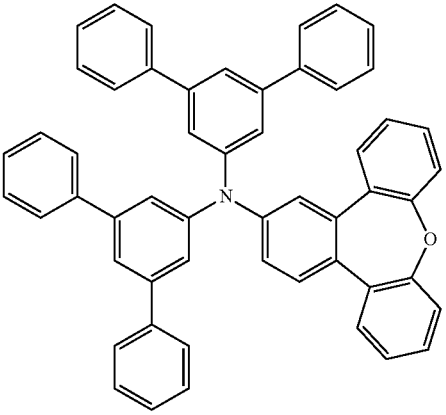<br>Compound 6 | 97.3% | 715.88 ($C_{57}H_{37}NO$) |
| Intermediate C4 | Intermediate C1 | 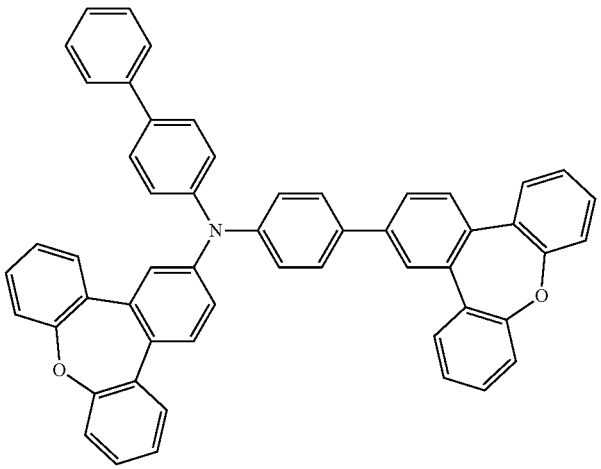<br>Compound 7 | 94.5% | 729.86 ($C_{54}H_{35}NO_2$) |

TABLE 5-continued
The reactants A and B used for preparing the novel compounds and their yields and MS data.
| Reactant A | Reactant B | Chemical Structure of Novel Compound | Yield (%) | Mass(M+) Theoretical (found) |
|---|---|---|---|---|
| Intermediate C4 | Intermediate B1 | 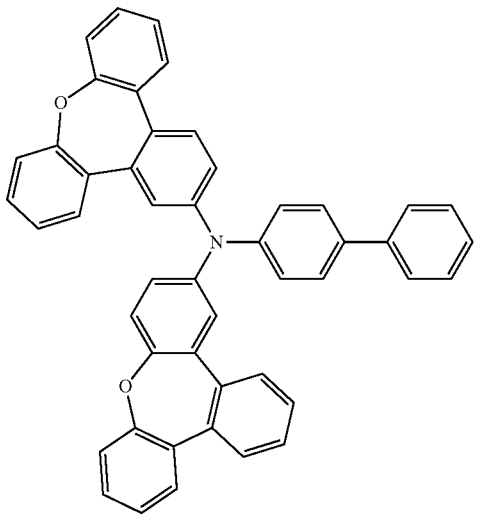 Compound 8 | 96.1% | 653.77 ($C_{48}H_{31}NO_2$) |
| Intermediate C5 | Intermediate B1 | 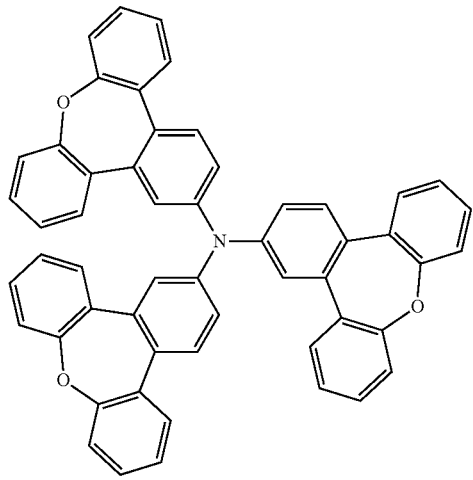 Compound 9 | 88.5% | 743.84 ($C_{54}H_{33}NO_3$) |

TABLE 5-continued
The reactants A and B used for preparing the novel compounds and their yields and MS data.
| Reactant A | Reactant B | Chemical Structure of Novel Compound | Yield (%) | Mass(M+) Theoretical (found) |
|---|---|---|---|---|
| Intermediate C5 | Intermediate C1 | 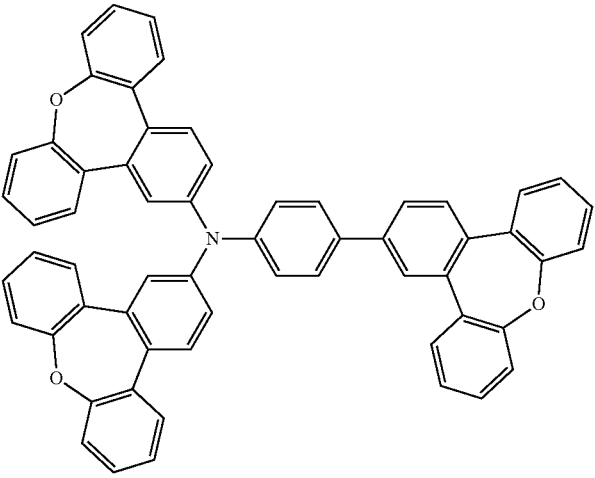 Compound 10 | 91.8% | 819.94 (C$_{60}$H$_{37}$NO$_3$) |
| Intermediate A5 | Intermediate B1 | 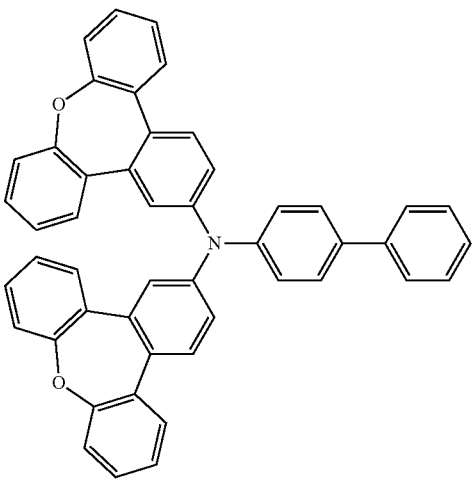 Compound 11 | 93.7% | 653.77 (C$_{48}$H$_{31}$NO$_2$) |

TABLE 5-continued
The reactants A and B used for preparing the novel compounds and their yields and MS data.
| Reactant A | Reactant B | Chemical Structure of Novel Compound | Yield (%) | Mass(M+) Theoretical (found) |
|---|---|---|---|---|
| Intermediate A5 | Intermediate C1 | 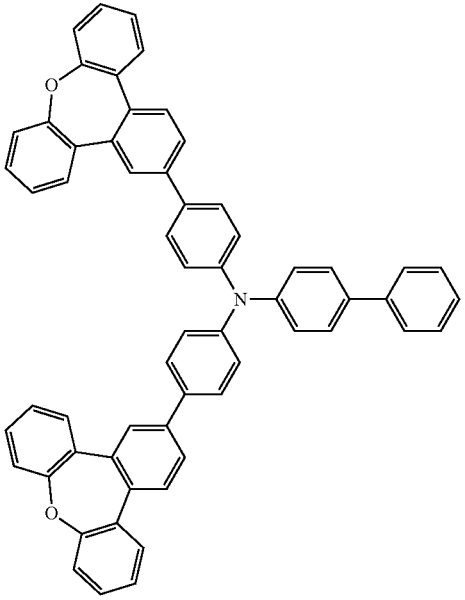<br>Compound 12 | 88.3% | 805.96 ($C_{60}H_{39}NO_2$) |
| Intermediate A6 | Intermediate C2 | 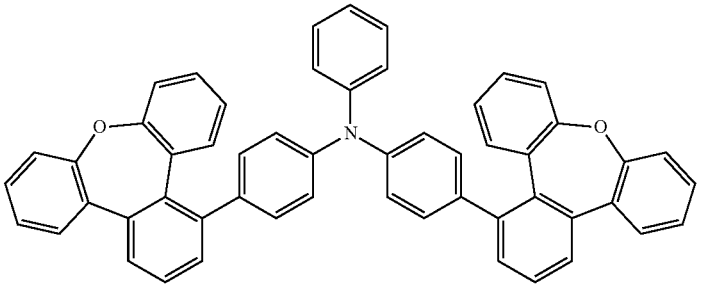<br>Compound 13 | 84.6% | 729.86 ($C_{54}H_3NO_2$) |
| Intermediate A2 | Intermediate B1 | 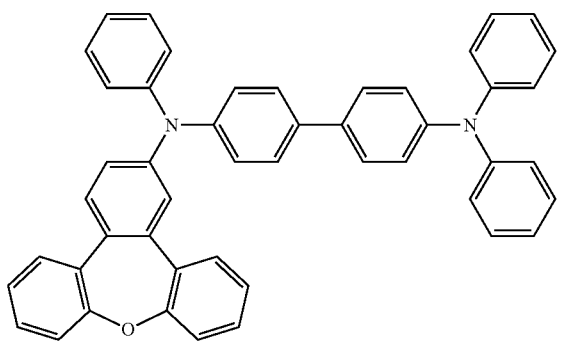<br>Compound 14 | 91.5% | 654.8 ($C_{48}H_{34}N_2O$) |

TABLE 5-continued

The reactants A and B used for preparing the novel compounds and their yields and MS data.

| Reactant A | Reactant B | Chemical Structure of Novel Compound | Yield (%) | Mass(M+) Theoretical (found) |
|---|---|---|---|---|
| Intermediate A3 | Intermediate B1 | Compound 15 | 83.3% | 820.97 ($C_{60}H_{40}N_2O_2$) |
| Intermediate A4 | Intermediate B1 | Compound 16 | 86.9% | 820.97 ($C_{60}H_{40}N_2O_2$) |
| Intermediate A4 | Intermediate C1 | Compound 17 | 87.9% | 973.16 ($C_{72}H_{48}N_2O_2$) |

TABLE 5-continued
The reactants A and B used for preparing the novel compounds and their yields and MS data.
| Reactant A | Reactant B | Chemical Structure of Novel Compound | Yield (%) | Mass(M+) Theoretical (found) |
|---|---|---|---|---|
| Intermediate A2 | Intermediate C1 | 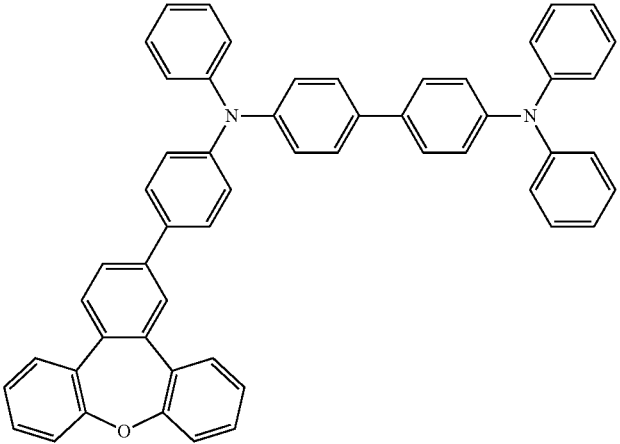 Compound 18 | 90.3% | 730.89 ($C_{54}H_{38}N_2O$) |
| Intermediate B1 | Intermediate A18 | 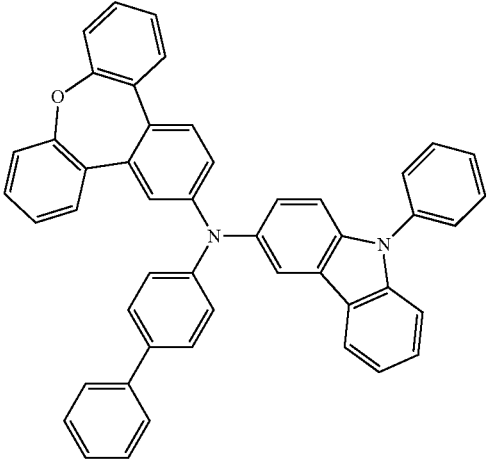 Compound 19 | 92.6% | 652.78 ($C_{48}H_{32}N_2O$) |

TABLE 5-continued
The reactants A and B used for preparing the novel compounds and their yields and MS data.
| Reactant A | Reactant B | Chemical Structure of Novel Compound | Yield (%) | Mass(M+) Theoretical (found) |
|---|---|---|---|---|
| Intermediate C1 | Intermediate A18 | 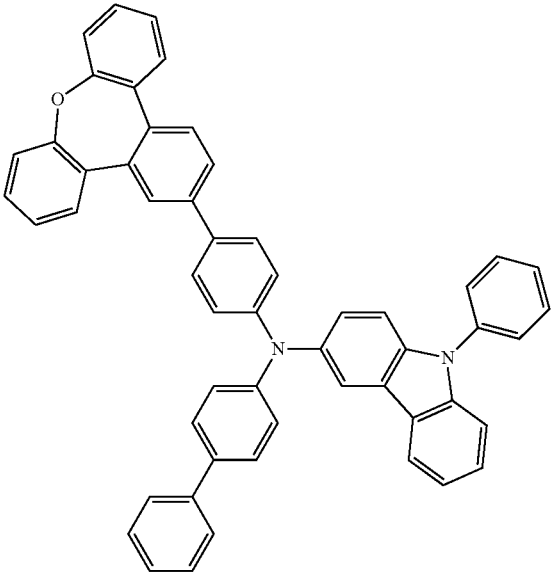<br>Compound 20 | 89.4% | 728.88 ($C_{54}H_{36}N_2O$) |
| Intermediate C2 | Intermediate A18 | 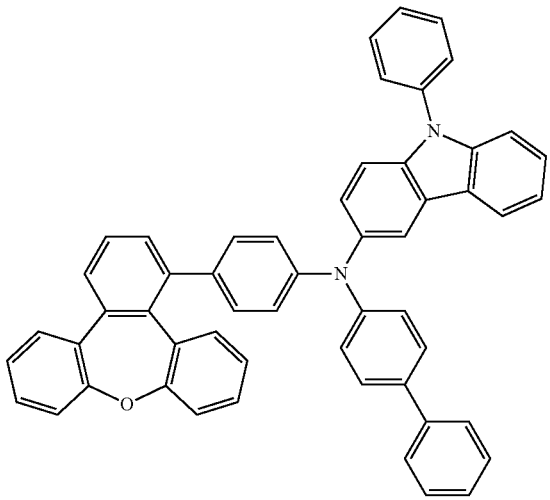<br>Compound 21 | 87.6% | 894.07 ($C_{66}H_{43}N_3O$) |

TABLE 5-continued

The reactants A and B used for preparing the novel compounds and their yields and MS data.

| Reactant A | Reactant B | Chemical Structure of Novel Compound | Yield (%) | Mass(M+) Theoretical (found) |
|---|---|---|---|---|
| Intermediate B1 | Intermediate A8 | Compound 22 | 89.7% | 741.88 ($C_{54}H_{35}N_3O$) |
| Intermediate C1 | Intermediate A8 | Compound 23 | 90.3% | 817.97 ($C_{60}H_{39}N_3O$) |

TABLE 5-continued
The reactants A and B used for preparing the novel compounds and their yields and MS data.
| Reactant A | Reactant B | Chemical Structure of Novel Compound | Yield (%) | Mass(M+) Theoretical (found) |
|---|---|---|---|---|
| Intermediate B1 | Intermediate A16 | 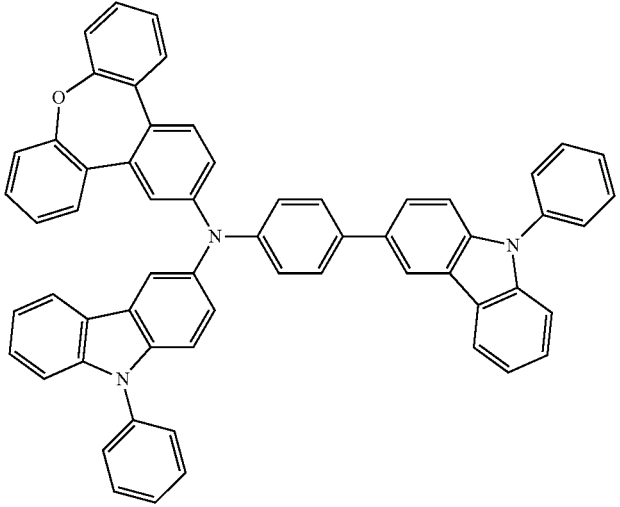<br>Compound 24 | 87.9% | 817.97 (C$_{60}$H$_{39}$N$_3$O) |
| Intermediate C1 | Intermediate A16 | 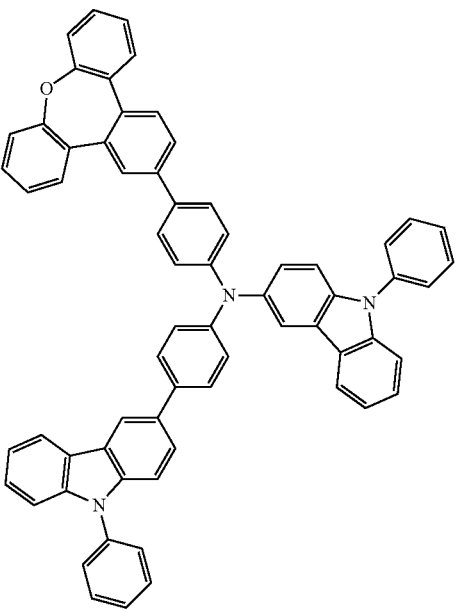<br>Compound 25 | 92.6% | 894.07 (C$_{66}$H$_{43}$N$_3$O) |

TABLE 5-continued
The reactants A and B used for preparing the novel compounds and their yields and MS data.
| Reactant A | Reactant B | Chemical Structure of Novel Compound | Yield (%) | Mass(M+) Theoretical (found) |
|---|---|---|---|---|
| Intermediate B1 | Intermediate A17 | 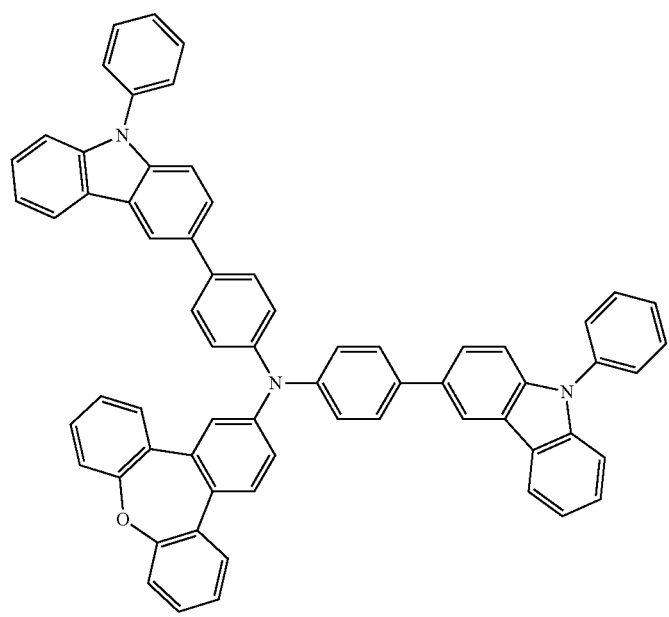<br>Compound 26 | 91.0% | 894.07 ($C_{66}H_{43}N_3O$) |
| Intermediate B1 | Intermediate A19 | 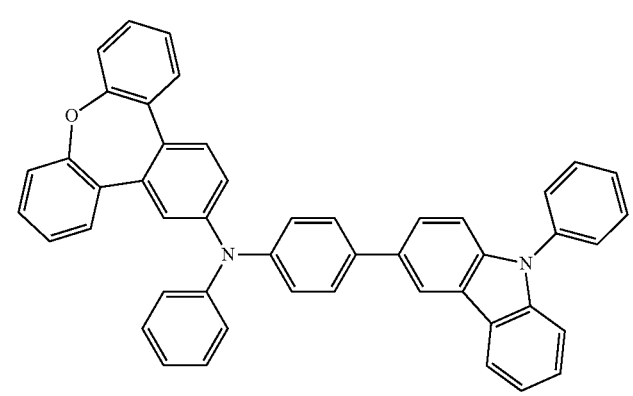<br>Compound 27 | 93.7% | 652.78 ($C_{48}H_{32}N_2O$) |

TABLE 5-continued
The reactants A and B used for preparing the novel compounds and their yields and MS data.
| Reactant A | Reactant B | Chemical Structure of Novel Compound | Yield (%) | Mass(M+) Theoretical (found) |
|---|---|---|---|---|
| Intermediate B1 | Intermediate A20 | 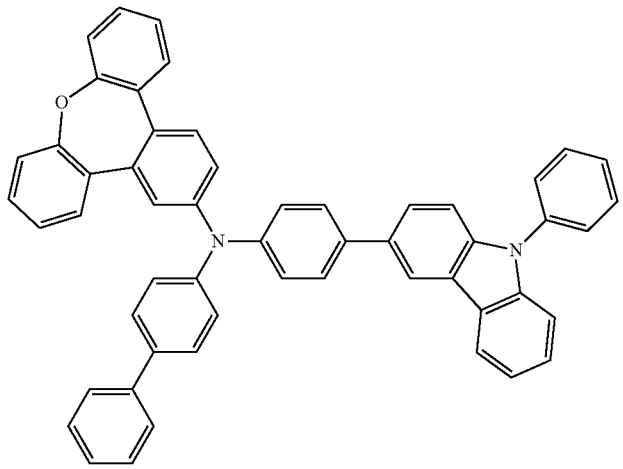<br>Compound 28 | 90.9% | 728.88 ($C_{54}H_{36}N_2O$) |
| Intermediate C1 | Intermediate A20 | 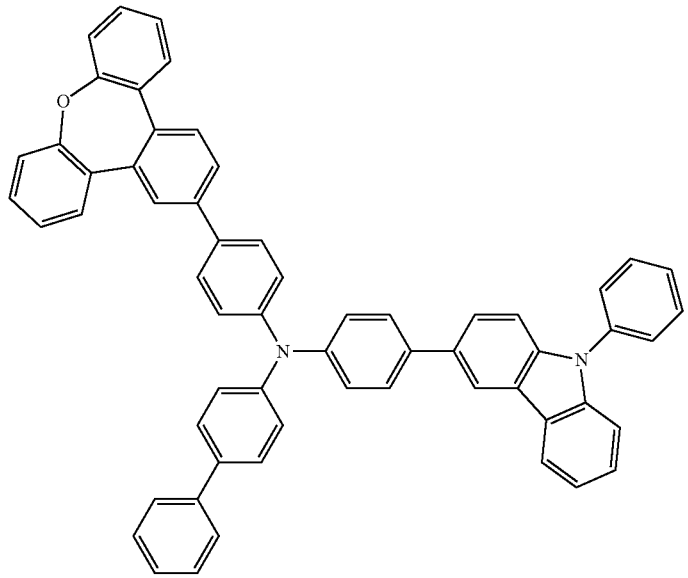<br>Compound 29 | 88.8% | 804.97 ($C_{60}H_{40}N_2O$) |

TABLE 5-continued
The reactants A and B used for preparing the novel compounds and their yields and MS data.
| Reactant A | Reactant B | Chemical Structure of Novel Compound | Yield (%) | Mass(M+) Theoretical (found) |
|---|---|---|---|---|
| Intermediate B1 | Intermediate A12 | 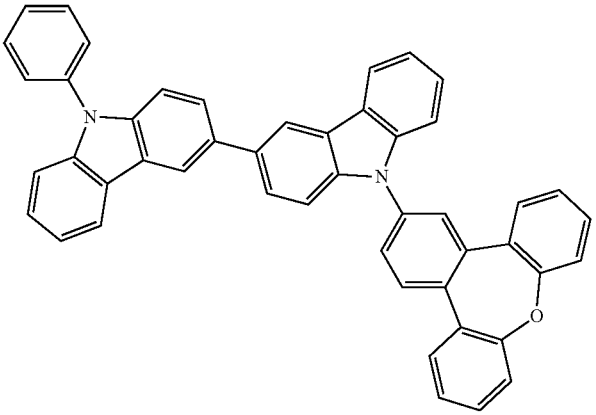<br>Compound 30 | 95.0% | 650.76 ($C_{48}H_{30}N_2O$) |
| Intermediate A10 | Intermediate C5 | 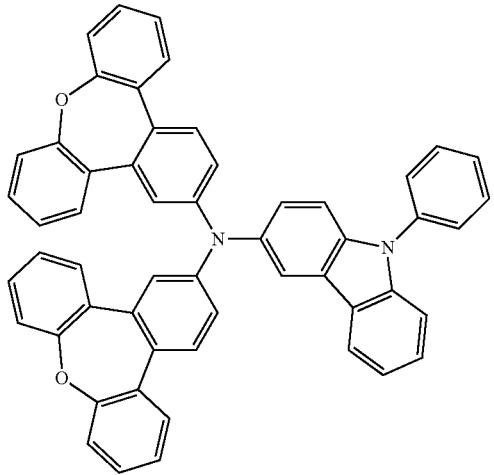<br>Compound 31 | 92.5% | 742.86 ($C_{54}H_{34}N_2O_2$) |

TABLE 5-continued
The reactants A and B used for preparing the novel compounds and their yields and MS data.
| Reactant A | Reactant B | Chemical Structure of Novel Compound | Yield (%) | Mass(M⁺) Theoretical (found) |
|---|---|---|---|---|
| Intermediate C1 | Intermediate C7 | 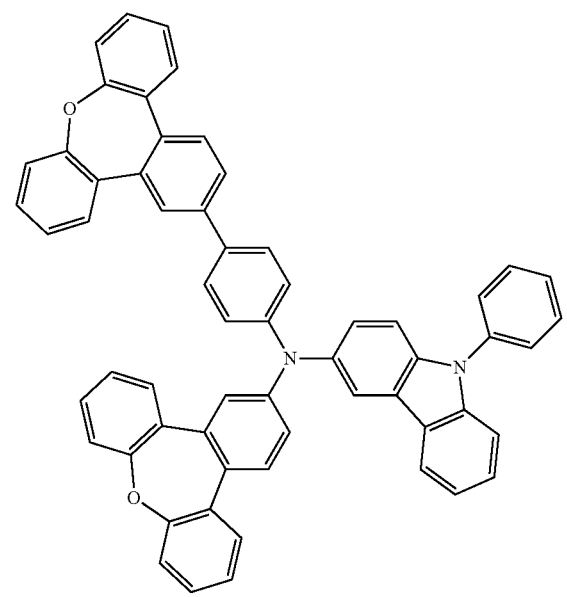<br>Compound 32 | 87.9% | 818.96 ($C_{60}H_{38}N_2O_2$) |
| Intermediate A14 | Intermediate C5 | 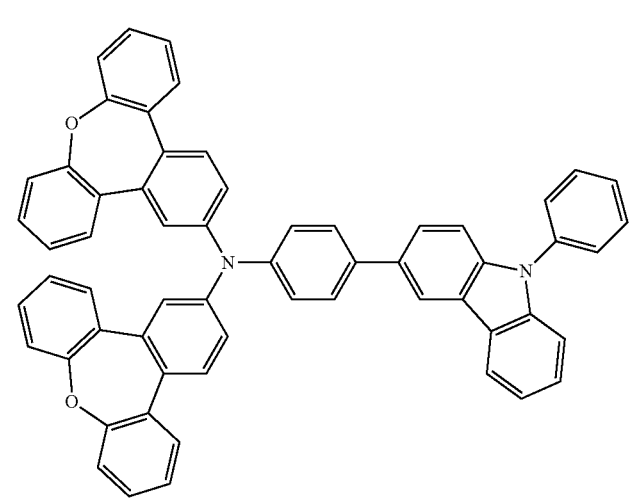<br>Compound 33 | 93.3% | 818.96 ($C_{60}H_{38}N_2O_2$) |

TABLE 5-continued
The reactants A and B used for preparing the novel compounds and
their yields and MS data.
| Reactant A | Reactant B | Chemical Structure of Novel Compound | Yield (%) | Mass(M⁺) Theoretical (found) |
|---|---|---|---|---|
| Intermediate B3 | Intermediate C8 | 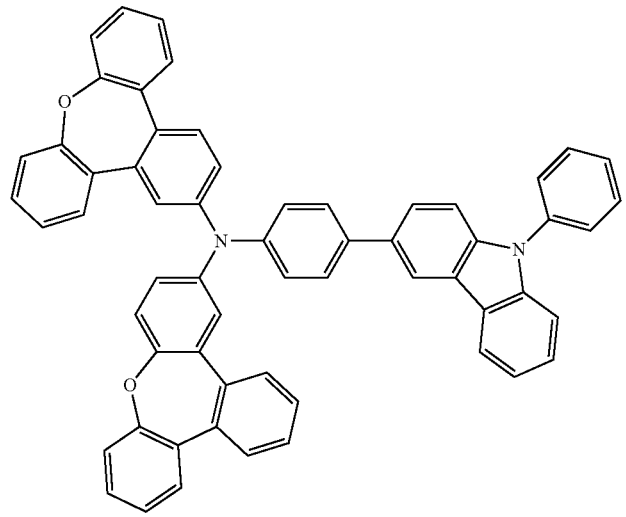<br>Compound 34 | 82.5% | 895.05 ($C_{66}H_{42}N_2O_2$) |
| Intermediate C1 | Intermediate C8 | 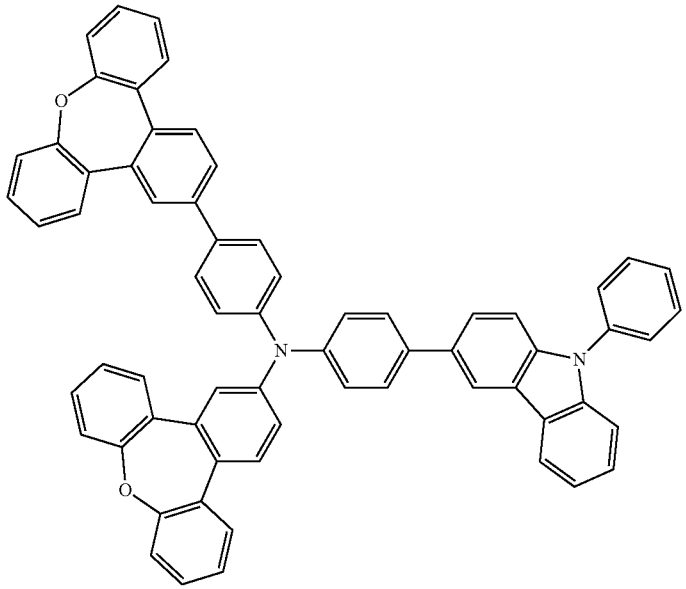<br>Compound 35 | 88.6% | 895.05 ($C_{66}H_{42}N_2O_2$) |

TABLE 5-continued
The reactants A and B used for preparing the novel compounds and their yields and MS data.
| Reactant A | Reactant B | Chemical Structure of Novel Compound | Yield (%) | Mass(M+) Theoretical (found) |
|---|---|---|---|---|
| Intermediate B1 | Intermediate A29 | 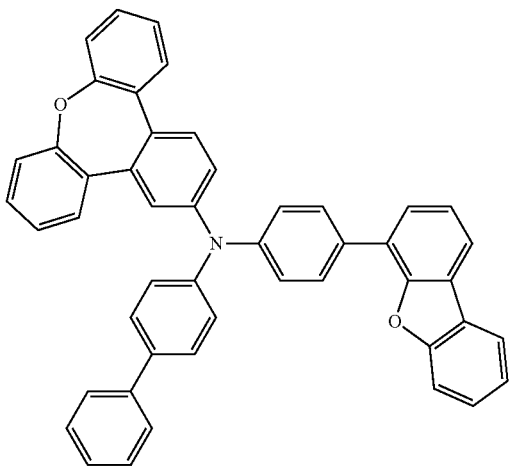 Compound 36 | 90.1% | 653.77 ($C_{48}H_{31}NO_2$) |
| Intermediate C1 | Intermediate A29 | 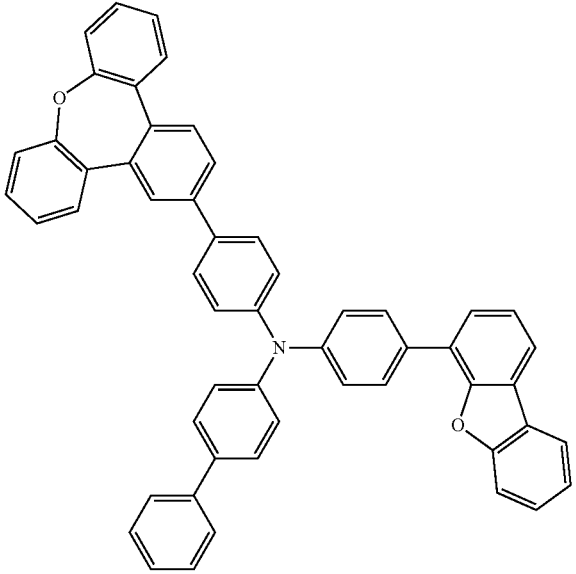 Compound 37 | 91.3% | 729.86 ($C_{54}H_{35}NO_2$) |

TABLE 5-continued
The reactants A and B used for preparing the novel compounds and their yields and MS data.
| Reactant A | Reactant B | Chemical Structure of Novel Compound | Yield (%) | Mass(M+) Theoretical (found) |
|---|---|---|---|---|
| Intermediate C2 | Intermediate A29 | 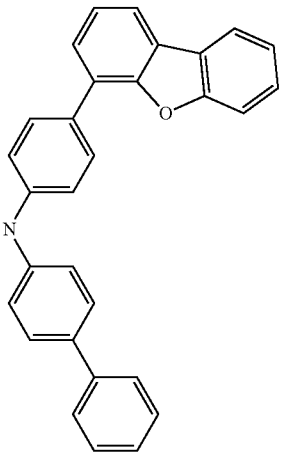Compound 38 | 86.3% | 729.86 ($C_{54}H_{35}NO_2$) |
| Intermediate B1 | Intermediate A30 | 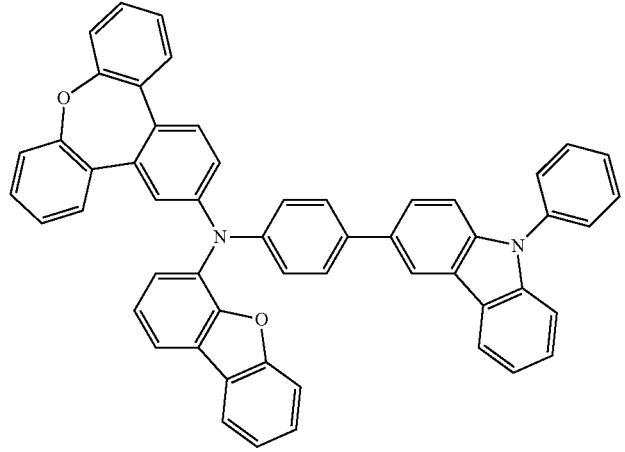Compound 39 | 88.4% | 742.86 ($C_{54}H_{34}N_2O_2$) |
| Intermediate B1 | Intermediate A31 | 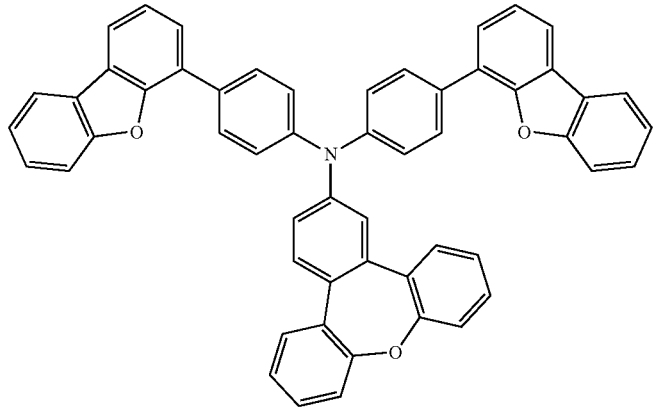Compound 40 | 94.5% | 743.84 ($C_{54}H_3.NO3$) |

TABLE 5-continued
The reactants A and B used for preparing the novel compounds and their yields and MS data.
| Reactant A | Reactant B | Chemical Structure of Novel Compound | Yield (%) | Mass(M+) Theoretical (found) |
|---|---|---|---|---|
| Intermediate B3 | Intermediate C9 | 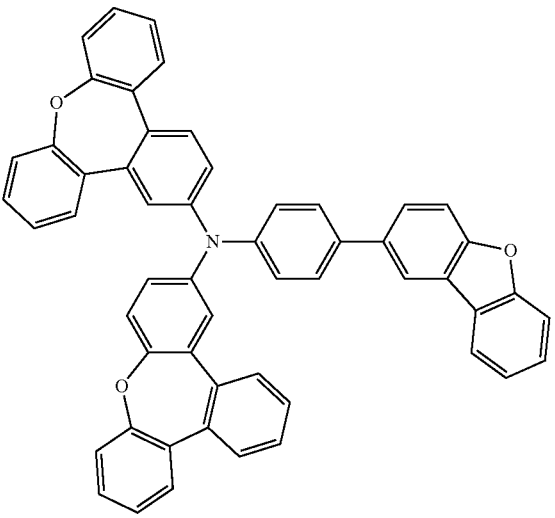<br>Compound 41 | 94.5% | 743.84 ($C_{54}H_{33}NO_3$) |
| Intermediate B1 | Intermediate A27 | 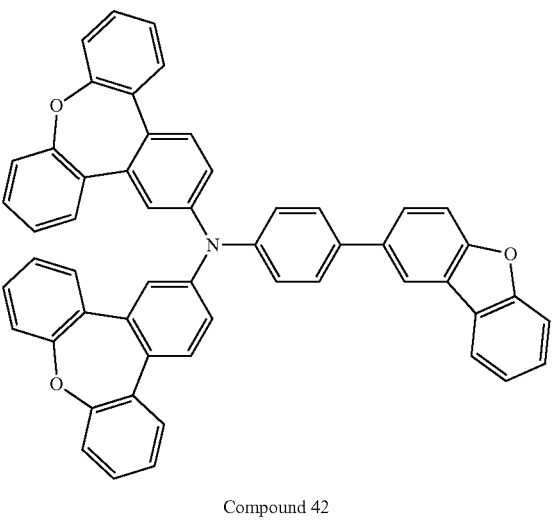 [SMILES: c1ccc2c(c1)Oc1ccccc1-c1cc(N(c3ccc(-c4ccc5oc6ccccc6c5c4)cc3)c3ccc4c(c3)-c3ccccc3Oc3ccccc3-4)ccc1-2]<br>Compound 42 | 91.3% | 743.84 ($C_{54}H_{33}NO_3$) |

TABLE 5-continued

The reactants A and B used for preparing the novel compounds and their yields and MS data.

| Reactant A | Reactant B | Chemical Structure of Novel Compound | Yield (%) | Mass(M+) Theoretical (found) |
|---|---|---|---|---|
| Intermediate C1 | Intermediate A32 | Compound 43 | 86.5% | 818.96 ($C_{60}H_{38}N_2O_2$) |

Preparation of OLED Devices

A glass substrate coated with ITO layer in a thickness of 1500 Å was placed in distilled water containing a detergent dissolved therein, and was ultrasonically washed. The detergent was a product manufactured by Fischer Co., and the distilled water was distilled water filtered twice through a filter (Millipore Co.). After the ITO layer had been washed for 30 minutes, it was ultrasonically washed twice with distilled water for 10 minutes. After the completion of washing, the glass substrate was ultrasonically washed with isopropyl alcohol, acetone and methanol solvents and then dried, after which it was transported to a plasma cleaner. Then the substrate was cleaned with oxygen plasma for 5 minutes, and then transferred to a vacuum evaporator.

After that, various organic materials and metal materials were sequentially deposited on the ITO substrate to obtain the OLED device of each of the following Examples and Comparative Examples. The vacuum degree during the deposition was maintained at $1\times10^{-6}$ to $3\times10^{-7}$ torr. Herein, the ITO substrate was deposited with a first hole injection layer (HIL-1), a second hole injection layer (HIL-2), a first hole transporting layer (HTL-1), a second hole transporting layer (HTL-2), a blue/green/red emission layer (BEL/GEL/REL), an electron transporting layer (ETL), an electron injection layer (EIL), and a cathode (Cthd).

Herein, HAT was a material for forming HIL-1; the foresaid novel compounds, HI-2, and HI-2' might be the material for forming HIL-2; the foresaid novel compounds and commercial HT-1, HT-2, or HT-2' might be the material for forming HTL-1 or HTL-2; ET was materials for forming ETL; Liq was a material for forming ETD and EIL. RH/GH/BH were host material for forming REL/GEL/BEL, and RD/GD/BD-1 or BD-2 were dopant for forming REL/GEL/BEL. The detailed chemical structures of foresaid commercial materials were listed in Table 6, and the novel compounds of the present invention were listed in Table 5.

TABLE 6 chemical structures of commercial materials for OLED devices.

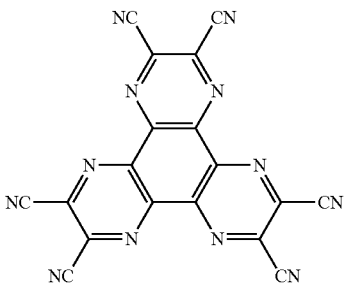 [SMILES: N#Cc1nc2c3nc(C#N)c(C#N)nc3c3nc(C#N)c(C#N)nc3c2nc1C#N]

HAT

TABLE 6-continued
chemical structures of commercial materials for OLED devices.
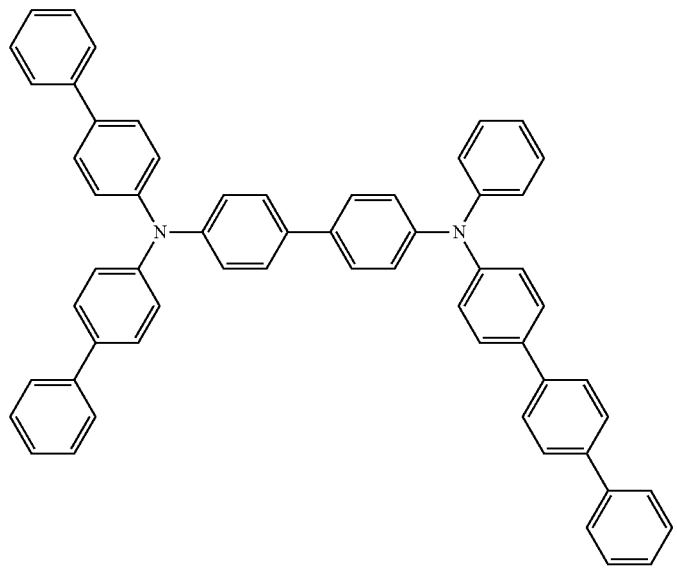 [SMILES: c1ccc(-c2ccc(-c3ccc(N(c4ccccc4)c4ccc(-c5ccc(N(c6ccc(-c7ccccc7)cc6)c6ccc(-c7ccccc7)cc6)cc5)cc4)cc3)cc2)cc1]
HI-2
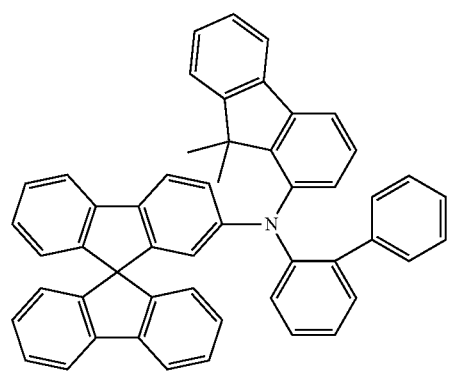 [SMILES: CC1(C)c2ccccc2-c2cccc(N(c3ccc4c(c3)C3(c5ccccc5-c5ccccc53)c3ccccc3-4)c3ccccc3-c3ccccc3)c21]
HT-1
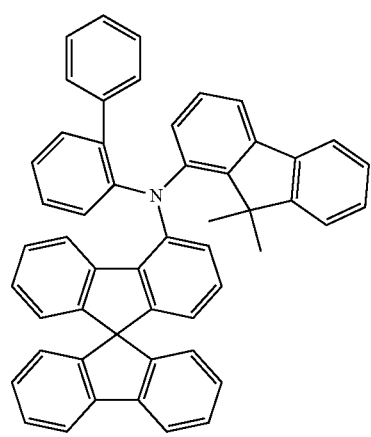 [SMILES: CC1(C)c2ccccc2-c2cccc(N(c3ccccc3-c3ccccc3)c3cccc4c3-c3ccccc3C43c4ccccc4-c4ccccc43)c21]
HT-2

TABLE 6-continued
chemical structures of commercial materials for OLED devices.
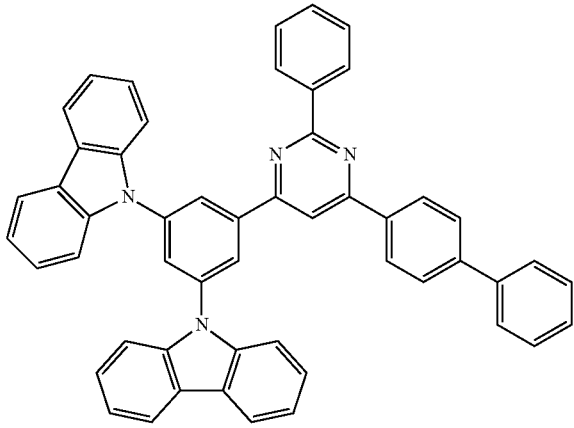 [SMILES: c1ccc(-c2ccc(-c3cc(-c4cc(-n5c6ccccc6c6ccccc65)cc(-n5c6ccccc6c6ccccc65)c4)nc(-c4ccccc4)n3)cc2)cc1] ET
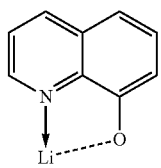 Liq
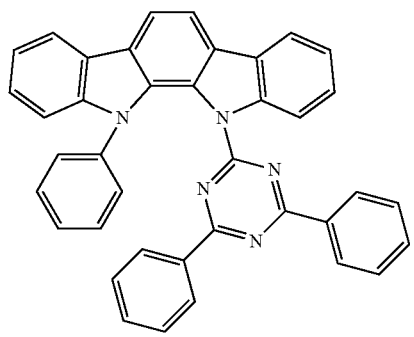 [SMILES: c1ccc(-c2nc(-c3ccccc3)nc(-n3c4ccccc4c4ccc5c6ccccc6n(-c6ccccc6)c5c43)n2)cc1] RH
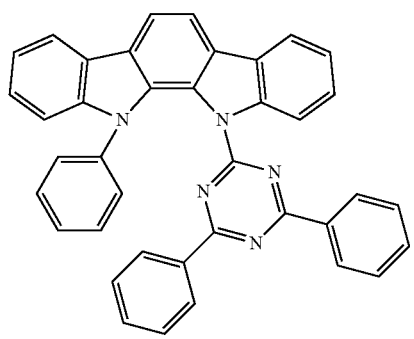 [SMILES: c1ccc(-c2nc(-c3ccccc3)nc(-n3c4ccccc4c4ccc5c6ccccc6n(-c6ccccc6)c5c43)n2)cc1] GH
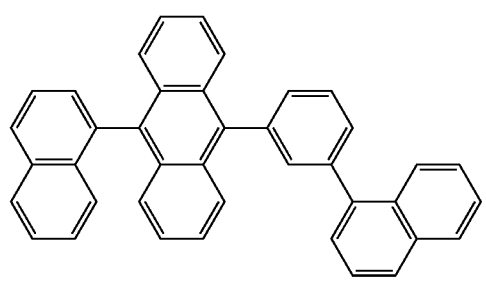 [SMILES: c1cc(-c2cccc3ccccc23)cc(-c2c3ccccc3c(-c3cccc4ccccc34)c3ccccc23)c1] BH TABLE 6-continued
chemical structures of commercial materials for OLED devices.
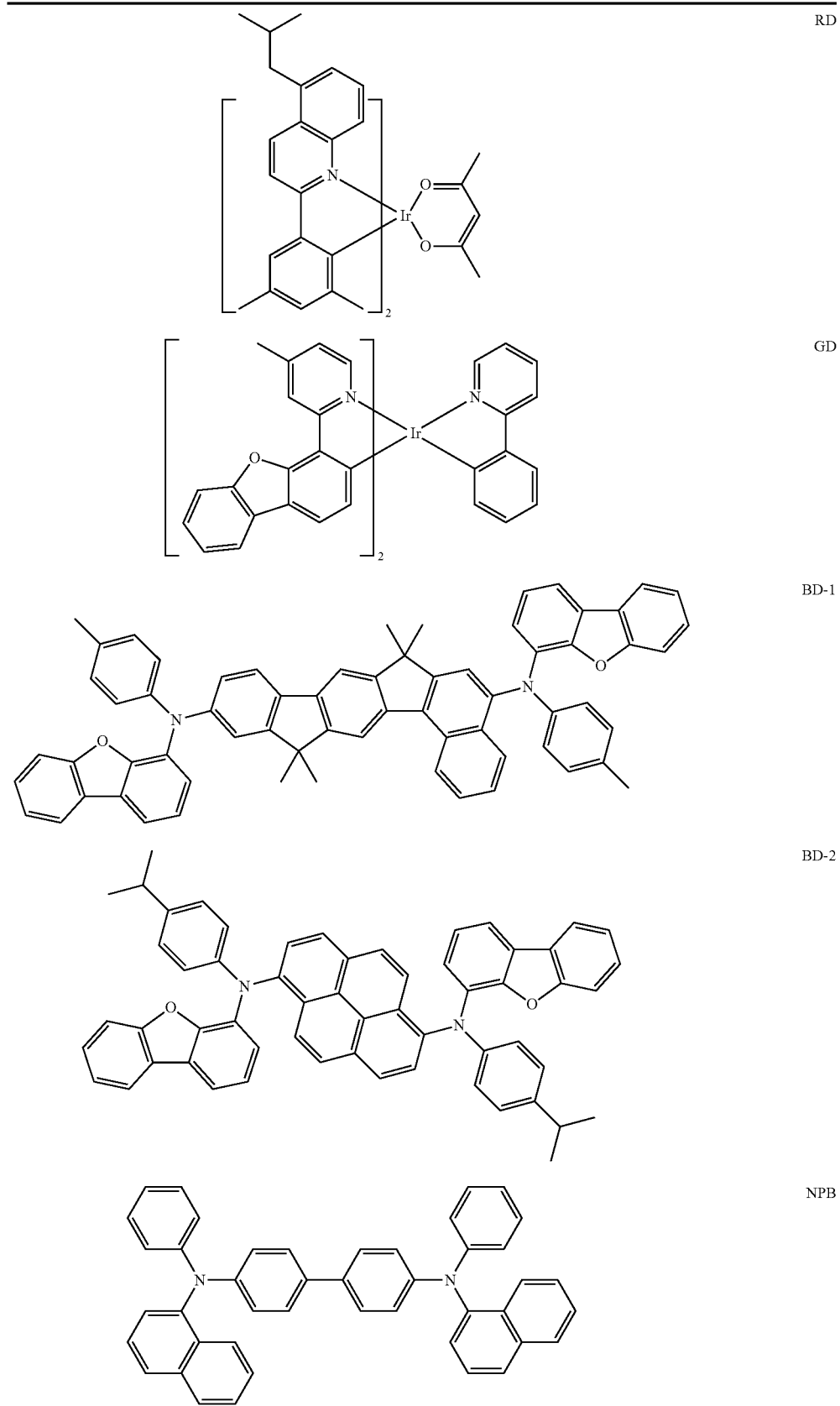
RD
GD
BD-1
BD-2
NPB TABLE 6-continued chemical structures of commercial materials for OLED devices.

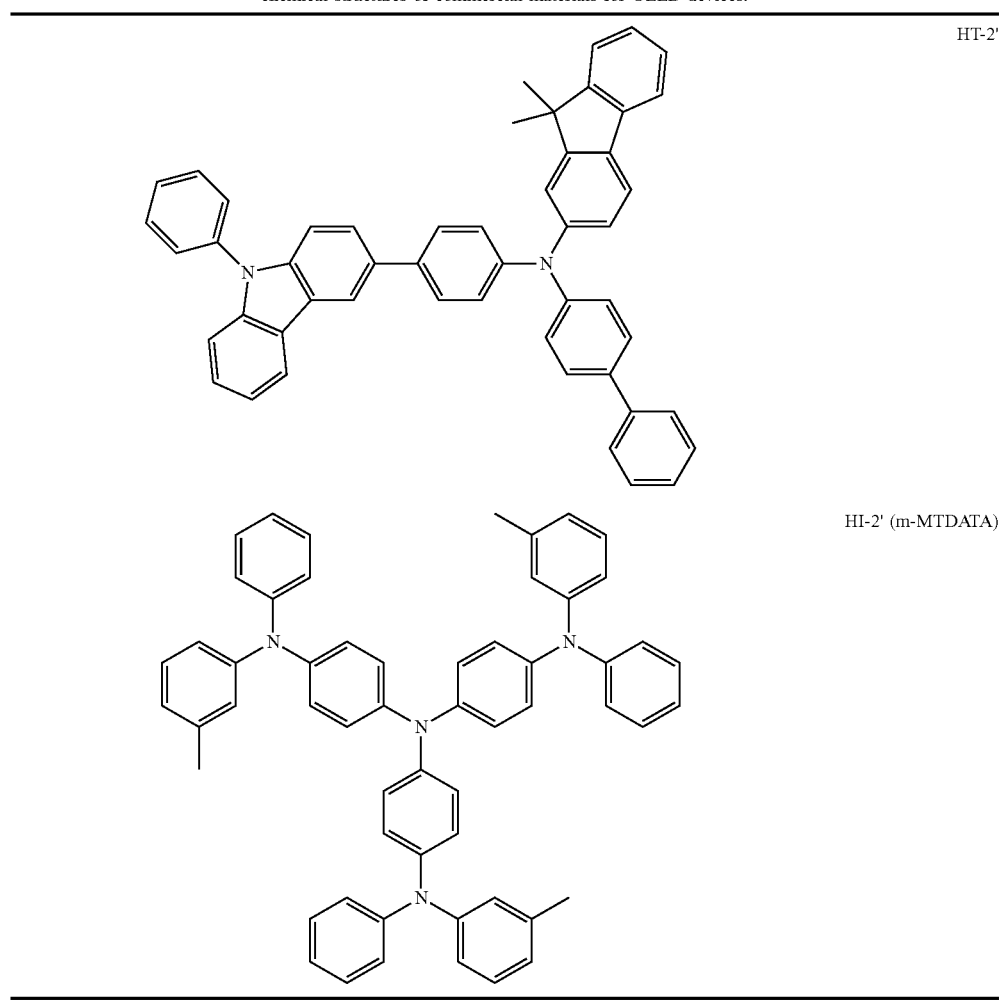

HT-2'

HI-2' (m-MTDATA)

Preparation of Red OLED Devices

To prepare the red OLED device, multiple organic layers were respectively deposited on the ITO substrate according to the sequence as listed in Table 7, and the materials and the thicknesses of the organic layers in red OLED devices were also listed in Table 7.

TABLE 7 coating sequence, materials and thickness of the organic layers in red OLED device.

| Coating Sequence | Layer | Material | Thickness |
|---|---|---|---|
| 1 | HIL-1 | HAT | 100 Å |
| 2 | HIL-2 | HI-2 or novel compound doped with 5.0 wt % of HAT | 2100 Å |
| 3 | HTL-1 | Commercial HT-1 or novel compound | 100 Å |
| 4 | HTL-2 | Commercial HT-2 or novel compound | 100 Å |
| 5 | REL | RH doped with 3.5 wt % of RD | 300 Å |
| 6 | ETL | ET doped with 35.0 wt % of Liq | 350 Å |
| 7 | EIL | Liq | 15 Å |
| 8 | Cthd | Al | 1500 Å |

Preparation of Green OLED Devices

To prepare the green OLED device, multiple organic layers were respectively deposited on the ITO substrate according to the sequence as listed in Table 8, and the materials and the thicknesses of the organic layers in green OLED devices were also listed in Table 8.

TABLE 8 coating sequence, materials and thickness of the layers in green OLED device.

| Coating Sequence | Layer | Material | Thickness |
|---|---|---|---|
| 1 | HIL-1 | HAT | 100 Å |
| 2 | HIL-2 | HI-2 or novel compound doped with 5.0 wt % of HAT | 1300 Å |
| 3 | HTL-1 | Commercial HT-1 or novel compound | 100 Å |
| 4 | HTL-2 | Commercial HT-2 or novel compound | 100 Å |
| 5 | GEL | GH doped with 10.0 wt % of GD | 400 Å |
| 6 | ETL | ET doped with 35.0 wt % of Liq | 350 Å |
| 7 | EIL | Liq | 15 Å |
| 8 | Cthd | Al | 1500 Å |

Preparation of Blue OLED Devices

To prepare the blue OLED device, multiple organic layers were respectively deposited on the ITO substrate according to the sequence as listed in Table 9, and the materials and the thicknesses of the organic layers in blue OLED devices were also listed in Table 9.

TABLE 9 coating sequence, materials and thickness of the layers in blue OLED device.

| Coating Sequence | Layer | Material | Thickness |
|---|---|---|---|
| 1 | HIL-1 | HAT | 100 Å |
| 2 | HIL-2 | HI-2 or novel compound doped with 5.0 wt % of HAT | 750 Å |
| 3 | HTL-1 | Commercial HT-1 or novel compound | 100 Å |
| 4 | HTL-2 | Commercial HT-2 or novel compound | 100 Å |
| 5 | BEL | BH doped with 3.5 wt % of BD-1 or BD-2 | 250 Å |
| 6 | ETL | ET doped with 35.0 wt % of Liq | 250 Å |
| 7 | EIL | Liq | 15 Å |
| 8 | Cthd | Al | 1500 Å |

Performance of OLED Device

To evaluate the performance of OLED devices, red, green, and blue OLED devices were measured by PR650 as photometer and Keithley 2400 as power supply. Color coordinates (x,y) were determined according to the CIE chromaticity scale (Commission Internationale de L'Eclairage, 1931). The results were shown in Tables 10 to 12. For the blue and red OLED devices, the data were collected at 1000 nits. For the green OLED devices, the data were collected at 3000 nits.

In the first test example, the materials of HL-2, HTL-1, and HTL-2, color and data of CIE, driving voltage, and current efficiency of Examples 1 to 13 (E1 to E13) and Comparative Examples 1 to 3 (C1 to C3) were listed in Table 10. The difference between the examples and the comparative examples was the material of the HIL-2.

TABLE 10 materials of HIL-2, HTL-1, and HTL-2, voltage, CIE (x, y) and current efficiency (E) of OLED devices of Examples 1 to 13 and Comparative Examples 1 to 3.

| Example No. | Material HIL-2 | HTL-1 | HTL-2 | Voltage (V) | CIE (x, y) | E (cd/A) |
|---|---|---|---|---|---|---|
| E1 | Compound 24 | HT1 | HT-2 | 5.33 | B(0.136, 0.171) | 10.9 |
| E2 | Compound 25 | HT-1 | HT-2 | 5.27 | B(0.137, 0.163) | 9.59 |
| E3 | Compound 26 | HT-1 | HT-2 | 4.73 | B(0.136, 0.166) | 12.7 |
| E4 | Compound 43 | HT-1 | HT-2 | 6.11 | B(0.136, 0.174) | 8.99 |
| E5 | Compound 19 | HT-1 | HT-2 | 5.73 | B(0.136, 0.176) | 10.7 |
| C1 | m-MTDATA | HT-1 | HT-2 | 6.81 | B(0.14, 0.187) | 4.59 |
| E6 | Compound 24 | HT-1 | HT-2 | 3.29 | G(0.312, 0.640) | 62 |
| E7 | Compound 25 | HT-1 | HT-2 | 4.08 | G(0.312, 0.638) | 67.8 |
| E8 | Compound 26 | HT-1 | HT-2 | 3.71 | G(0.308, 0.641) | 64.3 |
| E9 | Compound 19 | HT-1 | HT-2 | 4.19 | G(0.322, 0.634) | 63 |
| C2 | m-MTDATA | HT-1 | HT-2 | 4.22 | G(0.325, 0.631) | 55.5 |
| E10 | Compound 16 | HT-1 | HT-2 | 4.59 | R(0.659, 0.339) | 24.4 |
| E11 | Compound 25 | HT-1 | HT-2 | 4.85 | R(0.662, 0.336) | 22.1 |
| E12 | Compound 26 | HT-1 | HT-2 | 4.36 | R(0.659, 0.339) | 22.4 |
| E13 | Compound 19 | HT-1 | HT-2 | 4.95 | R(0.661, 0.338) | 22.7 |
| C3 | m-MTDATA | HT-1 | HT-2 | 5.1 | R(0.656, 0.341) | 20.4 |

In the above Table 10, the materials of HTL-1 of Examples were all commercial HT-1 as shown in Table 6, and the materials of HTL-2 of Examples were all commercial HT-2 as shown in Table 6. The dopants of BELs of blue OLEDs of E1 to E5 and C1 were BD-1.

According to the results of Table 10, in comparison with the commercial hole injection material m-MTDATA, adopting the novel compound of the present invention as the hole injection material can reduce the driving voltage and improve the current efficiency of the red, green, or blue OLEDs. It demonstrated that the novel compound of the present invention is suitable as a hole injection material for any color OLEDs, and allows the OLEDs using the same to have low driving voltage and improved current efficiency.

In the second test example, the materials of HIL-2, HTL-1, and HTL-2, color and data of CIE, driving voltage, and current efficiency of Examples 14 to 69 (E14 to E69) and Comparative Examples 4 to 9 (C4 to C9) were listed in Table 11. The major difference between the examples and the comparative examples was the material of the HTL-1. The material of the hole injection layer of E14 to E69 and C4 to C9 was commercial HI-2 as listed in Table 6.

TABLE 11 materials of dopant of emission layer, HTL-1, and HTL-2, voltage, CIE (x, y) and current efficiency (E) of OLED devices of Examples 14 to 69 and Comparative Examples 4 to 9.

| Exp | Dopant of emission layer | Material HTL-1 | HTL-2 | Voltage (V) | CIE (x, y) | E (cd/A) |
|---|---|---|---|---|---|---|
| E14 | BD-1 | compound 1 | HT-2 | 4.25 | B(0.136, 0.178) | 13 |
| E15 | BD-1 | compound 2 | HT-2 | 4.34 | B(0.136, 0.188) | 13.2 |
| E16 | BD-1 | compound 9 | HT-2 | 4.6 | B(0.136, 0.181) | 12.4 |
| E17 | BD-1 | compound 15 | HT-2 | 4.47 | B(0.136, 0.173) | 13.3 |
| E18 | BD-1 | compound 12 | HT-2 | 4.4 | B(0.136, 0.171) | 12.1 |
| E19 | BD-1 | compound 27 | HT-2 | 4.33 | B(0.136, 0.178) | 12.7 |
| E20 | BD-1 | compound 28 | HT-2 | 4.52 | B(0.136, 0.184) | 11.6 |
| E21 | BD-1 | compound 29 | HT-2 | 4.29 | B(0.136, 0.171) | 12 |
| E22 | BD-1 | compound 31 | HT-2 | 4.57 | B(0.136, 0.195) | 13 |
| E23 | BD-1 | compound 32 | HT-2 | 4.42 | B(0.136, 0.178) | 13.1 |
| E24 | BD-1 | compound 36 | HT-2 | 4.21 | B(0.136, 0.168) | 12.6 |
| E25 | BD-1 | compound 37 | HT-2 | 4.74 | B(0.137, 0.163) | 11 |
| E26 | BD-1 | compound 39 | HT-2 | 4.41 | B(0.135, 0.181) | 11.1 |
| E27 | BD-1 | compound 42 | HT-2 | 4.65 | B(0.136, 0.177) | 11.3 |
| E28 | BD-2 | compound 38 | HT-2 | 4.53 | B(0.13, 0.155) | 11 |
| E29 | BD-2 | compound 5 | HT-2 | 4.66 | B(0.13, 0.155) | 10.4 |
| E30 | BD-2 | compound 14 | HT-2 | 4.69 | B(0.130, 0.152) | 11.2 |
| E31 | BD-2 | compound 7 | HT-2 | 4.56 | B(0.129, 0.156) | 10.2 |
| E32 | BD-2 | compound 34 | HT-2 | 4.53 | B(0.13, 0.150) | 10.8 |
| C4 | BD-1 | NPB | HT-2 | 4.97 | B(0.129, 0.180) | 10.6 |
| C5 | BD-2 | NPB | HT-2 | 4.77 | B(0.129, 0.160) | 9.5 |
| E33 | GD | compound 1 | HT-2 | 3.36 | G(0.319, 0.637) | 75.9 |
| E34 | GD | compound 2 | HT-2 | 3.29 | G(0.319, 0.636) | 71.4 |
| E35 | GD | compound 14 | HT-2 | 3.33 | G(0.312, 0.639) | 70.5 |
| E36 | GD | compound 7 | HT-2 | 3.63 | G(0.308, 0.640) | 71.0 |
| E37 | GD | compound 8 | HT-2 | 3.46 | G(0.315, 0.638) | 81.7 |
| E38 | GD | compound 10 | HT-2 | 3.59 | G(0.309, 0.639) | 74.5 |
| E39 | GD | compound 9 | HT-2 | 3.59 | G(0.320, 0.636) | 73.7 |
| E40 | GD | compound 15 | HT-2 | 3.50 | G(0.320, 0.636) | 78.8 |
| E41 | GD | compound 17 | HT-2 | 3.18 | G(0.313, 0.639) | 71.3 |
| E42 | GD | compound 11 | HT-2 | 3.55 | G(0.312, 0.640) | 78.0 |
| E43 | GD | compound 27 | HT-2 | 3.42 | G(0.317, 0.638) | 76.3 |
| E44 | GD | compound 28 | HT-2 | 3.10 | G(0.315, 0.638) | 75.5 |
| E45 | GD | compound 29 | HT-2 | 3.30 | G(0.311, 0.640) | 74.3 |
| E46 | GD | compound 31 | HT-2 | 3.24 | G(0.32, 0.636) | 71.6 |
| E47 | GD | compound 33 | HT-2 | 3.12 | G(0.313, 0.639) | 74.0 |
| E48 | GD | compound 34 | HT-2 | 3.49 | G(0.312, 0.640) | 74.0 |
| E49 | GD | compound 36 | HT-2 | 3.26 | G(0.313, 0.639) | 70.6 |
| E50 | GD | compound 37 | HT-2 | 3.29 | G(0.31, 0.640) | 71.3 |
| E51 | GD | compound 40 | HT-2 | 3.50 | G(0.31 0.640) | 70.5 |
| E52 | GD | compound 42 | HT-2 | 3.39 | G(0.312, 0.640) | 74.3 |
| C6 | GD | NPB | HT-2 | 3.68 | G(0.317, 0.637) | 70.1 |
| C7 | GD | HT-1 | HT-2 | 5.64 | G(0.318, 0.637) | 69.4 |
| E53 | RD | compound 1 | HT-2 | 3.47 | R(0.662, 0.337) | 22.5 |
| E54 | RD | compound 2 | HT-2 | 3.36 | R(0.660, 0.339) | 23.8 |
| E55 | RD | compound 14 | HT-2 | 3.30 | R(0.661, 0.338) | 23.1 |
| E56 | RD | compound 7 | HT-2 | 3.58 | R(0.658, 0.340) | 24.0 |
| E57 | RD | compound 10 | HT-2 | 3.56 | R(0.659, 0.339) | 23.6 |
| E58 | RD | compound 9 | HT-2 | 3.63 | R(0.659, 0.339) | 24.7 |
| E59 | RD | compound 17 | HT-2 | 3.29 | R(0.662, 0.337) | 20.9 |
| E60 | RD | compound 11 | HT-2 | 3.61 | R(0.660, 0.339) | 22.8 |
| E61 | RD | compound 12 | HT-2 | 3.49 | R(0.661, 0.338) | 23.1 |

TABLE 11-continued materials of dopant of emission layer, HTL-1, and HTL-2, voltage, CIE (x, y) and current efficiency (E) of OLED devices of Examples 14 to 69 and Comparative Examples 4 to 9.

| Exp | Dopant of emission layer | Material HTL-1 | HTL-2 | Voltage (V) | CIE (x, y) | E (cd/A) |
|---|---|---|---|---|---|---|
| E62 | RD | compound 27 | HT-2 | 3.58 | R(0.662, 0.337) | 23.4 |
| E63 | RD | compound 28 | HT-2 | 3.32 | R(0.659, 0.340) | 23.7 |
| E64 | RD | compound 29 | HT-2 | 3.39 | R(0.66, 0.339) | 24.0 |
| E65 | RD | compound 31 | HT-2 | 3.38 | R(0.663, 0.335) | 23.5 |
| E66 | RD | compound 33 | HT-2 | 3.25 | R(0.659, 0.340) | 24.1 |
| E67 | RD | compound 36 | HT-2 | 3.35 | R(0.659, 0.340) | 22.9 |
| E68 | RD | compound 37 | HT-2 | 3.36 | R(0.658, 0.340) | 23.0 |
| E69 | RD | compound 42 | HT-2 | 3.55 | R(0.661, 0.338) | 25.2 |
| C8 | RD | NPB | HT-2 | 3.67 | R(0.661, 0.330) | 21.3 |
| C9 | RD | HT-1 | HT-2 | 3.69 | R(0.667, 0.332) | 20.7 |

In the third test example, the materials of HTL-1, and HTL-2, color and data of CIE, driving voltage, and current efficiency of Examples 70 to 81 (E70 to E81) and Comparative Examples 10 to 15 (C10 to C15) were listed in Table 12. The major difference between the examples and the comparative examples was the material of the HTL-2. The material of the hole injection layer of E70 to E83 and C10 to C15 was commercial HI-2 as listed in Table 6 and the material of the dopant of BEL of E70 to E72, C10, and C11 was BD-2 as listed in Table 6.

TABLE 12 materials of HTL-1 and HTL-2, voltage, CIE (x, y) and current efficiency (E) of OLED devices of Examples 70 to 81 and Comparative Examples 10 to 15.

| Exp | Material HTL-1 | HTL-2 | Voltage (V) | CIE (x, y) | E (cd/A) |
|---|---|---|---|---|---|
| E70 | HT-1 | compound 1 | 4.12 | B(0.135, 0.165) | 11.4 |
| E71 | HT-1 | compound 3 | 4.11 | B(0.128, 0.156) | 11.4 |
| E72 | HT-1 | compound 13 | 4.08 | B(0.13, 0.144) | 10.9 |
| C10 | HT-1 | HT-2' | 4.49 | B(0.129, 0.169) | 9.1 |
| C11 | HT-1 | HT-2 | 4.14 | B(0.129, 0.151) | 10.4 |
| E73 | HT-1 | compound 1 | 3.16 | G(0.317, 0.638) | 75.0 |
| E74 | HT-1 | compound 3 | 3.41 | G(0.318, 0.636) | 70.0 |
| E75 | HT-1 | compound 6 | 3.51 | G(0.315, 0.637) | 71.8 |
| E76 | HT-1 | compound 13 | 3.42 | G(0.314, 0.632) | 72.4 |
| C12 | HT-1 | HT-2' | 3.82 | G(0.312, 0.639) | 48.6 |
| C13 | HT-1 | HT-2 | 5.64 | G(0.318, 0.637) | 69.4 |
| E77 | HT-1 | compound 1 | 3.36 | R(0.663, 0.336) | 21.3 |
| E78 | HT-1 | compound 3 | 3.51 | R(0.659, 0.339) | 21.4 |
| E79 | HT-1 | compound 11 | 3.24 | R(0.661, 0.338) | 22.7 |
| E80 | HT-1 | compound 13 | 3.36 | R(0.657, 0.342) | 24.9 |
| E81 | HT-1 | compound 41 | 3.6 | R(0.655, 0.343) | 28.4 |
| C14 | HT-1 | HT-2 | 3.69 | R(0.667, 0.332) | 20.7 |
| C15 | HT-1 | HT-2' | 6.43 | R(0.635, 0.354) | 6.88 |

According to the results of Tables 11 and 12, in comparison with the commercial hole transport material such as HT-1, HT-2 or HT-2', adopting the novel compound of the present invention as the hole transport material can reduce the driving voltage and improve the current efficiency of the red, green, or blue OLEDs. The beneficial effects of adopting the novel compounds as hole transport material can be found from the results of E14 to E27 in comparison with C4, the results of E28 to E32 in comparison with C5, the results of E33 to E52 in comparison with C6 and C7, the results of E53 to E69 in comparison with C8 and C9 as listed in Table 11. Likely, the beneficial effects of adopting the novel compounds as hole transport material also can be found from the results of E70 to E72 in comparison with C10 and C11, the results of E73 to E76 in comparison with C12 and C13, and the results of E77 to E81 in comparison with C14 and C15 as listed in Table 12. It demonstrated that the novel compound of the present invention is suitable as a hole transport material for any color OLEDs, and allows the OLEDs using the same to have low driving voltage and improved current efficiency.

Even though numerous characteristics and advantages of the present invention have been set forth in the foregoing description, together with details of the structure and features of the invention, the disclosure is illustrative only. Changes may be made in the details, especially in matters of quantity, position, and arrangement of substitution groups within the principles of the invention to the full extent indicated by the broad general meaning of the terms in which the appended claims are expressed.

What is claimed is:

1. A compound represented by the following Formula (I):

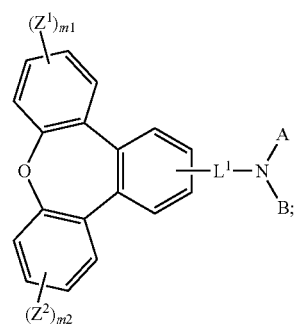

Formula (I)

wherein A is -$L^2$-$R^a$ and B is -$L^3$-$R^b$, or A and B are joined together and bonded to the nitrogen atom in Formula (I) to form a substituted or unsubstituted N-carbazolyl group;

$L^1$, $L^2$, and $L^3$ are each independently a single bond or an arylene group having 6 to 60 ring carbon atoms;

$R^a$ and $R^b$ are the same or different, and $R^a$ and $R^b$ are each independently selected from the group consisting of:
—Ar-Q,

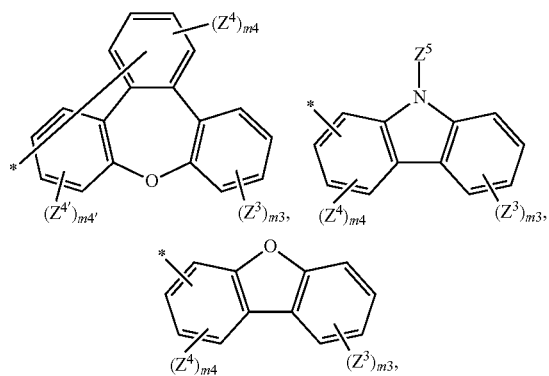

-continued

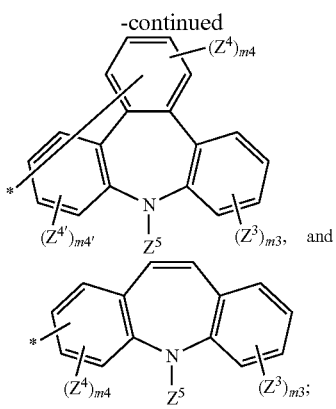

Ar is an arylene group having 6 to 60 ring carbon atoms;
Q is selected from the group consisting of: a hydrogen atom, a deuterium atom, and

$Q^1$ and $Q^2$ are the same or different, and $Q^1$ and $Q^2$ are each independently selected from the group consisting of: a substituted or unsubstituted aryl group having 6 to 60 ring carbon atoms,

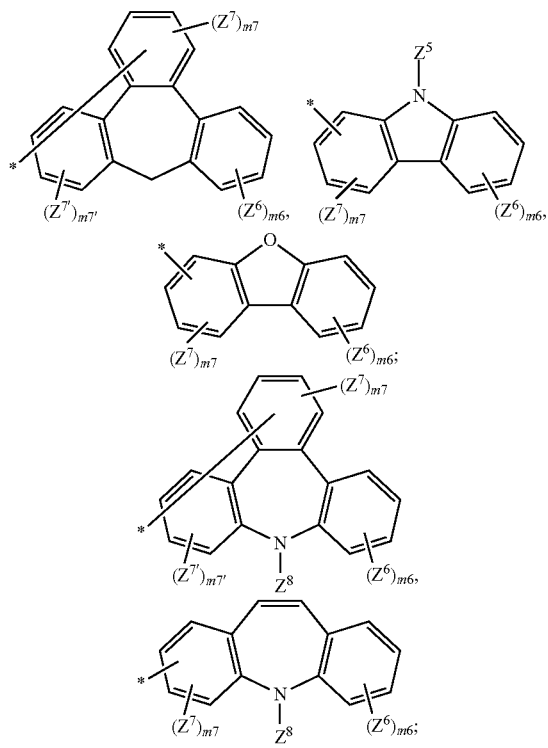

m1, m2, m3, and m6 are each independently an integral of 0 to 4, and m4, m4', m7, and m7' are each independently an integral of 0 to 3;
$Z^1$ to $Z^4$, $Z^{4'}$, $Z^6$, $Z^7$, and $Z^{7'}$ are each independently selected from the group consisting of: a deuterium atom, a trifluoromethyl group, a halogen group, a cyano group, a nitro group, an alkyl group having 1 to 40 carbon atoms, an alkenyl group having 2 to 40 carbon atoms, an alkynyl group having 2 to 40 carbon atoms, a cycloalkyl group having 3 to 60 ring carbon atoms, a heterocycloalkyl group having 3 to 60 ring carbon atoms, an aryl group having 6 to 60 ring carbon atoms, a heteroaryl group having 3 to 60 ring carbon atoms, an alkoxy group having 1 to 40 carbon atoms, an aryloxy group having 6 to 60 ring carbon atoms, an alkylsilyl group having 1 to 40 carbon atoms, an arylsilyl group having 6 to 60 ring carbon atoms, an alkylboron group having 1 to 40 carbon atoms, an arylboron group having 6 to 60 ring carbon atoms, a phosphine group having 1 to 40 carbon atoms, and a phosphine oxide group having 1 to 40 carbon atoms;
$Z^5$ and $Z^8$ are each independently selected from the group consisting of: a hydrogen atom, a deuterium atom, an alkyl group having 1 to 40 carbon atoms, an alkenyl group having 2 to 40 carbon atoms, an alkynyl group having 2 to 40 carbon atoms, a cycloalkyl group having 3 to 60 ring carbon atoms, a heterocycloalkyl group having 3 to 60 ring carbon atoms, an aryl group having 6 to 60 ring carbon atoms, and a heteroaryl group having 3 to 60 ring carbon atoms.

2. The compound as claimed in claim 1, wherein the compound is represented by

Formula (I-I)

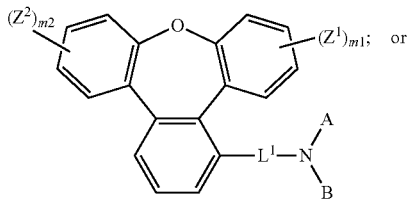

Formula (I-II)

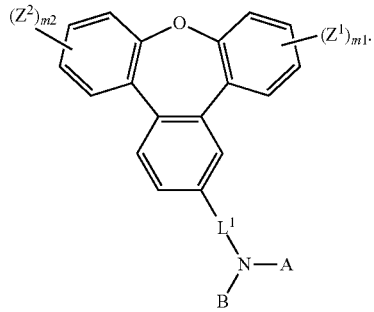

3. The compound as claimed in claim 1, wherein the compound is represented by

Formula (I-III)

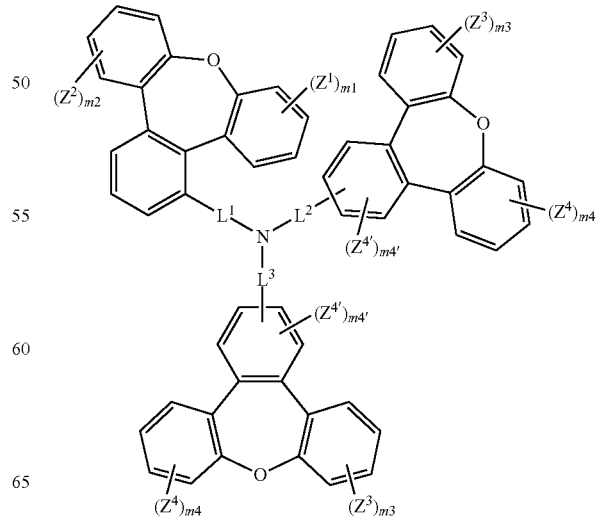

Formula (I-IV)
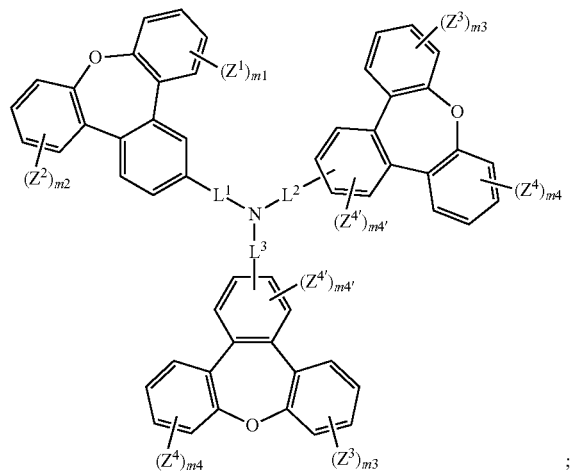
Formula (I-V)
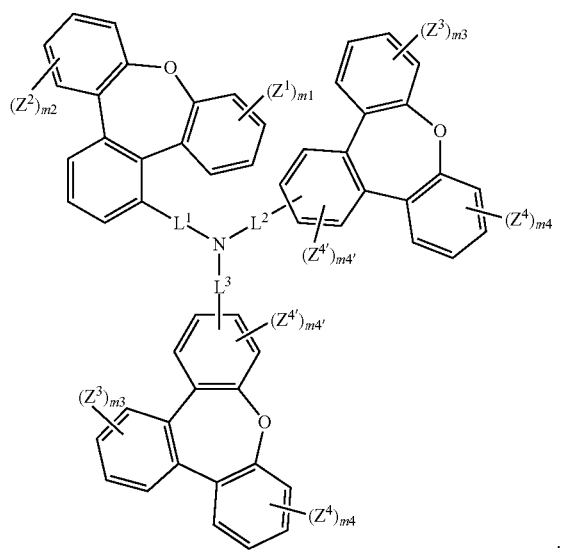
Formula (I-VI)
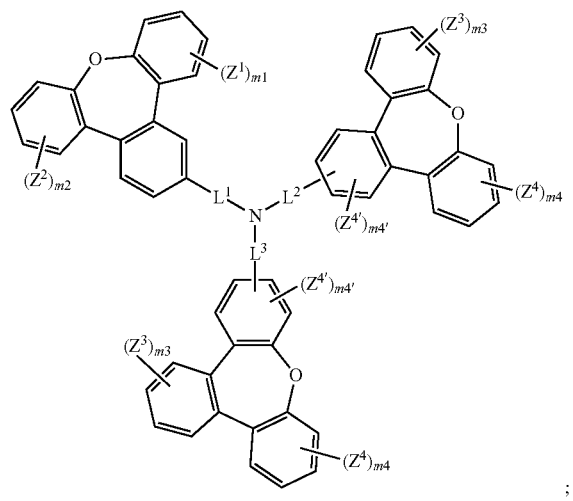
Formula (I-VII)
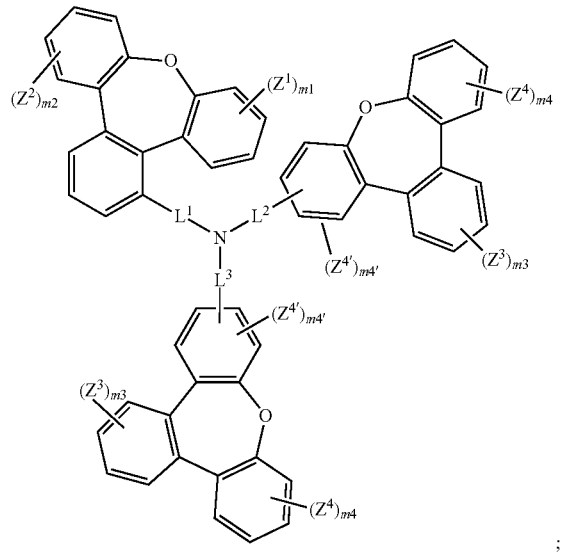
Formula (I-VIII)
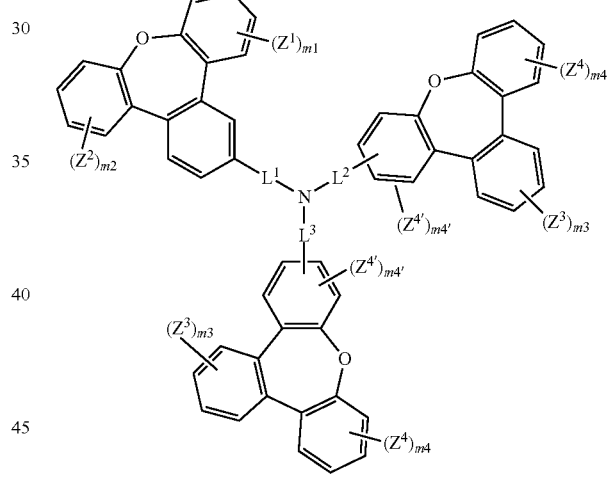
Formula (I-IX)
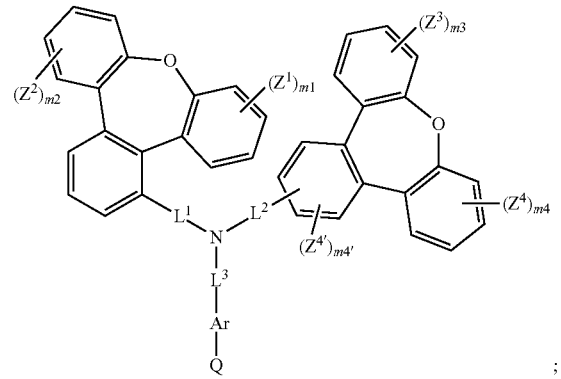

Formula (I-X)
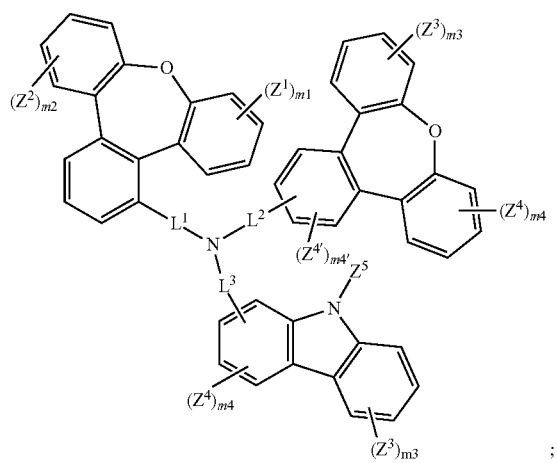
Formula (I-XI)
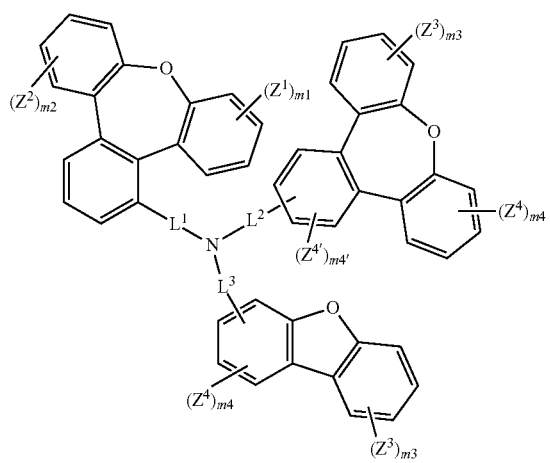
Formula (I-XII)
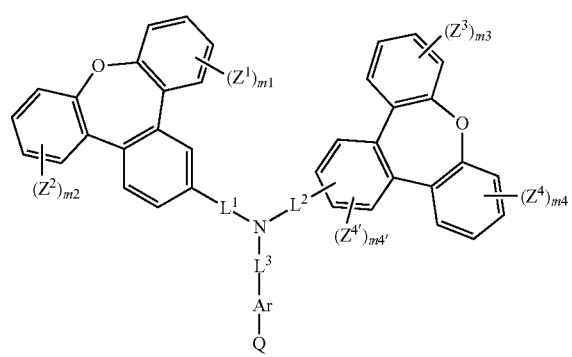
Formula (I-XIII)
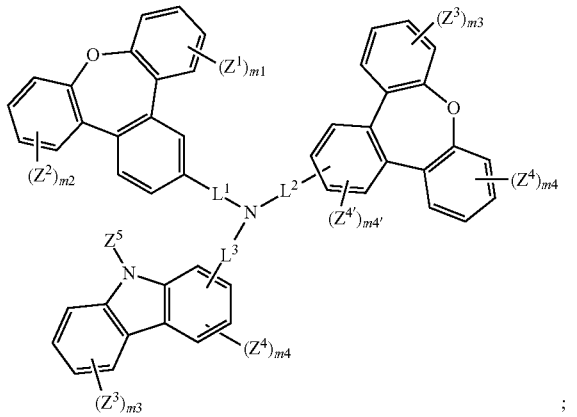
Formula (I-XIV)
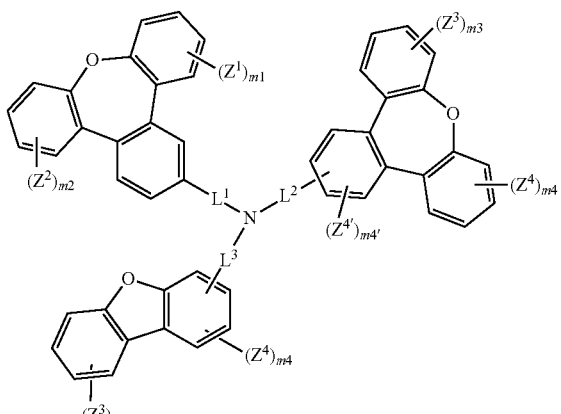
Formula (I-XV)
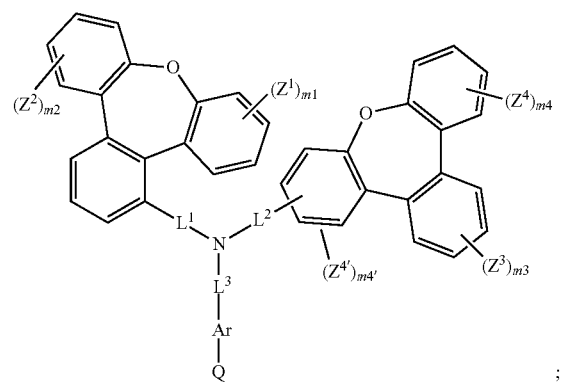

Formula (I-XVI)
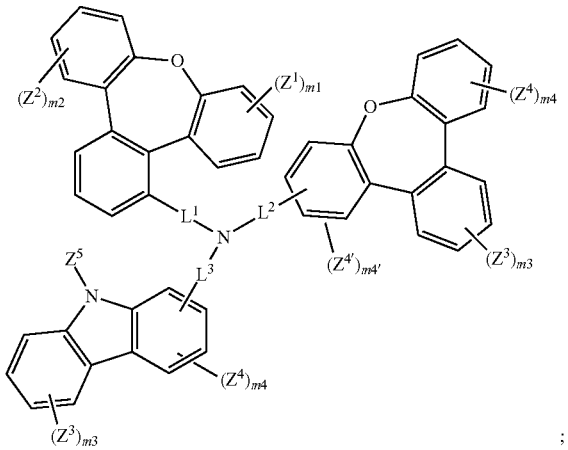
Formula (I-XVII)
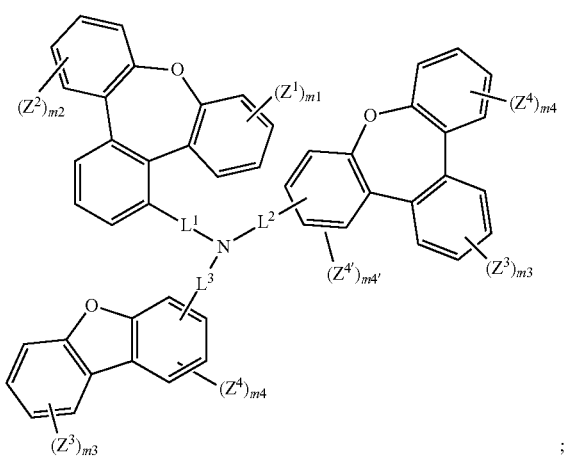
Formula (I-XVIII)
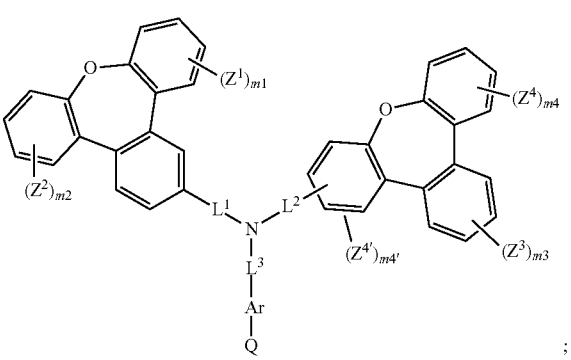
Formula (I-XIX)
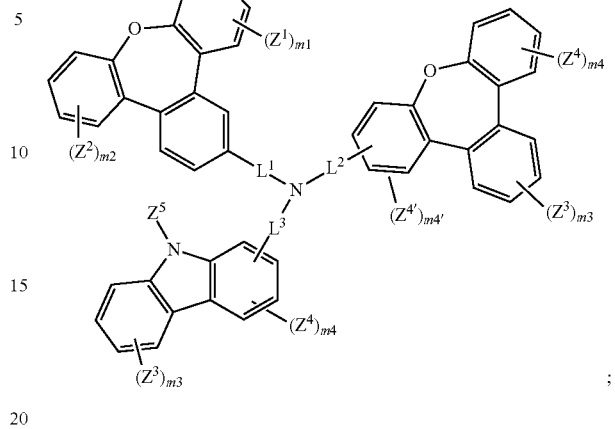
Formula (I-XX)
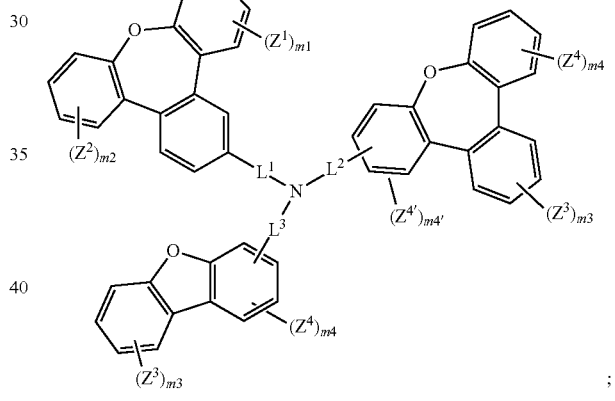
Formula (I-XXI)
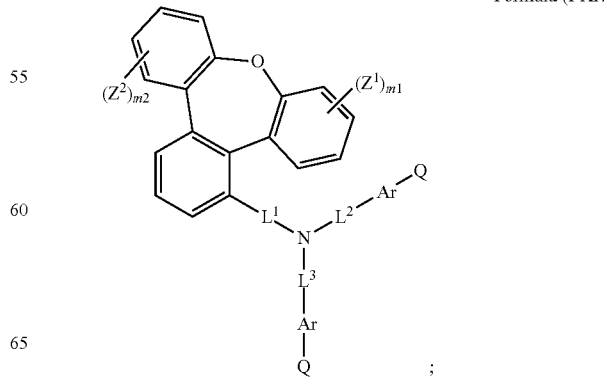

Formula (I-XXII)
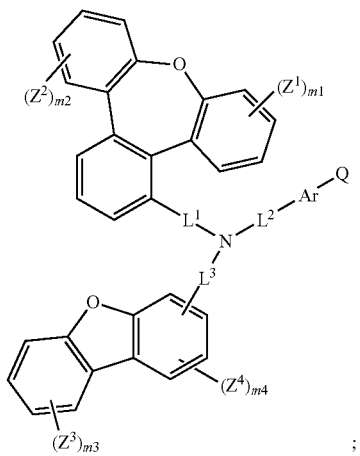
Formula (I-XXV)
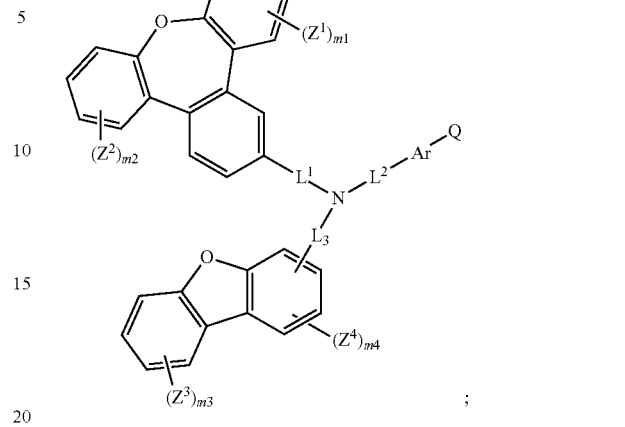
Formula (I-XXIII)
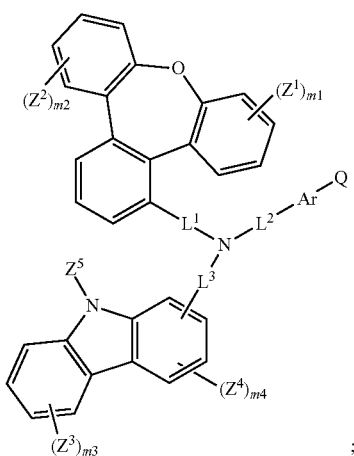
Formula (I-XXVI)
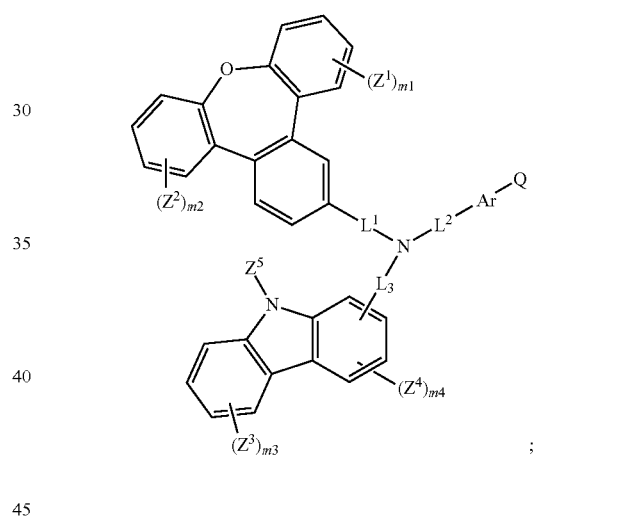
Formula (I-XXIV)
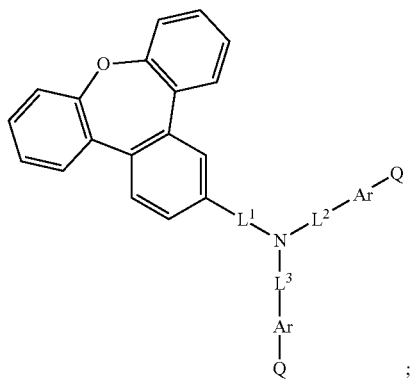
Formula (I-XXVII)
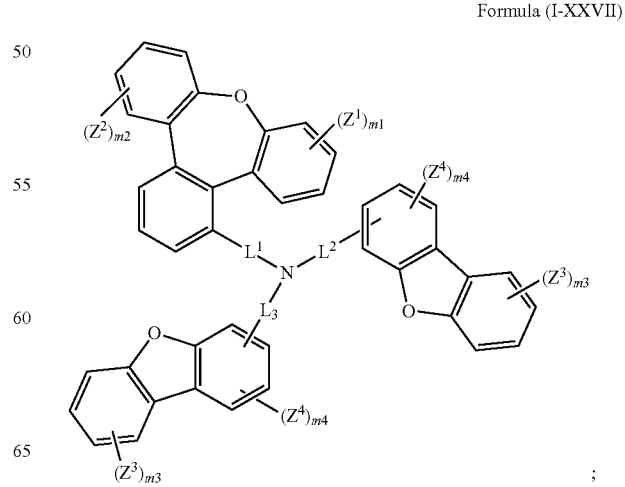

Formula (I-XXVII)
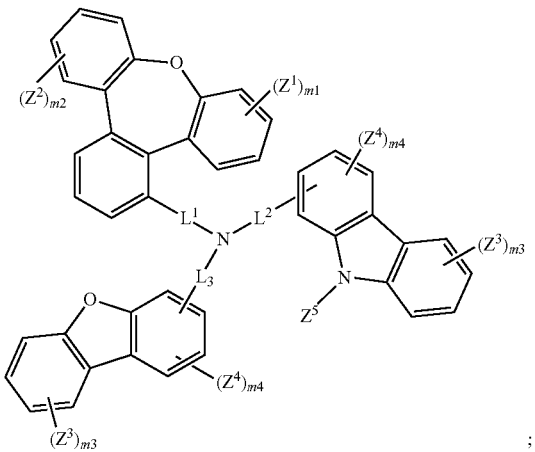
;
Formula (I-XXIX)
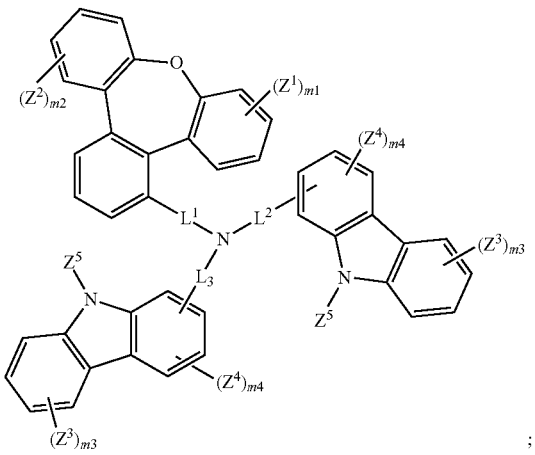
;
Formula (I-XXX)
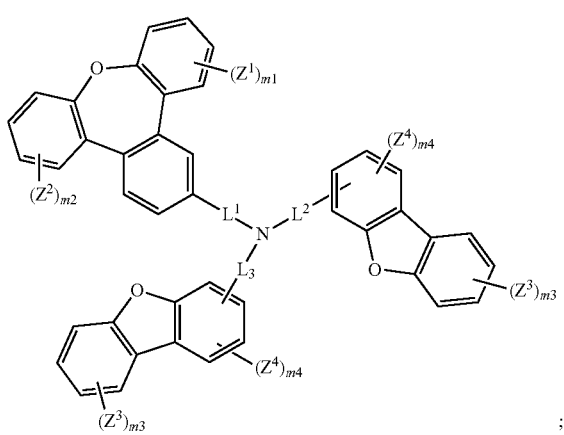
;
Formula (I-XXXI)
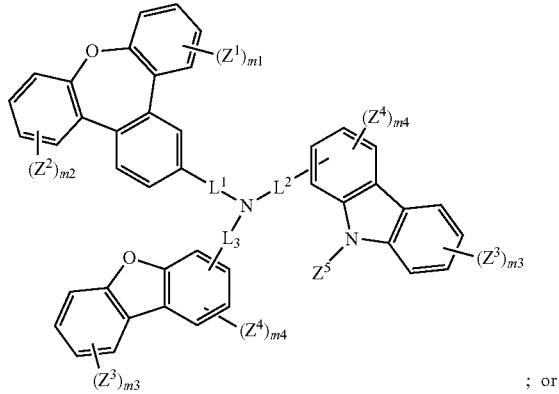
; or
Formula (I-XXXII)
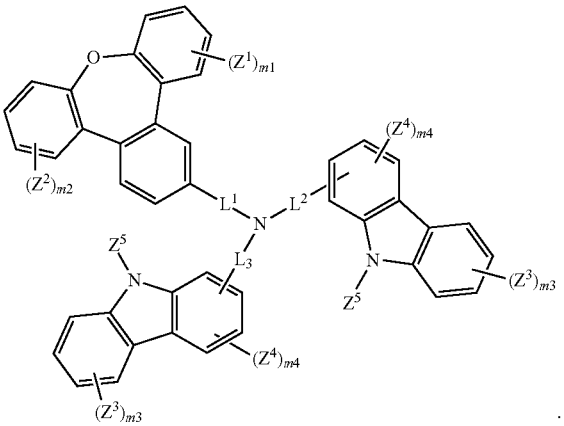
.
4. The compound as claimed in claim 1, wherein the compound is represented by
Formula (I-XXXIII)
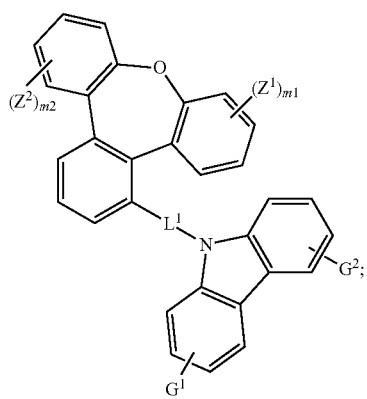

Formula (I-XXXIV)

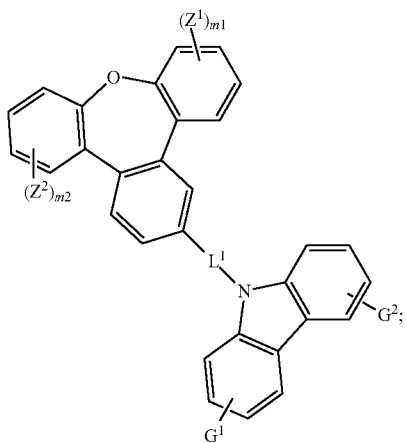

wherein G¹ and G² are the same or different, and G¹ and G² are each independently selected from the group consisting of: a hydrogen atom, a deuterium atom, an alkyl group having 1 to 40 carbon atoms, an alkenyl group having 2 to 40 carbon atoms, an alkynyl group having 2 to 40 carbon atoms, a cycloalkyl group having 3 to 60 ring carbon atoms, a heterocycloalkyl group having 3 to 60 ring carbon atoms, an aryl group having 6 to 60 ring carbon atoms, and a heteroaryl group having 3 to 60 ring carbon atoms.

5. The compound as claimed in claim 1, wherein the compound is represented by

Formula (I-XXXV)

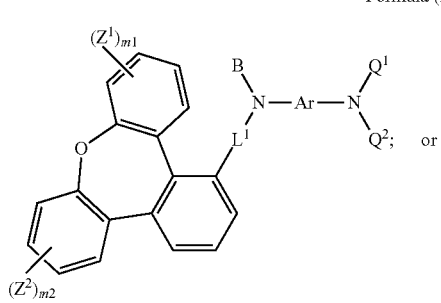

Formula (I-XXXVI)

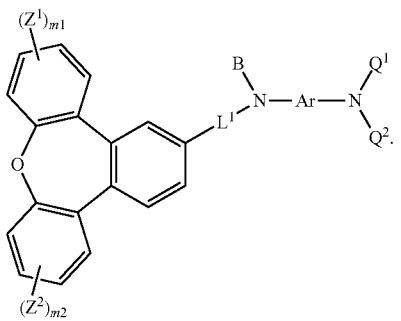

6. The compound as claimed in claim 5, wherein Q¹ and Q² are each independently selected from the group consisting of: a substituted or unsubstituted phenyl group, a substituted or unsubstituted biphenylyl group, a substituted or unsubstituted terphenyl group, a substituted or unsubstituted naphthyl group, a substituted or unsubstituted phenanthryl group, a substituted or unsubstituted anthryl group, a substituted or unsubstituted benzanthryl group, a substituted or unsubstituted pyrenyl group, a substituted or unsubstituted fluorenyl group, and any deuterated analogs thereof.

7. The compound as claimed in claim 5, wherein Q¹ and Q² are each independently selected from the group consisting of:

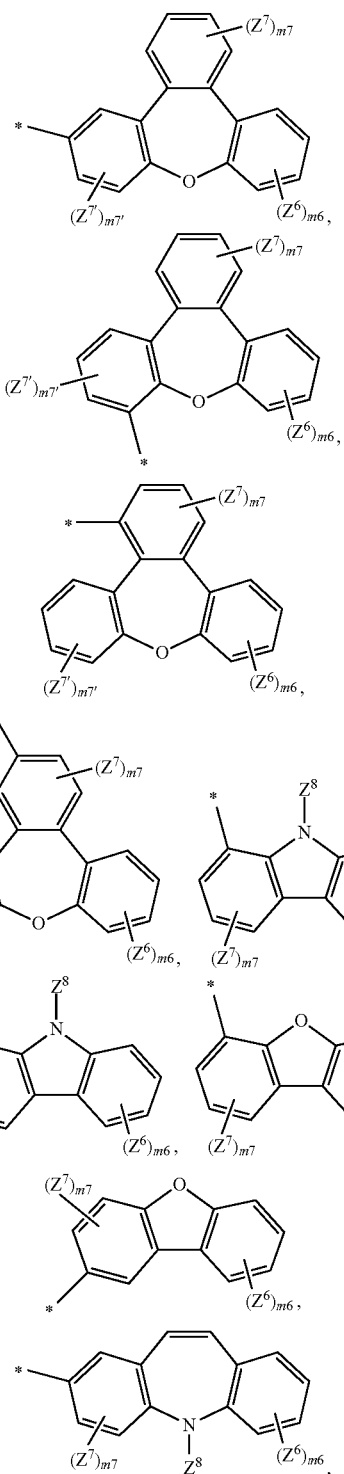

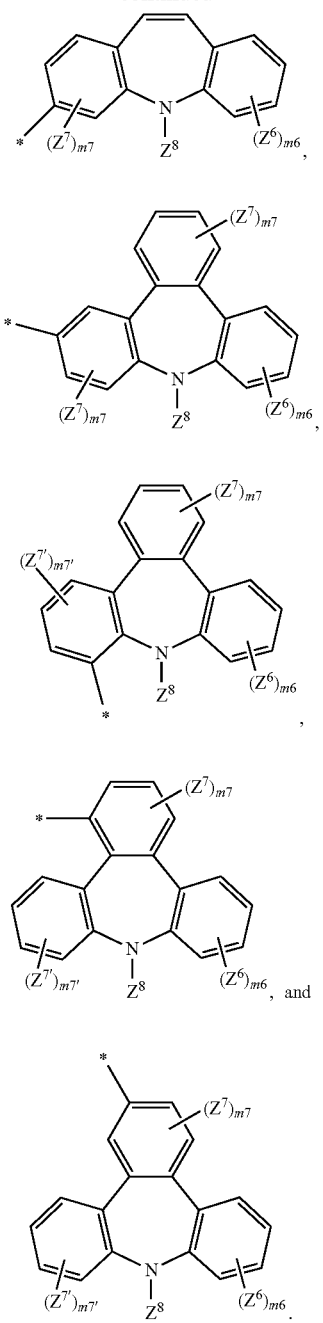
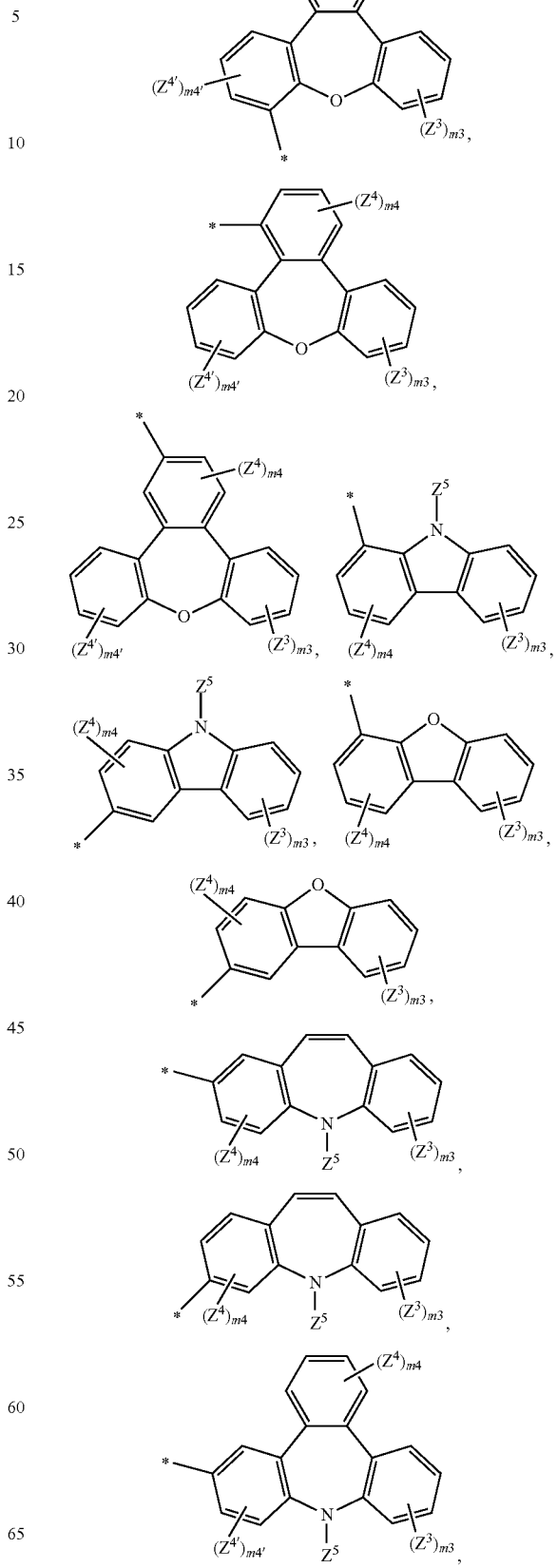
8. The compound as claimed in claim 1, wherein $R^a$ and $R^b$ are each independently selected from the group consisting of: —Ar-Q,
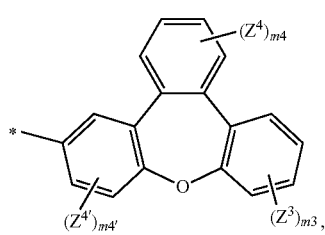

-continued

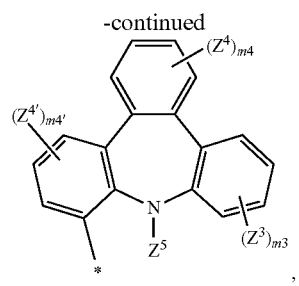

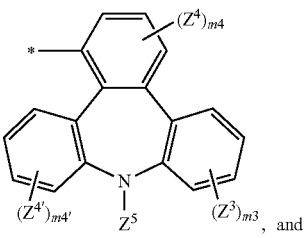, and

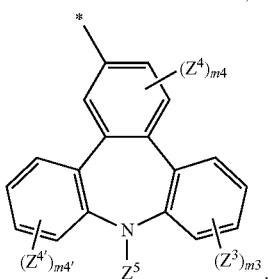.

9. The compound as claimed in claim 1, wherein —Ar-Q is selected from the group consisting of:

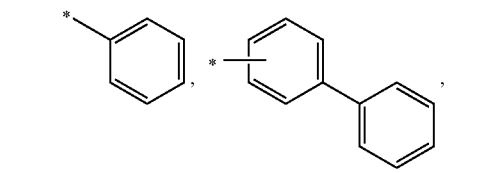

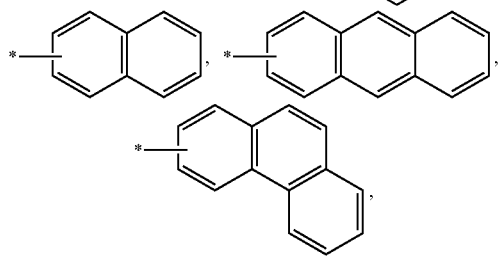

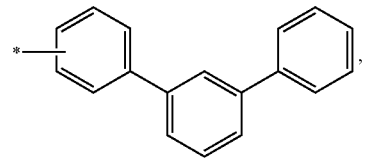

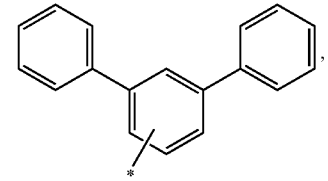

-continued

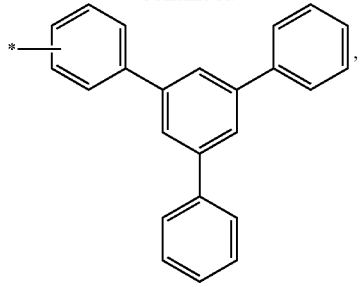

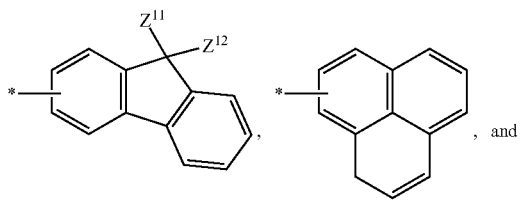, and

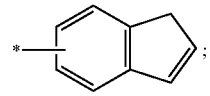;

wherein $Z^{11}$ and $Z^{12}$ are each independently selected from the group consisting of: a hydrogen atom, a deuterium atom, a methyl group, an ethyl group, a propyl group, a butyl group, a pentyl group, a hexyl group and a phenyl group.

10. The compound as claimed in claim 1, wherein $L^1$, $L^2$, and $L^3$ are each independently selected from the group consisting of:

a single bond,

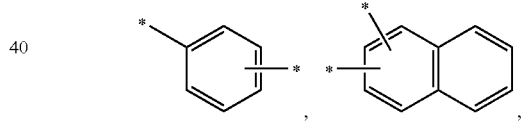

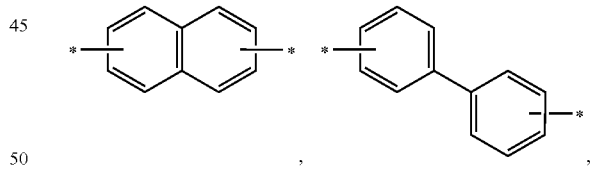

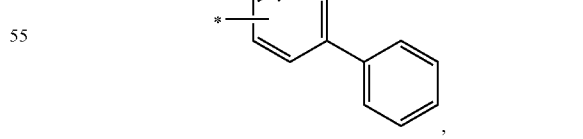

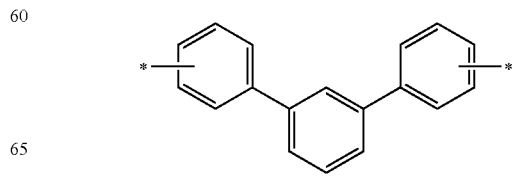

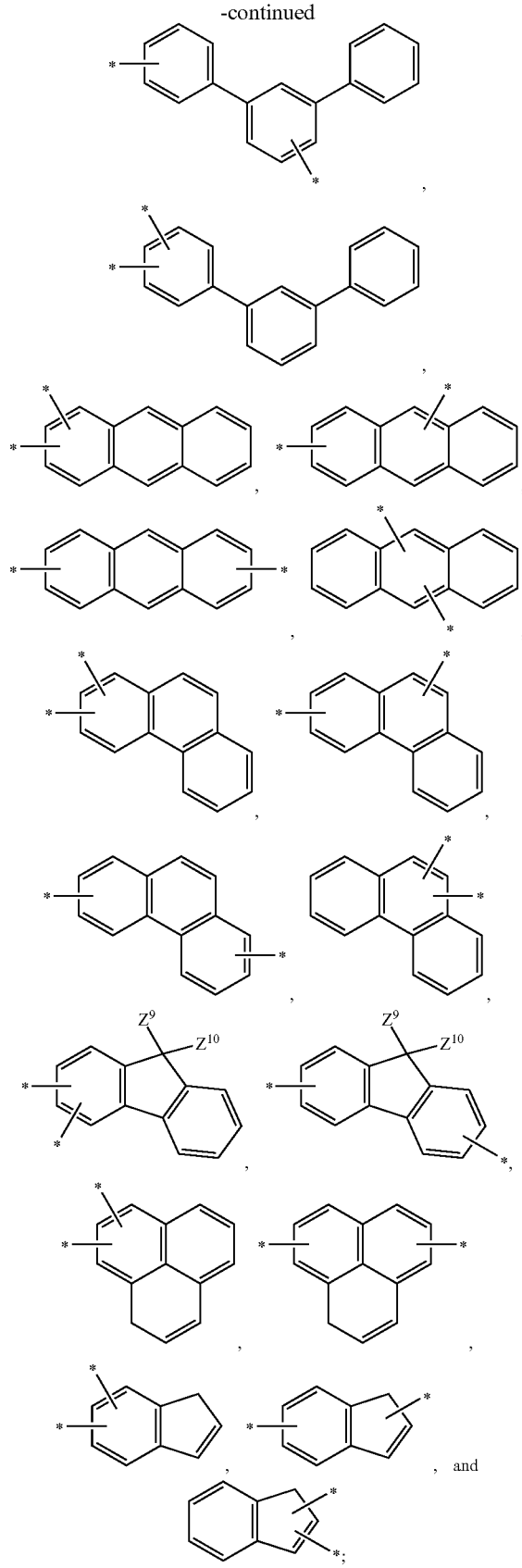
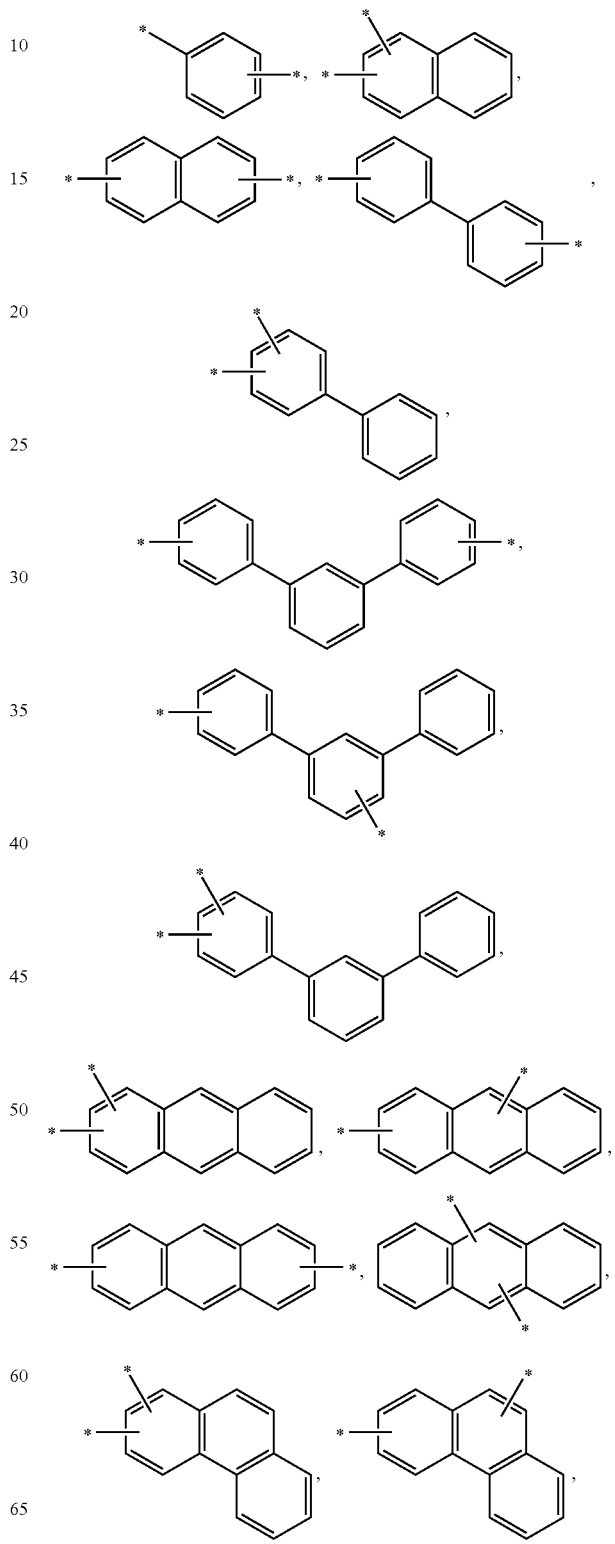
atom, a methyl group, an ethyl group, a propyl group, a butyl group, a pentyl group, a hexyl group and a phenyl group.
11. The compound as claimed in claim 1, wherein Ar is selected from the group consisting of:
wherein $Z^9$ and $Z^{10}$ are each independently selected from the group consisting of: a hydrogen atom, a deuterium 189
-continued

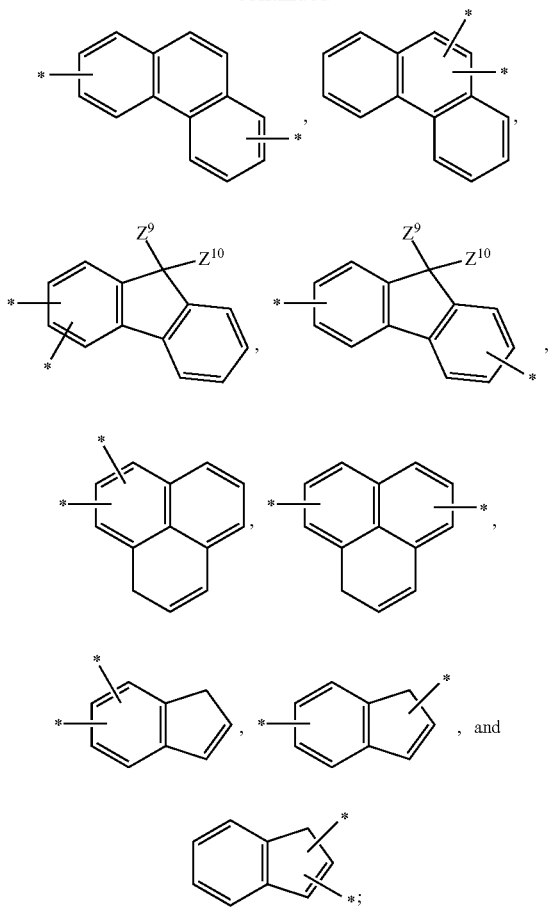

wherein $Z^9$ and $Z^{10}$ are each independently selected from the group consisting of: a hydrogen atom, a deuterium atom, a methyl group, an ethyl group, a propyl group, a butyl group, a pentyl group, a hexyl group and a phenyl group.

12. The compound as claimed in claim 1, wherein $L^1$, $L^2$, and $L^3$ are the same.

13. The compound as claimed in claim 1, wherein the compound is selected from the group consisting of:

Compound 1

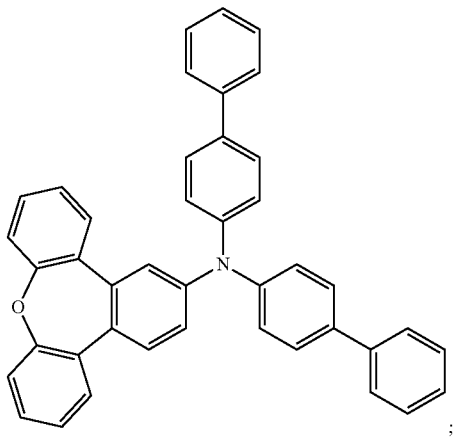

;

190
-continued

Compound 2

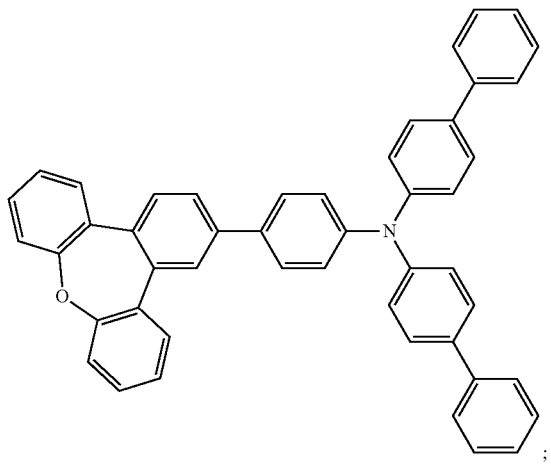

;

Compound 3

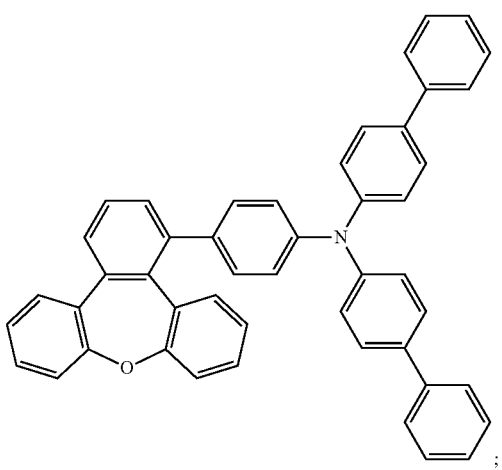

;

Compound 4

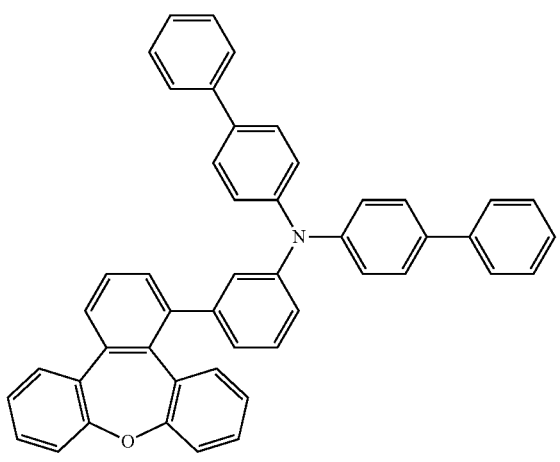

;

Compound 5
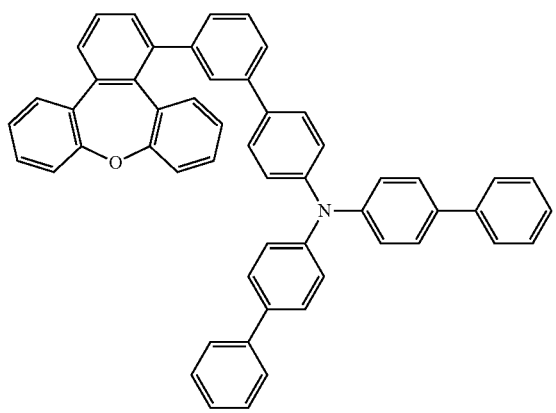
Compound 6
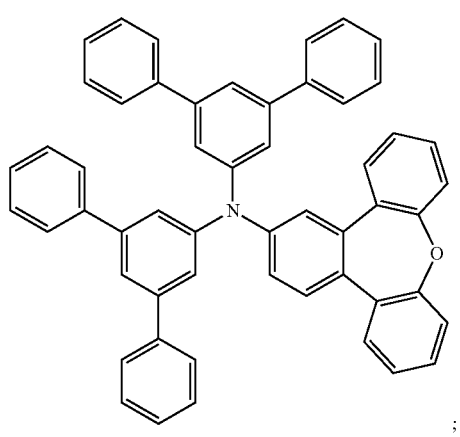
Compound 7
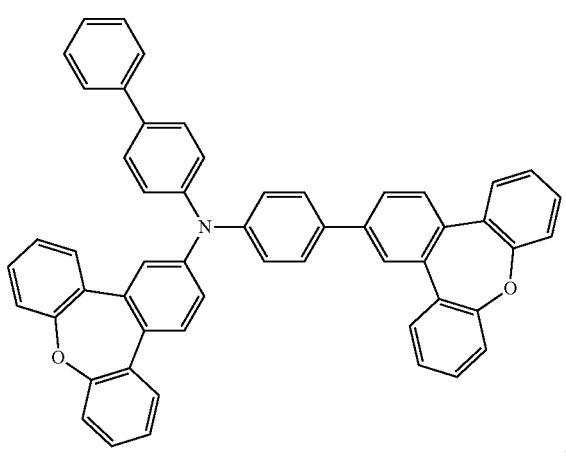
Compound 8
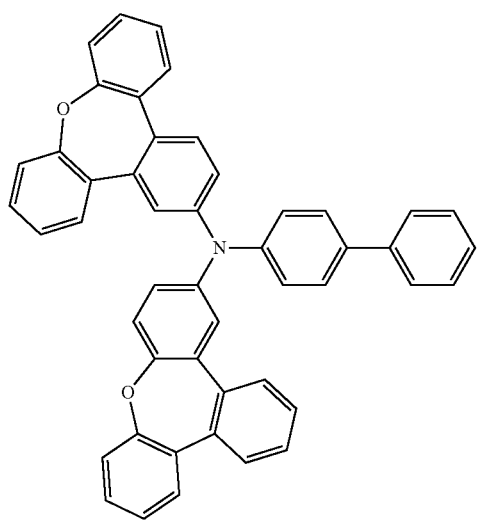
Compound 9
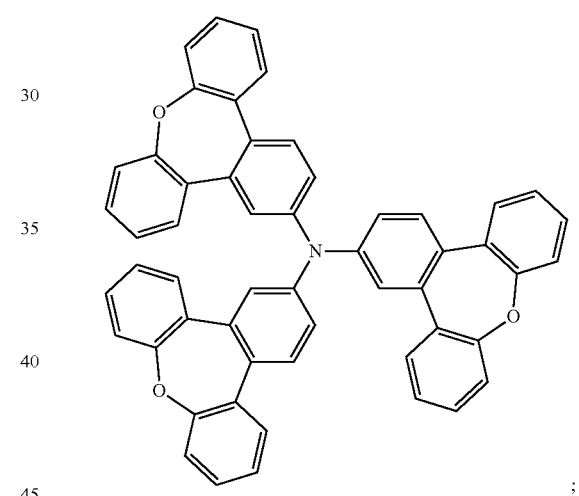
Compound 10
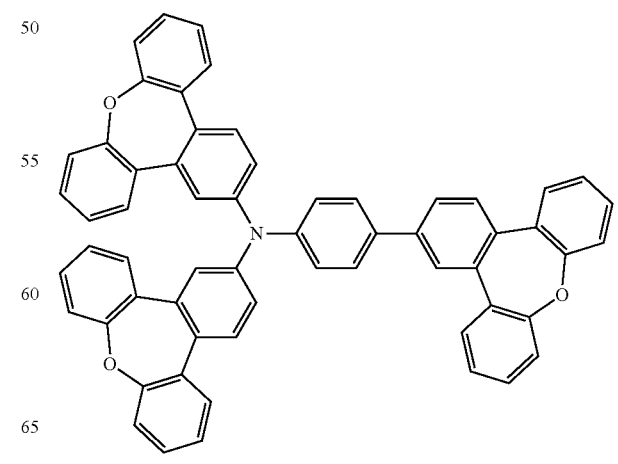

Compound 11
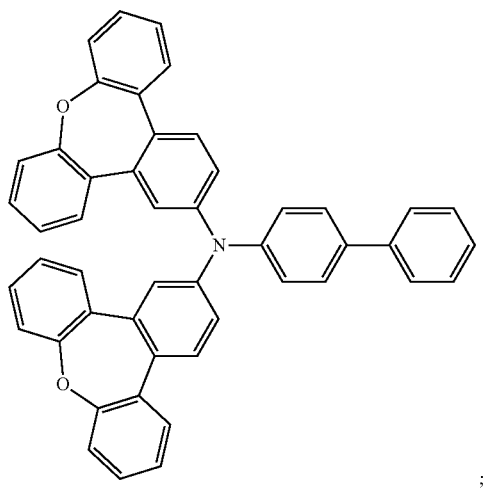
Compound 12
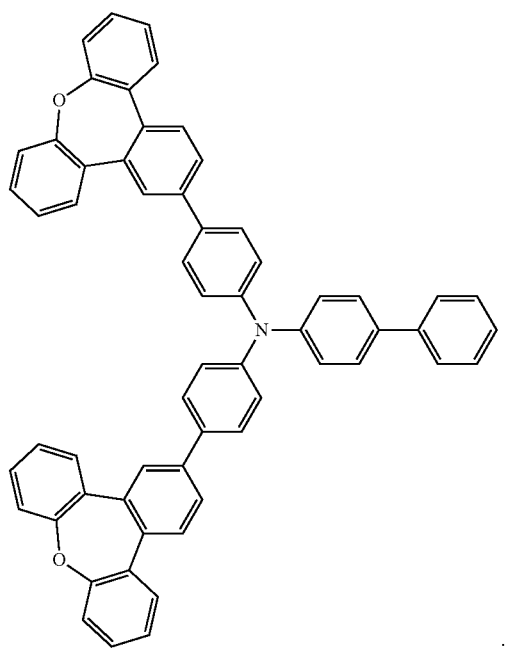
Compound 13
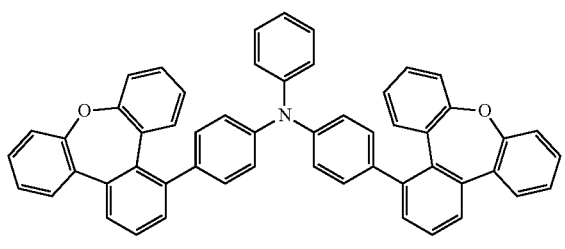
Compound 14
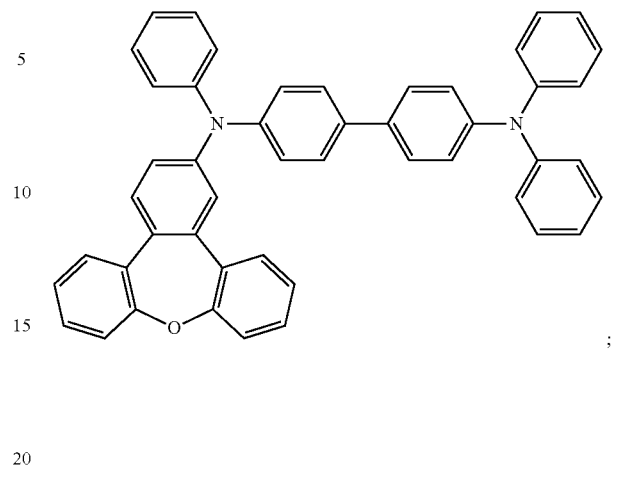
Compound 15
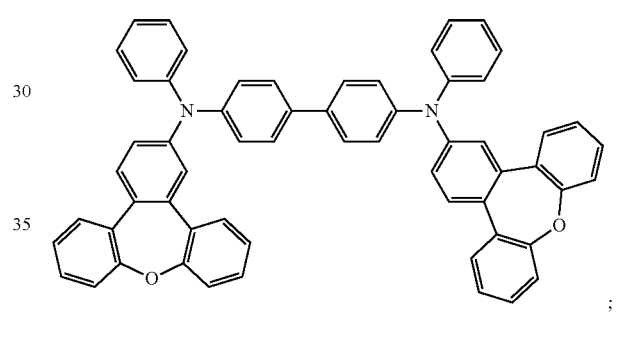
Compound 16
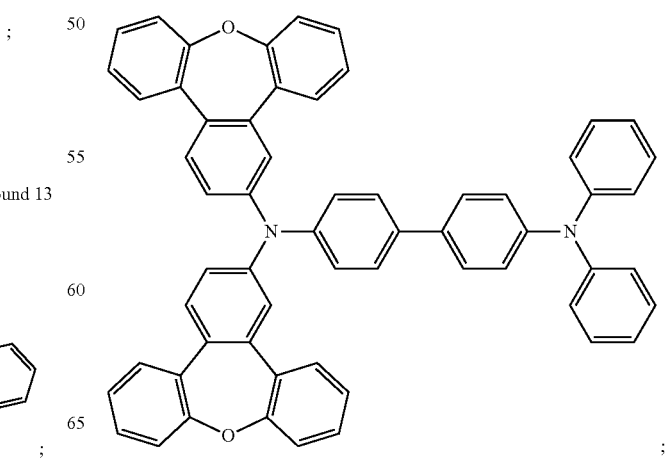

Compound 17
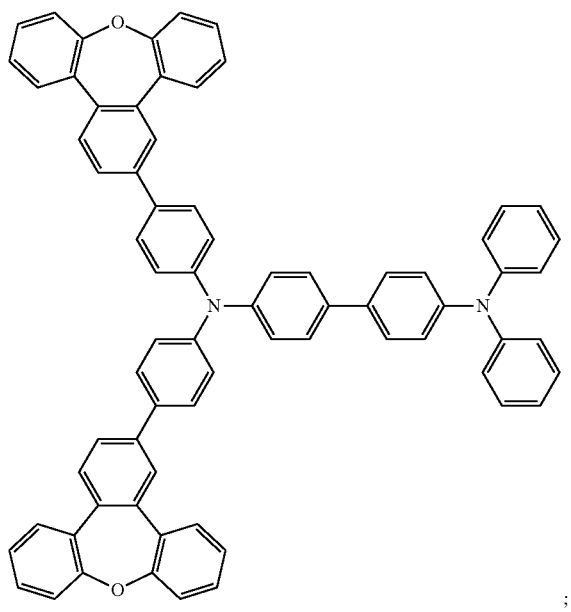
;
Compound 18
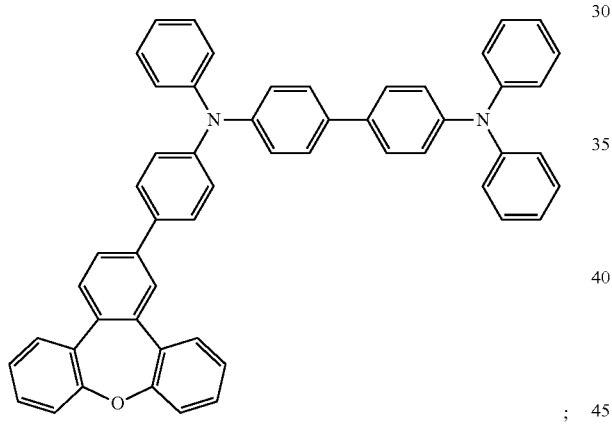
;
Compound 19
Compound 20
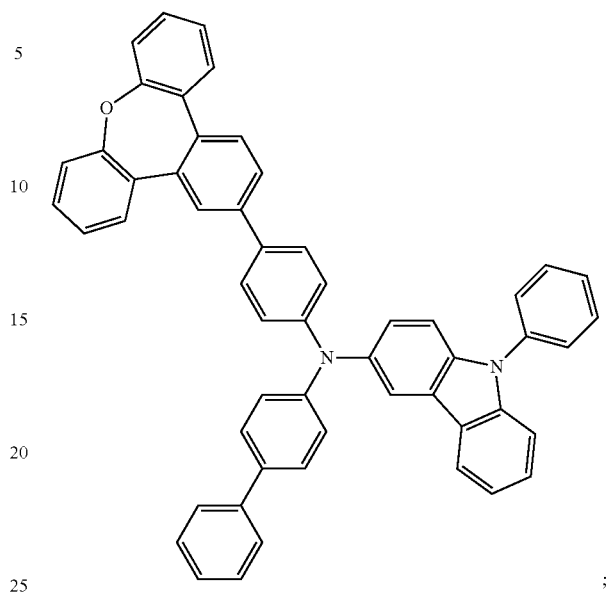
;
Compound 21
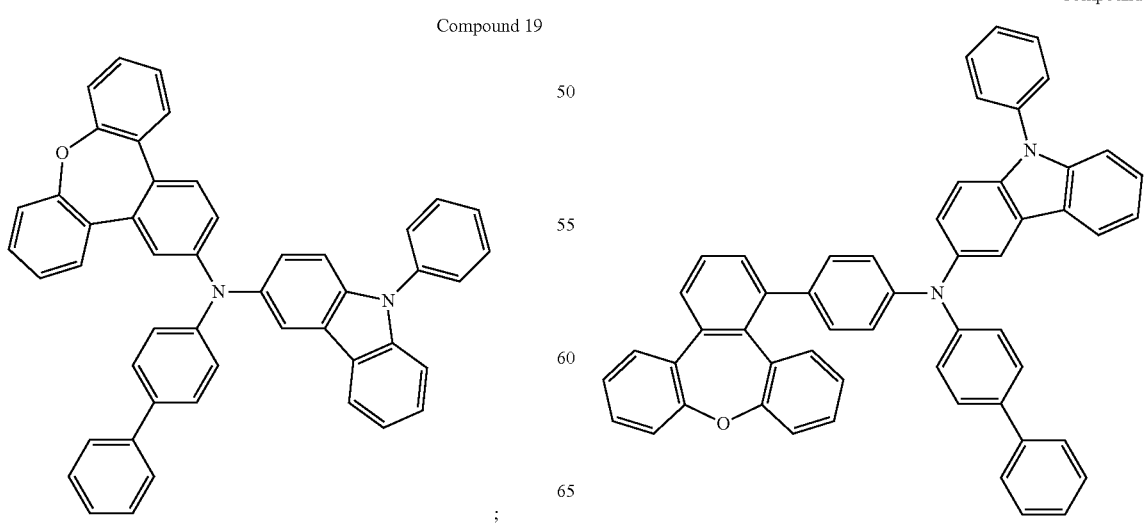
;

Compound 22
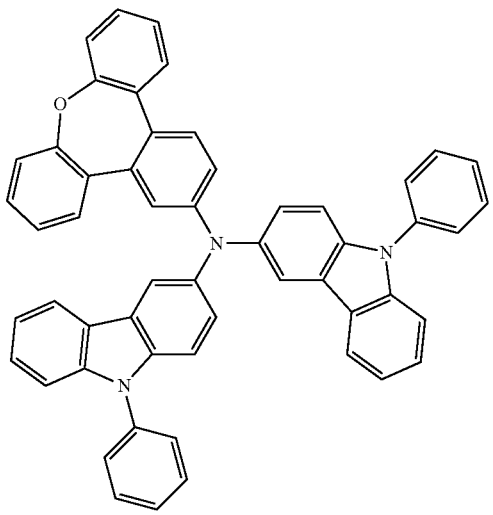
;
Compound 23
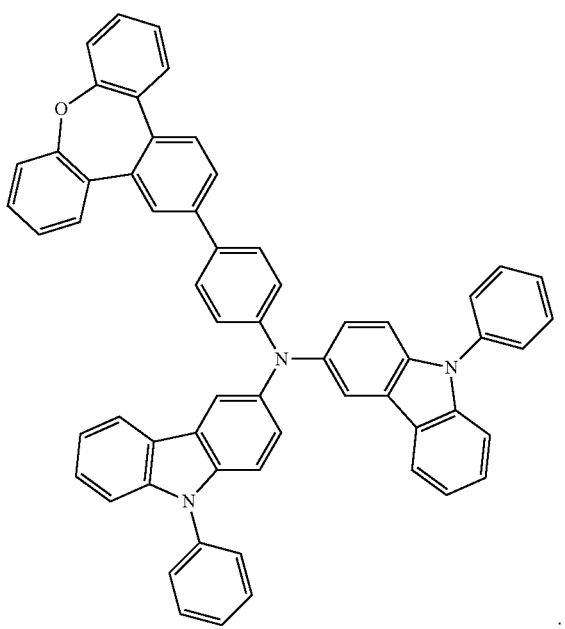
;
Compound 24
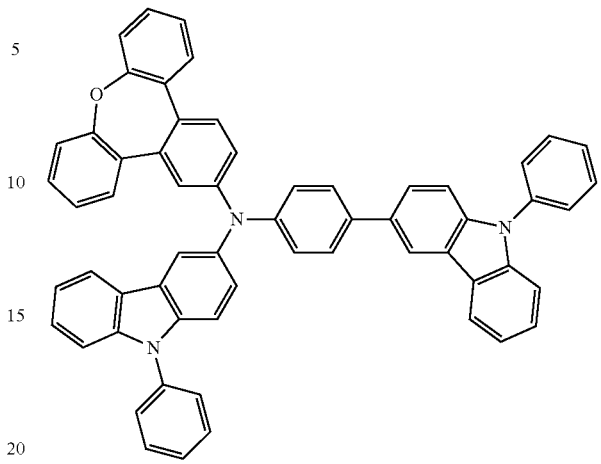
;
Compound 25
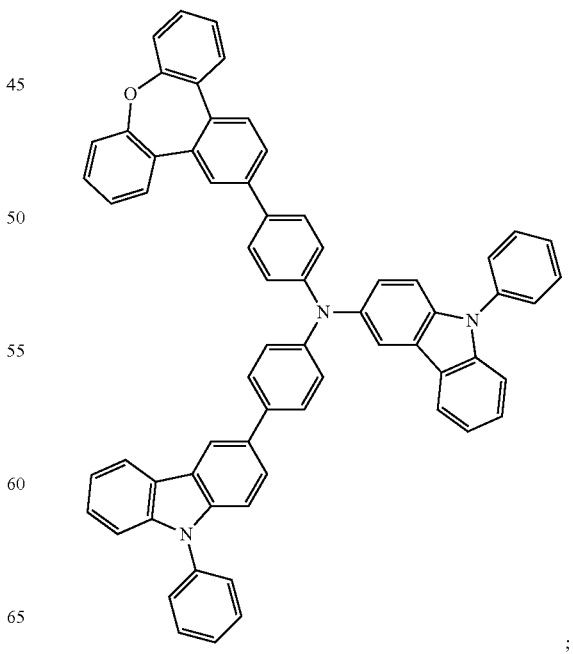
;

Compound 26
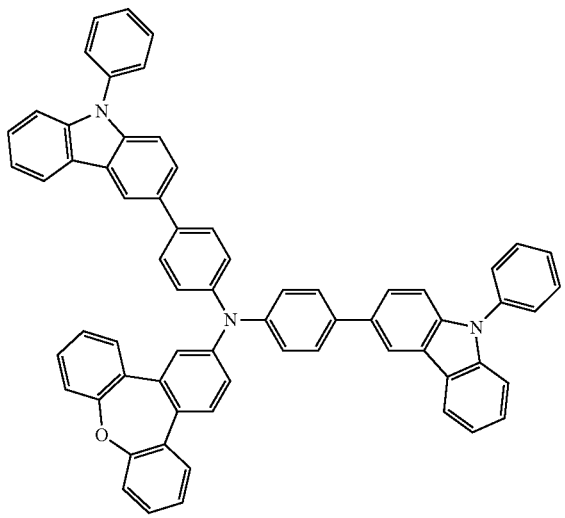
Compound 27
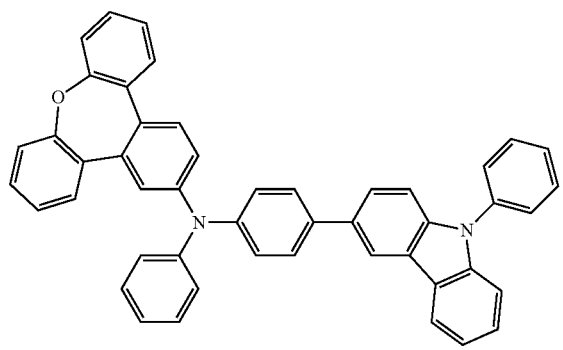
Compound 28
Compound 29
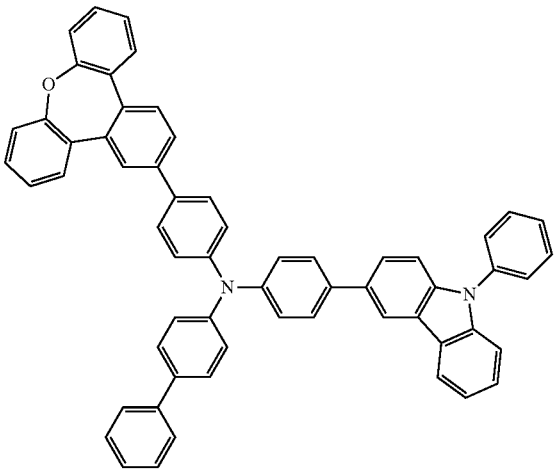
Compound 30
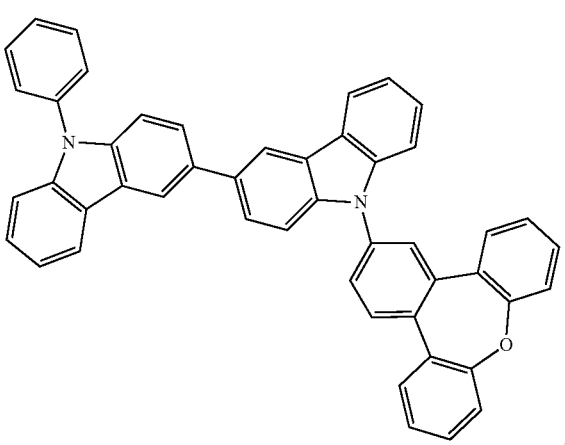
Compound 31
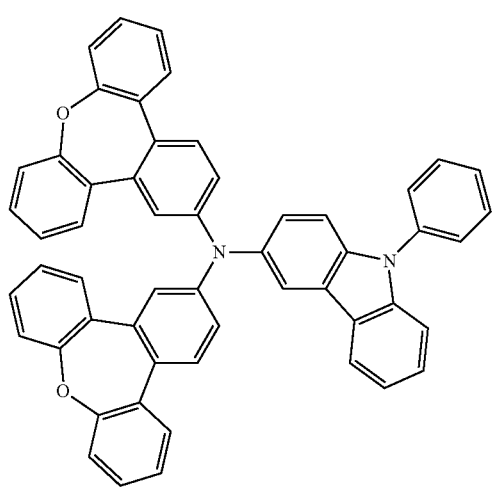

Compound 32
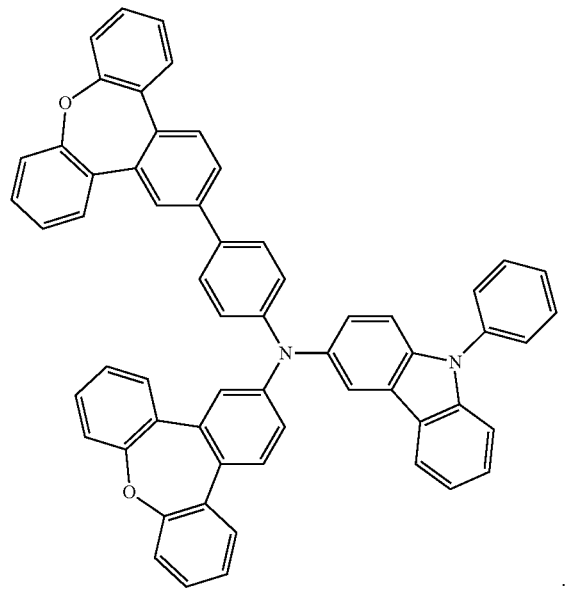
Compound 33
Compound 34
Compound 35
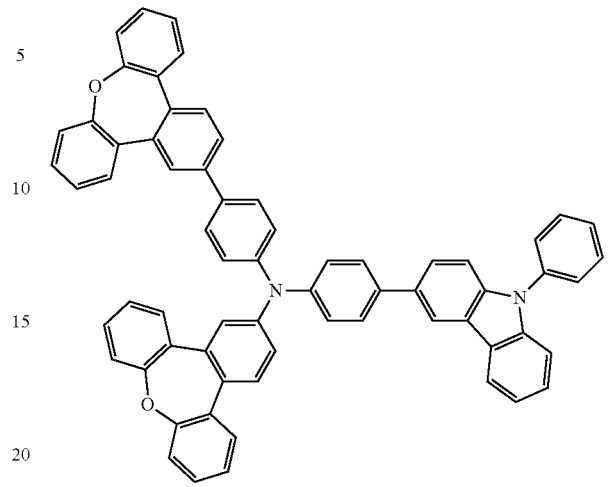
Compound 36
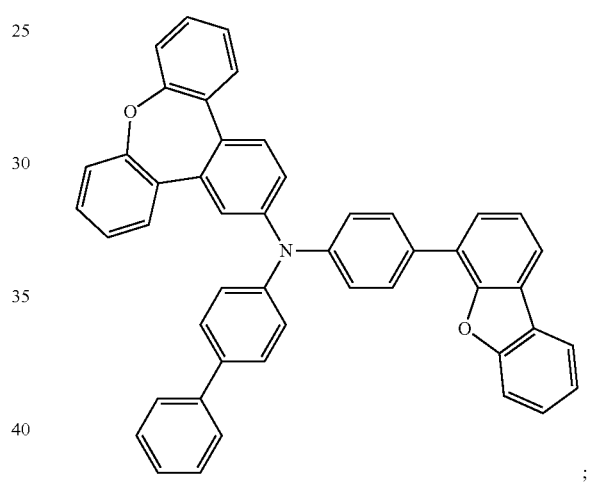
Compound 37
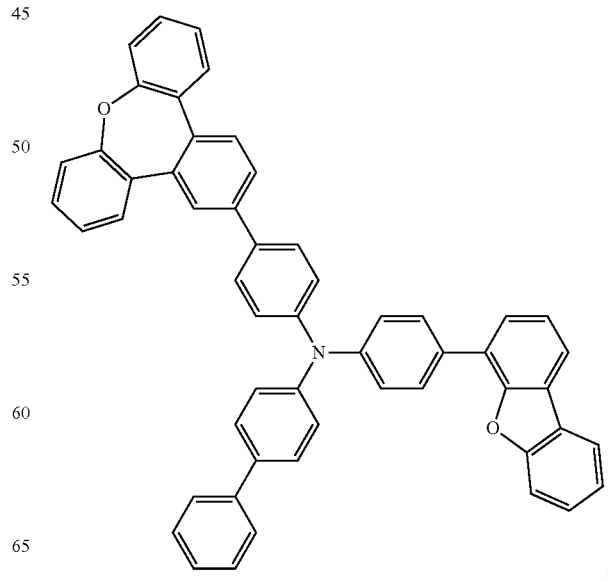

Compound 38
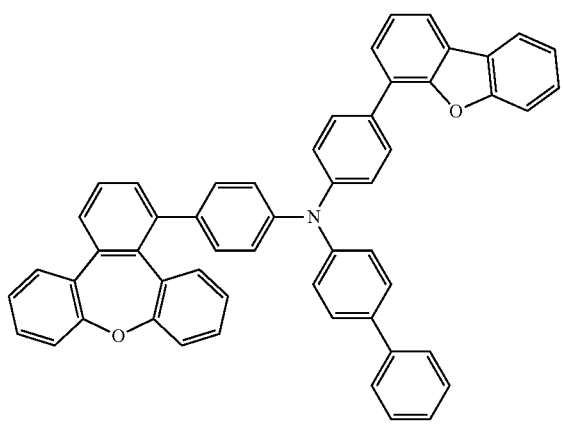
Compound 39
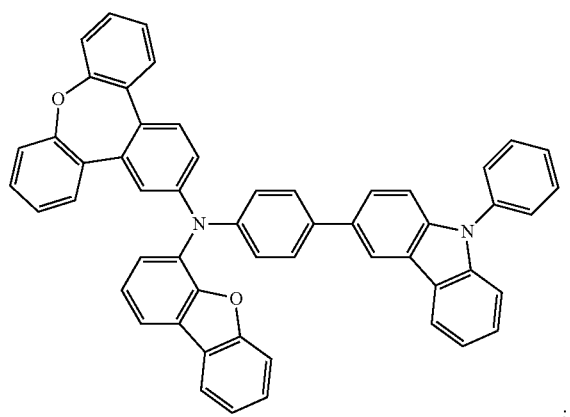
Compound 40
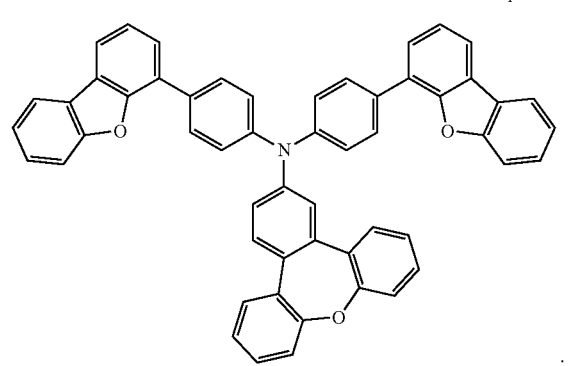
Compound 41
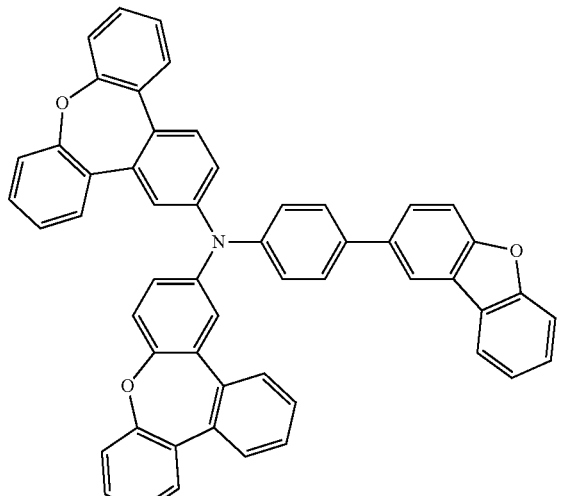
Compound 42
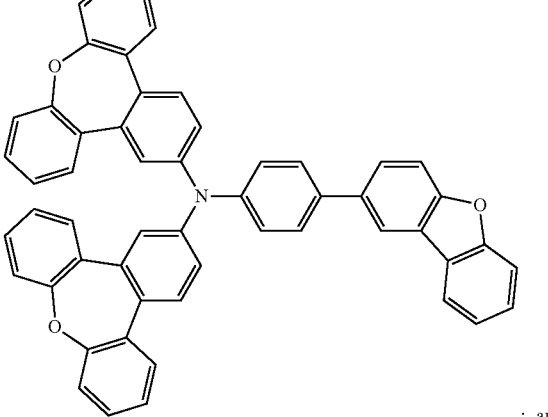
; and
Compound 43
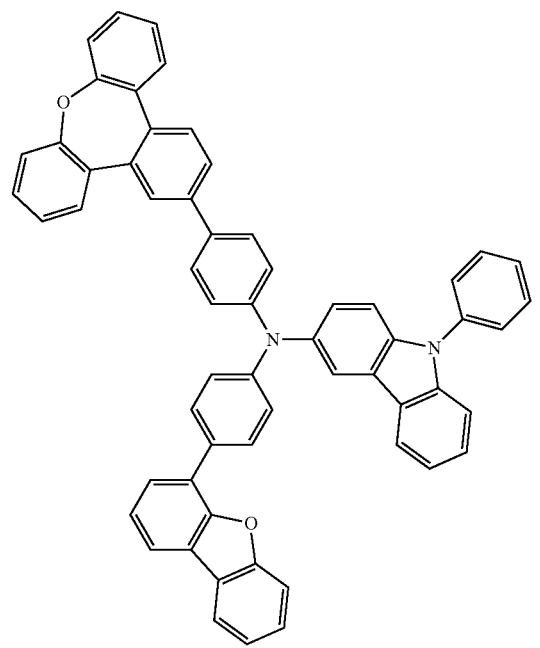
.

14. An organic electronic device, comprising a first electrode, a second electrode, and an organic layer disposed between the first electrode and the second electrode, wherein the organic layer comprises the compound as claimed in claim 1.

15. The organic electronic device as claimed in claim 14, wherein the organic electronic device is an organic light emitting device.

16. The organic electronic device as claimed in claim 15, wherein the organic light emitting device comprises:
   a hole injection layer formed on the first electrode;
   a hole transport layer formed on the hole injection layer, wherein the organic layer is the hole transport layer;
   an emission layer formed on the hole transport layer;
   an electron transport layer formed on the emission layer, and
   an electron injection layer formed between the electron transport layer and the second electrode.

17. The organic electronic device as claimed in claim 15, wherein the organic light emitting device comprises:
   a hole injection layer formed on the first electrode, wherein the organic layer is the hole injection layer,
   a hole transport layer formed on the hole injection layer,
   an emission layer formed on the hole transport layer;
   an electron transport layer formed on the emission layer, and
   an electron injection layer formed between the electron transport layer and the second electrode.

18. The organic electronic device as claimed in claim 15, wherein the organic light emitting device comprises:
   a hole injection layer formed on the first electrode;
   a hole transport layer formed on the hole injection layer;
   an emission layer formed on the hole transport layer;
   an electron transport layer formed on the emission layer; and
   an electron injection layer formed between the electron transport layer and the second electrode;
   wherein the organic layer is the hole injection layer and the hole transport layer.

19. The organic electronic device as claimed in claim 15, wherein the organic light emitting device comprises:
   a hole injection layer formed on the first electrode;
   a hole transport layer formed on the hole injection layer,
   an electron blocking layer formed on the hole transport layer, wherein the organic layer is the electron blocking layer;
   an emission layer formed on the electron blocking layer,
   an electron transport layer formed on the emission layer; and
   an electron injection layer formed between the electron transport layer and the second electrode.

20. The organic electronic device as claimed in claim 14, wherein the compound is selected from the group consisting of:

Compound 1

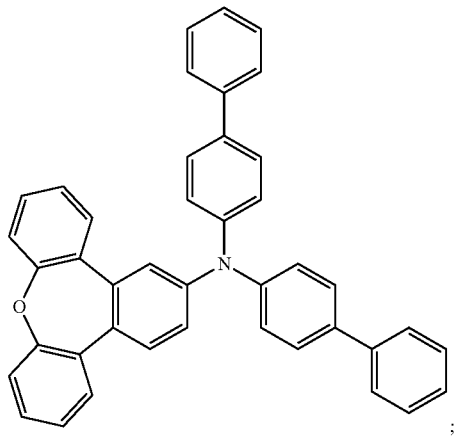

;

Compound 2

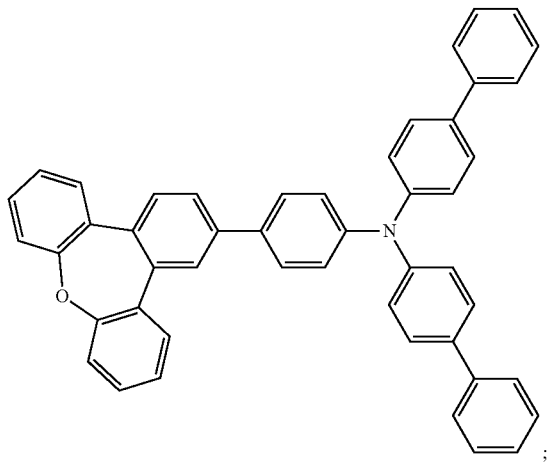

;

Compound 3

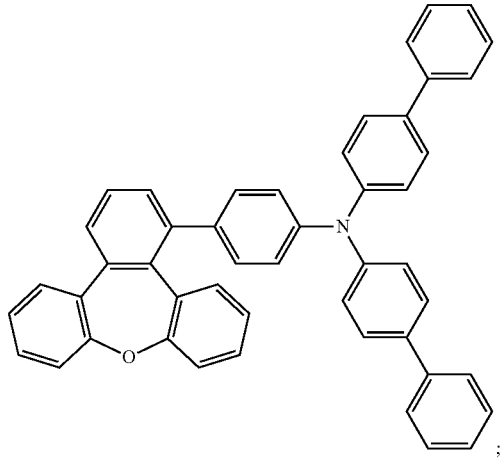

;

Compound 4
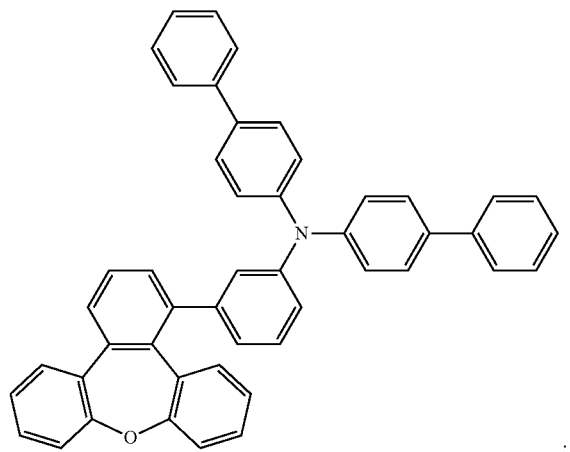
;
Compound 5
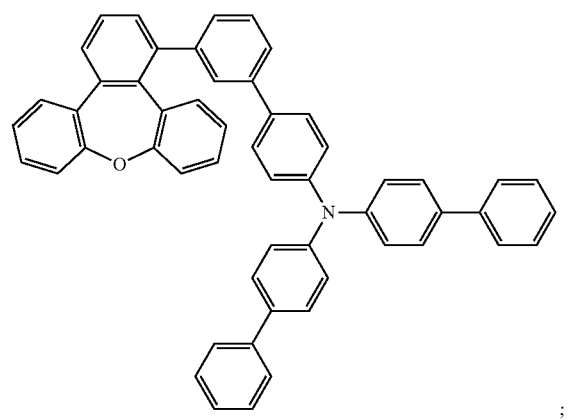
;
Compound 6
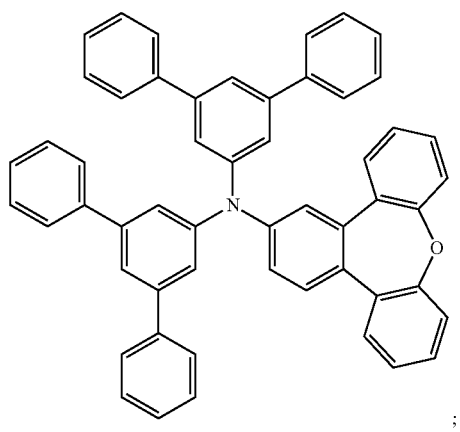
;
Compound 7
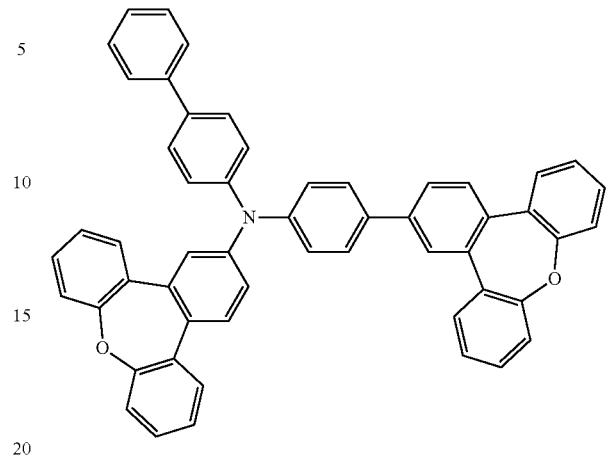
;
Compound 8
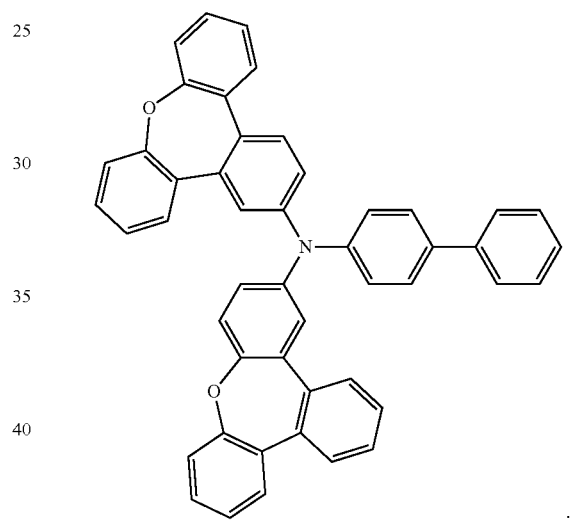
;
Compound 9
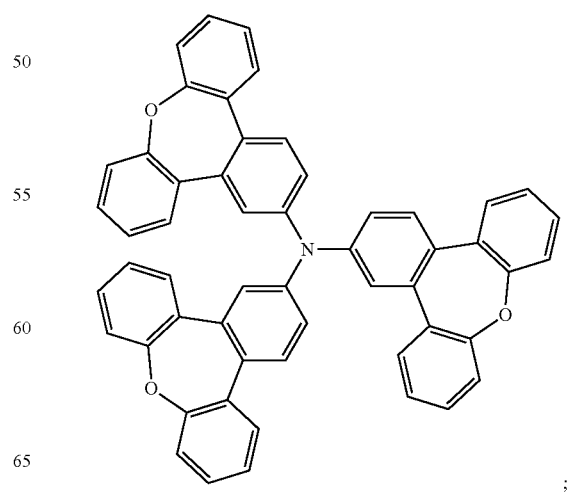
;

Compound 10
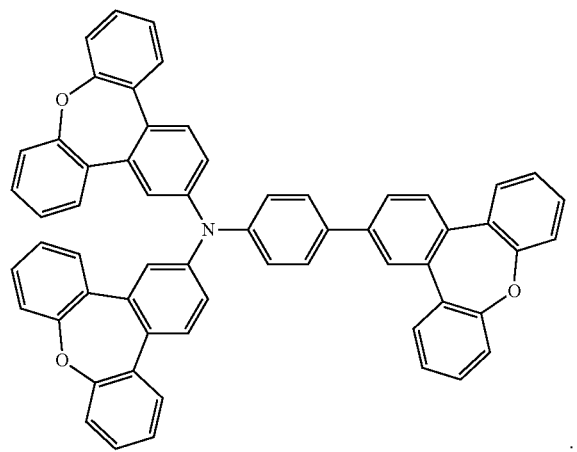
Compound 11
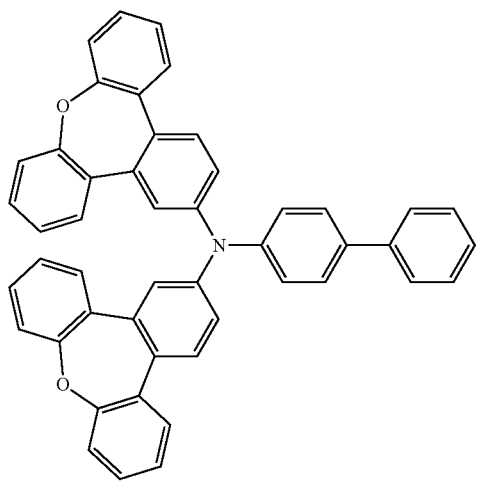
Compound 12
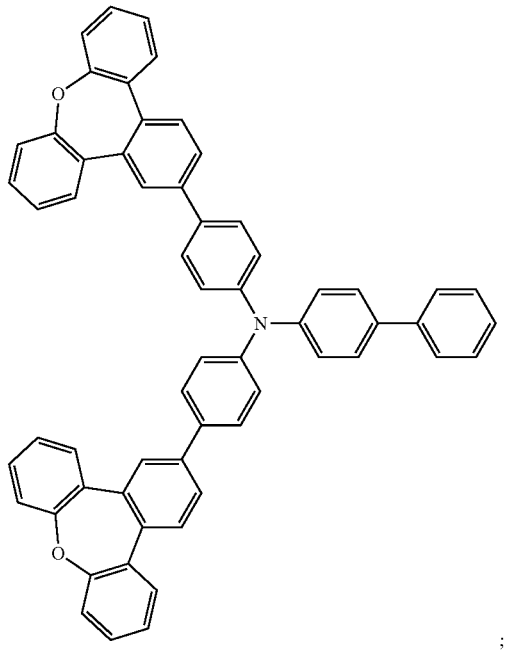
Compound 13
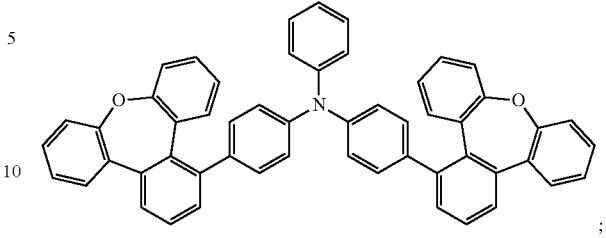
Compound 14
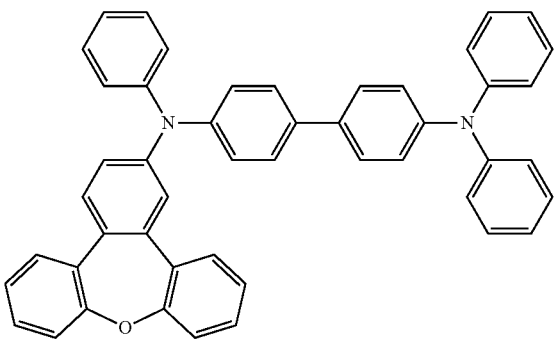
Compound 15
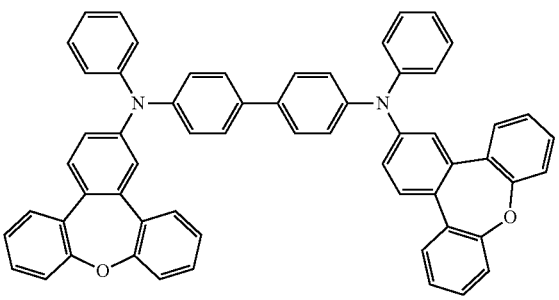
Compound 16
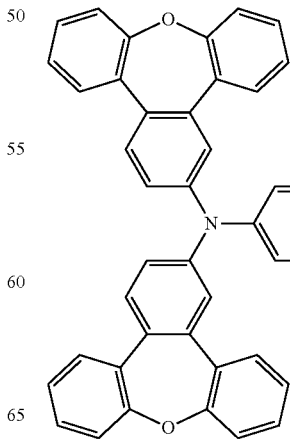

Compound 17
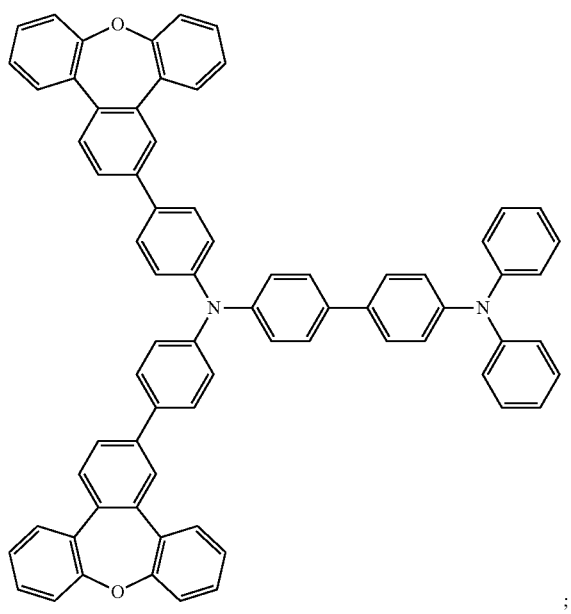
Compound 18
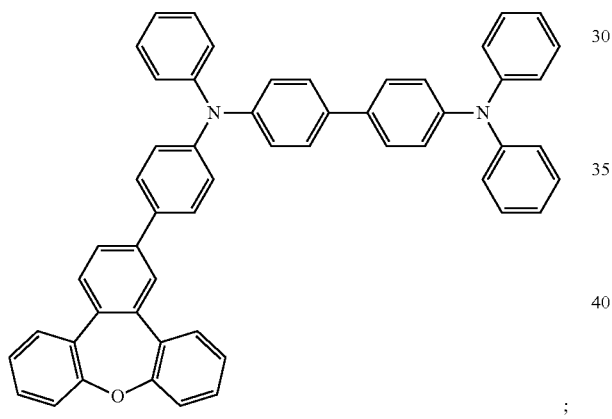
Compound 19
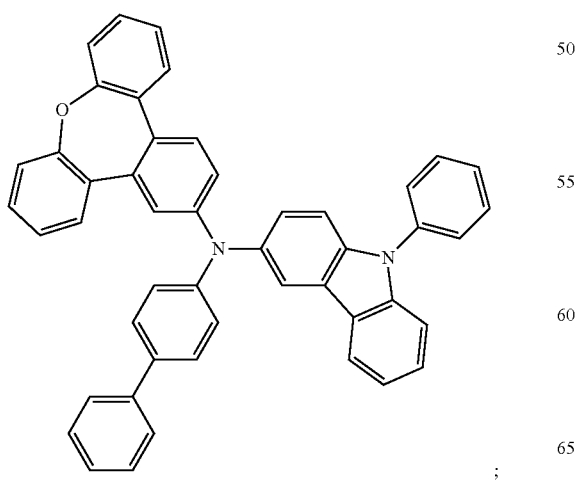
Compound 20
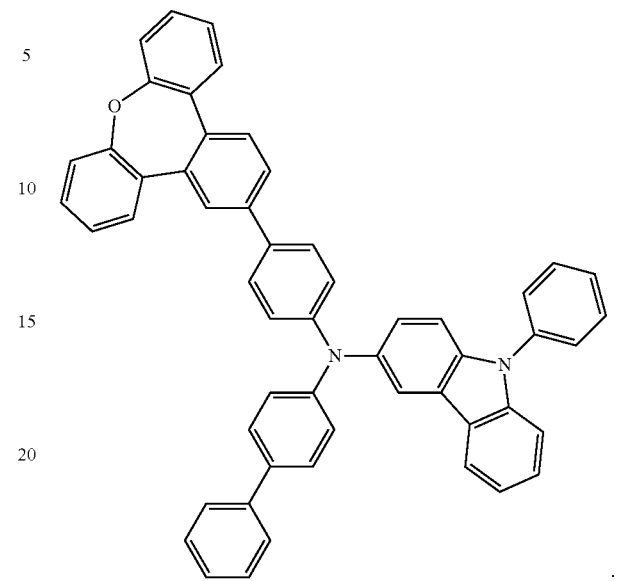
Compound 21
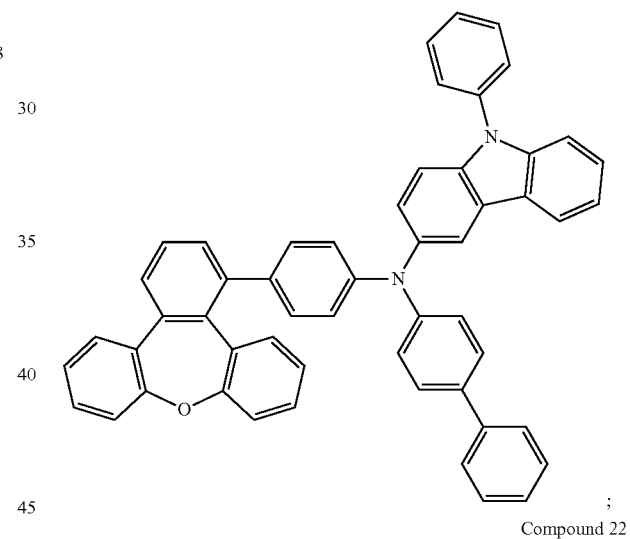
Compound 22
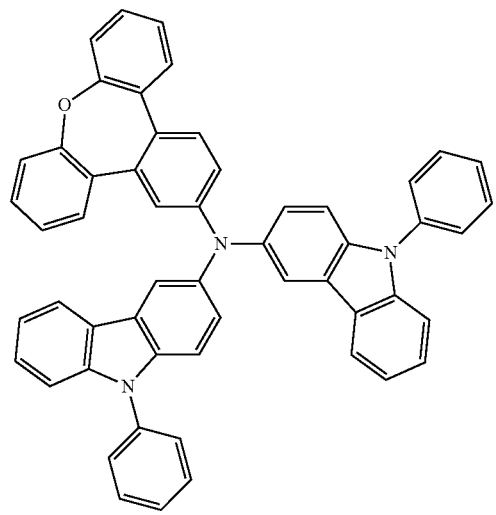

Compound 23
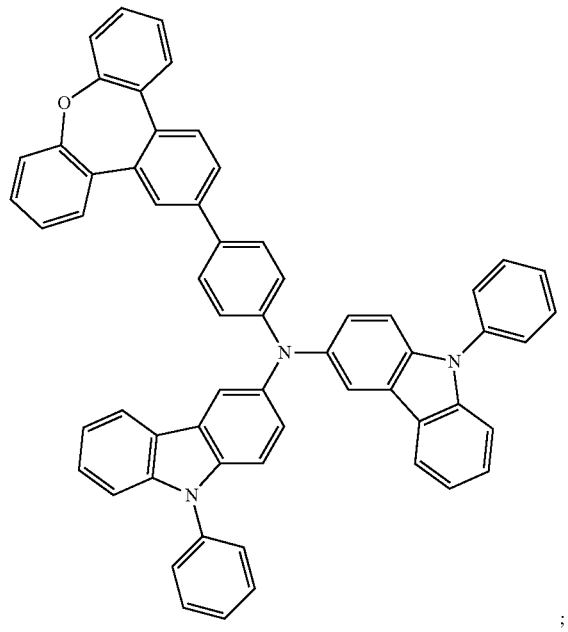
Compound 25
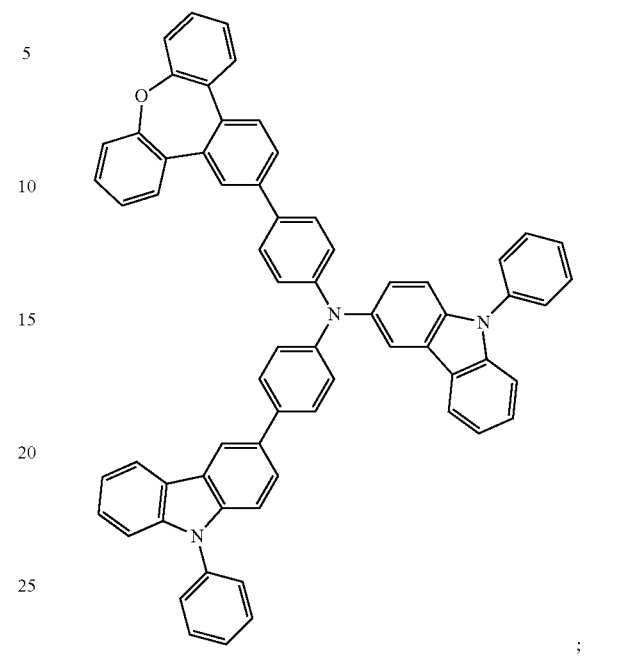
Compound 26
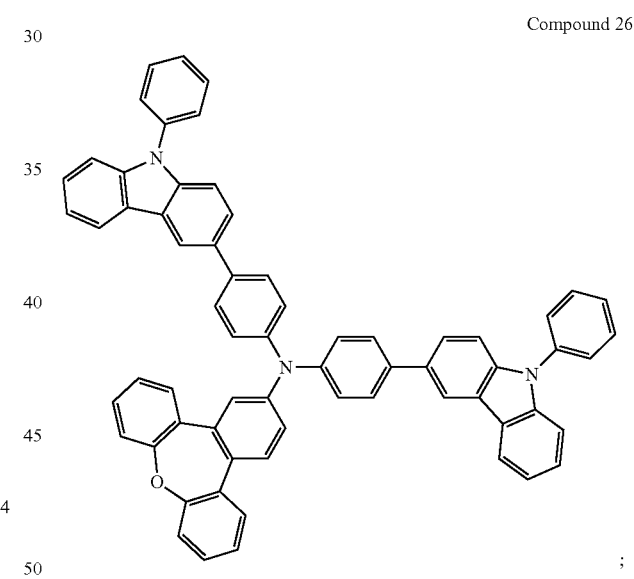
Compound 24
Compound 27
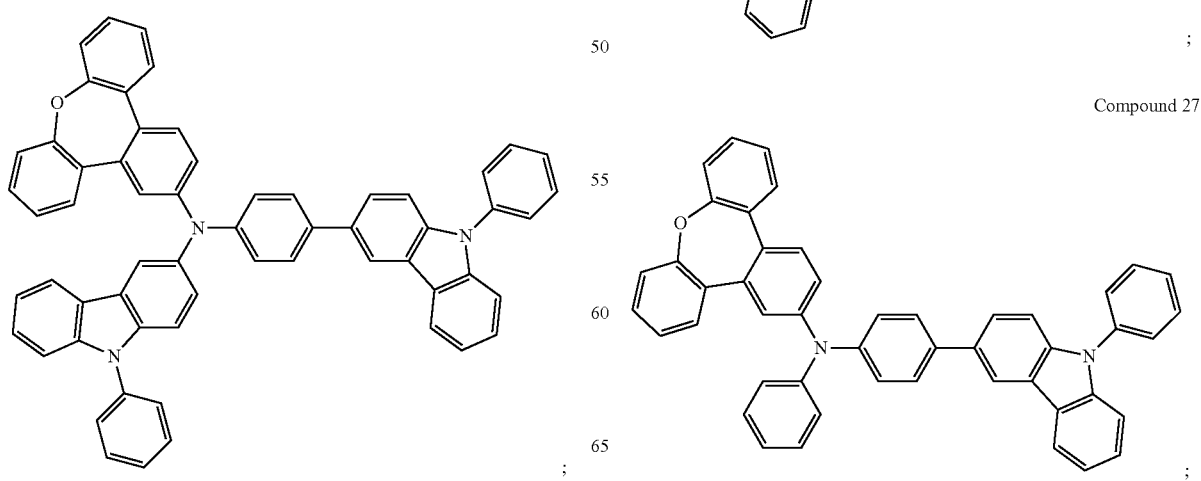

Compound 28
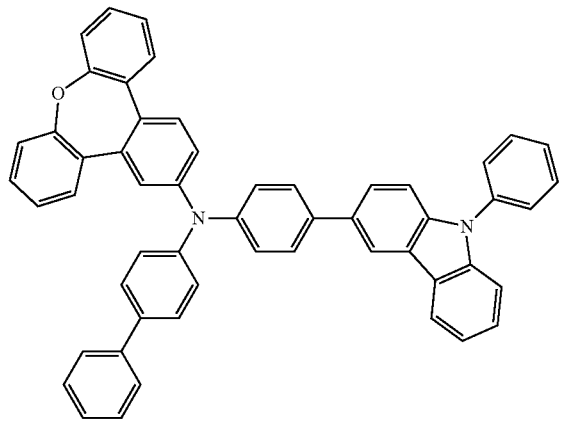
Compound 29
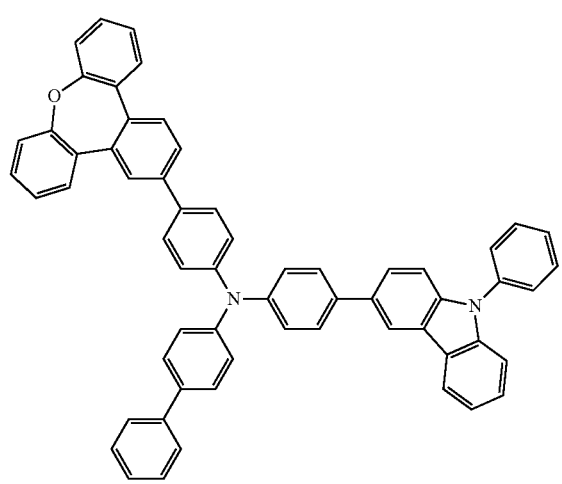
Compound 30
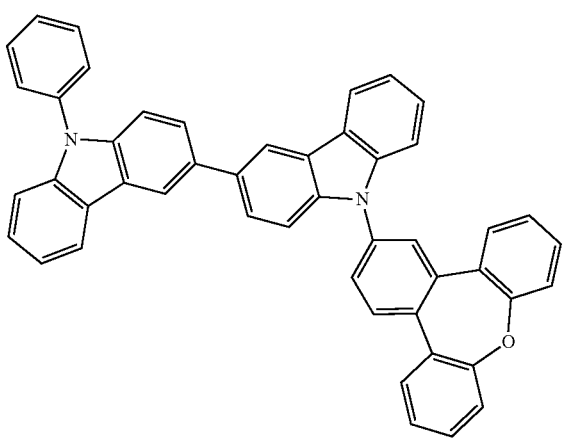
Compound 31
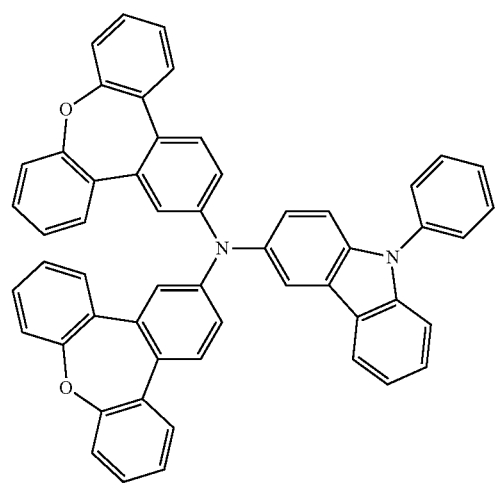
Compound 32
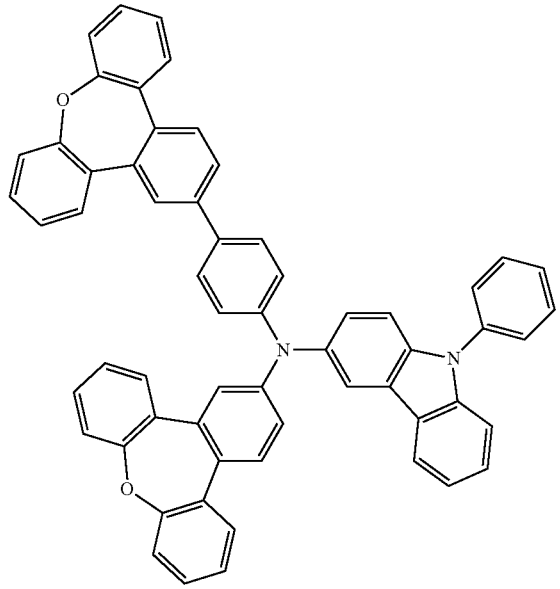
Compound 33
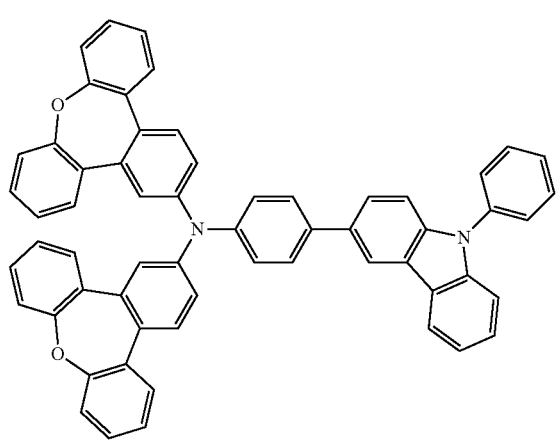

Compound 34
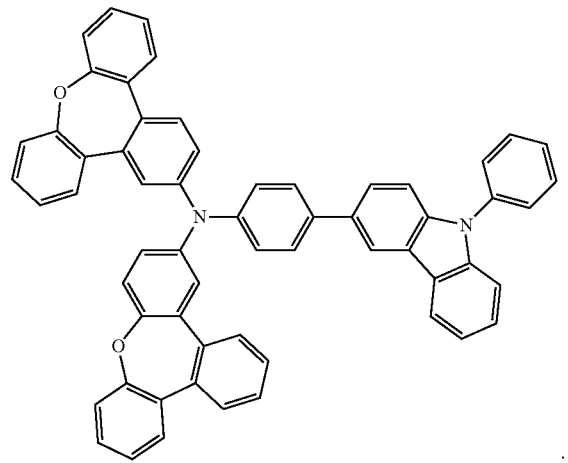
Compound 35
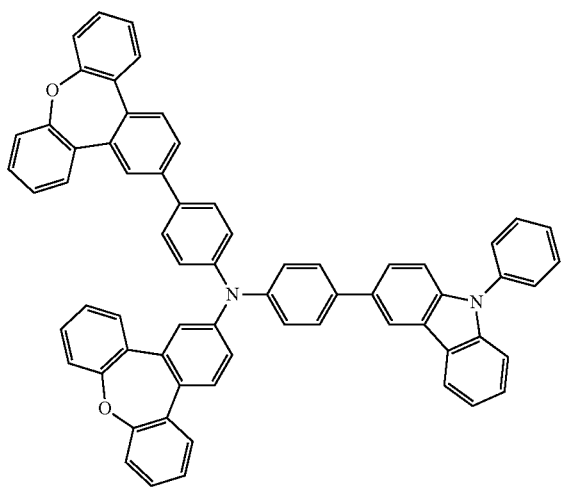
Compound 36
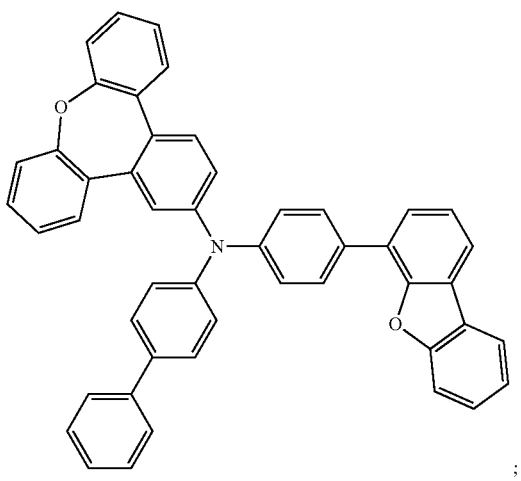
Compound 37
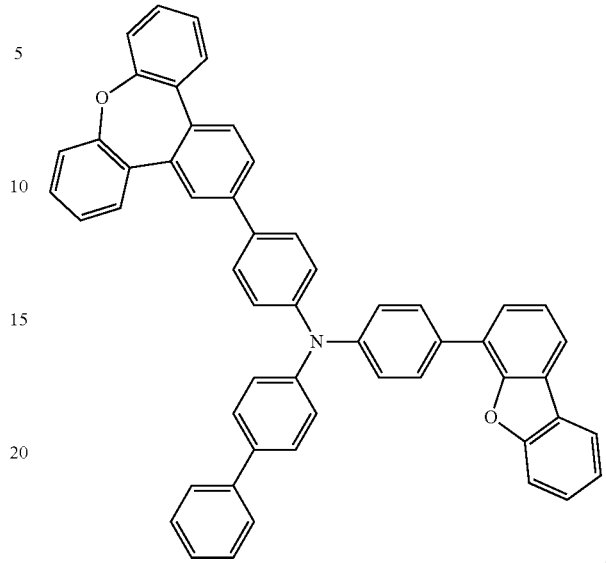
Compound 38
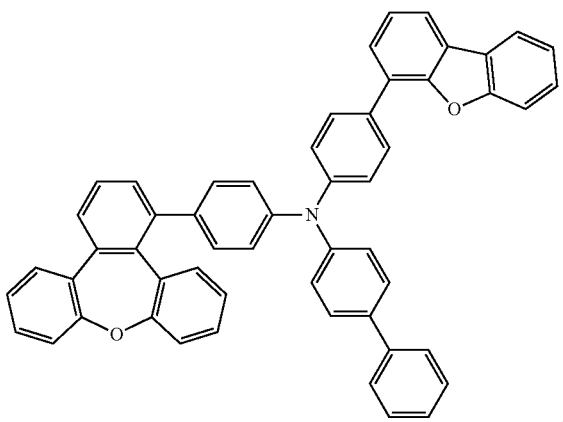
Compound 39
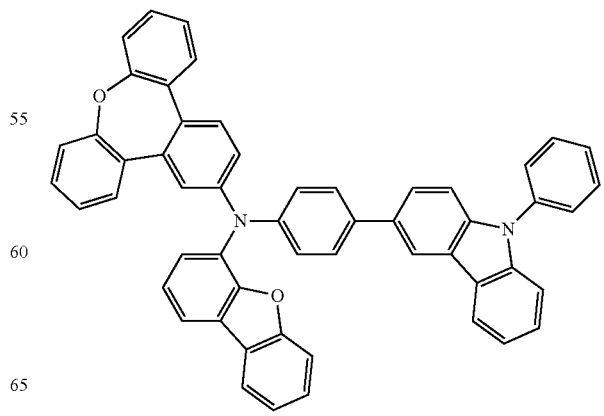

Compound 40
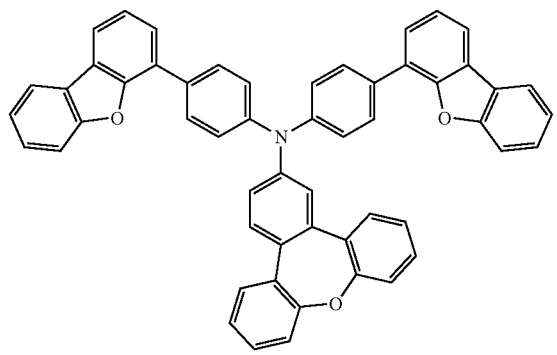
Compound 41
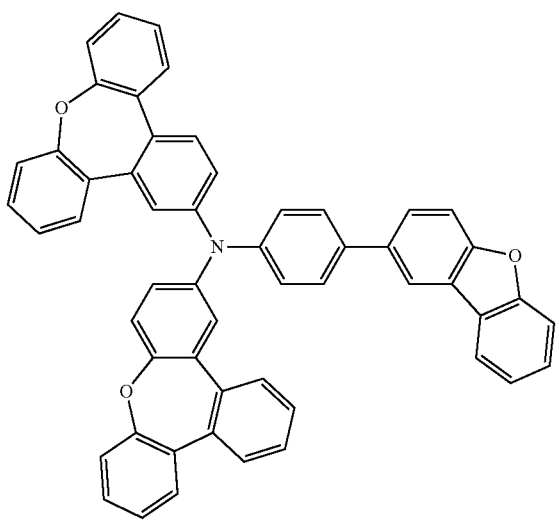
Compound 42
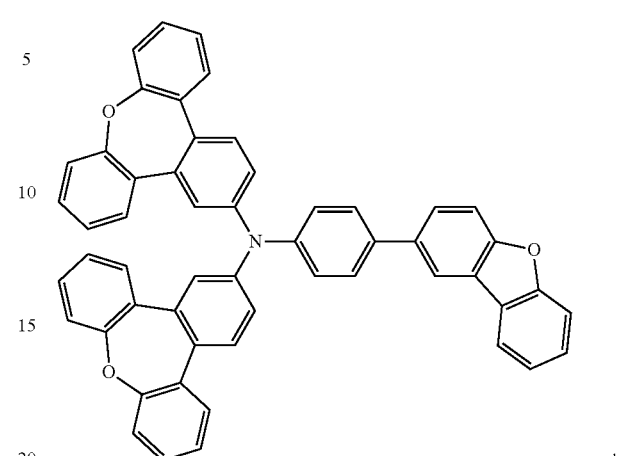
; and
Compound 43
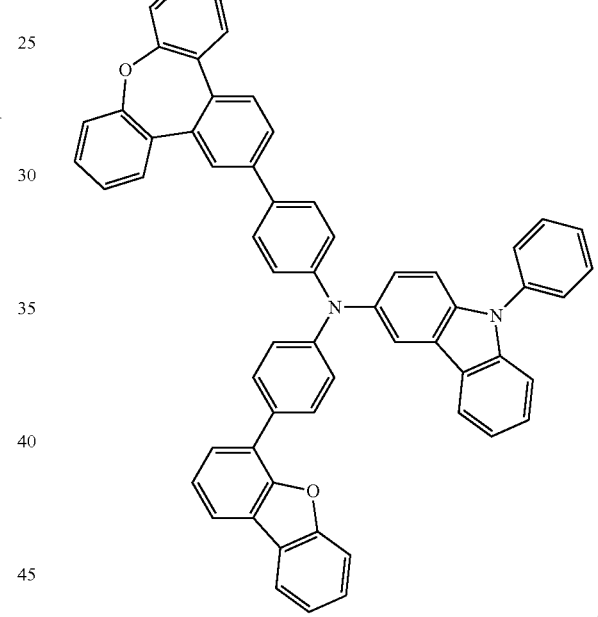
* * * * *